(12) United States Patent  (10) Patent No.: US 7,538,084 B2
Molino et al.  (45) Date of Patent: May 26, 2009

(54) CYCLOSPORINS

(75) Inventors: Bruce F. Molino, Slingerlands, NY (US); Simon N. Haydar, Apex, NY (US); Zhicai Yang, Schenectady, NY (US); Peter C. Michels, Prospect Heights, IL (US); Michael S. Hemenway, Vernon Hills, IL (US); Joseph O. Rich, Glenview, IL (US); Yuri Khmelnitsky, Addison, IL (US)

(73) Assignee: AMR Technology, Inc., Manchester Center, VT (US)

( * ) Notice: Subject to any disclaimer, the term of this patent is extended or adjusted under 35 U.S.C. 154(b) by 86 days.

(21) Appl. No.: 10/802,013

(22) Filed: Mar. 16, 2004

(65) Prior Publication Data

US 2004/0235716 A1  Nov. 25, 2004

Related U.S. Application Data

(60) Provisional application No. 60/455,727, filed on Mar. 17, 2003.

(51) Int. Cl.
  *A61K 38/00* (2006.01)
(52) U.S. Cl. ....................................................... 514/11
(58) Field of Classification Search ........................ None
  See application file for complete search history.

(56) References Cited

U.S. PATENT DOCUMENTS

| | | | |
|---|---|---|---|
| 4,210,581 A | 7/1980 | Riiegger et al. | |
| 4,288,431 A | 9/1981 | Traber et al. | |
| 4,384,996 A | 5/1983 | Bollinger et al. | |
| 4,396,542 A | 8/1983 | Wenger | |
| 4,554,351 A | 11/1985 | Wenger | |
| 4,639,434 A | 1/1987 | Wenger et al. | |
| 4,649,047 A | 3/1987 | Kaswan | |
| 4,703,033 A | 10/1987 | Seebach | |
| 4,727,035 A | 2/1988 | Mahoney | |
| 4,764,503 A | 8/1988 | Wenger | |
| 4,771,122 A | 9/1988 | Seebach | |
| 4,798,823 A * | 1/1989 | Witzel ........................ | 514/11 |
| 4,814,323 A | 3/1989 | Andrieu et al. | |
| 4,839,342 A | 6/1989 | Kaswan | |
| 4,885,276 A | 12/1989 | Witzel | |
| 5,030,739 A | 7/1991 | Foricher et al. | |
| 5,116,816 A | 5/1992 | Dreyfuss et al. | |
| 5,169,773 A | 12/1992 | Rosenthaler et al. | |
| 5,284,826 A | 2/1994 | Eberle | |
| 5,318,901 A | 6/1994 | Patchett et al. | |
| 5,411,952 A | 5/1995 | Kaswan | |
| 5,525,590 A | 6/1996 | Bollinger et al. | |
| 5,643,870 A | 7/1997 | Boelsterli et al. | |
| 5,767,069 A | 6/1998 | Ko et al. | |
| 5,834,266 A | 11/1998 | Crabtree et al. | |
| 5,840,900 A | 11/1998 | Greenwald et al. | |
| 5,846,514 A | 12/1998 | Foster et al. | |
| 5,869,337 A | 2/1999 | Crabtree et al. | |
| 5,869,709 A | 2/1999 | Marwah et al. | |
| 5,948,693 A | 9/1999 | Rich et al. | |
| 5,948,884 A | 9/1999 | Luchinger | |
| 5,981,479 A | 11/1999 | Ko et al. | |
| 5,994,299 A | 11/1999 | Barriere et al. | |
| 6,255,100 B1 | 7/2001 | Ko et al. | |
| 6,506,777 B1 | 1/2003 | Finke et al. | |
| 6,605,593 B1 | 8/2003 | Naicker et al. | |
| 6,613,729 B1 | 9/2003 | Naicker et al. | |
| 6,613,739 B1 | 9/2003 | Naicker et al. | |
| 6,686,454 B1 | 2/2004 | Yatscoff et al. | |
| 6,723,339 B2 | 4/2004 | Meinzer et al. | |
| 6,767,555 B2 | 7/2004 | Ambuhl et al. | |
| 6,784,156 B2 | 8/2004 | Or et al. | |
| 6,809,077 B2 | 10/2004 | Or et al. | |

(Continued)

FOREIGN PATENT DOCUMENTS

BR  9603738-5 A  5/1998

(Continued)

OTHER PUBLICATIONS

Buetler et al., "Does Cyclosporin A Generate Free Radicals?" *TIPS*, 21:288-290 (2000).

(Continued)

*Primary Examiner*—Anish Gupta
*Assistant Examiner*—Marcela M Cordero Garcia
(74) *Attorney, Agent, or Firm*—Nixon Peabody LLP

(57) ABSTRACT

The compounds of the present invention are represented by the chemical structure found in Formula I:

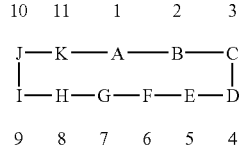

Formula I where A is an amino acid of Formula II:

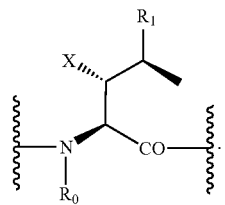

Formula II or a pharmaceutically acceptable salt thereof, with $R_0$, $R_1$, B, C, D, E, F, G, H, I, J, and K defined herein.

8 Claims, No Drawings

U.S. PATENT DOCUMENTS

| | | | |
|---|---|---|---|
| 6,844,459 B2 | 1/2005 | Hauer et al. | |
| 6,927,208 B1 * | 8/2005 | Wenger et al. | 514/9 |
| 6,979,671 B2 | 12/2005 | Or et al. | |
| 6,998,385 B2 | 2/2006 | Naicker et al. | |
| 7,012,064 B2 | 3/2006 | Or et al. | |
| 7,012,065 B2 | 3/2006 | Or et al. | |
| 7,060,672 B2 | 6/2006 | Naicker et al. | |
| 2002/0127198 A1 | 9/2002 | Rothbard et al. | |
| 2002/0128470 A1 | 9/2002 | Fuenfschilling et al. | |
| 2002/0132763 A1 | 9/2002 | Naicker et al. | |
| 2002/0142946 A1 | 10/2002 | Or et al. | |
| 2003/0022831 A1 | 1/2003 | Rothbard et al. | |
| 2003/0087813 A1 | 5/2003 | Or et al. | |
| 2003/0104992 A1 | 6/2003 | Or et al. | |
| 2003/0109425 A1 | 6/2003 | Or et al. | |
| 2003/0109426 A1 | 6/2003 | Or et al. | |
| 2003/0139326 A1 | 7/2003 | Naicker et al. | |
| 2003/0166515 A1 | 9/2003 | Or et al. | |
| 2003/0171264 A1 | 9/2003 | Naicker et al. | |
| 2003/0186855 A1 | 10/2003 | Or et al. | |
| 2003/0212249 A1 | 11/2003 | Naicker et al. | |
| 2003/0220234 A1 | 11/2003 | Naicker et al. | |
| 2004/0087496 A1 | 5/2004 | Kim et al. | |
| 2004/0110666 A1 | 6/2004 | Or et al. | |
| 2004/0157768 A1 | 8/2004 | Or et al. | |
| 2004/0220091 A1 | 11/2004 | Adam et al. | |
| 2004/0235716 A1 * | 11/2004 | Molino et al. | 514/11 |
| 2004/0247624 A1 | 12/2004 | Unger et al. | |
| 2004/0266669 A1 | 12/2004 | Wu et al. | |
| 2005/0176628 A1 | 8/2005 | Naicker et al. | |
| 2005/0192214 A1 | 9/2005 | Naicker et al. | |
| 2006/0035821 A1 | 2/2006 | Hunt et al. | |
| 2006/0035822 A1 | 2/2006 | Hunt et al. | |
| 2006/0035828 A1 | 2/2006 | Elmaleh | |
| 2006/0052290 A1 | 3/2006 | Naicker et al. | |
| 2006/0069015 A1 * | 3/2006 | Molino et al. | 514/9 |
| 2006/0069016 A1 * | 3/2006 | Molino et al. | 514/9 |
| 2006/0074015 A1 | 4/2006 | Molino et al. | |
| 2006/0135414 A1 | 6/2006 | Naicker et al. | |
| 2006/0217309 A1 | 9/2006 | Naicker et al. | |
| 2007/0232530 A1 | 10/2007 | Molino | |
| 2007/0232531 A1 | 10/2007 | Molino | |
| 2007/0232532 A1 | 10/2007 | Molino | |
| 2008/0021197 A1 | 1/2008 | Molino et al. | |
| 2008/0153744 A1 | 6/2008 | Molino et al. | |

FOREIGN PATENT DOCUMENTS

| | | |
|---|---|---|
| CA | 1106303 A2 | 8/1981 |
| CA | 1292962 C | 12/1991 |
| CA | 2076291 AA | 2/1993 |
| CA | 2096892 A | 11/1993 |
| CA | 2086267 AA | 6/1994 |
| CH | 628872 A | 3/1982 |
| CH | 630061 A | 5/1982 |
| CH | 630062 A | 5/1982 |
| CH | 637123 A | 7/1983 |
| CH | 640520 A | 1/1984 |
| CS | 277471 B6 | 3/1993 |
| CS | 277472 B6 | 3/1993 |
| CZ | 280552 B6 | 2/1996 |
| CZ | 280553 B6 | 2/1996 |
| DE | 2455859 A1 | 6/1975 |
| DE | 2648121 A1 | 5/1977 |
| DE | 2819094 A1 | 11/1978 |
| DE | 285793 A5 | 1/1991 |
| DE | 295245 A5 | 10/1991 |
| DE | 295870 A | 11/1991 |
| DE | 295871 A | 11/1991 |
| DE | 4032268 A1 | 4/1992 |
| DE | 4236237 A1 | 4/1994 |
| DE | 19933173 A1 | 1/2001 |
| DE | 102004011988 A1 | 9/2005 |
| EP | 0 034 567 | 11/1984 |
| EP | 283801 A2 | 9/1988 |
| EP | 300785 A2 | 1/1989 |
| EP | 375454 A1 | 6/1990 |
| EP | 444897 A1 | 9/1991 |
| EP | 471295 A1 | 2/1992 |
| EP | 473961 A2 | 3/1992 |
| EP | 487289 A2 | 5/1992 |
| EP | 642799 A1 | 3/1995 |
| EP | 0 484 281 B2 | 11/2000 |
| FR | 2640641 A1 | 6/1990 |
| FR | 2757520 A1 | 6/1998 |
| FR | 2757521 A1 | 6/1998 |
| FR | 2757522 A1 | 6/1998 |
| FR | 2851471 A1 | 8/2004 |
| GB | 2205317 A1 | 12/1988 |
| GB | 2206119 A1 | 12/1988 |
| GB | 2207678 A1 | 2/1989 |
| GB | 2212499 A1 | 7/1989 |
| GB | 2227244 A1 | 7/1990 |
| JP | 57063093 A2 | 4/1982 |
| JP | 05271267 A2 | 10/1993 |
| JP | 07278187 A2 | 10/1995 |
| JP | 10279596 A2 | 10/1998 |
| JP | 2002080394 A2 | 3/2002 |
| JP | 2005198543 A2 | 7/2005 |
| JP | 2005325061 A2 | 11/2005 |
| KR | 161664 B1 | 11/1998 |
| KR | 2002089300 A | 11/2002 |
| RU | 2144017 C1 | 1/2000 |
| WO | WO 90/06763 | 6/1990 |
| WO | WO 92/06998 | 4/1992 |
| WO | WO 92/13094 | 8/1992 |
| WO | WO 92/13569 | 8/1992 |
| WO | WO 93/07150 | 4/1993 |
| WO | WO 94/18317 | 8/1994 |
| WO | WO 94/25606 | 11/1994 |
| WO | WO 95/02684 | 1/1995 |
| WO | WO 96/06111 | 2/1996 |
| WO | WO 96/06857 | 3/1996 |
| WO | WO 96/27607 | 9/1996 |
| WO | WO 96/40758 | 12/1996 |
| WO | WO 97/04005 | 2/1997 |
| WO | WO 97/11092 | 3/1997 |
| WO | WO 97/46575 | 12/1997 |
| WO | WO 98/03192 | 1/1998 |
| WO | WO 98/07713 | 2/1998 |
| WO | WO 98/08956 | 3/1998 |
| WO | WO 98/46247 | 10/1998 |
| WO | WO 98/49193 | 11/1998 |
| WO | WO 98/58927 | 12/1998 |
| WO | WO 99/02659 | 1/1999 |
| WO | WO 99/10373 | 3/1999 |
| WO | WO 99/10374 | 3/1999 |
| WO | WO 99/18120 | 4/1999 |
| WO | WO 99/21879 | 5/1999 |
| WO | WO 99/32512 | 7/1999 |
| WO | WO 99/62540 | 12/1999 |
| WO | WO 99/65933 | 12/1999 |
| WO | WO 99/67280 | 12/1999 |
| WO | WO 00/01715 | 1/2000 |
| WO | WO 00/08033 | 2/2000 |
| WO | WO 00/51558 | 9/2000 |
| WO | WO 00/67801 | 11/2000 |
| WO | WO 01/05819 A1 | 1/2001 |
| WO | WO 01/13957 A2 | 3/2001 |
| WO | WO 01/35913 A1 | 5/2001 |
| WO | WO 01/35914 A1 | 5/2001 |
| WO | WO 02/24865 A2 | 3/2002 |
| WO | WO 02/41858 A1 | 5/2002 |
| WO | WO 02/41859 A1 | 5/2002 |

| WO | WO 02/064106 A1 | 8/2002 |
| --- | --- | --- |
| WO | WO 02/065986 A2 | 8/2002 |
| WO | WO 02/067917 A1 | 9/2002 |
| WO | WO 02/069902 A2 | 9/2002 |
| WO | WO 02/076927 A2 | 10/2002 |
| WO | WO 02/085928 A2 | 10/2002 |
| WO | WO 02/092032 A1 | 11/2002 |
| WO | WO 02/092033 A1 | 11/2002 |
| WO | 02/100428 A1 | 12/2002 |
| WO | WO 03/030834 A2 | 4/2003 |
| WO | WO 03/032949 A1 | 4/2003 |
| WO | WO 03/033010 A1 | 4/2003 |
| WO | WO 03/033526 A2 | 4/2003 |
| WO | WO 03/033527 | 4/2003 |
| WO | WO 03/034980 A2 | 5/2003 |
| WO | WO 03/049772 A2 | 6/2003 |
| WO | WO 03/070755 A2 | 8/2003 |
| WO | WO 2004/050687 A2 | 6/2004 |
| WO | WO 2004/072108 A1 | 8/2004 |
| WO | WO 2004/082629 A2 | 9/2004 |
| WO | WO 2004/089960 A2 | 10/2004 |
| WO | WO 2004/096236 A2 | 11/2004 |
| WO | WO 2004/100960 A2 | 11/2004 |
| WO | WO 2005/000879 A1 | 1/2005 |
| WO | WO 2005/021028 A1 | 3/2005 |
| WO | WO 2005/046575 A2 | 5/2005 |
| WO | WO 2005/097164 A2 | 10/2005 |
| WO | WO 2006/005580 A1 | 1/2006 |
| WO | WO 2006/005610 A1 | 1/2006 |
| WO | WO 2006/014872 A2 | 2/2006 |
| WO | 2006/039163 | 4/2006 |
| WO | 2006/039164 | 4/2006 |
| WO | 2006/041631 | 4/2006 |
| WO | WO 2006/063470 A1 | 6/2006 |
| WO | WO 2006/066416 A1 | 6/2006 |
| WO | WO 2006/071618 A1 | 7/2006 |
| WO | 2007/112345 | 10/2007 |
| WO | 2007/112352 | 10/2007 |
| WO | 2007/112357 | 10/2007 |

OTHER PUBLICATIONS

Christians et al., "Cyclosporin Metabolism in Transplant Patients," *Pharmac. Ther.*, 57:291-345 (1993).

Foster, "Deuterium Isotope Effects in Studies of Drug Metabolism," *TIPS*, 5:524-527 (1984).

Fritz-Langhals et al., "Synthesis of Aromatic Aldehydes by Laccase-Mediator Assisted Oxidation," *Tetrahedron Letters*, 39:5955-5956 (1998).

Henke et al., "Cyclosporine A Inhibits ATP Net Uptake of Rat Kidney Mitochondria," *Biochemical Pharmacology*, 43(5):1021-1024 (1992).

Park et al., "A Semi-Synthetic Approach to Olefinic Analogs of Amino Acid One (MeBMT) in Cyclosporin A," *Tetrahedron Letters*, 30(32):4215-4218 (1989).

Paolini, "Cyclosporin A and Free Radical Generation," *Trends in Pharmacological Sciences*, 22(1):14-15 (2001).

Punniyamurthy et al., "Cobalt Catalysed Allylic and Benzylic Oxidations with Dioxygen in the Presence of Ethyl 2-Oxocyclopentanecarboxylate," *Tetrahedron Letters*, 35(23):4003-4006 (1994).

Seebach et al., "Modification of Cyclosporin A (CS): Generation of an Enolate at the Sarcosine Residue and Reactions with Electrophiles," *Helvetica Chimica Acta*, 76:1564-1590 (1993).

Seebach et al., "Thiocyclosporins: Preparation, Solution and Crystal Structure, and Immunosuppressive Activity," *Helvetica Chimica Acta*, 74:1953-1990 (1991).

Serkova et al., "The Novel Immunosuppressant SDZ-RAD Protects Rat Brain Slices from Cyclosporine-Induced Reduction of High-Energy Phosphate," *British Journal of Pharmacology*, 129:485-492 (2000).

Serino et al., "Oxygen Radical Formation by the Cytochrome P450 Systems as a Cellular Mechanism for Cyclosporine Toxicity," *Transplantation Proceedings*, 26:2916-2917 (1994).

Snyder et al., "Immunophilins and the Nervous System," *Nature Medicine*, 1(1):32-37 (1995).

Steiner et al., "Neurotrophic Actions of Nonimmunosuppressive Analogues of Immunosuppressive Drugs FK506, Rapamycin and Cyclosporin A," *Nature Medicine*, 3(4):421-428 (1997).

Wenger, "Structures of Cyclosporine and Its Metabolites," *Transplantation Proceedings*, 22(3):1104-1108 (1990).

Xu et al., "Redox Chemistry in Laccase-Catalyzed Oxidation of N-Hydroxy Compounds," *Applied and Environmental Microbiology*, 66(5):2052-2056 (2000).

Abel et al., "ISATX247: A Novel Calcineurin Inhibitor," *J. Heart Lung Transplantation*, 20(2):161 (2001) (abstract).

Aspeslet et al., "ISA$_{TX}$247: A Novel Calcineurin Inhibitor," *Transplantation Proceedings*, 33:1048-1051 (2001).

Khanna et al., "TGF-β: A Link Between Immunosuppression, Nephrotoxicity, and CsA," *Transplantation Proceedings*, 30:944-945 (1998).

Wenger, "60. Synthesis of Cyclosporine: Total Syntheses of 'Cyclosporin A' and 'Cyclosporin H', Two Fungal Metabolites Isolated from the Species *Tolypocladium Inflatum* GAMS," *Helvetica Chimica Acta*, 67(2):502-525 (1984).

Traber, "122. Die Struktur von Cyclosporin C," *Helvetica Chimica Acta*, 60(4):1247-1255 (1977) (English Abstract Only).

Traber, "2. Neue Cyclosporine aus *Tolypocladium inflatum* Die Cyclosporine K-Z," *Helvetica Chimica Acta*, 70:13-36 (1987) (English Abstract Only).

Traber, "162. Isolierung und Strukturermittlung der neuen Cyclosporine E, F, G, H und I," *Helvetica Chimica Acta*, 65(5):1655-1677 (1982) (English Abstract Only).

Eberle et al., "Preparation of Sulfhydryl Cyclosporin A," *J. Org. Chem.*, 60:2610-2612 (1995).

Snyder et al., "Neural Actions of Immunophilin Ligands," *TIPS*, 19:21-26 (1998).

Loor, "Valspodar: Current Status and Perspectives," *Exp. Opin. Invest. Drugs*, 8(6):807-835 (1999).

Traber et al., "Cyclosporins—New Analogues by Prescursor Directed Biosynthesis," *J. of Antibiotics*, 42(4):591-597 (1989).

Ko et al., "53. Solid-Phase Total Synthesis of Cyclosporine Analogues," *Helvetica Chimica Acta*, 80:695-705 (1997).

Kallen et al., "12 Cyclosporins: Recent Developments in Biosynthesis, Pharmacology and Biology, and Clinical Applications," *Biotechnology*, Second Edition, Rehm et al, eds., pp. 535-591 (1997).

Mlynar et al., "The Non-Immunosuppressive Cyclosporin A Analogue SDZ NIM 811 Inhibits Cyclophilin A Incorporation Into Virions and Virus Replication in Human Immunodeficiency Virus Type 1-Infected Primary and Growth-Arrested T Cells," *J. General Virology*, 78(4):825-835 (1997).

Loor, "Cyclosporins and Related Fungal Products in the Reversal of P-Glycoprotein-Mediated Multidrug Resistance," in *Multidrug Resistance in Cancer Cells*, Gupta et al, eds., John Wiley and Sons Ltd: Chichester, pp. 385-412 (1996).

Potthast et al., "A Novel Method for the Conversion of Benzyl Alcohols to Benzaldehydes by Laccase-Catalyzed Oxidation," *J. Molecular Catalysis A*, 108:5-9 (1996).

Offenzeller et al., "Biosynthesis of the Unusual Amino Acid (4R)-4-[(E)-2-Butenyl]-4-methyl-L-threonine of Cyclosporin A: Enzymatic Analysis of the Reaction Sequence Including Identification of the Methylation Precursor in a Polyketide Pathway," *Biochemistry* 35:8401-8412 (1996).

Clark & Yorio, "Ophthalmic Drug Discovery," *Nat. Rev. Drug Discov.* 2(6):448-459 (2003).

Dumont, "ISAtx-247 Isotechnika/Roche," *Curr. Opin. Investig. Drugs* 5(5):542-550 (2004).

Eckstein & Fung, "A New Class of Cyclosporin Analogues for the Treatment of Asthma," *Expert Opin. Investig. Drugs* 12(4):647-653 (2003).

Lazarova et al., "Synthesis and Biological Evaluation of Novel Cyclosporin A Analogues: Potential Soft Drugs for the Treatment of Autoimmune Diseases," *J. Med. Chem.* 46:674-676 (2003).

Aebi et al., "Synthesis, Conformation, and Immunosuppressive Activities of Three Analogs of Cyclosporin A Modified in the 1-Position," *Journal of Medicinal Chemistry* 33(3):999-1009 (1990), Abstract only.

Agathos et al., "Enhancement of Cyclosporin Production in a Tolypocladium inflatum Strain After Epichlorohydrin Treatment," *Journal of Biotechnology* 13(1):73-81 (1990), Abstract only.

Agathos et al., "The Fungal Production of Cyclosporins," *Annals of the New York Academy of Sciences*, 506(Biochem. Eng. 5):657-662 (1987), Abstract only.

Alberg et al., "Structure-Based Design of a Cyclophilin-Calcineurin Bridging Ligand," *Science* (Washington, DC, United States) 262(5131):248-250 (1993), Abstract only.

Andres et al., "Interaction of Lead(II) With Highly-Dentate Linear and Cyclic Polyamines," *Journal of the Chemical Society, Dalton Transactions: Inorganic Chemistry* (23):3507-3513 (1972-1999) (1993), Abstract only.

Angell et al. "Innovation and Perspectives in Solid Phase Synthesis & Combinatorial Libraries: Peptides, Proteins and Nucleic Acids—Small Molecule Organic Chemical Diversity, Collected Papers," in Epton, ed. *International Symposium*, 5th, London, Sep. 2-6, 1997 (1999), Meeting Date 1997, Mayflower Scientific Ltd.: Kingswinford, pp. 135-138, Abstract only.

Angell et al., "Solid-Phase Synthesis of Cyclosporin Peptides," *Journal of the American Chemical Society* 117(27):7279-7280 (1995), Abstract only.

Angell, "The Solid-Phase Synthesis Of Cyclosporin A Analogs," Diss. Abstr. Int., B 1997, 57(9):5657(1996), Abstract only.

Belshaw et al. "Cell-Specific Calcineurin Inhibition by a Modified Cyclosporin," *Journal of the American Chemcial Society* 119(7):1805-1806 (1997), Abstract only.

Belshaw et al., "Controlling Protein Association and Subcellular Localization With a Synthetic Ligand That Induces Heterodimerization of Proteins," *Proceedings of the National Academy of Sciences of the United States of America*, 93(10):4604-4607 (1996), Abstract only.

Belshaw et al., "Rational Design of Orthogonal Receptor-Ligand Combinations," *Angewandte Chemie, International Edition In English*, 34(19):2129-2132 (1995), Abstract only.

Bencini et al., "Anaerobic Complexation of Colbalt(II) by [3k]aneNk (k=7-12) Polyazacycloalkanes," *Inorganic Chemistry* 28(12):2480-2482 (1989), Abstract only.

Bencini et al., "Synthesis and Ligational Properties of the Two Very Large Polyazacycloalkanes [33]aneN11 and [36]aneN12 Forming Trinuclear Copper(II) Complexes," *Inorganic Chemistry* 27(1):176-180 (1988), Abstract only.

Bencini et al., "Thermodynamic and Structural Aspects of the Interaction Between Macrocyclic Polyammonium Cations and Complexed Anions," *Inorganic Chemistry* 31(10):1902-1908 (1992), Abstract only.

Billich et al., Enzymic Synthesis of Cyclosporin A,: *Journal of Biological Chemistry* 262(36):17258-17259 (1987), Abstract only.

Billich et al., "Novel Cyclosporin Derivatives Featuring Enhanced Skin Penetration Despite Increased Molecular Weight," *Bioorganic and Medicinal Chemistry* 13(9):3157-3167 (2005), Abstract only.

Bohnstedt, "This Synthesis And Biological Activities Of Novel Backbone-Modified Analogs Of Cyclosporin A," Diss. Abstr. Int. B 1995, 55(11), 4848 (1994), Abstract only.

Brooks et al., "Preparative Chromatographic Purification of Cyclosporine Metabolites," *Clinical Chemistry* (Washington, DC, United States) 39(3):457-466 (1993), Abstract only.

Brugghe et al., "Simultaneous Multiple Synthesis and Selective Conjugation of Cyclized Peptides Derived from a Surface Loop of a Meningococcal Class 1 Outer Membrane Protein," *International Journal of Peptide & Protein Research* 43(2), 166-172 (1994), Abstract only.

Buchta et al., "A Cyclosporin From Mycelium Sterilae," *Phytochemistry* 48(7):1195-1198 (1998), Abstract only.

Burtscher et al., "Synthesis of [S-[1-14C]val7]VALSPODAR: Application of (+)/(−)-[13,14Cn]BABS and (+)/(−)-[13,14Cn]DPMGBS," *Journal of Labelled Compounds & Radiopharmaceuticals* 43(3):205-216 (2000), Abstract only.

Cacalano et al., "Antibodies to Cyclosporine A (CsA) by a Novel Route and Their Use to Monitor Cyclosporine Levels by Radioimmunoassay (RIA)," *Journal of Immunological Methods* 118(2):257-263 (1989), Abstract only.

Carry et al., "Semisynthetic Di- and Tri-Functionalized Non-Immunosuppressive Cyclosporin A Derivatives as Potential Anti-HIV 1 Drugs," *Synlett* (2):316-320 (2004), Abstract only.

Cerny et al., "Synthesis of [ω-3H-MeBmt1]-Cyclosporin A," *Journal of Labelled Compounds & Radiopharmaceuticals* 41(4):267-272 (1998), Abstract only.

Chen et al., "A Sensitive Enzyme Immunoassay for Cyclosporin A Using Antibodies Generated Against A Novel Hapten," *Research Communications in Molecular Pathology and Pharmacology* 88(3):317-326 (1995), Abstract only.

Cho et al., "Water Soluble Cyclosporine Monomethoxy Poly(Ethyleneglycol) Conjugates as Potential Prodrugs," *Archives of Pharmacal Research* 27(6):662-669 (2004), Abstract only.

Chu et al., "A New Producer of Cyclosporin C," *Zhongguo Kangshengsu Zazhi* 23(1):1-5, 16 (1998), Abstract only.

Chu et al., "Production of Cyclosporin C by Gliomastix luzulae Isolated From Different Areas of China," *Zhongguo Kangshengsu Zazhi* 23(2):116-120 (1998), Abstract only.

Chu et al., "Screening of Antifungal Substances with Immunosuppressive Activity by Special Morphological Abnormalities of *Aspergillus clavatus*," *Zhongguo Kangshengsu Zazhi* 23(3):193-196 (1998), Abstract only.

Coates et al., "Radioimmunoassay of Salivary Cyclosporine With Use of Iodine-125-Labeled Cyclosporine," *Clinical Chemistry* (Washington, DC, United States), 34(8):1545-1551 (1988), Abstract only.

Colucci et al., "Synthesis of D-Lysine8-Cyclosporine A. Further Characterization of BOP-Cl in the 2-7 Hexapeptide Fragment Synthesis," *Journal of Organic Chemistry* 55(9): 2895-2903 (1990), Abstract only.

Dai et al., "Study of the Reaction Between Cyclosporine A and 4-Benzoylbenzoic Acid," *Jingxi Huagong* 18(3):135-137 (2001), Abstract only.

Donatsch et al., "A Radioimmunoassay to Measure Cyclosporin A in Plasma and Serum Samples," *Journal of Immunoassay* 2(1):19-32 (1981), Abstract only.

Dreyfuss et al., "Cyclosporin A and C. New Metabolites From Trichoderma polysporum (Link ex Pers.) Rifai," *European Journal of Applied Microbiology* 3(2):125-133 (1976), Abstract only.

Dugave, "Study of the cis-trans Isomerization of the Amino-Acyl Prolyl Peptide Bond: Application to the Design of Novel Inhibitors of Immunophilins," *Current Organic Chemistry* 6(15):1397-1431 (2002), Abstract only.

Durette et al., "A study of the Correlation Between Cyclophilin Binding and in Vitro Immunosuppressive Activity of Cyclosporine A and Analogs," *Transplantation Proceedings* 20(2, Suppl. 2):51-57 (1988), Abstract only.

Eberle et al., "Bridged Cyclosporins," *Journal of Organic Chemistry* 60(15):4868-4872 (1995), Abstract only.

Eberle et al., "Cyclosporin A: Regioselective Ring Opening and Fragmentation Reactions via Thioamides. A Route to Semisynthetic Cyclosporins," *Journal of Organic Chemistry* 59(24):7249-7258 (1994), Abstract only.

Eberle et al., "Modifications of the MeBmt Side Chain of Cyclosporin A," *Bioorganic & Medicinal Chemistry Letters* 5(15):1725-1728 (1995), Abstract only.

Eberle et al., "Preparation and in Vitro Activities of Ethers of [D-Serine]8-cyclosporin," *Journal of Medicinal Chemistry* 38(11):1853-1864 (1995), Abstract only.

Eberle et al., "Preparation of [D-cysteine]8-Cyclosporin Via Intramolecular Sulfur Transfer Reaction," *Journal of Organic Chemistry* 58(3):673-677 (1993), Abstract only.

Eberle et al., "Preparation of Functionalized Ethers of Cyclosporin A," *Tetrahedron Letters* 35(35):6477-6480 (1994), Abstract only.

Eberle et al., "Synthesis of the Main Metabolite (OL-17) of Cyclosporin A," *Journal of Organic Chemistry*, 57(9):2689-2691 (1992), Abstract only.

Endo et al., "Solution-Phase Synthesis and Structural Analysis of N-Desmethylated Cyclosporin O Analogs," *Peptide Science* 39:383-386 Volume Date 2002, (2003), Abstract only.

Evers et al., "Synthesis of Non-Immunosuppressive Cyclophilin-Binding Cyclosporin A Derivatives as Potential Anti-HIV-1 Drugs," *Bioorganic & Medicinal Chemistry Letters* 13(24):4415-4419 (2003), Abstract only.

Fang et al., "Separation of Cyclosporins by High Speed Counter Current Chromatography," *Zhongguo Kangshengsu Zazhi* 30(1):48-51 (2005), Abstract only.

French et al., "New Fluorescent Derivatives of Cyclosporin for Use in Immunoassays," *Journal of Pharmaceutical and Biomedical Analysis* 10(1):23-30 (1992), Abstract only.

Galpin et al., "Synthesis of Cyclosporin Analogs," *Tetrahedron Letters* 28(51):6517-6520 (1987), Abstract only.

Galpin et al., "Synthetic Studies of Cyclosporin Analogs," *Tetrahedron* 44(6):1783-1794 (1988), Abstract only.

Gfeller et al., "Improvement of Detection Sensitivity of Cyclosporin A by Derivatization With 2-Naphthylselenyl Chloride," *Helvetica Chimica Acta* 63(3):728-732 (1980), Abstract only.

Giger et al., "Design and Synthesis of a Transition State Analog of a Metalloporphyrin-Catalysed Oxidation Reaction," *Journal of Porphyrins and Phthalocyanines* 6(5):362-365 (2002), Abstract only.

Grote et al. "A Practical Method for the Synthesis of a Cyclosporine-Fluorescein Conjugate," *Organic Process Research & Development*, 9(6):822-824 (2005), Abstract only.

Guichou et al., "Pseudo-Prolines (ΨPro): Direct Insertion of ΨPro Systems Into Cysteine Containing Peptides," *Tetrahedron Letters* 43(24):4389-4390 (2002), Abstract only.

Hamel et al., "Cyclosporin A Prodrugs: Design, Synthesis and Biophysical Properties," *Journal of Peptide Research* 63(2):147-154 (2004), Abstract only.

Hamel et al., "Water-Soluble Prodrugs of Cyclosporine A With Tailored Conversion Rates," *Journal of Peptide Research* 65(3):364-374 (2005), Abstract only.

Hensens et al., "The Preparation of [2-deutero-3-fluoro-D-Ala8]Cyclosporin A by Directed Biosynthesis," *Journal of Antibiotics* 45(1):133-135 (1992), Abstract only.

Hornich et al., "Variation of Amino Acids Within the Cyclosporin-Cyclophilin Binding Domain. Synthesis of a 21-Membered Cyclopeptolide," *Scientia Pharmaceutica* 64(3/4):463-470 (1996), Abstract only.

Hu et al., "Cyclosporin Analogs Modified in the 3,7,8-Positions: Substituent Effects on Peptidylprolyl Isomerase Inhibition and Immunosuppressive Activity Are Nonadditive," *Journal of Medicinal Chemistry* 38(21):4164-4170 (1995), Abstract only.

Hu, "Synthesis And Biological Properties Of Novel Cyclosporine Analogs," Diss. Abstr. Int. B 1995, 55(7), 2743 (1994), Abstract only.

Hubler et al., "Synthetic Routes to NEtXaa4-Cyclosporin A Derivatives as Potential Anti-HIV I Drugs," *Tetrahedron Letters* 41(37):7193-7196 (2000), Abstract only.

Husi et al., "Prediction of Substrate-Specific Pockets in Cyclosporin Synthetase," *FEBS Letters* 414(3):532-536 (1997), Abstract only.

Jegorov et al., "An Unusual Side Chain C-C Cleavage at the MeBmt Amino Acid in Cyclosporin A," *Amino Acids* 10(2):145-151 (1996), Abstract only.

Jegorov et al., "Cyclosporins from *Tolypocladium terricola*," *Phytochemistry* 38(2):403-407 (1995), Abstract only.

Jegorov et al., "Cyclosporins of Symmetry P21—a Series of Clathrates," *Journal of Inclusion Phenomena and Macrocyclic Chemistry* 37(1-4):137-153 (2000), Abstract only.

Jegorov et al., "Synthesis and Crystal Structure Determination of Cyclosporin H," *Collection of Czechoslovak Chemical Communications* 65(8):1317-1329 (2000), Abstract only.

Jiang et al., "Synthesis of Biotinylated Cyclosporin A and Studies on its Interaction With Human Cyclophilin A," *Huaxue Xuebao* 59(10):1745-1750 (2001), Abstract only.

Kanoh et al., Photo-Cross-Linked Small-Molecule Affinity Matrix for Facilitating Forward and Reverse Chemical Genetics *Angewandte Chemie, International Edition* 44(28):4282 (2005) [Erratum], Abstract only.

Kanoh et al., Photo-Cross-Linked Small-Molecule Affinity Matrix for Facilitating Forward and Reverse Chemcial Genetics, *Angewandte Chemie, International Edition* 44(23):3559-3562 (2005), Abstract only.

Keller et al., "Pseudoprolines (ΨPro) in Drug Design: Direct Insertion of ΨPro Systems Into Cyclosporin C," *Chemistry—A European Journal* 6(23):4358-4363 (2000), Abstract only.

Kobel et al., "Directed Biosynthesis of Cyclosporins," *European Journal of Applied Microbiology and Biotechnology* 14(4):237-240 (1982), Abstract only.

Koeck et al., "Novel Backbone Conformatioin of Cyclosporin A: The Complex With Lithium Chloride," *Journal of the American Chemical Society* 114(7):2676-2686 (1992), Abstract only.

Kratochvil et al., "Crystal Structures of Cyclosporin Derivatives: O-acetyl-(4R)-4-(E-2-butyl)-4,N-Dimethyl-L-Threonyl-Cyclosporin A and O-Acetyl-(4R)-4-[E-2-(4-Bromobutyl)]-4,N-Dimethyl-L-Threonyl-Cyclosporin A," *Collection of Czechoslovak Chemical Communications* 64(1):89-98 (1999), Abstract only.

Kuhnt et al., "Microbial Biotransformation Products of Cyclosporin A," *Journal of Antibiotics* 49(8):781-787 (1996), Abstract only.

Lee et al., "Synthesis and Immunosuppressive Activities of Conformationally Restricted Cyclosporin Lactam Analogs," *International Journal of Peptide & Protein Research* 35(5):481-494 (1990), Abstract only.

Levitsky et al. "Selective Inhibition of Engineered Receptors Via Proximity-Accelerated Alkylation," *Organic Letters* 5(5):693-696 (2003), Asbtract only.

Levitsky et al., "Exo-Mechansim Proximity-Accelerated Alkylations: Investigations of Linkers, Electrophiles and Surface Mutations in Engineered Cyclophilin-Cyclosporin Systems," *ChemBioChem* 6(5):890-899 (2005), Abstract only.

Lhoest et al., "Isolation, Identification and Immunosuppressive Activity of a New IMM-125 Metabolite From Human Liver Microsomes. Identification of its Cyclophilin A-IMM-125 Metabolite Complex by Nanospray Tandem Mass Spectrometry," *Journal of Mass Spectrometry* 33(10):936-942 (1998), Abstract only.

Li et al., "The Development of Highly Efficient Onium-Type Peptide Coupling Reagents Based Upon Rational Molecular Design," *Journal of Peptide Research* 58(2):129-139 (2001), Abstract only.

Li et al., "Total Synthesis of Cyclosporin O Both in Solution and in the Solid Phase Using Novel Thiazolium-, Immonium-, and Pyridinium-Type Coupling Reagents: BEMT, BDMP, and BEP," *Journal of Organic Chemistry* 65(10):2951-2958 (2000), Abstract only.

Liu et al., "Preparation of Cyclosporine A Immunogen," *Sichuan Daxue Xuebao, Ziran Kexueban* 38(3):407-411 (2001), Abstract only.

Liu et al., "Semipreparative Chromatographic Separation Of Cyclosporin G Metabolites Generated by Microsomes from Rabbits Treated With Rifampicin," *Journal of Pharmacological and Toxicological Methods* 35(3):121-129 (1996), Abstract only.

Liu et al., "Structural Characterization of two Novel Oxidative Derivatives of Cyclopsporine Generated by a Chemical Method," *Clinical Biochemistry* 31(3):173-180 (1998), Abstract only.

Lu et al., "Modification of Cyclosporin A and Conjugation of Its Derivative to HPMA Coplymers," *Bioconjugate Chemistry* 12(1):129-133 (2001), Abstract only.

Lu et al., "Synthesis of Bioadhesive Lectin-HPMA Copolymer-Cyclosporin Conjugates," *Bioconjugate Chemistry* 11(1):3-7 (2000), Abstract only.

Lynch, "The Search For Cyclophilin Inhibitors: The Design And Synthesis Of Conformationally Constrained Scaffolds," Diss. Abstr. Int., B 1995, 56(2)828 (1995), Abstract only.

Magni et al., "Hydrolytic Conditions for the Formation of Open-Chain Oligopeptides from Cyclosporin A," *Journal of Peptide Research* 49(3):191-194 (1997), Abstract only.

Mahoney et al., "Derivatives of Cyclosporin Compatible With Antibody-Based Assays: I. The Generation of [125I]-Labeled Cyclosporin," *Clinical Chemistry* (Washington, DC, United States), 31(3):459-462 (1985), Abstract only.

McIntyre et al., "ISA-247," *Drugs of the Future* 29(7):680-686 (2004), Abstract only.

Mikol et al., "The Role of Water Molecules in the Structure-Based Design of (5-Hydroxynorvaline)-2-cyclosporin: Synthesis, Biological Activity, and Crystallographic Analysis with Cyclophilin A," *Journal of Medicinal Chemistry* 38(17):3361-3367 (1995), Abstract only.

Muamba et al. "Peptides: The Wave of the Future," in Lebl eds., *Proceedings of the Second International and the Seventeenth American Peptide Symposium*, San Diego, CA, Jun. 9-14, 2001, 130-131 (2001), Abstract only.

Ohta et al., "Production of Human Metabolites of Cyclosporin A, AM1, AM4N and AM9, by Microbial Conversion," *Journal of Bioscience and Bioengineering* 99(4):390-395 (2005), Abstract only.

Okada et al., "Properties and the Inclusion Behavior of 6-O-α-D-Galactosyl- and 6-O-α-D-Mannosyl- Cyclodextrins," *Chemical & Pharmaceutical Bulletin* 47(11):1564-1568 (1999), Abstract only.

Papageorgiou et al., "Anti HIV-1 Activity of a Hydrophilic Cyclosporine Derivative With Improved Affinity to Cyclophilin," *Bioorganic & Medicinal Chemistry Letters* 6(4):497 (1996) [Erratum], Abstract only.

Papageorgiou et al., "Anti HIV-1 Activity of a Hydrophilic Cyclosporine Derivative With Improved Binding Affinity to Cyclophilin A," *Bioorganic & Medicinal Chemistry Letters* 6(1):23-26 (1996), Abstract only.

Papageorgiou et al., "Calcineurin has a Very Tight-Binding Pocket for the Side Chain of Residue 4 of Cyclosporin," *Bioorganic & Medicinal Chemistry Letters* 4(2):267-272 (1994), Abstract only.

Papageorgiou et al., "Conformational Control of Cyclosporin Through Substitution of the N-5 position. A new class of cyclosporin antagonists," *Bioorganic & Medicinal Chemistry* 5(1):187-192 (1997), Abstract only.

Papageorgiou et al., "Derivatives of Cyclosporin at Position 2 as Probes for Cyclophilin," *Bioorganic & Medicinal Chemistry Letters* 3(12):2559-64 (1993), Abstract only.

Papageorgiou et al., "Improved Binding Affinity for Cyclophilin A by a Cyclosporin Derivative Singly Modified at Its Effector Domain," *Journal of Medicinal Chemistry* 37(22):3674-3676 (1994), Abstract only.

Paprica et al., "Preparation of Novel Cyclosporin A Derivatives," *Bioconjugate Chemistry* 3(1):32-36 (1992), Abstract only.

Patchett et al., "Analogs of Cyclosporin A Modified at the D-Ala8 Position," *Journal of Antibiotics* 45(1):94-102 (1992), Abstract only.

Patiny et al., "Structure-Activity Studies of Novel D-Ser8-Cyclosporin A Derivatives As Potential Anti-HIV Drugs," *Peptides 2002, Proceedings of the European Peptide Symposium, 27th*, Benedetti et al. (eds) 1020-1021 (2002), Abstract only.

Patiny et al., "Synthesis and Characterization of Constrained Cyclosporin A Derivatives Containing a Pseudo-Proline Group," *Tetrahedron* 59(28):5241-5249 (2003), Abstract only.

Pflanz et al., "Induction and Rapid Screening of Monoclonal Antibodies Against Cyclosporin A," *Immunology Letters*, 18(4):241-245 (1988), Abstract only.

Pohl et al., "Crystal Structures of Two Modifications of [3,O-Didehydro-MeBmt1,Val2]Cyclosporin and Comparison of Three Different X-Ray Data Sets," *Helvetica Chimica Acta* 78(2):355-366 (1995), Abstract only.

Radeke et al., "Additive and Synergistic Effects of Cyclosporine Metabolites on Glomerular Mesangial Cells," *Kidney International* 39(6):1255-1266 (1991), Abstract only.

Raman Dissertation, 338 pp. Avail.: UMI, Order No. DA9809876 From: Diss. Abstr. Int., B 1998, 59(3), 1117 (1997), Abstract only.

Raman et al., "Methods to Circumvent a Difficult Coupling in the Solid-Phase Synthesis of Cyclosporine Analogs," *Journal of Organic Chemistry* 63(17):5734-5735 (1998), Abstract only.

Rich et al., "Synthesis and Antimitogenic Activities of Four Analogs of Cyclosporin A Modified in the 1-Position," *Journal of Medicinal Chemistry* 29(6):978-984 (1986), Abstract only.

Rich et al., "Synthesis, Biological Activity, and Conformational Analysis of (2S,3R,4S)-MeBmt-Cyclosporin, A Novel 1-Position Epimer of Cyclosporin A," *Journal of Medicincal Chemistry* 32(8):1982-1987 (1989), Abstract only.

Rihova et al., "Cytotoxic and Cytostatic Effects on Anti-Thy 1.2 Targeted Doxorubicin and Cyclosporin A," *Journal of Controlled Release* 40(3):303-319 (1996), Abstract only.

Roedl et al., "Lipoprotein-Induced Modulation of Cyclosporine A-Mediated Immunosuppression," *European Journal of Clinical Investigation* 20(3):248-252 (1990), Abstract only.

Romanova et al., "Synthesis of Cyclosporin A Fragment 8-11," *Ukrainskii Khimicheskii Zhurnal (Russian Edition)* 55(5):527-530 (1989), Abstract only.

Rothbard et al., "Conjugation of Arginine Oligomers to Cyclosporin A Facilitates Topical Delivery and Inhibition of Inflammation," *Nature Medicine* New York 6(11):1253-1257 (2000), Abstract only.

Rothe et al., in Brunfeldt, ed., *Pept., Proc. Eur. Pept. Symp.*, 16th Meeting Date 1980, Scriptor: Copenhagen, Den pp. 258-263 (1981), Abstract only.

Rozycki et al., "New Cyclosporin A Analog: Synthesis and Immunosuppressive Activity," *Molecular Immunology* 29(9):1043-1047 (1992), Abstract only.

Ruegger et al., "Cyclosporin A, A Peptide Metabolite From Trichoderma polysporum (Link ex Pers.) Rifai, With Immunosuppressive Activity," *Helvetica Chimica Acta* 59(4):1075-1092 (1976), Abstract only.

Sakamoto et al., "FR901459, a Novel Immunosuppressant Isolated From Stachybotrys chartarum No. 19392. Taxonomy of the Producing Organism, Fermentation, Isolation, Physico-Chemical Properties and Biological Activities," *Journal of Antibiotics* 46(12):1788-1798 (1993), Abstract only.

Shevchenko et al., "Synthesis of Tritiated Cyclosporin A and FK-506 by Metal-Catalyzed Hydrogen Isotope Exchange," *Journal of Labelled Compounds & Radiopharmaceuticals* 47(7):407-414 (2004), Abstract only.

Shevchenko et al., Synthesis of Tritium-Labeled Immunodepressants Containing Double Bonds by Isotope Exchange with Tritium Water, *Radiochemistry* (Moscow) (*Translation of Radiokhimiya*) 41(1):85-88 (1999), Abstract only.

Smulik et al., "Synthesis of Cyclosporin A-Derived Affinity Reagents by Olefin Metathesis," *Organic Letters* 4(12):2051-2054 (2002), Abstract only.

Stabler et al., "Chemiluminescence Immunoassay of Cyclopsorine in Whole Blood," *Clinical Chemistry* (Washington, DC, United States), 36(6):906-908 (1990), Abstract only.

Sun et al., "Synthesis, Conformation, and Immunosuppressive Activity of Cyclosporines That Contain ε-Oxygen (4R)-4-[(E)-butenyl]-4,N-Dimethyl-L-Threonine Analogs in the 1-Position," *Journal of Medicinal Chemistry* 33(5):1443-1452 (1990), Abstract only.

Sun, "Synthesis Of Cyclosporin Analogs Modified in the 1-Position," Diss. Abstr. Int. B 1990, 50(12, Pt. 1), 5637 (1989), Abstract only.

Tamolang et al., "A Rifampicin-Induced Hepatic Microsomal Enzyme System for the Generation of Cyclosporine Metabolites," *Pharmacological Research* 32(3):141-148 (1995), Abstract only.

Thern et al., "Peptides: The Wave of the Future," in Lebl, eds., *Proceedings of the Second International and the Seventeenth American Peptide Symposium*, San Diego, CA, Jun. 9-14, 2001, 244-245 (2001), Abstract only.

Thern et al., "Triphosgene as Highly Efficient Reagent for the Solid-Phase Coupling of N-Alkylated Amino Acids-Total Synthesis of Cyclosporin O," *Tetrahedron Letters* 43(28):5013-5016 (2002), Abstract only.

Traber et al., "[MeIle4]Cyclosporin, a Novel Natural Cyclosporin With Anti-HIV Activity: Structural Elucidation, Biosynthesis and Biological Properties," *Antiviral Chemistry & Chemotherapy* 5(5):331-339 (1994), Asbtract only.

Traber et al., "New Cyclopeptides From Trichoderma polysporum (Link ex. Pers.) Rifai: Cyclosporins B, D and E," *Helvetica Chimica Acta* 60(5):1568-1578 (1977), Abstract only.

Traber et al., "Novel Cyclosporins from Tolypocladium inflatum. Cyclosporins K-Z," *Helvetica Chimica Acta* 70(1):13-36 (1987), Abstract only.

Traber et al., "Occurrence of Cyclosporins and Cyclosporin-Like Peptolides in Fungi," *Journal of Industrial Microbiology & Biotechnology* 17(5/6):397-401 (1996), Abstract only.

Traber et al., "The Structure of Cyclosporin C." *Helvetica Chimica Acta* 60(4):1247-1255 (1977), Abstract only.

Tung et al., "Synthesis and Biological Properties of a High Specific Activity Radioiodinated, Photolabile Cyclosporin," *UCLA Symposia on Molecular and Cellular Biology, New Series*, 86(Synth. Pept.), pp. 321-335 (1989), Abstract only.

Tuominen et al., "Separation of Cyclosporins by High-Performance Liquid Chromatography and Mass Spectrometric Study of Cyclosporin Metabolites," *Rapid Communications in Mass Spectrometry* 12(16):1085-1091 (1998), Abstract only.

Vedejs et al., "Solution-Phase Synthesis of a Hindered N-Methylated Tetrapeptide Using Bts-Protected Amino Acid Chlorides: Efficient Coupling and Methylation Steps Allow Purification by Extraction," *Journal of Organic Chemistry* 65(8):2309-2318 (2000), Abstract only.

Wei et al., "Synthesis and Neurotrophic Activity of Nonimmunosuppressant Cyclosporin A Derivatives," *Bioorganic & Medicinal Chemistry Letters* 14(17):4549-4551 (2004), Abstract only.

Wenger et al., "Cyclosporine: Chemistry, Structure-Activity Relationships and Mode of Action," *Progress in Clinical Biochemistry and Medicine* 3:157-191 (1986), Abstract only.

Wenger et al., "Structure of Cyclosporine and its Metabolites: Total Synthesis of Cyclosporine Metabolites Formed by Oxidation at Positions 4 and 9 of Cyclosporine. Preparation of Leucine-4-Cyclosporine, (γ-hydroxy)-N-Methylleucine-9-Cyclosporine and Leucine-4-(γ-hydroxy)-N-Methylleucine-9-Cyclosporine," *Chimia* 46(7-8):314-322 C (1992), Abstract only.

Wenger, "Synthesis of Ciclosporin and Analogs: Structural and Conformational Requirements for Immunosuppressive Activity," *Progress in Allergy* 38(Ciclosporin):46-64 (1986), Abstract only.

Wenger, "Synthesis of Cyclosporin and Analogs: Structure, Activity, Relationships of New Cyclosporin Derivatives," *Transplantation Proceedings* 15(4, Suppl. 1-2)2230-2241 (1983), Abstract only.

Wu et al., "Preparation of Cyclosporin A Immunogen," *Journal of Chinese Pharmaceutical Sciences* 11(3):78-82 (2002), Abstract only.

Yamada et al., "Single-Step N-Methylation of Hindered Peptides: Total Synthesis of Cyclosporin O," *Peptide Science* 41:591-594 Volume Date 2004, (2005), Abstract only.

Paeshuyse et al., "Potent and Selective Inhibition of Hepatitis C Virus Replication by the Non-Immunosuppressive Cyclosporin Analogue DEBIO-025," *Antiviral Research* 65(3):A41 (2005).

Nakagawa et al., "Specific Inhibition of Hepatitis C Virus Replication by Cyclosporin A," *Biochem. Biophys. Res. Commun.* 313:42-47 (2004).

Inoue et al., "Combined Interferon α2b abd Cyclosporin A in the Treatment of Chronic Hepatitis C: Controlled Trial," *J. Gastroenterol.* 38:567-572 (2003).

Bandera et al., "Immunomodulants in HIV Infection," *Expert Opin. Ther. Patents* 15(9):1115-1131 (2005).

Bartz et al., "Inhibition of Human Immunodeficiency Virus Replication by Non-Immunosuppressive Analogs of Cyclosporin A," *Proc. Natl. Acad. Sci. USA* 92:5381-5385 (1995).

Prelog et al., "Treatment of Psoriatic Arthritis with Cyclosporin A," *Acta Dermatovenerologica, Alpina, Pannonica et Adriatica*, 9(3):1-5 (2000).

The Merck Manual online version, www.merck.com/mmhe, Common Cold, pp. 1-3 (Oct. 27, 2004).

The Merck Manual online version, www.merck.com/mmhe, Viral Infections, pp. 1-4 (Mar. 20, 2005).

Rosenwirth et al., "Debio-025, A Novel Non-Immunosuppressive Cyclosporine Analog with Potent Anti-Human Immunodeficiency Virus Type 1 Activity: Pharmacological Properties and Mode of Action," *Antiviral Research*, 64(3):42-43 (2005).

DEB 025, ADIS Database, pp. 1-2 (Oct. 12, 2005).

Chakrabarty et al., "Therapy of Other Viral Infections: Herpes to Hepatitis," Dermatologic Therapy, 17:465-490 (2004).

\* cited by examiner

CYCLOSPORINS

This application claims the benefit of U.S. Provisional Patent Application Ser. No. 60/455,727, filed Mar. 17, 2003, which is hereby incorporated by reference in its entirety.

FIELD OF THE INVENTION

The present invention relates to novel derivatives of the cyclosporin family of compounds, cyclosporin A in particular, methods for preparing such derivatives, pharmaceutical compositions comprising such derivatives, and methods of using such derivatives for treatment of various diseases.

BACKGROUND OF THE INVENTION

Cyclosporin A, currently marketed as Neoral® and Sandimmune® (Novartis), is the most widely prescribed drug for the prevention of organ transplant rejection. Cyclosporin A has also demonstrated clinical efficacy in the treatment of autoimmune diseases such as rheumatoid arthritis, Crohn's disease, psoriasis, and Type I diabetes and chronic inflammatory diseases like asthma. Test results in many other preclinical studies indicate utility for cyclosporin A in other therapeutic areas.

Widespread use of cyclosporin A for clinical uses other than prevention of organ transplant rejection is limited, however, due to the drugs narrow therapeutic index. Long term toxicity from chronic administration of cyclosporin A is a serious drawback. Negative consequences associated with chronic treatment with cyclosporin A include nephrotoxicity, abnormal liver function, hirsutism, tremor, neurotoxicity, gastrointestinal discomfort, and other adverse effects. Toxicity associated with cyclosporin A usage has been attributed by many experts working in the immunosuppression therapeutic area as mechanism based. Cyclosporin A inhibits the ubiquitous serine/threonine phosphatase called calcineurin. Attempts to separate the immunosuppressive activity from toxicity through structural modification of cyclosporin A have, for the most part, been unsuccessful. Nevertheless, over the past decade, continued investigation into understanding cyclosporin's toxicity has provided other possible explanations that are independent of calcineurin inhibition.

Published results of recent research (Paolini et al., "Cyclosporin A and Free Radical Generation," *Trends in Pharmaceutical Sciences*, 22:14-15 (2001); Buetler et al., "Does Cyclosporin A Generate Free Radicals?" *Trends in Pharmaceutical Sciences*, 21:288-290 (2000)) suggest that cyclosporin A-mediated generation of reactive oxygen intermediates may be linked with the significant side effects that accompany use of this drug. Results of in vitro and in vivo studies indicate that although cyclosporin A is capable of generating reactive oxygen intermediates, the radicals formed are not derived directly from the cyclosporin A molecule, and are unlikely to stem from mitochondria or from cytochrome P450-mediated metabolism of cyclosporin A.

Novel cyclosporin A analogue, ISATX247, is a potent calcineurin inhibitor (Abel et al., "ISATX247: A Novel Calcineurin Inhibitor," *J. Heart Lung Transplant*, 20(2):161 (2001); Aspeslet et al., "ISATX247: A Novel Calcineurin Inhibitor," *Transplantation Proceedings*, 33(1-2):1048-1051 (2001)) and has demonstrated a reduced toxicity profile relative to cyclosporin A in animal studies. It remains to be shown if this translates into reduced toxicity in human. In PCT International Publication No. WO 99/18120 to Naicker et al., cyclosporin analogues were claimed, where the MeBmt[1] ((4R)-4-((E)-2-butenyl)-4, N-dimethyl-L-threonine) amino acid side chain of cyclosporin A has been structurally modified. Some of the most active compounds claimed in this publication have deuterium incorporated in place of one or more hydrogens in the side chain. Incorporation of deuterium is known to slow down metabolism of compounds in vivo, if hydrogen abstraction is the rate limiting step in the metabolism of the drug (Foster, "Deuterium Isotope Effects in Studies of Drug Metabolism," *Trends in Pharmaceutical Sciences*, 5:524-527 (1984)), and improve the pharmacokinetic properties of the molecule. Deuterium incorporation in cyclosporin A analogues may also block pathways responsible for generation of reactive oxygen intermediates in a manner not currently understood.

Other studies have implicated the role of transforming growth factor-β (TGF-β) in the nephrotoxicity of cyclosporin A (Khanna et al., "TGF-β: A Link Between Immunosuppression, Nephrotoxicity, and CsA," *Transplantation Proceedings*, 30:944-945 (1998)). Cyclosporin A induces expression of TGF-β, collagen and fibronectin genes in the kidney. TGF-β has a host of immunosuppressive effects that parallel the effects of cyclosporin A. However, TGF-β also causes the accumulation of extracellular matrix genes by increasing the expression of collagen and fibronectin, which is the hallmark of fibrosis. Because glomerulosclerosis (which occurs with chronic cyclosporin A use) is associated with an increase of extracellular matrix proteins, cyclosporin A-associated nephrotoxicity may be due to TGF-β induction. Novel analogues of cyclosporin A may have different effects on induction of gene expression of proteins like TGF-β and may demonstrate improved therapeutic index.

Therefore, it would be advantageous to have novel cyclosporin derivatives that are safe and effective for the treatment of a variety of diseases.

The present invention is directed to achieving these objectives.

SUMMARY OF THE INVENTION

The compounds of the present invention are represented by the chemical structure found in Formula (I):

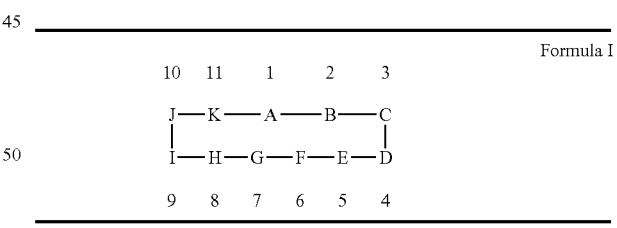

Formula I wherein A is an amino acid of Formula (II):

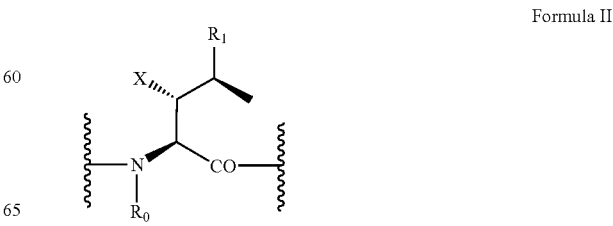

Formula II where:
$R_0$ is H or $CH_3$;
$R_1$=CHO;
C(=O)$OR_2$;
C(O)$NR_3R_4$;
CH=N—Y;
CH($NR_5R_6$)$R_7$;
CH($OR_8$)$R_9$;
CH($OR_{10}$)$_2$;
$CH_2SR_{11}$;
CH($SR_{12}$)$_2$;
$CR_{13}R_{14}R_{15}$;
CH=CHC(=O)Me;
$CH_2CH_2$C(=O)Me;
CH=CHCH($OR_{16}$)Me;
$CH_2CH_2$CH($OR_{16}$)Me;
CH=CHCH($NR_{17}R_{18}$)Me;
$CH_2CH_2$CH($NR_{17}R_{18}$)Me;
CH=CHC(=N—Y)Me;
$CH_2CH_2$C(=N—Y)Me;
CH=CHC($OR_{19}$)$_2$Me;
$CH_2CH_2$C($OR_{19}$)$_2$Me;
CH=CHC(=$CR_{20}R_{21}$)Me;
$CH_2$—$CH_2$C(=$CR_{20}R_{21}$)Me;
CH=CHC($SR_{22}$)$_2$Me;
$CH_2CH_2$C($SR_{22}$)$_2$Me;
CH=$CR_{23}R_{24}$;
$CH_2$CH$R_{23}R_{24}$;
CH=CHC(=O)$NR_{25}R_{26}$;
$CH_2CH_2$C(=O)$NR_{25}R_{26}$;
CH=CHC(=O)$OR_{26}$;
$CH_2CH_2$C(=O)$OR_{26}$;
CH=CHC(=O)$CH_2CH_2NR_{27}R_{28}$;
$CH_2CH_2$C(=O)$CH_2CH_2NR_{27}R_{28}$;
CH=CHC(=O)CH=CH$NR_{29}R_{30}$;
$CH_2CH_2$C(=O)CH=CH$NR_{29}R_{30}$;
CH=CH—C($OR_{31}$)$R_{32}$Me;
$CH_2CH_2$C($OR_{31}$)$R_{32}$Me;
CH=CHC(=O)$CH_2$C(OH)$R_{33}R_{34}$; or
$CH_2CH_2$C(=O)$CH_2$C(OH)$R_{33}R_{34}$;
$R_2$ and $R_{26}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring;
$(CH_2)_n$-heteroaryl ring;
$CH_2OCH_3$;
$CH_2SCH_3$;
$CH_2CH_2F$;
$CH_2CF_3$;
$CH_2CH_2CF_3$;
CH($CF_3$)$_2$; and
$CH_2OCH_2$OC(O)$CH_3$;
$R_3$, $R_4$, $R_5$, $R_6$, $R_{10}$, $R_{11}$, $R_{12}$, $R_{17}$, $R_{18}$, $R_{19}$, $R_{22}$, $R_{25}$, $R_{27}$, $R_{28}$, $R_{29}$, and $R_{30}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring; and
$(CH_2)_n$-heteroaryl ring;
$R_3$ and $R_4$, $R_5$ and $R_6$, $R_{10}$, $R_{12}$, $R_{17}$ and $R_{18}$, $R_{19}$, $R_{22}$, $R_{25}$ and $R_{26}$, $R_{27}$ and $R_{28}$, $R_{29}$ and $R_{30}$ are together —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$— that results in the formation of a cyclic moiety that contains the heteroatom or heteroatoms to which they are bound;
$R_8$, $R_{16}$, and $R_{31}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring;
$(CH_2)_n$-heteroaryl ring;
alkanoyl;
alkenoyl;
alkynoyl;
aryloyl;
arylalkanoyl;
alkylaminocarbonyl;
arylaminocarbonyl;
arylalkylaminocarbonyl;
alkyloxycarbonyl;
aryloxycarbonyl; and
arylalkyloxycarbonyl;
$R_7$, $R_9$, $R_{13}$, $R_{14}$, $R_{15}$, $R_{20}$, $R_{21}$, $R_{23}$, $R_{24}$, $R_{32}$, $R_{33}$, and $R_{34}$, are the same or different and independently selected from the group consisting of:
hydrogen;
deuterium;
halogen;
hydroxyl;
nitrile;
substituted and unsubstituted $C_1$-$C_6$-straight alkyl chain;
substituted and unsubstituted $C_2$-$C_6$-straight alkenyl chain;
substituted and unsubstituted $C_3$-$C_6$-branched alkyl chain;
substituted and unsubstituted $C_4$-$C_6$-branched alkenyl chain;
substituted and unsubstituted $C_2$-$C_6$-straight alkynyl chain;
substituted and unsubstituted $C_4$-$C_6$-branched alkynyl chain;
substituted and unsubstituted $C_4$-$C_6$-chain having alkenyl and alkynyl groups;
substituted and unsubstituted $C_3$-$C_7$-cycloalkyl;
substituted and unsubstituted $(CH_2)_p$—($C_3$-$C_7$-cycloalkyl);
substituted and unsubstituted aryl;
substituted and unsubstituted heteroaryl;
substituted and unsubstituted arylalkyl;
substituted and unsubstituted heteroarylalkyl;
COOH;
COO$R_2$; and
C(O)$NR_3R_4$;
n=0, 1, 2, 3, or 4;
p=0, 1, 2, or 3;
X=hydrogen;

hydroxyl; or
hydroxyl group derivatized with an alkanoyl, aryloyl, alkylaminocarbonyl, arylaminocarbonyl, arylalkylaminocarbonyl, alkyloxycarbonyl, aryloxycarbonyl, or arylalkyloxycarbonyl group;
Y=$C_1$-$C_6$ straight and branched chain alkyl;
  $C_3$-$C_6$ straight and branched chain alkenyl;
  arylalkyl;
  heteroarylalkyl;
  $C_1$-$C_6$ straight and branched chain alkyloxy;
  aryloxy;
  acyloxy;
  arylalkyloxy;
  $C_1$-$C_6$ straight and branched chain alkylamino;
  arylamino;
  arylalkylamino;
  heteroarylamino;
  heteroarylalkylamino;
  $C_1$-$C_6$ straight and branched chain alkylcarboxamido;
  arylcarboxamido;
  heteroarylcarboxamido;
  $C_1$-$C_6$ straight and branched chain alkylsulfonamido;
  arylsulfonamido;
  arylalkylsulfonamido;
  heteroarylsulfonamido;
  heteroarylalkylsulfonamido; or
  $NH_2C(O)NH$;
CO— in Formula II is covalently bound to an α-amino group of B in Formula I to form an amide linkage, and —N—$R_0$ in Formula II is covalently bound to a carboxylic acid of K to form an amide linkage;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine;
or a pharmaceutically acceptable salt thereof.

Another aspect of the present invention relates to a process for preparation of a product compound of the formula:

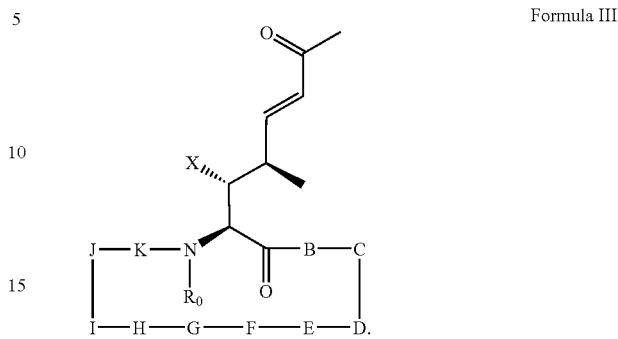

Formula III

The process involves biocatalytically converting a starting compound of the formula:

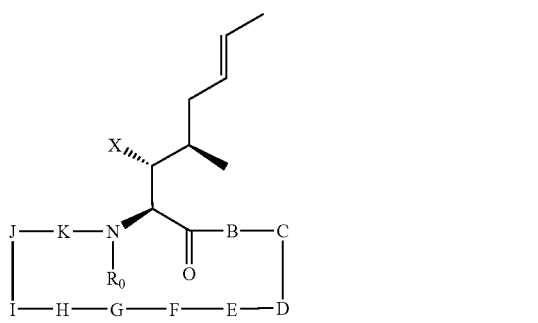

where:
$R_0$ is H or $CH_3$;
X=hydrogen;
  hydroxyl; or
  hydroxyl group derivatized with an alkanoyl, aryloyl, alkylaminocarbonyl, arylaminocarbonyl, arylalkylaminocarbonyl, alkyloxycarbonyl, aryloxycarbonyl, or arylalkyloxycarbonyl group;
B is an amino acid selected from the group consisting of:
  α-aminobutyric acid;
  alanine;
  threonine;
  valine;
  norvaline; and
  a modified α-aminobutyric acid, alanine, valine, or norvaline where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline where a carbon atom in a side chain is substituted with a hydroxyl group;

F is an amino acid selected from the group consisting of:
leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine, under conditions effective to produce the product compound.

Another aspect of the present invention relates to a process for preparation of a product compound of the formula:

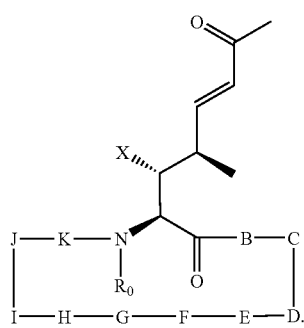

Formula III

The process involves chemically oxidizing a starting compound of the formula:

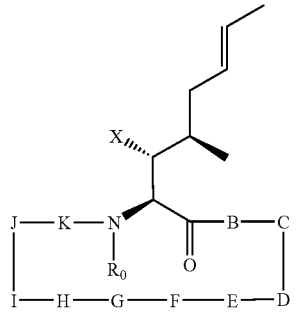

where:
$R_0$ is H or $CH_3$;
X=hydrogen;
  hydroxyl; or
  hydroxyl group derivatized with an alkanoyl, aryloyl, alkylaminocarbonyl, arylaminocarbonyl, arylalkylaminocarbonyl, alkyloxycarbonyl, aryloxycarbonyl, or arylalkyloxycarbonyl group;
B is an amino acid selected from the group consisting of:
  α-aminobutyric acid;
  alanine;
  threonine;
  valine;
  norvaline; and a modified α-aminobutyric acid, alanine, valine, or norvaline where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline;
  and a modified valine or norvaline where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

The present invention also relates to a process of preparation of a product compound of the formula:

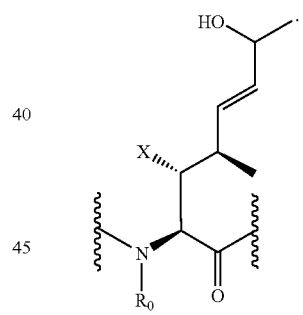

The process involves reducing a compound of the formula:

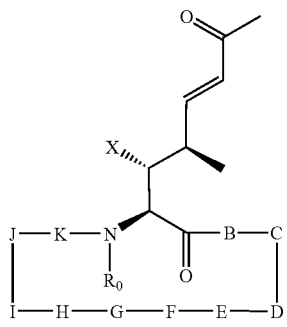

where:
X=OH;
R₀=CH₃;
B is an amino acid selected from the group consisting of:
  α-aminobutyric acid;
  alanine;
  threonine;
  valine;
  norvaline; and
  a modified α-aminobutyric acid, alanine, valine, or norvaline where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline;
  and a modified valine or norvaline where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

[chemical structure]

The process involves treating a compound of the formula:

[chemical structure]

under conditions effective to produce the product compound.

Another aspect of the present invention relates to a process of preparation of a product compound of the formula:

[chemical structure]

The process involves treating a compound of the formula:

[chemical structure]

under conditions effective to produce the product compound.

Another aspect of the present invention relates to a process of preparation of a product compound of the formula:

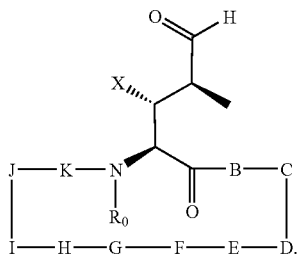

Formula V

The process involves treating a compound of the formula:

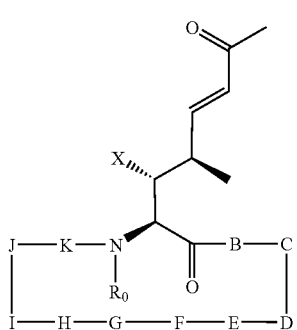

Formula III where:
$R_0$=$CH_3$;
X=OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;

I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

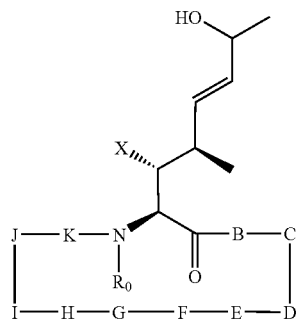

Formula V

The process involves treating a compound of the formula:

Formula IV where:
$R_0$=$CH_3$;
X=OH;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;

F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.
  Another aspect of the present invention relates to a process of preparation of a product compound of the formula:

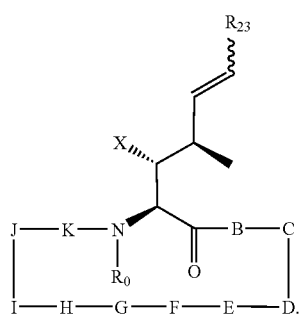

Formula VI

The process involves treating a compound of the formula:

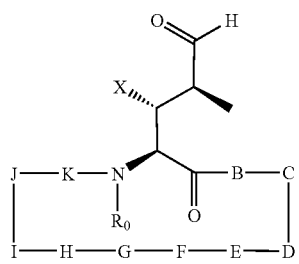

Formula V where:
$R_0$=CH$_3$;
$R_{23}$=hydrogen;
  deuterium;
  halogen;
  hydroxyl;
  nitrile;
  substituted and unsubstituted $C_1$-$C_6$-straight alkyl chain;
  substituted and unsubstituted $C_2$-$C_6$-straight alkenyl chain;
  substituted and unsubstituted $C_3$-$C_6$-branched alkyl chain;
  substituted and unsubstituted $C_4$-$C_6$-branched alkenyl chain;
  substituted and unsubstituted $C_2$-$C_6$-straight alkynyl chain;
  substituted and unsubstituted $C_4$-$C_6$-branched alkynyl chain;
  substituted and unsubstituted $C_4$-$C_6$-chain having alkenyl and alkynyl groups;
  substituted and unsubstituted $C_3$-$C_7$-cycloalkyl;
  substituted and unsubstituted $(CH_2)_p$—($C_3$-$C_7$-cycloalkyl);
  substituted and unsubstituted aryl;
  substituted and unsubstituted heteroaryl;
  substituted and unsubstituted arylalkyl;
  substituted and unsubstituted heteroarylalkyl;
  COOH;
  COOR$_2$; and
  C(O)NR$_3$R$_4$;
$R_2$=hydrogen;
  $C_1$-$C_6$-straight alkyl chain;
  $C_3$-$C_6$-straight alkenyl chain;
  $C_3$-$C_6$-branched alkyl chain;
  $C_4$-$C_6$-branched alkenyl chain;
  $C_3$-$C_6$-straight alkynyl chain;
  $C_3$-$C_7$-cycloalkyl;
  CH$_2$—($C_3$-$C_7$-cycloalkyl);
  (CH$_2$)$_n$-aryl ring;
  (CH$_2$)$_n$-heteroaryl ring;
  CH$_2$OCH$_3$;
  CH$_2$SCH$_3$;
  CH$_2$CH$_2$F;
  CH$_2$CF$_3$;
  CH$_2$CH$_2$CF$_3$;
  CH(CF$_3$)$_2$; and
  CH$_2$OCH$_2$OC(O)CH$_3$;
$R_3$ and $R_4$ are the same or different and independently selected from the group consisting of:
  hydrogen;
  $C_1$-$C_6$-straight alkyl chain;
  $C_3$-$C_6$-straight alkenyl chain;
  $C_3$-$C_6$-branched alkyl chain;
  $C_4$-$C_6$-branched alkenyl chain;
  $C_3$-$C_6$-straight alkynyl chain;
  $C_3$-$C_7$-cycloalkyl;
  CH$_2$—($C_3$-$C_7$-cycloalkyl);
  (CH$_2$)$_n$-aryl ring; and
  (CH$_2$)$_n$-heteroaryl ring;
$R_3$ and $R_4$ are together —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$— that results in the formation of a cyclic moiety that contains the heteroatom or heteroatoms to which they are bound;
n=0, 1, 2, 3 or 4;
p=0, 1, 2, or 3;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

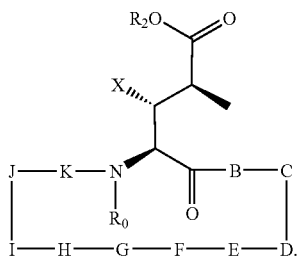

The process involves treating a compound of the formula:

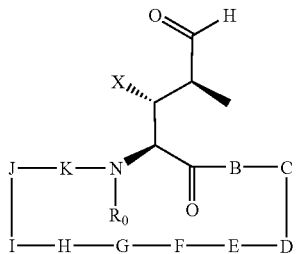

Formula V where:
$R_0$=$CH_3$;
$R_2$=hydrogen;
  $C_1$-$C_6$-straight alkyl chain;
  $C_3$-$C_6$-straight alkenyl chain;
  $C_3$-$C_6$-branched alkyl chain;
  $C_4$-$C_6$-branched alkenyl chain;
  $C_3$-$C_6$-straight alkynyl chain;
  $C_3$-$C_7$-cycloalkyl;
  $CH_2$—($C_3$-$C_7$-cycloalkyl);
  $(CH_2)_n$-aryl ring;
  $(CH_2)_n$-heteroaryl ring;
  $CH_2OCH_3$;
  $CH_2SCH_3$;
  $CH_2CH_2F$;
  $CH_2CF_3$;
  $CH_2CH_2CF_3$;
  $CH(CF_3)_2$; and
  $CH_2OCH_2OC(O)CH_3$;
n=0, 1, 2, 3 or 4;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

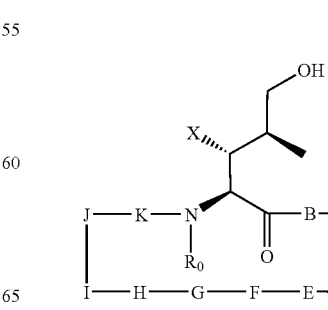

The process involves treating a compound of the formula:

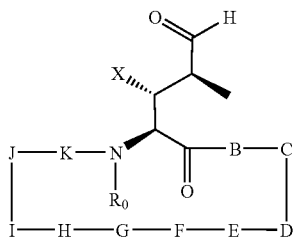

Formula V where:
$R_0$=CH$_3$;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

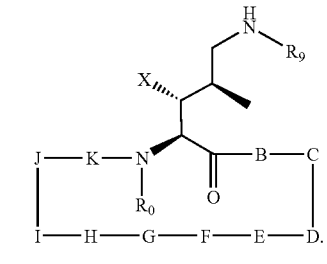

The process involves treating a compound of the formula:

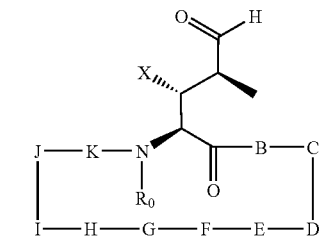

Formula V where:
$R_0$ =CH$_3$;
$R_9$=hydrogen;
  deuterium;
  halogen;
  hydroxyl;
  nitrile;
  substituted and unsubstituted C$_1$-C$_6$-straight alkyl chain;
  substituted and unsubstituted C$_2$-C$_6$-straight alkenyl chain;
  substituted and unsubstituted C$_3$-C$_6$-branched alkyl chain;
  substituted and unsubstituted C$_4$-C$_6$-branched alkenyl chain;
  substituted and unsubstituted C$_2$-C$_6$-straight alkynyl chain;
  substituted and unsubstituted C$_4$-C$_6$-branched alkynyl chain;
  substituted and unsubstituted C$_4$-C$_6$-chain having alkenyl and alkynyl groups;
  substituted and unsubstituted C$_3$-C$_7$-cycloalkyl;
  substituted and unsubstituted (CH$_2$)$_p$—(C$_3$-C$_7$-cycloalkyl);
  substituted and unsubstituted aryl;
  substituted and unsubstituted heteroaryl;
  substituted and unsubstituted arylalkyl;
  substituted and unsubstituted heteroarylalkyl;
  COOH;
  COOR$_2$; and
  C(O)NR$_3$R$_4$;
$R_2$=hydrogen;
  C$_1$-C$_6$-straight alkyl chain;
  C$_3$-C$_6$-straight alkenyl chain;
  C$_3$-C$_6$-branched alkyl chain;
  C$_4$-C$_6$-branched alkenyl chain;
  C$_3$-C$_6$-straight alkynyl chain;
  C$_3$-C$_7$-cycloalkyl;
  CH$_2$—(C$_3$-C$_7$-cycloalkyl);
  (CH$_2$)$_n$-aryl ring;

$(CH_2)_n$-heteroaryl ring;
$CH_2OCH_3$;
$CH_2SCH_3$;
$CH_2CH_2F$;
$CH_2CF_3$;
$CH_2CH_2CF_3$;
$CH(CF_3)_2$; and
$CH_2OCH_2OC(O)CH_3$;

$R_3$ and $R_4$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring; and
$(CH_2)_n$-heteroaryl ring;

$R_3$ and $R_4$ are together $-CH_2CH_2-$, $-CH_2CH_2CH_2-$, $-CH_2CH_2CH_2CH_2-$, $-CH_2CH_2CH_2CH_2CH_2-$ and $-CH_2CH_2CH_2CH_2CH_2CH_2-$ that results in the formation of a cyclic moiety that contains the heteroatom or heteroatoms to which they are bound;
n=0, 1, 2, 3 or 4;
p=0, 1, 2, or 3;
X=OH or OAc;
B is an amino acid selected from the group consisting of:
α-aminobutyric acid;
alanine;
threonine;
valine;
norvaline; and
a modified α-aminobutyric acid, alanine, valine, or norvaline, where a carbon atom in a side chain is substituted with a hydroxyl group;
C is a sarcosine;
D is an amino acid selected from the group consisting of:
leucine;
N-methyl leucine;
valine;
γ-hydroxy-N-methyl leucine; and
γ-hydroxy leucine;
E is an amino acid selected from the group consisting of:
valine;
norvaline; and
a modified valine or norvaline, where a carbon atom in a side chain is substituted with a hydroxyl group;
F is an amino acid selected from the group consisting of:
leucine;
N-methyl leucine;
γ-hydroxy-N-methyl leucine; and
γ-hydroxy leucine;
G is α-aminobutyric acid or alanine;
H is D-alanine;
I and J are independently selected from the group consisting of:
leucine;
N-methyl leucine;
γ-hydroxy-N-methyl leucine; and
γ-hydroxy leucine; and
K is N-methyl valine or valine,
under conditions effective to produce the product compound.

Another aspect of the present invention relates to a process of preparation of a product compound of the formula:

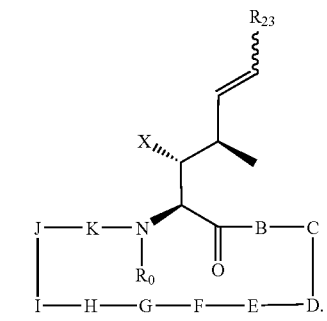

Formula VI

The process involves treating a compound of the formula:

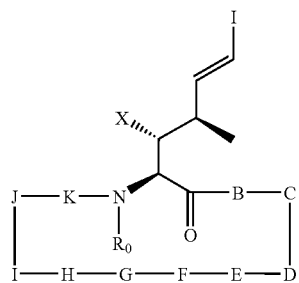

where:
$R_0$=$CH_3$;
$R_{23}$=hydrogen;
deuterium;
halogen;
hydroxyl;
nitrile;
substituted and unsubstituted $C_1$-$C_6$-straight alkyl chain;
substituted and unsubstituted $C_2$-$C_6$-straight alkenyl chain;
substituted and unsubstituted $C_3$-$C_6$-branched alkyl chain;
substituted and unsubstituted $C_4$-$C_6$-branched alkenyl chain;
substituted and unsubstituted $C_2$-$C_6$-straight alkynyl chain;
substituted and unsubstituted $C_4$-$C_6$-branched alkynyl chain;
substituted and unsubstituted $C_4$-$C_6$-chain having alkenyl and alkynyl groups;
substituted and unsubstituted $C_3$-$C_7$-cycloalkyl;
substituted and unsubstituted $(CH_2)_p$—($C_3$-$C_7$-cycloalkyl);
substituted and unsubstituted aryl;
substituted and unsubstituted heteroaryl;
substituted and unsubstituted arylalkyl;
substituted and unsubstituted heteroarylalkyl;
COOH;
$COOR_2$; and
$C(O)NR_3R_4$;
$R_2$=hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;

$C_3$-$C_6$-straight alkynyl chain;
$C_3$-$C_7$-cycloalkyl;
$CH_2$—($C_3$-$C_7$-cycloalkyl);
$(CH_2)_n$-aryl ring;
$(CH_2)_n$-heteroaryl ring;
$CH_2OCH_3$;
$CH_2SCH_3$;
$CH_2CH_2F$;
$CH_2CF_3$;
$CH_2CH_2CF_3$;
$CH(CF_3)_2$; and
$CH_2OCH_2OC(O)CH_3$;
$R_3$ and $R_4$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring; and
$(CH_2)_n$-heteroaryl ring;
$R_3$ and $R_4$ are together —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$— that results in the formation of a cyclic moiety that contains the heteroatom or heteroatoms to which they are bound;
n=0, 1, 2, 3 or 4;
p=0, 1, 2, or 3;
X=OH or OAc;
B is an amino acid selected from the group consisting of:
α-aminobutyric acid;
alanine;
threonine;
valine;
norvaline; and
a modified α-aminobutyric acid, alanine, valine, or norvaline, where a carbon atom in a side chain is substituted with a hydroxyl group;
C is a sarcosine;
D is an amino acid selected from the group consisting of:
leucine;
N-methyl leucine;
valine;
γ-hydroxy-N-methyl leucine; and
γ-hydroxy leucine;
E is an amino acid selected from the group consisting of:
valine;
norvaline; and
a modified valine or norvaline, where a carbon atom in a side chain is substituted with a hydroxyl group;
F is an amino acid selected from the group consisting of:
leucine;
N-methyl leucine;
γ-hydroxy-N-methyl leucine; and
γ-hydroxy leucine;
G is α-aminobutyric acid or alanine;
H is D-alanine;
I and J are independently selected from the group consisting of:
leucine;
N-methyl leucine;
γ-hydroxy-N-methyl leucine; and
γ-hydroxy leucine; and K is N-methyl valine or valine,
under conditions effective to produce the product compound.

Another aspect of the present invention relates to a process of preparation of a product compound of the formula:

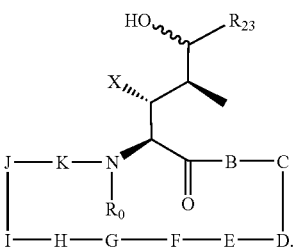

Formula IX

The process involves treating a compound of the formula:

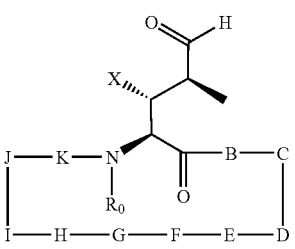

Formula V where:
$R_0$=$CH_3$;
$R_{23}$=hydrogen;
deuterium;
halogen;
hydroxyl;
nitrile;
substituted and unsubstituted $C_1$-$C_6$-straight alkyl chain;
substituted and unsubstituted $C_2$-$C_6$-straight alkenyl chain;
substituted and unsubstituted $C_3$-$C_6$-branched alkyl chain;
substituted and unsubstituted $C_4$-$C_6$-branched alkenyl chain;
substituted and unsubstituted $C_2$-$C_6$-straight alkynyl chain;
substituted and unsubstituted $C_4$-$C_6$-branched alkynyl chain;
substituted and unsubstituted $C_4$-$C_6$-chain having alkenyl and alkynyl groups;
substituted and unsubstituted $C_3$-$C_7$-cycloalkyl;
substituted and unsubstituted $(CH_2)_p$—($C_3$-$C_7$-cycloalkyl);
substituted and unsubstituted aryl;
substituted and unsubstituted heteroaryl;
substituted and unsubstituted arylalkyl;
substituted and unsubstituted heteroarylalkyl;
COOH;
$COOR_2$; and
$C(O)NR_3R_4$;
$R_2$=hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;

CH$_2$—(C$_3$-C$_7$-cycloalkyl);
(CH$_2$)$_n$-aryl ring;
(CH$_2$)$_n$-heteroaryl ring;
CH$_2$OCH$_3$;
CH$_2$SCH$_3$;
CH$_2$CH$_2$F;
CH$_2$CF$_3$;
CH$_2$CH$_2$CF$_3$;
CH(CF$_3$)$_2$; and
CH$_2$OCH$_2$OC(O)CH$_3$;
R$_3$ and R$_4$ are the same or different and independently selected from the group consisting of:
hydrogen;
C$_1$-C$_6$-straight alkyl chain;
C$_3$-C$_6$-straight alkenyl chain;
C$_3$-C$_6$-branched alkyl chain;
C$_4$-C$_6$-branched alkenyl chain;
C$_3$-C$_6$-straight alkynyl chain;
C$_3$-C$_7$-cycloalkyl;
CH$_2$—(C$_3$-C$_7$-cycloalkyl);
(CH$_2$)$_n$-aryl ring; and
(CH$_2$)$_n$-heteroaryl ring;
R$_3$ and R$_4$ are together —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$— that results in the formation of a cyclic moiety that contains the heteroatom or heteroatoms to which they are bound;
n=0, 1, 2, 3 or 4;
p=0, 1, 2, or 3;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

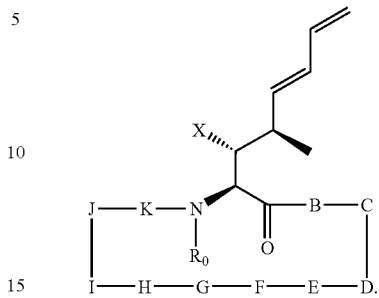

The process involves treating a compound of the formula:

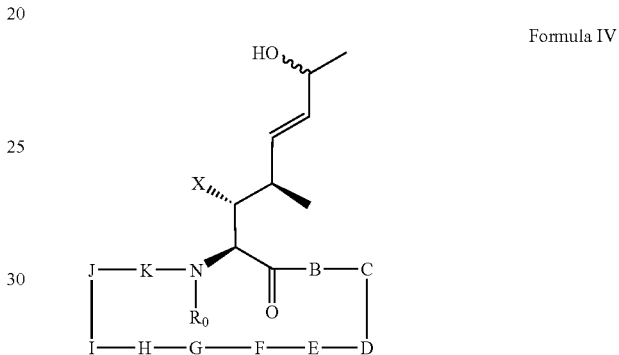

Formula IV where:
R$_0$=CH$_3$;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;
F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;

I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

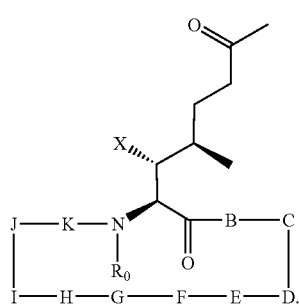

Formula XI

The process involves treating a compound of the formula:

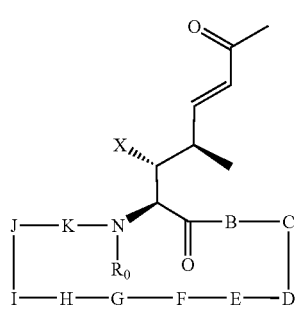

Formula III where:
$R_0$=CH$_3$;
X=OH or OAc;
B is an amino acid selected from the group consisting of:
  α-aminobutyric acid;
  alanine;
  threonine;
  valine;
  norvaline; and
  a modified α-aminobutyric acid, alanine, valine, or norvaline, where a carbon atom in a side chain is substituted with a hydroxyl group;
C is a sarcosine;
D is an amino acid selected from the group consisting of:
  leucine;
  N-methyl leucine;
  valine;
  γ-hydroxy-N-methyl leucine; and
  γ-hydroxy leucine;
E is an amino acid selected from the group consisting of:
  valine;
  norvaline; and
  a modified valine or norvaline, where a carbon atom in a side chain is substituted with a hydroxyl group;

F is an amino acid selected from the group consisting of:
  leucine;
  N-methyl leucine;
  γ-hydroxy-N-methyl leucine; and
  γ-hydroxy leucine;
G is α-aminobutyric acid or alanine;
H is D-alanine;
I and J are independently selected from the group consisting of:
  leucine;
  N-methyl leucine;
  γ-hydroxy-N-methyl leucine; and
  γ-hydroxy leucine; and
K is N-methyl valine or valine,
under conditions effective to produce the product compound.

Another aspect of the present invention relates to a process of preparation of a product compound of the formula:

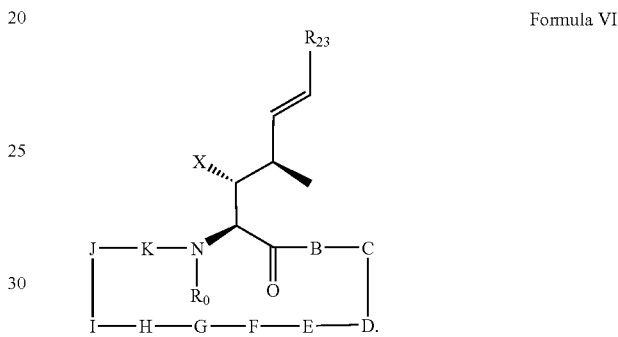

Formula VI

The process involves treating a compound of the formula:

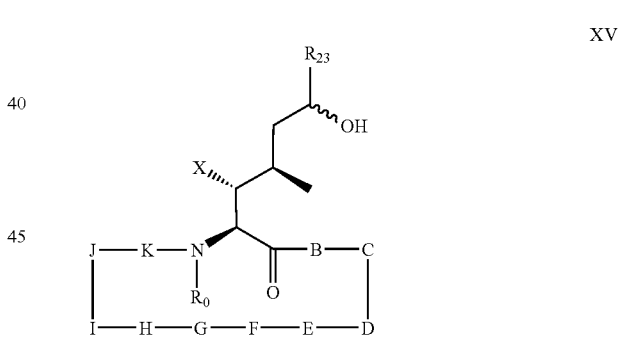

XV where:
$R_0$=CH$_3$;
$R_{23}$=hydrogen;
  deuterium;
  halogen;
  hydroxyl;
  nitrile;
  substituted and unsubstituted C$_1$-C$_6$-straight alkyl chain;
  substituted and unsubstituted C$_2$-C$_6$-straight alkenyl chain;
  substituted and unsubstituted C$_3$-C$_6$-branched alkyl chain;
  substituted and unsubstituted C$_4$-C$_6$-branched alkenyl chain;
  substituted and unsubstituted C$_2$-C$_6$-straight alkynyl chain;
  substituted and unsubstituted C$_4$-C$_6$-branched alkynyl chain;

substituted and unsubstituted $C_4$-$C_6$-chain having alkenyl and alkynyl groups;
substituted and unsubstituted $C_3$-$C_7$-cycloalkyl;
substituted and unsubstituted $(CH_2)_p$—($C_3$-$C_7$-cycloalkyl);
substituted and unsubstituted aryl;
substituted and unsubstituted heteroaryl;
substituted and unsubstituted arylalkyl;
substituted and unsubstituted heteroarylalkyl;
COOH;
$COOR_2$; and
$C(O)NR_3R_4$;

$R_2$=hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring;
$(CH_2)_n$-heteroaryl ring;
$CH_2OCH_3$;
$CH_2SCH_3$;
$CH_2CH_2F$;
$CH_2CF_3$;
$CH_2CH_2CF_3$;
$CH(CF_3)_2$; and
$CH_2OCH_2OC(O)CH_3$;

$R_3$ and $R_4$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring; and
$(CH_2)_n$-heteroaryl ring;

$R_3$ and $R_4$ are together —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$— that results in the formation of a cyclic moiety that contains the heteroatom or heteroatoms to which they are bound;
n=0, 1, 2, 3 or 4;
p=0, 1, 2, or 3;
X=OH or OAc;
B is an amino acid selected from the group consisting of:
α-aminobutyric acid;
alanine;
threonine;
valine;
norvaline; and
a modified α-aminobutyric acid, alanine, valine, or norvaline, where a carbon atom in a side chain is substituted with a hydroxyl group;
C is a sarcosine;
D is an amino acid selected from the group consisting of:
leucine;
N-methyl leucine;
valine;
γ-hydroxy-N-methyl leucine; and
γ-hydroxy leucine;
E is an amino acid selected from the group consisting of:
valine;
norvaline; and
a modified valine or norvaline, where a carbon atom in a side chain is substituted with a hydroxyl group;
F is an amino acid selected from the group consisting of:
leucine;
N-methyl leucine;
γ-hydroxy-N-methyl leucine; and
γ-hydroxy leucine;
G is α-aminobutyric acid or alanine;
H is D-alanine;
I and J are independently selected from the group consisting of:
leucine;
N-methyl leucine;
γ-hydroxy-N-methyl leucine; and
γ-hydroxy leucine; and
K is N-methyl valine or valine,
under conditions effective to produce the product compound.

The present invention discloses cyclosporin analogues that are safe and effective for the treatment of a variety of diseases. Some of the cyclosporin compounds of the present invention possess potent immunosuppressive activity comparable with known cyclosporins, especially cyclosporin A, as well as other naturally occurring cyclosporins or known synthetic cyclosporin analogues. The cyclosporin analogues of the present invention are produced by a chemical transformation of cyclosporins that possess the MeBmt$^1$ ((4R)-4-((E)-2-butenyl)-4, N-dimethyl-L-threonine) amino acid, including cyclosporin A. Cyclosporin analogues, especially those of CsA, of the present invention include the incorporation of deuterium in the hydrocarbon side chains of the Bmt$^1$ ((4R)-4-((E)-2-butenyl)-4-methyl-L-threonine) amino acid. Many members of the cyclosporin family contain the Bmt$^1$ and MeBmt$^1$ amino acid.

The present invention discloses chemical processes that rely on the use of an oxidative biocatalyst or chemical oxidation conditions to yield derivatives of cyclosporins containing structural modifications to the Bmt$^1$ side chain. The net effect is the conversion of the (E)-2-butenyl terminus of the Bmt$^1$ amino acid to a methyl vinyl ketone moiety. The cyclosporin methyl vinyl ketone derived from cyclosporin A has never been reported before. The methyl vinyl ketone derivatives of other members of the cyclosporin family are also unknown. The cyclosporin A methyl vinyl ketone displays significant immunosuppressive activity in the mixed lymphocyte reaction assay in murine splenocytes and human T-lymphocytes.

The present invention also describes the utility of cyclosporin A methyl vinyl ketone as a synthetic intermediate that is converted to additional cyclosporin derivatives. The methyl vinyl ketone is a versatile functional group that can undergo facile chemical transformation to a wide range of unique cyclosporin analogues with variations at the one amino acid position. While many analogues of cyclosporins, especially cyclosporin A, have been synthesized with modifications at the Bmt$^1$ amino acid since Wenger's landmark total synthesis of CsA (Wenger, "Total Synthesis of Cyclosporin A and Cyclosporin H, Two Fungal Metabolites Isolated from the Species *Tolypocladium inflatum* GAMS," *Helv. Chim. Acta*, 67:502-525 (1984); U.S. Pat. No. 4,396,542 to Wenger, which are hereby incorporated by reference in their entirety), this synthetic route used for CsA analogue preparation is lengthy. As a result, the number of derivatives that have been prepared with Bmt$^1$ structural variations has been limited. Even considering the number of cyclosporin analogues with variations at the Bmt$^1$ amino acid that have already been synthesized and tested, there is still considerable room for further exploration of structure activity relationships on this important part of the cyclosporin molecule. The production of cyclosporin A methyl vinyl ketone gives synthetic access to many novel cyclosporin analogues more efficiently in only a few chemical steps starting from cyclosporin A.

DETAILED DESCRIPTION OF THE INVENTION

The compounds of the present invention are derived from members of the cyclosporin family, especially cyclosporin A. The cyclosporin family is intended to include all natural cyclosporins produced and isolated as metabolites from the strains of fungi, *Tolypocladium niveum*, *Tolypcladium inflatum*, and *Cyclindrocarpon lucidum* (Traber et al., "Die Struktur von Cyclosporin C," *Helv. Chim. Acta*, 60:1247-1255 (1977); Traber et al., "Isolierung und Strukturermittlung der neuen Cyclosporine E, F, G, H, und I," *Helv. Chim. Acta*, 65:1655-1677 (1982); Traber et al., "2. Neue Cyclosporine aus *Tolypocladium inflatum* Die Cyclosporine K-Z," *Helv. Chim. Acta*, 70:13-36 (1987), which are hereby incorporated by reference in their entirety). Other natural cyclosporins have also been isolated by the application of modified fermentation culture techniques (Traber et al., "Cyclosporins-New Analogues by Precursor Directed Biosynthesis," *J. Antibiotics*, XLII:591-597 (1989), which is hereby incorporated by reference in its entirety).

The structure of cyclosporin A, a cycloundecapeptide, and the position numbering for each amino acid in the ring is shown below:

TABLE 1

Cyclosporins

Cy A or CsA = Cyclosporin (Sandimmune ®) = Cyclosporin A
Cy B = [Ala$^2$]Cy A
Cy C = [Thr$^2$]Cy A
Cy D = [Val$^2$]Cy A
Cy E = [Val$^{11}$]Cy A
Cy F = [Deoxy-MeBmt$^1$]Cy A
Cy G = [Nva$^2$]Cy A
Cy H = [D-MeVal$^{11}$]Cy A
Cy I = [Val2, Leu$^{10}$]Cy A
Cy K = [Deoxy-MeBmt$^1$, Val$^2$]Cy A
Cy L = [Bmt$^1$]Cy A
Cy M = [Nva$^2$, Nva$^5$]Cy A
Cy N = [Nva$^2$, Nva$^{10}$]Cy A
Cy O = [MeLeu$^1$, Nva$^2$]Cy A
Cy P = [Bmt$^1$, Thr$^2$]Cy A
Cy Q = [Val$^4$]Cy A
Cy R = [Leu?, Leu?] Cy A
Cy S = [Nva$^2$, Nva$^5$]Cy A
Cy T = [Leu$^{10}$]Cy A
Cy U = [Leu$^6$]Cy A
Cy V = [Abu$^7$]Cy A
Cy W = [Thr$^2$, Val$^{11}$]Cy A
Cy X = [Nva$^2$, Leu$^9$]Cy A
Cy Y = [Nva$^2$, Leu$^6$]Cy A
Cy Z = [N-Methyl-2-amino-octanoic acid$^1$]Cy A

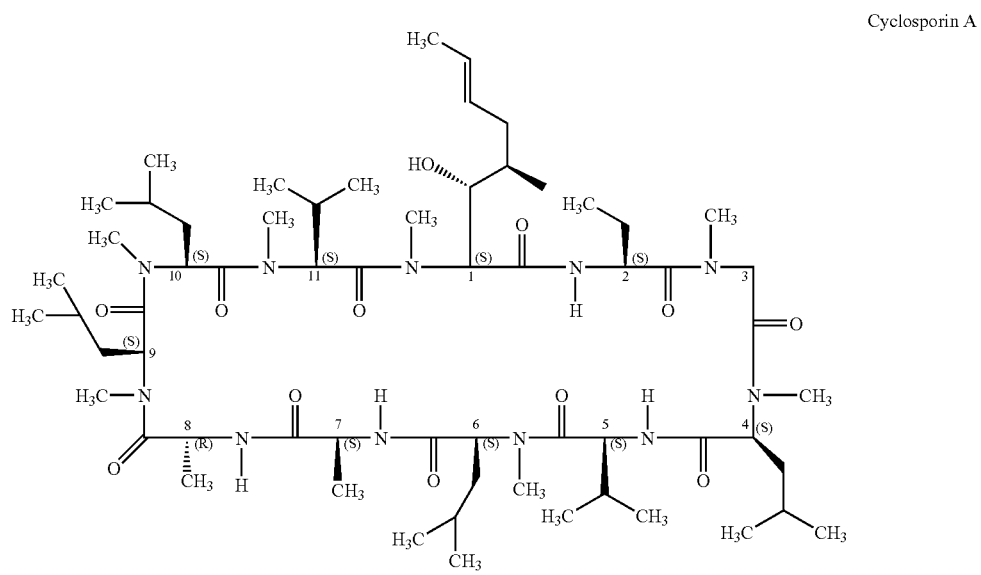

Cyclosporin A

Cyclosporin A is the most prominent member of the cyclosporin family of compounds. Therefore, names and abbreviations for other members of the cyclosporin family are often based on cyclosporin A. For example, cyclosporin B can be designated as [Ala$^2$]Cy A or (Ala$^2$)-Cs A, which indicates that the amino acid alanine is present at the two position instead of the amino acid, α-aminobutyric acid (Abu), that is present at the two position in cyclosporin A.

Important members of the cyclosporin family that have been isolated and characterized are shown in Table 1.

Novel compounds of the present invention are derived from cyclosporins like the ones shown, especially cyclosporin A, where the position one amino acid is:

(a) MeBmt$^1$ (acronym for (4R)-4-((E)-2-butenyl)-4, N-dimethyl-L-threonine; systematic name is (2S,3R,4R,6E)-3-hydroxy-4-methyl-2-(methylamino)-6-octenoic acid, also called N-Methyl-butenyl-threonine);

(b) Deoxy-MeBmt$^1$ (systematic name is (2S,3R,4R,6E)-4-methyl-2-(methylamino)-6-octenoic acid;

(c) Bmt¹ (acronym for (4R)-4-((E)-2-butenyl)-4-methyl-L-threonine; systematic name is (2S,3R,4R,6E)-3-hydroxy-4-methyl-2-(amino)-6-octenoic acid); or (d) Deoxy-Bmt¹ (systematic name is (2S,3R,4R,6E)-4-methyl-2-(amino)-6-octenoic acid).

The family of cyclosporins also extends to cyclosporin derivatives that do not occur in nature and, here, have been prepared by total synthetic and semi-synthetic methods. Many novel cyclosporin analogues have been prepared by total synthetic methods, allowing for the incorporation of natural or unnatural amino acids for one or more of the eleven amino acids of the cycloundecapeptide. (U.S. Pat. No. 4,396,542 to Wenger; U.S. Pat. No. 4,639,434 to Wenger et al.; European Patent Application No. 34567 to Wenger; Ko et al., "Solid Phase Total Synthesis of Cyclosporin Analogs," *Helv. Chim. Acta,* 80(3):695-705 (1997); U.S. Pat. No. 5,948,693 to Rich et al., which are hereby incorporated by reference in their entirety). Cyclosporin analogues prepared by total synthesis belong to the cyclosporin family.

Semi-synthetic methods have been applied to cyclosporins, leading to the preparation of many chemical derivatives of cyclosporins (Seebach et al., "Modification of Cyclosporin A: Generation of an Enolate at the Sarcosine Residue with Electrophiles," *Helv. Chim. Acta,* 76:1564-1590 (1993); Park et al., "A Semi-synthetic Approach to Olefinic Analogs of Amino Acid One (MeBmt) in Cyclosporin A," *Tetrahedron Lett.,* 30:4215-4218 (1989); Eberle et al., "Preparation of Sulfhydryl Cyclosporin A," *J. Org. Chem.,* 60:2610-2612 (1995); PCT Application Publication No. WO 99/65933 to Ellmerer-Mueller et al., which are hereby incorporated by reference in their entirety). Cyclosporin analogues prepared by semi-synthesis belong to the cyclosporin family.

Novel compounds of the present invention are derived from the cyclosporin family that include the unnatural cyclosporins like the ones that were prepared by total synthetic or semi-synthetic methods in the above cited references, but are not limited to the unnatural cyclosporins in these references.

The compounds of the present invention are represented by the chemical structure found in Formula I:

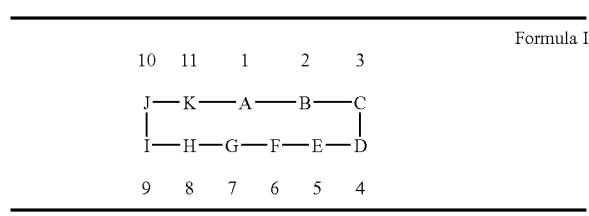

Formula I where A is an amino acid of Formula II:

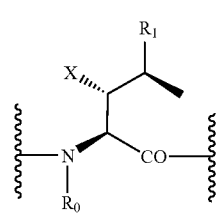

Formula II where:
$R_0$ is H or $CH_3$;
$R_1$=CHO;
C(=O)$OR_2$;
C(O)$NR_3R_4$;
CH=N—Y;
CH($NR_5R_6$)$R_7$;
CH($OR_8$)$R_9$;
CH($OR_{10}$)$_2$;
$CH_2SR_{11}$;
CH($SR_{12}$)$_2$;
$CR_{13}R_{14}R_{15}$;
CH=CHC(=O)Me;
$CH_2CH_2$C(=O)Me;
CH=CHCH($OR_{16}$)Me;
$CH_2CH_2$CH($OR_{16}$)Me;
CH=CHCH($NR_{17}R_{18}$)Me;
$CH_2CH_2$CH($NR_{17}R_{18}$)Me;
CH=CHC(=N—Y)Me;
$CH_2CH_2$C(=N—Y)Me;
CH=CHC($OR_{19}$)$_2$Me;
$CH_2CH_2$C($OR_{19}$)$_2$Me;
CH=CHC(=$CR_{20}R_{21}$)Me;
$CH_2$—$CH_2$C(=$CR_{20}R_{21}$)Me;
CH=CHC($SR_{22}$)$_2$Me;
$CH_2CH_2$C($SR_{22}$)$_2$Me;
CH=$CR_{23}R_{24}$;
$CH_2$CH$R_{23}R_{24}$;
CH=CHC(=O)$NR_{25}R_{26}$;
$CH_2CH_2$C(=O)$NR_{25}R_{26}$;
CH=CHC(=O)$OR_{26}$;
$CH_2CH_2$C(=O)$OR_{26}$;
CH=CHC(=O)$CH_2CH_2NR_{27}R_{28}$;
$CH_2CH_2$C(=O)$CH_2CH_2NR_{27}R_{28}$;
CH=CHC(=O)CH=CH$NR_{29}R_{30}$;
$CH_2CH_2$C(=O)CH=CH$NR_{29}R_{30}$;
CH=CH—C($OR_{31}$)$R_{32}$Me;
$CH_2CH_2$C($OR_{31}$)$R_{32}$Me;
CH=CHC(=O)$CH_2$C(OH)$R_{33}R_{34}$; or
$CH_2CH_2$C(=O)$CH_2$C(OH)$R_{33}R_{34}$;

$R_2$ and $R_{26}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
($CH_2$)$_n$-aryl ring;
($CH_2$)$_n$-heteroaryl ring;
$CH_2OCH_3$;
$CH_2SCH_3$;
$CH_2CH_2$F;
$CH_2CF_3$;
$CH_2CH_2CF_3$;
CH($CF_3$)$_2$; and
$CH_2OCH_2OC(O)CH_3$;

$R_3$, $R_4$, $R_5$, $R_6$, $R_{10}$, $R_{11}$, $R_{12}$, $R_{17}$, $R_{18}$, $R_{19}$, $R_{22}$, $R_{25}$, $R_{27}$, $R_{28}$, $R_{29}$, and $R_{30}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;

$C_3$-$C_6$-straight alkynyl chain;
$C_3$-$C_7$-cycloalkyl;
$CH_2$—($C_3$-$C_7$-cycloalkyl);
$(CH_2)_n$-aryl ring; and
$(CH_2)_n$-heteroaryl ring;

$R_3$ and $R_4$, $R_5$ and $R_6$, $R_{10}$, $R_{12}$, $R_{17}$ and $R_{18}$, $R_{19}$, $R_{22}$, $R_{25}$ and $R_{26}$, $R_{27}$ and $R_{28}$, $R_{29}$ and $R_{30}$ are together —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$— that results in the formation of a cyclic moiety that contains the heteroatom or heteroatoms to which they are bound;

$R_8$, $R_{16}$, and $R_{31}$ are the same or different and independently selected from the group consisting of:
hydrogen;
$C_1$-$C_6$-straight alkyl chain;
$C_3$-$C_6$-straight alkenyl chain;
$C_3$-$C_6$-branched alkyl chain;
$C_4$-$C_6$-branched alkenyl chain;
$C_3$-$C_6$-straight alkynyl chain;
$C_3$-$C_7$-cycloalkyl;
$CH_2$—($C_3$-$C_7$-cycloalkyl);
$(CH_2)_n$-aryl ring;
$(CH_2)_n$-heteroaryl ring;
alkanoyl;
alkenoyl;
alkynoyl;
aryloyl;
arylalkanoyl;
alkylaminocarbonyl;
arylaminocarbonyl;
arylalkylaminocarbonyl;
alkyloxycarbonyl;
aryloxycarbonyl; and
arylalkyloxycarbonyl;

$R_7$, $R_9$, $R_{13}$, $R_{14}$, $R_{15}$, $R_{20}$, $R_{21}$, $R_{23}$, $R_{24}$, $R_{32}$, $R_{33}$, and $R_{34}$, are the same or different and independently selected from the group consisting of:
hydrogen;
deuterium;
halogen;
hydroxyl;
nitrile;
substituted and unsubstituted $C_1$-$C_6$-straight alkyl chain;
substituted and unsubstituted $C_2$-$C_6$-straight alkenyl chain;
substituted and unsubstituted $C_3$-$C_6$-branched alkyl chain;
substituted and unsubstituted $C_4$-$C_6$-branched alkenyl chain;
substituted and unsubstituted $C_2$-$C_6$-straight alkynyl chain;
substituted and unsubstituted $C_4$-$C_6$-branched alkynyl chain;
substituted and unsubstituted $C_4$-$C_6$-chain having alkenyl and alkynyl groups;
substituted and unsubstituted $C_3$-$C_7$-cycloalkyl;
substituted and unsubstituted $(CH_2)_p$—($C_3$-$C_7$-cycloalkyl);
substituted and unsubstituted aryl;
substituted and unsubstituted heteroaryl;
substituted and unsubstituted arylalkyl;
substituted and unsubstituted heteroarylalkyl;
COOH;
$COOR_2$; and
$C(O)NR_3R_4$;
n=0, 1, 2, 3, or 4;
p=0, 1, 2, or 3;
X=hydrogen;
hydroxyl; or
hydroxyl group derivatized with an alkanoyl, aryloyl, alkylaminocarbonyl, arylaminocarbonyl, arylalkylaminocarbonyl, alkyloxycarbonyl, aryloxycarbonyl, or arylalkyloxycarbonyl group;

Y=$C_1$-$C_6$ straight and branched chain alkyl;
$C_3$-$C_6$ straight and branched chain alkenyl;
arylalkyl;
heteroarylalkyl;
$C_1$-$C_6$ straight and branched chain alkyloxy;
aryloxy;
acyloxy;
arylalkyloxy;
$C_1$-$C_6$ straight and branched chain alkylamino;
arylamino;
arylalkylamino;
heteroarylamino;
heteroarylalkylamino;
$C_1$-$C_6$ straight and branched chain alkylcarboxamido;
arylcarboxamido;
heteroarylcarboxamido;
$C_1$-$C_6$ straight and branched chain alkylsulfonamido;
arylsulfonamido;
arylalkylsulfonamido;
heteroarylsulfonamido;
heteroarylalkylsulfonamido; or
$NH_2C(O)NH$;

CO— in Formula II is covalently bound to an α-amino group of B in Formula I to form an amide linkage, and —N—$R_0$ in Formula II is covalently bound to a carboxylic acid of K to form an amide linkage;

B is an amino acid selected from the group consisting of:
α-aminobutyric acid;
alanine;
threonine;
valine;
norvaline; and
a modified α-aminobutyric acid, alanine, valine, or norvaline, wherein a carbon atom in a side chain is substituted with a hydroxyl group;

C is a sarcosine;
D is an amino acid selected from the group consisting of:
leucine;
N-methyl leucine;
valine;
γ-hydroxy-N-methyl leucine; and
γ-hydroxy leucine;

E is an amino acid selected from the group consisting of:
valine;
norvaline; and
a modified valine or norvaline, wherein a carbon atom in a side chain is substituted with a hydroxyl group;

F is an amino acid selected from the group consisting of:
leucine;
N-methyl leucine;
γ-hydroxy-N-methyl leucine; and
γ-hydroxy leucine;

G is α-aminobutyric acid or alanine;
H is D-alanine;
I and J are independently selected from the group consisting of:
leucine;
N-methyl leucine;
γ-hydroxy-N-methyl leucine; and
γ-hydroxy leucine; and K is N-methyl valine or valine;
or a pharmaceutically acceptable salt thereof.

The term "$C_1$-$C_6$-straight alkyl chain" as used herein refers to saturated, straight chain hydrocarbon radicals containing between one and six carbon atoms. Examples include methyl, ethyl, propyl, n-butyl, n-pentyl, and n-hexyl.

The term "$C_3$-$C_6$-straight alkenyl chain" as used herein refers to straight chain hydrocarbon radicals containing between three and six carbon atoms with at least one carbon-carbon double bond. The term "$C_2$-$C_6$-straight alkenyl chain" as used herein refers to straight chain hydrocarbon radicals containing between two and six carbon atoms with at least one carbon-carbon double bond. Examples include ethylene, $CD=CD_2$, 2-propenyl, 3-butenyl, 4-pentenyl, 5-hexenyl, 2-butenyl, 2-pentenyl, 3-pentenyl, 2-hexenyl, 3-hexenyl, and 4-hexenyl.

The term "$C_3$-$C_6$-branched alkyl chain" as used herein refers to branched chain hydrocarbon radicals containing between three and six carbon atoms. Examples include, but are not limited to, isopropyl, isobutyl, tert-butyl, and neopentyl.

The term "$C_4$-$C_6$-branched alkenyl chain" as used herein refers to branched chain hydrocarbon radicals containing between four and six carbon atoms with at least one carbon-carbon double bond. Examples include 2-methyl-2-propenyl, 3-methyl-2-butenyl, and 4-methyl-3-pentenyl, and the like.

The term "$C_2$-$C_6$-straight alkynyl chain" as used herein refers to straight chain hydrocarbon radicals containing between three and six carbon atoms with a carbon-carbon triple bond. The term "$C_2$-$C_6$-branched alkynyl chain" as used herein refers to straight chain hydrocarbon radicals containing between four and six carbon atoms with a carbon-carbon triple bond. Examples include $C≡CH$, $C≡CCH_3$, $C≡CCH_2CH_3$, $C≡CCH_2C(CH_3)_2$, $CH_2C≡CH$, $CH_2C≡CCH_3$, and the like.

The term "$C_3$-$C_7$-cycloalkyl" as used herein refers to cyclic hydrocarbon radicals between three and seven carbon atoms. Examples include cyclopropyl, cyclobutyl, cyclopentyl, cyclohexyl, and cycloheptyl.

Substituents on straight and branched chain alkyl, straight and branched chain alkenyl, alkynyl chain and cycloalkyl chain are in any position and are independently selected from methyl, ethyl, $C_3$-$C_7$-cycloalkyl, substituted and unsubstituted aryl, substituted and unsubstituted heteroaryl, $CF_3$, F, Cl, Br, I, OH, $OCH_3$, OPh, $CO_2H$, $CO_2Me$, CN, $C(O)NH_2$, $C(O)NHCH_3$, $OC(O)CH_3$, $OCH_3$, $NH_2$, $NHCH_3$, $N(CH_3)_2$, NHPh, and $NHC(O)CH_3$. Carbon-hydrogen bonds of alkyl, alkenyl and alkynyl chains are replaced with carbon-deuterium and carbon-fluorine bonds to give polydeuterated and polyfluorinated alkyl, alkenyl, and alkynyl chains.

The term "aryl ring" as used herein refers to carbocyclic rings with the degree of unsaturation present as to impart aromaticity to the ring. Examples include substituted or unsubstituted phenyl rings, napthyl rings, and the like. Substituents (1-2 in number) are in any position and are independently selected from $CH_3$, $CH_3CH_2$, $CH(CH_3)_2$, OH, $OCH_3$, $OCH_2CH_3$, $OCF_3$, OPh, Ph, SH, $SCH_3$, SPh, $S(O)CH_3$, $S(O)$ Ph, $S(O_2)CH_3$, $S(O_2)$Ph, $NHCH_3$, $N(CH_3)_2$, NHPh, $NCH_3$Ph, $NO_2$, $NHC(O)CH_3$, $NHC(O)$Ph, F, Cl, Br, I, $CF_3$, CN, $C(O)CH_3$, $C(O)$Ph, $CO_2H$, $CO_2CH_3$, $C(O)NHCH_3$, $C(O)N(CH_3)_2$, $C(O)NHCH_2CH_2OH$, $CH_2CO_2H$, and $CH_2C(O)NH_2$.

The term "heteroaryl ring" used herein refers to a substituted or unsubstituted heterocyclic aromatic ring, which can be a five-member ring heterocycle, a six-member ring heterocycle, and ring-fused bicyclic heterocycle. Examples of heteroaryl rings include 2-pyridyl, 3-pyridyl, 4-pyridyl, 2-pyrimidyl, 4-pyrimidyl, 5-pyrimidyl, thiophene-2-yl, thiophene-3-yl, 2-furanyl, 3-furanyl, oxazol-2-yl, oxazol-4-yl, oxazol-5-yl, thiazol-2-yl, thiazol-4-yl; thiazol-5-yl, imidazol-2-yl, imidazol-4-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, 1,3,4-thiadiazol-2-yl, benzo[b]furan-2-yl, benzo[b]thiophene-2-yl, 2-pyrrolyl, 3-pyrrolyl, 1,3,5-triazin-2-yl, pyrazin-2-yl, pyridazin-3-yl, pyridazin-4-yl, 2-quinolinyl, 3-quinolinyl, 4-quinolinyl, 1-isoquinolinyl, 3-isoquinolinyl, 4-isoquinolinyl heterocyclic rings, and the like. The substituents (1-2 in number) are in any position and are independently selected from $CH_3$, $CH_3CH_2$, OH, $OCH_3$, $OCH_2CH_3$, $OCF_3$, OPh, Ph, SH, $SCH_3$, SPh, $S(O)CH_3$, $S(O)$Ph, $S(O_2)CH_3$, $S(O_2)$Ph, $NHCH_3$, $N(CH_3)_2$, NHPh, $NCH_3$Ph, $NO_2$, $NHC(O)CH_3$, $NHC(O)$Ph, F, Cl, Br, I, $CF_3$, CN, $C(O)CH_3$, $C(O)$Ph, $CO_2H$, $CO_2CH_3$, $C(O)NHCH_3$, $C(O)N(CH_3)_2$, $C(O)NHCH_2CH_2OH$; $CH_2CO_2H$, and $CH_2C(O)NH_2$.

The term "alkanoyl" used herein refers to a substituted or unsubstituted $C_1$-$C_6$-straight alkyl chain, a $C_3$-$C_6$-branched alkyl chain and a $C_3$-$C_7$-cycloalkyl group covalently bound to a carbonyl group. Examples include acetate, propionate, pivaloate, butyrate, isobutyrate, cyclohexane carboxylate, and the like.

The term "alkenoyl" used herein refers to a substituted or unsubstituted $C_3$-$C_6$-straight alkenyl chain covalently bound to a carbonyl group. Examples include acrylate, crotonate, methacrylate, 2,4-hexadienoate, and the like.

The term "alkynoyl used herein refers to a substituted or unsubstituted $C_3$-$C_6$-straight alkynyl chain covalently bound to a carbonyl group. Examples include propiolate, 2-butynoate, and the like. Substituents on alkanoyl, alkenoyl and alkynoyl chains are in any appropriate position and are independently selected from F, Cl, Br, I, OH, $CO_2H$, $CO_2Me$, CN, $C(O)NH_2$, $C(O)NHCH_3$, $OC(O)CH_3$, $OCH_3$, $NH_2$, $NHCH_3$, $N(CH_3)_2$, and $NHC(O)CH_3$.

The term "aryloyl" used herein refers to a substituted or unsubstituted aryl or heteroaryl ring. Examples of arylacyl groups include benzoyl, p-fluorobenzoyl, 2-naphthoyl, nicotinoyl, isonicotinoyl, and the like.

The term "arylalkanoyl" used herein refers to a substituted or unsubstituted aryl or heteroaryl ring covalently bound to an alkyl chain of one, two, three or four carbon atoms whereby one of the carbon atoms of the alkyl chain is covalently attached to a carbonyl group. The alkyl chain is substituted or unsubstituted, straight or branched, saturated or unsaturated. Examples of arylalkylacyl groups include phenylacetoyl, p-fluorophenylacetoyl, 2-phenylpropionoyl, mandeloyl, cinnamoyl, and the like.

The term "alkylaminocarbonyl" used herein refers to a substituted or unsubstituted $C_1$-$C_6$-straight alkyl chain, a $C_3$-$C_6$-branched alkyl chain, and a $C_3$-$C_7$-cycloalkyl group covalently bound to a nitrogen atom that is covalently bound to a carbonyl group. Examples of alkylaminoacyl groups include methylaminocarbonyl, ethylaminocarbonyl, isopropylaminocarbonyl, tert-butylaminocarbonyl, cyclopentylaminocarbonyl, cyclohexylaminocarbonyl, and the like.

The term "arylaminocarbonyl" used herein refers to a substituted or unsubstituted aryl or heteroaryl ring. Examples include phenylaminocarbonyl, (naphth-2-yl)aminocarbonyl, para-methoxyphenylaminocarbonyl, (pyrid-4-yl)aminocarbonyl, (pyrazin-2-yl)aminocarbonyl, and the like.

The term "arylalkylaminocarbonyl" used herein refers to a substituted or unsubstituted aryl or heteroaryl ring covalently bound to an alkyl chain of one, two, three or four carbon atoms whereby one of the carbon atoms of the alkyl chain is covalently bound to an amino group which is covalently bound to a carbonyl group. Examples include benzylaminocarbonyl, phenethylaminocarbonyl, α-methylbenzylaminocarbonyl, pyrid-4-yl methylaminocarbonyl, and the like.

The term "alkyloxycarbonyl" used herein refers to a substituted or unsubstituted $C_1$-$C_6$-straight alkyl chain, a $C_3$-$C_6$-branched alkyl chain, and a $C_3$-$C_7$-cycloalkyl group covalently bound to an oxygen atom that is covalently bound to a carbonyl group. The substituents are in any position and are independently selected from F, Cl, Br, I, OH, $CO_2H$, $CO_2Me$, CN, $C(O)NH_2$, $C(O)NHCH_3$, $OC(O)CH_3$, $OCH_3$, $SCH_3$, $NH_2$, $NHCH_3$, $N(CH_3)_2$, and $NHC(O)CH_3$. Examples include methoxycarbonyl, ethoxycarbonyl, tert-butyloxycarbonyl (BOC), and the like.

The term "aryloxycarbonyl" used herein refers to a substituted or unsubstituted aryl or heteroaryl ring. Examples include phenyloxycarbonyl, (naphth-2-yl)oxycarbonyl, para-methoxyphenyloxycarbonyl, (pyrid-4-yl)oxycarbonyl, (pyrazin-2-yl)oxycarbonyl, and the like.

The term "arylalkyloxycarbonyl" used herein refers to a substituted or unsubstituted aryl or heteroaryl ring covalently bound to an alkyl chain of one, two, three, or four carbon atoms whereby one of the carbon atoms of the alkyl chain is covalently bound to an oxygen atom which is covalently bound to a carbonyl group. Examples include benzyloxycarbonyl, phenethyloxycarbonyl, α-methylbenzyloxycarbonyl, (pyrid-4-yl)methyl oxycarbonyl, 9-fluorenylmethyl oxycarbonyl (FMOC), and the like.

The cyclosporin nomenclature and numbering systems used herein are those used by Kallen et al., "Cyclosporins: Recent Developments in Biosynthesis, Pharmacology and Biology, and Clinical Applications," In *Biotechnology*, second edition, Rehm et al., eds, pp. 535-591 (1997), which is hereby incorporated by reference in its entirety, and are shown below:

| Position numbering | Letter in Formula I | Amino acid in cyclosporin A |
|---|---|---|
| 1 | A | N-Methyl-butenyl-threonine (MeBmt) |
| 2 | B | α-Aminobutyric acid (Abu) |
| 3 | C | Sarcosine (Sar) |
| 4 | D | N-Methyl-leucine (MeLeu) |
| 5 | E | Valine (Val) |
| 6 | F | N-Methyl-leucine (MeLeu) |
| 7 | G | Alanine (Ala) |
| 8 | H | (D)-Alanine ((D)-Ala) |
| 9 | I | N-Methyl-leucine (MeLeu) |
| 10 | J | N-Methyl-leucine (MeLeu) |
| 11 | K | N-Methyl-valine (MeVal) |

The relationship between the position numbering and the "Letter in Formula I" has been arbitrarily assigned for the purpose of defining the structure of the compounds of the present invention and does not represent any known convention for designating amino acids in cyclosporin analogues as such.

The compounds of the present invention are derived from known compounds of the cyclosporin family, including cyclosporin A, or other cyclosporins that have in the first amino acid position (according to cyclosporin nomenclature) of the cycloundecapeptide the MeBmt[1], Deoxy-MeBmt[1], Deoxy-Bmt[1], or Bmt[1]. The novel compounds of the present invention all possess structurally modified amino acids at the one position. In addition to the modification to the amino acids at the one position, it is also within the scope of the present invention to include derivatives where structural changes have also been made simultaneously to one or more of the amino acids at positions two through eleven.

The present invention also provides novel chemical and biocatalytic processes for the preparation of novel cyclosporin derivatives. One such process involves the use of a biocatalyst for the conversion of members of the cyclosporin family, especially cyclosporin A, to novel cyclosporin derivatives that possess biological activity that make them useful as pharmaceutical compounds. This process involves the transformation of the MeBmt[1], in cyclosporin A for example, to a new amino acid residue (4R)-4-((E)-2-keto-3-butenyl)-4, N-dimethyl-L-threonine (also systematically named (2S,3R,4R,5E)-3-hydroxy-4-methyl-2-(methylamino)-7-oxo-5-octenoic acid). The net effect of this biocatalytic process is to convert the amino acid side chain terminus from the "(E)-2-butenyl" moiety to a terminal "methyl vinyl ketone", as shown below.

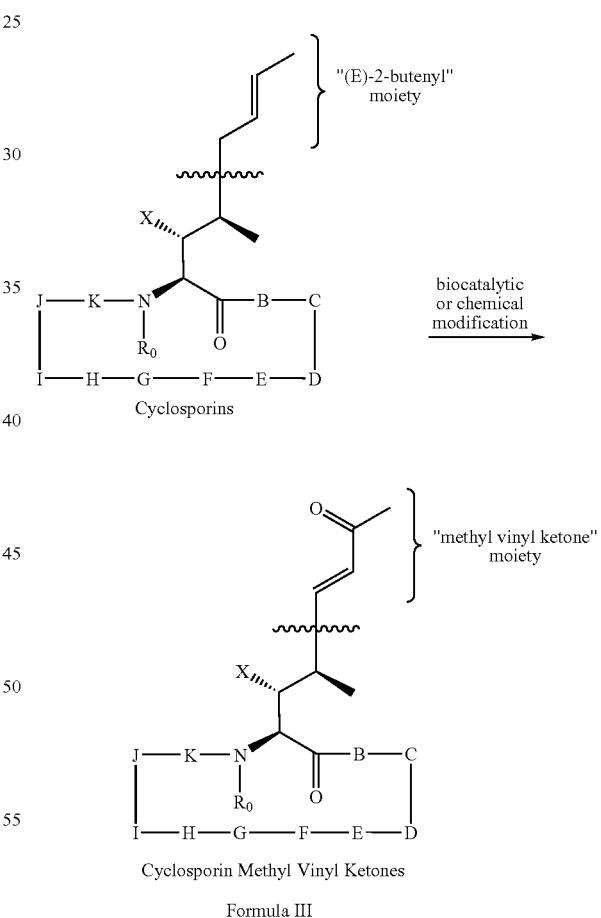

Formula III

The novel cyclosporin methyl vinyl ketone (Cs-MVK, Formula III) derivatives possess biological activities that make them useful as pharmaceutical agents to treat a variety of medical conditions or disorders. The methyl vinyl ketone functional group also makes these compounds useful synthetic intermediates from which to make additional novel derivatives, as shown below.

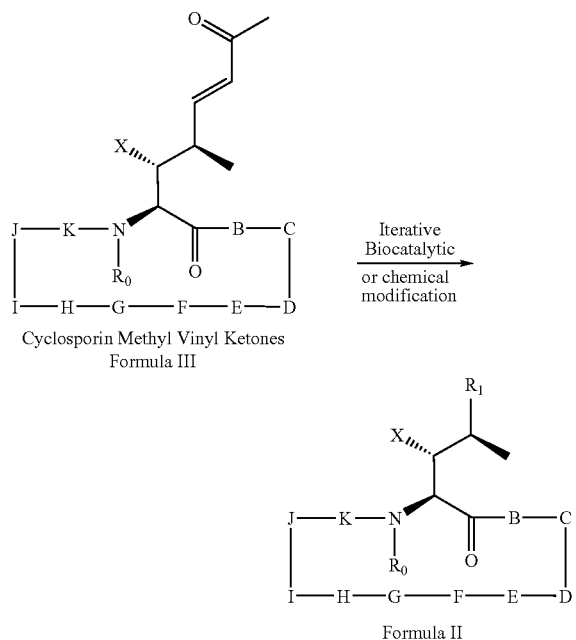

Cyclosporin Methyl Vinyl Ketones
Formula III

Iterative Biocatalytic or chemical modification

Formula II

Therefore, another aspect of the present invention relates to subjecting the compounds of Formula III to further chemical or biocatalytic manipulation, which leads to the production of novel compounds possessing pharmaceutical utility. Structural modifications produced by this iterative type of process are not restricted to the amino acid one position, but can take place on one or more of the other ten amino acids, positions two through eleven, around the cycloundecapeptide.

An alternative method for the preparation of the Cs-MVK derivatives is also disclosed, where a chemical oxidation that does not require the use of biocatalysts is performed to transform cyclosporins, including cyclosporin A, to the cyclosporin methyl vinyl ketones of Formula III.

It is well known that the amino acid at the one position (MeBmt[1], Deoxy-MeBmt[1] Deoxy-Bmt[1] or Bmt[1]) of the cycloundecapeptide of cyclosporins, including cyclosporin A, plays a very important role in the biological activity of the cyclosporins. As a result of these structural changes to the amino acid in the one position, the novel cyclosporin derivatives of the present invention possess pharmaceutical utility towards several therapeutic indications.

The cyclosporins are best known for their immunosuppressive effects exerted by their selective action on T-lymphocytes of the immune system. Compounds disclosed in the present invention that possess inhibitory activity against calcineurin, an intracellular protein phosphatase involved in the regulation of intracellular lymphocyte (T-cell) signaling in the mammalian immune system, display immunosuppressive activity in mammals. The drug interaction with calcineurin occurs with a complex between cyclophilin A (the intracellular receptor for cyclosporins) and cyclosporin A that first forms. The major consequence of calcineurin inhibition is that dephosphorylation of the transcription factor nuclear factor of activated T-cells (NF-AT) does not occur and transcription of the cytokine interleukin-2 (IL-2) is inhibited. In vitro and in vivo tests, the effect observed is the inhibition of T-cell proliferation and lymphocyte cell differentiation (T-lymphocytes to B-lymphocytes). Compounds disclosed in the present invention that have this biological activity profile are in the same class as cyclosporin A, and administration of these compounds suppresses the immune response in organ transplant patients and, thus, prevents allograft rejection. Compounds disclosed in the present invention in this class also possess utility in the treatment of autoimmune and chronic inflammatory diseases like asthma, rheumatoid arthritis, multiple sclerosis, psoriasis, and ulcerative colitis, to name only a few.

Another aspect of the present invention provides new cyclosporin A analogues that possess other useful biological activities that are dissociated from immunosuppressive activity. Some cyclosporin derivatives of the present invention retain good binding affinity toward cyclophilin A, but lack calcineurin inhibitory activity and, therefore, lack immunosuppressive activity. Cyclophilin A, like other cyclophilins, is a peptidyl-prolyl cis-trans isomerase (PPIase) which is important for protein folding or chaperone activities. Cyclosporin A and FK-506 have been shown to possess neurotrophic activity in mammals (Snyder et al., "Neural Actions of Immunophilin Ligands," *Trends in Pharmacological Sciences*, 19:21-26 (1998), which is hereby incorporated in its entirety). It has also been reported that analogues of cyclosporin A and FK-506 that lack immunosuppressive activity but retain potent PPIase inhibitory activity retain neurotrophic activity. This demonstrates the feasibility of dissociating the immunosuppressive and neurotrophic activities. These compounds have been shown to possess the therapeutic utility for the treatment of a wide range of neurodegenerative diseases like diabetic neuropathy, amyotrophic lateral sclerosis, spinal cord injury, Alzheimer's disease, Parkinson's disease, and stroke, to name a few. Compounds disclosed in the present invention possess similar biological activity profiles and, therefore, utilities.

Other cyclosporin derivatives devoid of immunosuppressive activity have shown the ability to disrupt the human immunodeficiency virus (HIV) life cycle, e.g., SDZ NIM 811 (Mlynar et al., "The Non-immunosuppressive Cyclosporin A Analog SDZ NIM 811 Inhibits Cyclophilin A Incorporation Into Virions and Virus Replication in Human Immunodeficiency Virus Type 1 Infected Primary and Growth-Arrested T Cells," *J. Gen. Virol.*, 78(4):825-835 (1997), which is hereby incorporated by reference in its entirety). Binding to cyclophilin A is a prerequisite for HIV-1 inhibition by cyclosporins. Cyclophilin A was demonstrated to bind to HIV-1 p24gag and this cyclophilin-Gag interaction leads to the incorporation of cyclophilin A into HIV-1 virions. Compounds disclosed in the present invention that function in a manner like SDZ NIM 811 inhibit this protein interaction, which is likely to be the molecular basis for their antiviral activity.

While much of the biological activity described above requires cyclosporins, like cyclosporin A, to cross the cell plasma membrane and interact with intracellular protein targets like the cyclophilins and calcineurin, some biological activities result from the interaction of cyclosporins with proteins in the plasma membrane. Cyclosporin A is a broad and relatively unselective inhibitor of seven transmembrane-G-protein coupled receptors (7-TM-GPCR) and 12 transmembrane (TM) channels and transporters. One of these transporters is the multidrug resistance-1 P-glycoprotein (MDR1-encoded Pgp), a 12 TM ATP binding cassette (ABC) transporter. The cell specific expression of the MDR1 Pgp sustains house-keeping functions (e.g., at the blood-brain barrier), toxin exclusion (e.g., in the gut), and toxic metabolites clearance (e.g., in the liver), but MDR1 Pgp is also a flippase for selective membrane phospholipids (Loor, "Cyclosporins and Related Fungal Products in the Reversal of P-Glycoprotein-Mediated Multidrug Resistance," In *Multidrug Resistance in Cancer Cells*, Gupta et al., eds. pp 387-412, John Wiley & Sons Ltd.: Chichester (1996), which is hereby incorporated by reference in its entirety). This Pgp activity also restricts anticancer drug accumulation by the cells, causing the MDR phenotype of some tumor cells. Several cyclosporin derivatives were found to behave as highly potent and selective inhibitors of drug transport by the MDR1 Pgp. One such cyclosporin derivative, known as Valspodar ([3'-keto-MeBmt$^1$, Val2]-CsA), is more potent and selective than CsA (Loor, "Valspodar: Current Status and Perspectives," *Exp. Opin. Invest. Drugs*, B 8:807-835 (1999), which is hereby incorporated by reference in its entirety). Several cyclosporin derivatives disclosed in the present invention, like Valspodar, lack immunosuppressive activity (and other collateral activities of CsA), and are useful for chemosensitization of MDR tumor cells.

Other cyclosporin derivatives disclosed in the present invention possess anti-fungal and anti-parasitic activity. Further, other compounds disclosed in the present invention possess immunostimulatory activity.

The compounds disclosed in the present invention may be administered neat or with a pharmaceutical carrier to warm blooded mammals. Compounds disclosed in the present invention can be administered to patients for the treatment of immunoregulatory disorders, autoimmune disease, HIV infection, neurodegenerative disease, for the prevention of organ transplant rejection, and for the chemosensitization of tumor cells resistant to chemotherapy.

For treatment of the above mentioned diseases, therapeutically effective doses of cyclosporin compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutical excipients. As used herein, the term "pharmaceutical excipient" means a non-toxic, inert solid, semi-solid or liquid filler, diluent, encapsulating material, or formulation auxiliary of any type. Some examples of pharmaceutical excipients are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), compounds of the present invention may be administered in suppository or enema form, in solution in particular, for example in vegetable oil or in an oily system for use as a retention enema.

Compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of compounds of the present invention employed for the treatment of the maladies identified in the present invention will vary depending on the site of treatment, the particular condition to be treated, the severity of the condition, the subject to be treated (who may vary in body weight, age, general health, sex, and other factors) as well as the effect desired.

Dosage levels ranging from about 0.05 mg to about 50 mg per kilogram of body weight per day are useful for the treatment of the conditions or diseases identified in the present invention. This means the amount of the compound disclosed in the present invention that is administered will range from 2.5 mg to about 2.5 gm per patient per day.

The amount of active ingredient that may be combined with the pharmaceutical carrier materials to produce a single dosage form will vary depending upon the host treated and the particular mode of administration. For example, a formulation intended for the oral administration of humans may contain from 2.5 mg to 2.5 gm of active compound of the present invention compounded with an appropriate and convenient amount of carrier material which may vary from about 5 to 95 percent of the total composition. Dosage unit forms will generally contain between from about 5 mg to about 500 mg of active compound of the present invention. Dosage for topical preparation will, in general be less (one tenth to one hundredth) of the dose required for an oral preparation.

The Synthesis of Novel Cyclosporin A Derivatives

The starting materials for the preparation of novel cyclosporin derivatives of the present invention are members of the cyclosporin family, including cyclosporin A (CsA). Selective oxidation of the MeBmt$^1$, deoxy-MeBmt$^1$, Bmt$^1$, or deoxy-Bmt$^1$ side chain of a cyclosporin can be achieved biocatalytically by the use of enzymes from the laccase family.

Laccases (EC 1.10.3.2) are multi-copper oxidases that can catalyze the oxidation of a range of reducing substances with concomitant reduction of molecular oxygen (Xu et al, "Redox Chemistry in Laccase-Catalyzed Oxidation of N-Hydroxy Compounds," *Applied and Environmental Microbiology*, 66:2052-2056 (2000), which is hereby incorporated by reference in its entirety). It has been shown that many compounds that would appear to possess comparable redox potentials are not laccase substrates due to unfavorable kinetics. Under certain conditions, however, these compounds can be indirectly oxidized by laccase through the mediation of small, redox active laccase substrates. Some known mediators of laccase catalysis are 2,2'-azinobis(3-ethylbenzothiazoline)-6-sulfonic acid (ABTS) and N-hydroxy compounds such as 1-hydroxybenzotriazole (HOBT), violuric Acid (VA) and N-hydroxyacetanilide (NHA).

Laccase from *Trametes versicolor* in combination with mediators, such as ABTS, NHA, and HOBT, are used as bleaching agents for lignin degradation and pulp bleaching in the paper industry. In organic synthesis, laccase mediated oxidation is used for the transformation of an aromatic methyl group to an aromatic aldehyde (Fritz-Langhals et al., "Synthesis of Aromatic Aldehydes by Laccase-Mediator Assisted Oxidation," *Tetrahedron Lett.*, 39:5955-5956 (1998), which is hereby incorporated by reference in its entirety) as well as the conversion of a benzyl alcohol to benzaldehyde (Potthast et al., "A Novel Method for the Conversion of Benzyl Alcohols to Benzaldehydes by Laccase-Catalyzed Oxidation," *J. Mol. Cat., A* 108:5-9 (1996), which is hereby incorporated by reference in its entirety).

The HOBT-mediated laccase oxidation of cyclosporins is a novel application for the laccase enzyme. Treatment of cyclosporins, including cyclosporin A, with HOBT-mediated laccase oxidation conditions results in the preparation of cyclosporin methyl vinyl ketones (Cs-MVK) of Formula III. The net effect of this biocatalytic process is to convert the position one amino acid side chain terminus from the "(E)-2-butenyl" moiety to a terminal "methyl vinyl ketone," as shown in Scheme 1.

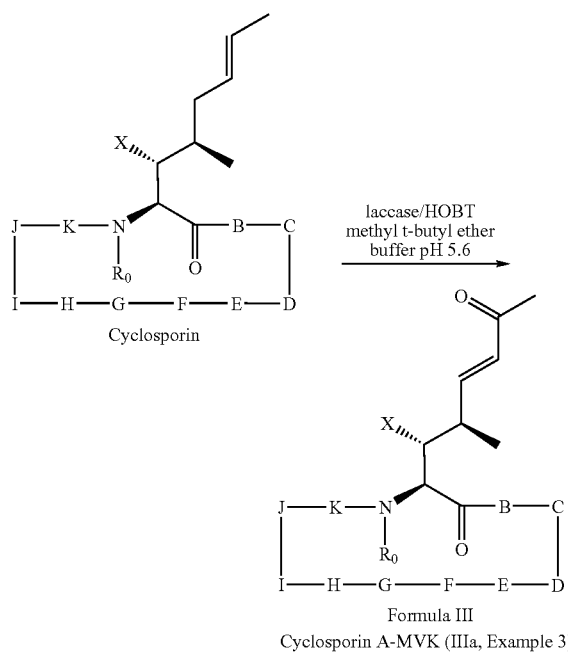

Cyclosporin A-MVK (IIIa, Example 3)

The more likely products that are expected oxidation are products of allylic oxidation of the methyl or methylene positions, i.e., primary or secondary alcohols and more highly oxidized products arising from these, i.e., aldehydes or ketones. These expected products, however, are minor reaction products at best. The formation of the Cs-MVK (Formula III) as the major product via the HOBT-mediated laccase oxidation is unexpected and unprecedented. This biocatalytic process works best using HOBT as the mediator, however the present invention includes the use of other known mediators like ABTS, VA, NHA, or other mediators known in the art. Also, the present invention includes the use of laccase enzyme from other known sources, e.g., *Trametes villosa, Pleurotus ostreatus, Polyporus versicolor*, or other known organisms from which laccase has been found.

The selective oxidation of the MeBmt[1], deoxy-MeBmt[1], Bmt[1], or deoxy-Bmt[1] side chains of cyclosporins to Cs-MVKs (compounds of Formula III) can also be practiced by chemical transformation that does not require the use of a biocatalyst such as the laccase enzyme. Punniyamurthy et al., "Cobalt Catalyzed Allylic and Benzylic Oxidations with Dioxygen in the Presence of Ethyl 2-Oxocyclopentanecarboxylate," *Tetrahedron Lett.*, 35:4003-4006 (1994), which is hereby incorporated by reference in its entirety, has reported this type of functional group transformation, where cis-2-octene is converted to 2-keto-oct-3-ene using a catalytic amount of cobalt (II) Schiff's base complex [bis(salicylidene-N-(methyl-3-hydroxypropionate))] and molecular oxygen, as a "surprising" result.

One embodiment of the present invention relates to a process for effecting allylic oxidation which utilizes an alkali metal periodate and an alkyl hydroperoxide (see U.S. Pat. No. 5,869,709 to Marwah et al., which is hereby incorporated by reference in its entirety). Cyclosporin A, when subjected to treatment with t-butyl peroxide and sodium periodate in acetone or methyl isobutyl ketone at room temperature or with gentle heating, results in the formation of the CsA MVK (IIIa) product, as shown in Scheme 2.

While the periodate/peroxide conditions described above are effective for reaction scales of a gram or less of cyclosporin starting materials, the yield of the Cs-MVK product are lower when the reaction is run on larger scale with significant amounts of unreacted cyclosporine isolated. Further optimization of the periodate/peroxide conditions involves the use of t-butyl hydroperoxide (50-100 equivalents), potassium periodate (5-10 equivalents), and a crown ether (18-crown-6, 4-10 equivalents) in an acetone-benzene-water (1.0:1.0:1.5) solvent mixture at room temperature for three days. The oxidation of cyclosporins proceed under these novel conditions on a multigram scale in nearly complete conversion of the cyclosporin starting materials to Cs-MVK products in good yields.

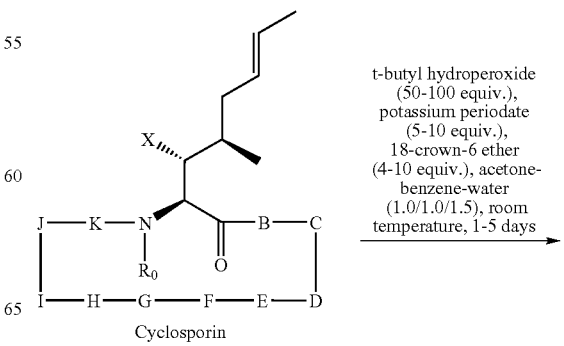

-continued

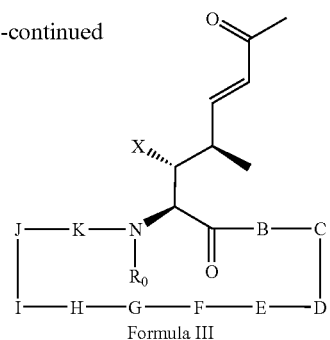

Formula III
Cyclosporin A-MVK (IIIa, Examples 4-6)
Cyclosporin C-MVK (IIIb, Example 7)
Cyclosporin D-MVK (IIIc, Example 8)

Another embodiment of the present invention relates to an oxidation condition for allylic groups that utilizes catalytic N-hydroxydicarboxylic acid imides, e.g., N-hydroxyphthalimide, dibenzoyl peroxide, refluxing acetone or isobutyl methyl ketone and air (see U.S. Pat. No. 5,030,739 to Foricher et al., which is hereby incorporated by reference in its entirety). These conditions are appealing because of the use of a similar N-hydroxy mediator used in the biocatalytic process. When cyclosporin A is subjected to these conditions, the desired product, CsA-MVK (IIIa), is detected by proton NMR analysis of the reaction mixture, but the major product isolated is an N-hydroxyphthalimide CsA adduct. Upon resubjecting this adduct to the reaction conditions, CsA MVK is isolated as the major product. It is important to note that Cs-MVK products isolated by either of the chemical methods described in the present invention would not be predicted based on the products reported in the previously cited patents.

Further chemical modification of Cs-MVK products of the present invention can be performed by sodium borohydride reduction of the ketone to give a diastereomeric mixture (1:1) of cyclosporin alcohols, referred to as cyclosporin alcohols A (IVa-A) and B (IVa-B) shown in Scheme 3. The cyclosporin alcohols (IVa-A & IVa-B) are separable by semi-preparative reverse phase HPLC (C8 column). Cyclosporin alcohol "isomer A" when subjected to treatment with acetic anhydride, DMAP and pyridine in dichloromethane gives a mixture of cyclosporin alcohol monoacetyl ester 1, cyclosporin alcohol monoacetyl ester 2 and cyclosporin alcohol diacetate of IVa-A. The products are purified and separated by semi-preparative reverse phase HPLC (C8 column). Selective acylation of CsA alcohol "isomer B" is performed by enzymatic acylation with a lipase in an organic solvent. The lipase can be from *Pseudomonas cepacia* or *Pseudomonas fluorescens*, and can be a native lipase or a genetically modified lipase. In another embodiment, the lipase can be immobilized to a solid support. Examples of the organic solvent are methyl-tert-butyl ether, toluene, pyridine, or mixtures thereof, and mixtures with N,N-dimethyl formamide. When the CsA alcohol "isomer B" (IVa-B) is stirred in methyl tert-butyl ether with vinyl butyrate and immobilized lipases AH and AK, the monobutyrate ester of IVa-B is prepared.

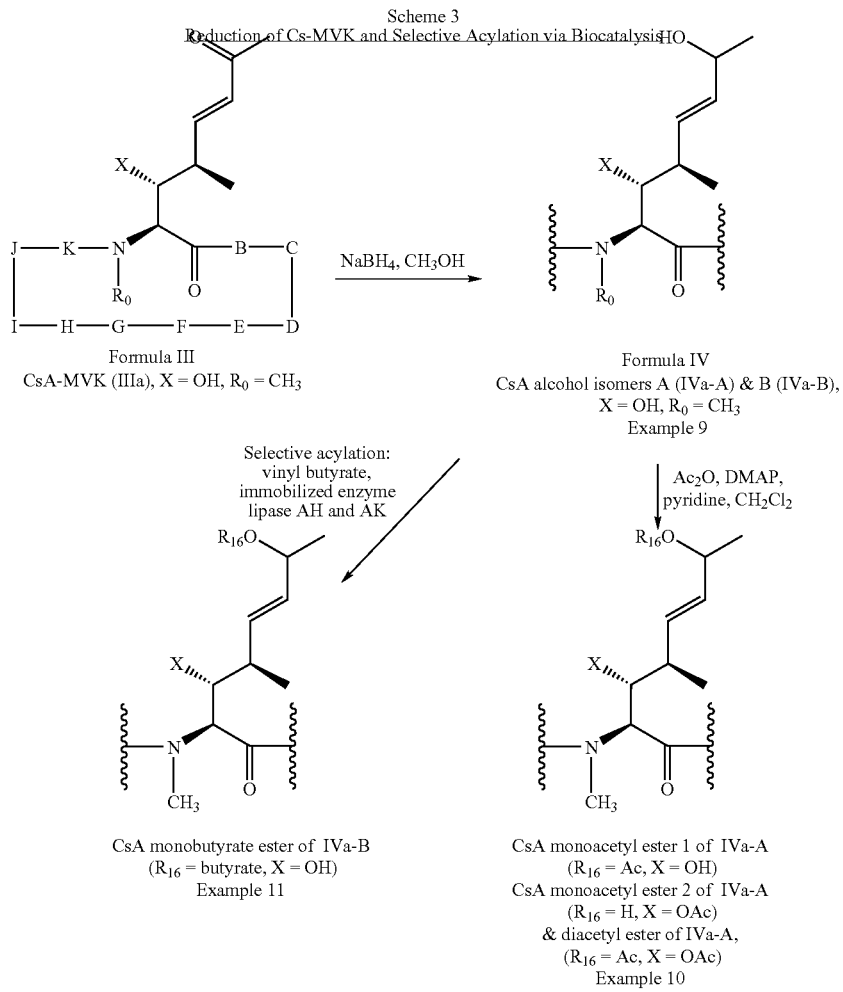

Scheme 3
Reduction of Cs-MVK and Selective Acylation via Biocatalysis

Other cyclosporin derivatives disclosed in the present invention can be prepared by applying biocatalytic or chemical methods in an iterative process. Scheme 4 shows CsA-MVK (IIIa), when incubated with *Saccharopolyspora hirsute* subspecie *hirsuta* (Microbe no. 27875-ATCC), leading to the formation of γ-hydroxy-MeLeu[4] CsA-MVK (see Example 12). It is also possible to reverse the order of biocatalytic reactions by first modifying cyclosporin A, e.g., converting CsA to [γ-hydroxy-MeLeu[9]]CsA by incubation of CsA with *Streptomyces catenulae* (Microbe no. 23893-ATCC) (see Example 13). Then, upon isolation and purification by reversed phase semi-preparative (C8) chromatography, [γ-hydroxy-MeLeu[9]]CsA is subjected to HOBT-mediated laccase c oxidation to produce [γ-hydroxy-MeLeu[9]] CsA-MVK (see Example 14).

Scheme 4
Application of Iterative Biocatalysis to Cyclosporin A

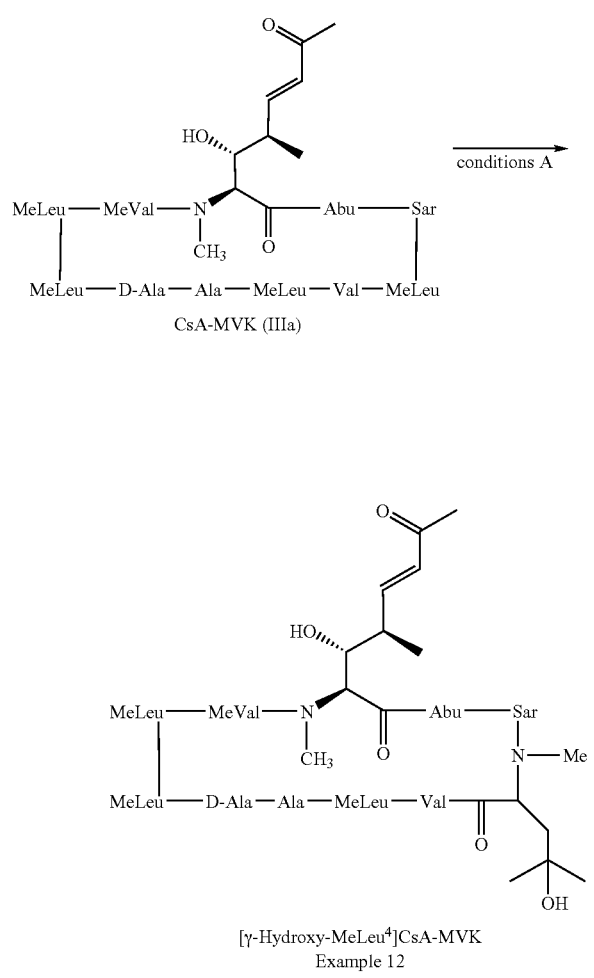

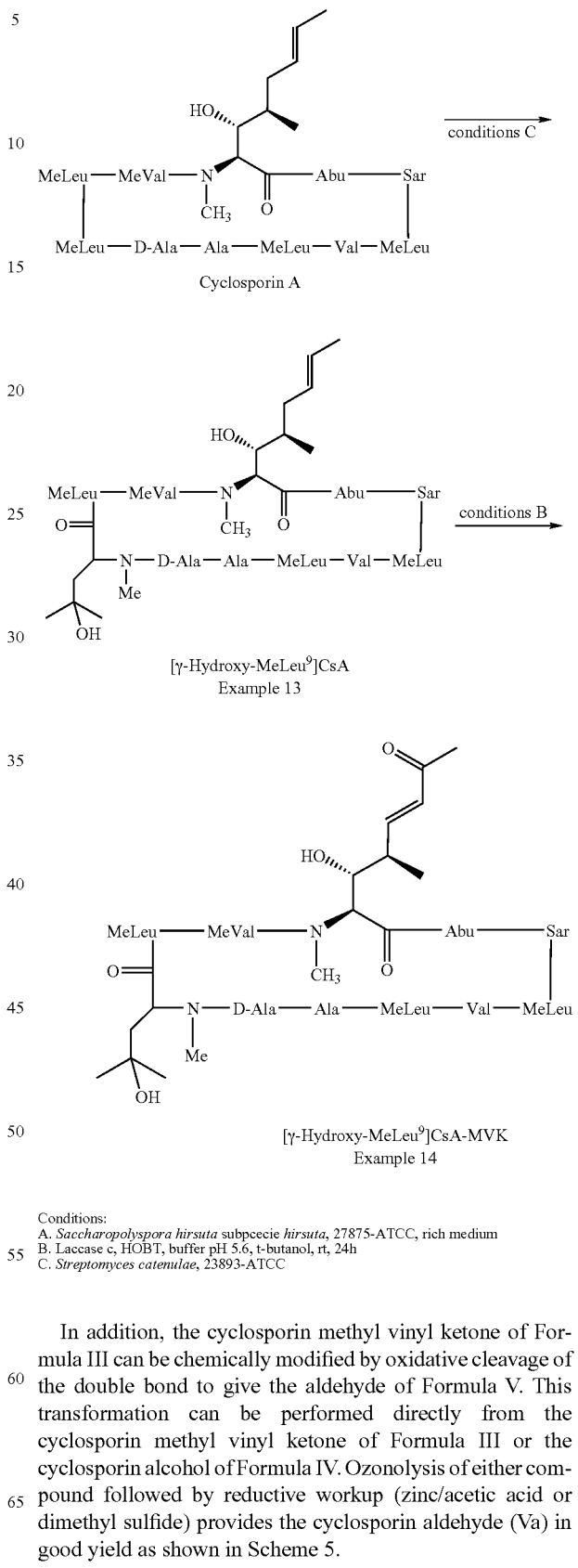

Conditions:
A. *Saccharopolyspora hirsuta* subpcecie *hirsuta*, 27875-ATCC, rich medium
B. Laccase c, HOBT, buffer pH 5.6, t-butanol, rt, 24h
C. *Streptomyces catenulae*, 23893-ATCC In addition, the cyclosporin methyl vinyl ketone of Formula III can be chemically modified by oxidative cleavage of the double bond to give the aldehyde of Formula V. This transformation can be performed directly from the cyclosporin methyl vinyl ketone of Formula III or the cyclosporin alcohol of Formula IV. Ozonolysis of either compound followed by reductive workup (zinc/acetic acid or dimethyl sulfide) provides the cyclosporin aldehyde (Va) in good yield as shown in Scheme 5.

Scheme 5
Oxidative Cleavage of Double Bond Leading to Cyclosporin Aldehyde

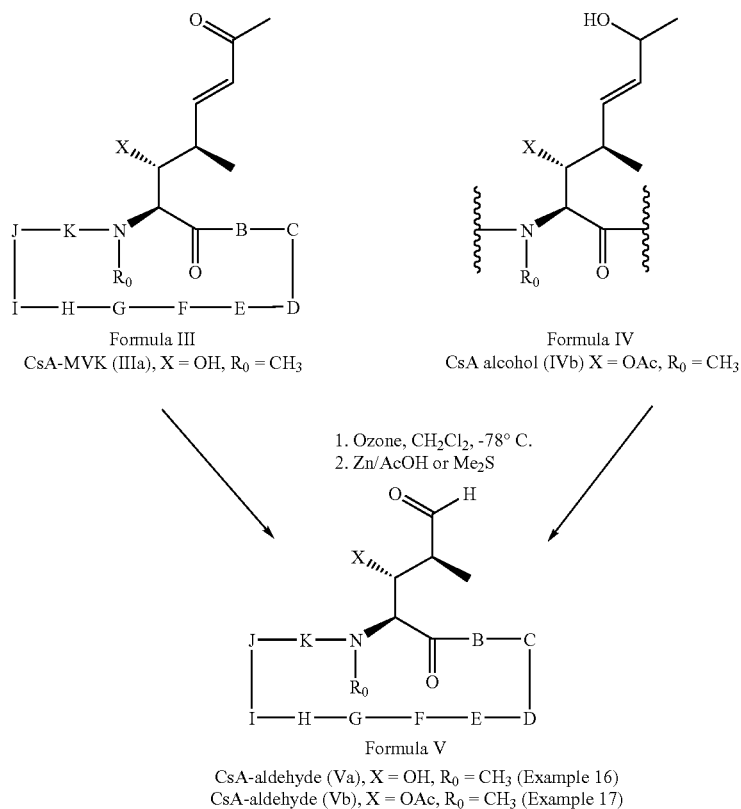

Formula III
CsA-MVK (IIIa), X = OH, R$_0$ = CH$_3$

Formula IV
CsA alcohol (IVb) X = OAc, R$_0$ = CH$_3$

1. Ozone, CH$_2$Cl$_2$, -78° C.
2. Zn/AcOH or Me$_2$S

Formula V
CsA-aldehyde (Va), X = OH, R$_0$ = CH$_3$ (Example 16)
CsA-aldehyde (Vb), X = OAc, R$_0$ = CH$_3$ (Example 17)

The cyclosporin aldehyde of Formula V provides another useful 15 synthetic intermediate from which to prepare novel cyclosporin derivatives of the present invention. Phosporous ylide chemistry, i.e., the Wittig reaction and Wittig-Homer-Emmons reaction, can be successfully performed on the cyclosporin aldehyde, as shown in Scheme 6. This chemistry converts the aldehyde to a substituted olefin of Formula VI, thus extending the carbon chain and introducing a variety of novel substituents attached to the olefin.

Scheme 6
Phosphorus Ylide Chemistry on Cyclosporin Aldehyde

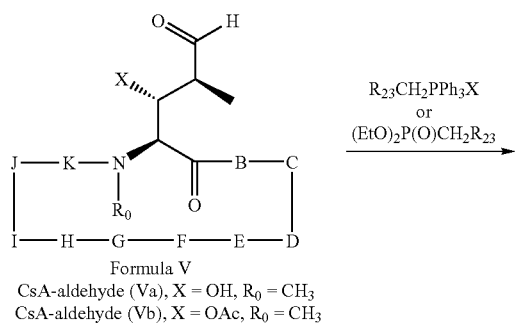

Formula V
CsA-aldehyde (Va), X = OH, R$_0$ = CH$_3$
CsA-aldehyde (Vb), X = OAc, R$_0$ = CH$_3$ R$_{23}$CH$_2$PPh$_3$X
or
(EtO)$_2$P(O)CH$_2$R$_{23}$ -continued

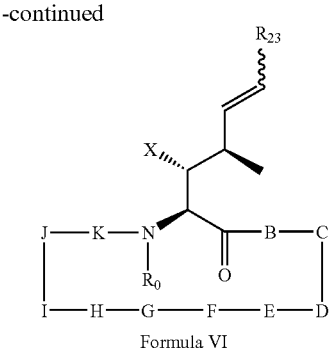

Formula VI

There is an abundance of phosphorous ylide precursors available commercially or readily prepared by following procedures found in the chemistry literature. Several representatives of this class of reagents that are utilized in the present invention are as follows:

Iodomethyltriphenyphosphonium iodide;
Methyltriphenylphosphonium bromide;
[3-(Dimethylamino)propyl]triphenylphosphonium bromide;
n-Propyltriphenylphosphonium bromide;
(3,3-Dimethylallyl)triphenylphosphonium bromide;

Methyl diethylphosphonoacetate;
Diethyl cyanomethylphosphonate;
Trans-2-butenyltriphenylphosphonium bromide, to name only a few. The above list is not intended to limit the scope of the present invention to the use of these reagents only.

The reactive ylide species in the Wittig or Wittig-Homer-Emmons reaction are typically generated by treatment of the above phosphonium salts or phosphonates with a strong base. Examples of bases that can be used in the present invention include sodium hydride or sodium bis(trimethylsilyl)amide. Typically, a large excess (5 to 15 equivalents) of the phosphorous ylide is used to react with compounds of Formula V. Reaction temperatures are often maintained between −78° C. and 0° C. The compounds of Formula VI isolated from this reaction may exist as cis and trans isomers of the alkene.

Examples of compounds of Formula VI include the following compound:

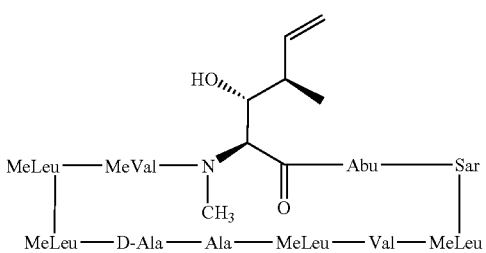

as well as other compounds where the position one amino acids are of the following formulas:

Example 19

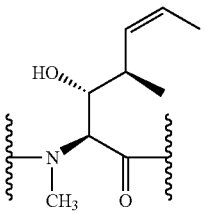

Example 20

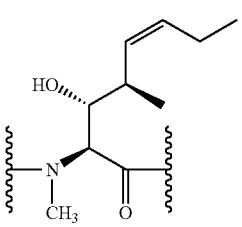

Example 21

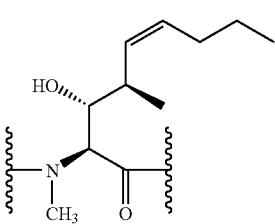

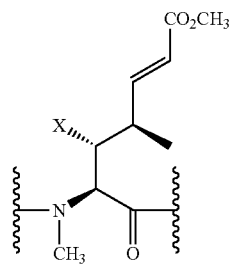

Example 22 (X = OAc)
Example 23 (X = OH)

Example 24

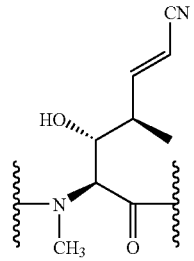

Example 25

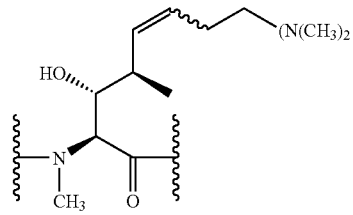

Example 26

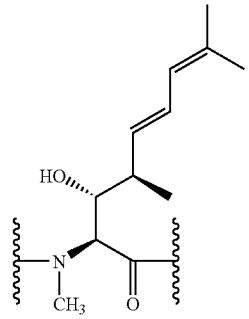

Example 27

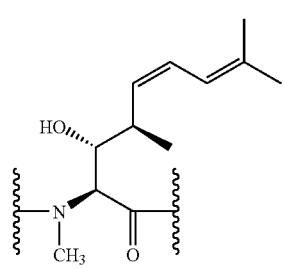

Example 28

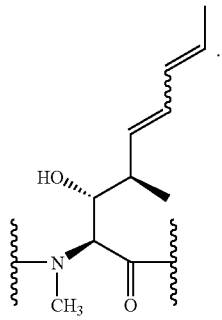

Scheme 8

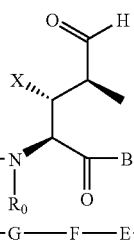

Formula V
CsA aldehyde (Va), X = OH, $R_0$ = CH$_3$

NaBH$_4$
MeOH
→

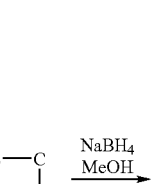

CsA diol (Example 30)

acid chloride
or acid anhydride
pyridine

Another aspect of the present invention relates to the transformation of cyclosporin aldehyde of Formula V into the corresponding carboxylic acid and its derivatives, such as carboxylic esters and amides. Treatment of cyclosporin aldehyde (Va) with tert-butyl hypochlorite, followed by addition of methanol and pyridine produces the cylosporin ester (Scheme 7).

Scheme 7

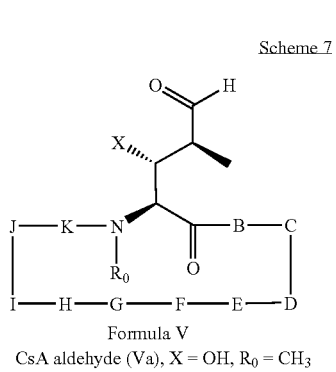

Formula V
CsA aldehyde (Va), X = OH, $R_0$ = CH$_3$ 1. t-BuOCl
   CCl$_4$
2. MeOH
   pyridine
→

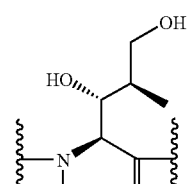

Formula VII
CsA monoester

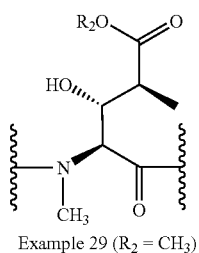

Example 29 ($R_2$ = CH$_3$)

Reduction of cyclosporine aldyhyde (Va) with sodium borohydride provides cyclosporine diol in quantative yield (Scheme 8). Further chemical modification of the diol can be performed by selective esterfication on the primary alcohol with various acid chlorides or acid anhydrides in the presence of pyridine to afford mono-esters of Formula VII.

Examples of compounds of Formula VII include the following compounds:

Example 31

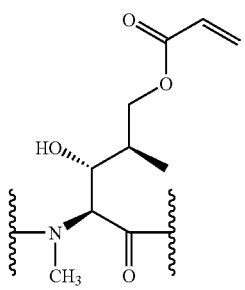

-continued

Example 32

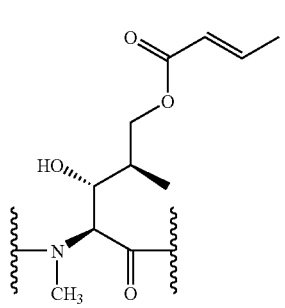

Example 33

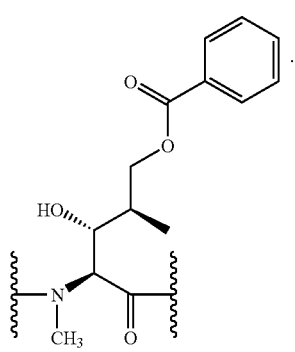

Another aspect of the present invention relates to the preparation of cyclosporine amines and amine derivatives from cyclosporine aldehyde (Va). Reductive amination of CsA aldehyde (Va) with ammonium acetate and sodium cyanoborohydride in the presence of acetic acid in methanol generates cyclosporine amine ($R_9$=H), while treatment of aldehyde (Va) with methylamine followed by reduction with sodium borohydride produces cyclosporine methylamine ($R_9$=$CH_3$), as shown in Scheme 9. Further modifications of cyclosporin amine or cyclosporine methylamine include alkylation or acylation to generate amine derivatives of Formula VIII. The alkylation can be accomplished by reacting the cyclosporin amine or cyclosporine methylamine in the presence of an alkyl halide such as alkyl bromide, alkyl chloride, or alkyl iodide. Alternatively, the acylation can be accomplished by reacting the cyclosporin amine or cyclosporine methylamine in the presence of an acid anhydride or acid chloride, or in the presence of a sulfonic acid anhydride or sulfonyl chloride.

Scheme 9

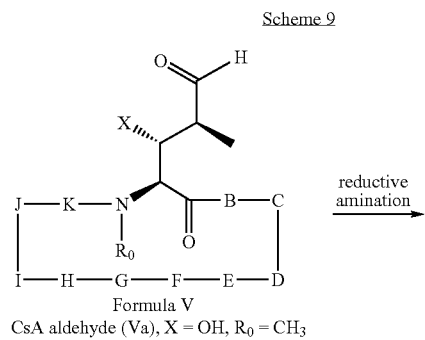

Formula V
CsA aldehyde (Va), X = OH, $R_0$ = $CH_3$

-continued

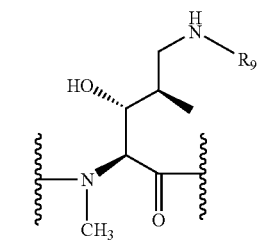

Example 34 ($R_9$ = H)
Example 35 ($R_9$ = $CH_3$)

alkylation
or
acylation

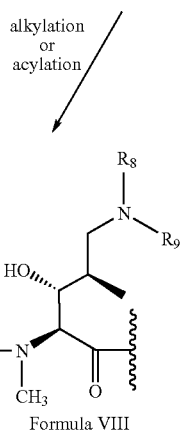

Formula VIII

Examples of compounds of Formula VIII include the following compounds:

Example 36

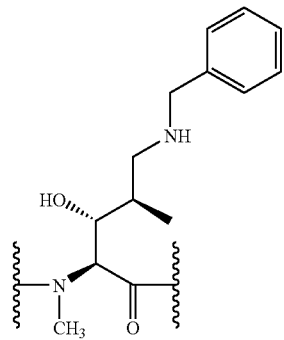

Example 37

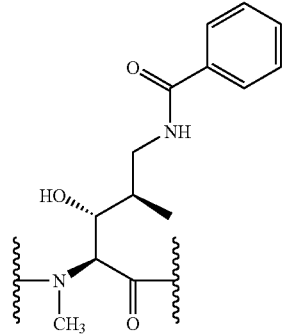

-continued

Example 38

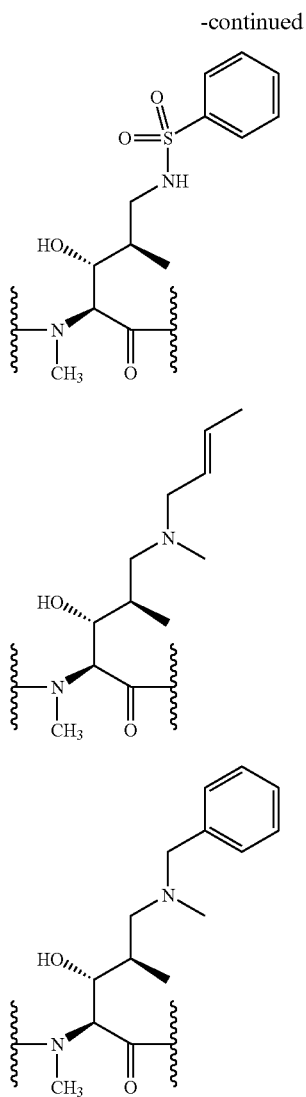

Example 39

Example 40

-continued

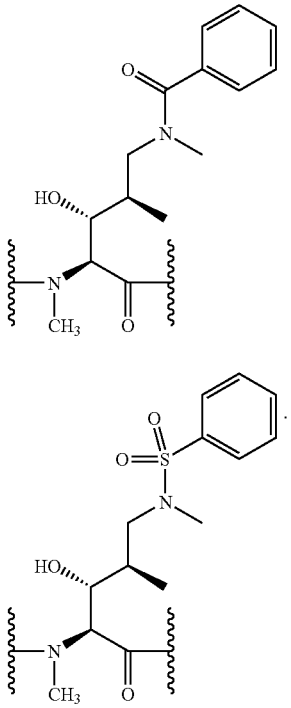

Example 41

Example 42

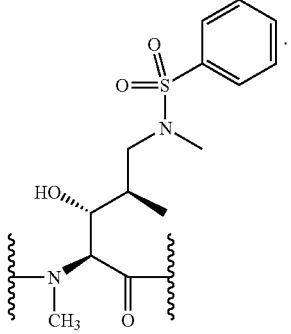

Another aspect of the present invention relates to the preparation of novel cyclosporine vinyl halides via Wittig reaction or Takai reaction (Scheme 10). Wittig reaction of CsA aldehyde (Va) with phosphorous ylide that can be generated from iodomethyltriphenylphosphonium iodide and sodium bis(trimethylsilyl)amide affords cis-isomer of cyclosporine vinyl iodide. The trans-isomer of cyclosporine vinyl iodide can be prepared by treatment of the aldehyde (Va) with iodoform in the presence of chromium(II) chloride. Other cyclosporine vinyl halides, such as vinyl bromide and vinyl chloride, can be also prepared using the methods outlined in Scheme 10.

Scheme 10

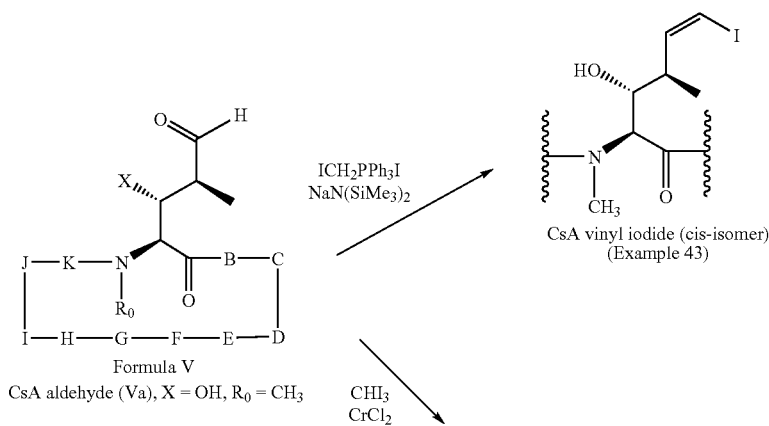

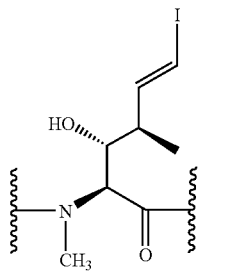

CsA vinyl iodide (trans-isomer)
(Example 44)

Further chemical modification on cyclosporine vinyl iodide includes palladium mediated coupling with organotin or organozinc reagents to provide novel cyclosporine olefin of Formula VI, as shown in Scheme 11.

Scheme 11

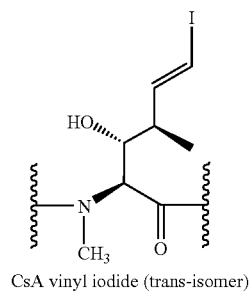

CsA vinyl iodide (trans-isomer)

organotin reagents
or
organozinc reagents
Pd(PPh$_3$)$_4$
or
Pd(PPh$_3$)$_2$Cl$_2$

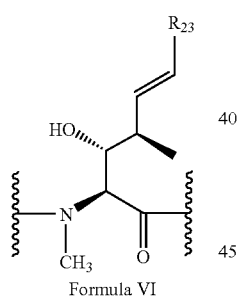

Formula VI

Examples of compounds of Formula VI include the following compounds:

Example 45

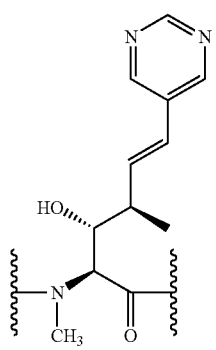

Example 46

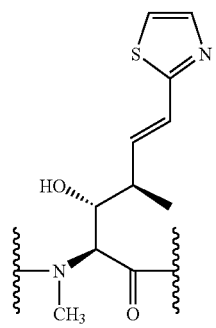

Example 47

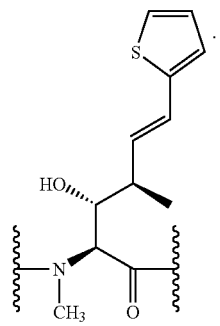

Another aspect of the present invention relates to the preparation of the novel cyclosporine diol of Formula IX by treatment of cyclosporine aldehyde of Formula V with various Grignard reagents at −78° C. or organozinc reagents at 0° C. (Scheme 12). Many organozinc reagents are commercially available or can be generated from the corresponding Grignard reagents and zinc chloride.

Scheme 12

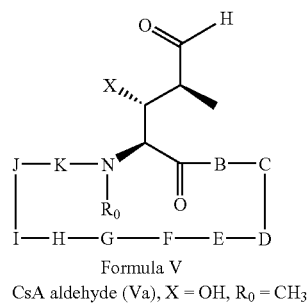
Formula V
CsA aldehyde (Va), X = OH, R₀ = CH₃

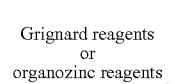
Grignard reagents or organozinc reagents

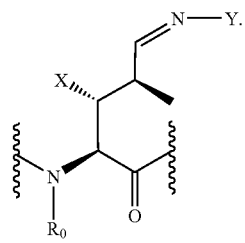

The present invention also discloses compounds prepared from cyclosporin A aldehyde (Va), where the position one amino acid is an amino acid of the following formula:

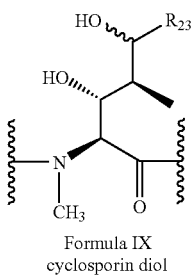
Formula IX
cyclosporin diol

Examples of compounds of Formula IX include the following compounds:

Other examples of compounds prepared from cyclosporin A aldehyde (Va) include the following compounds:

Example 48
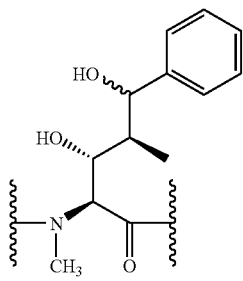

Example 50
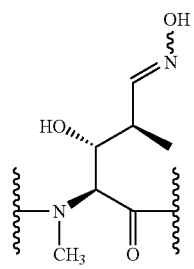

Example 49
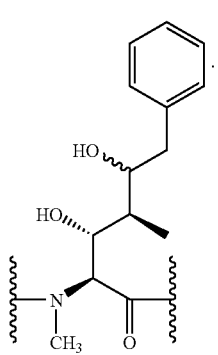

Example 51
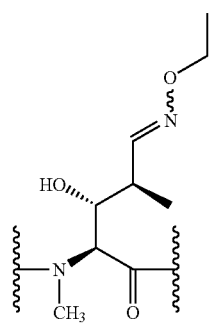

Example 52
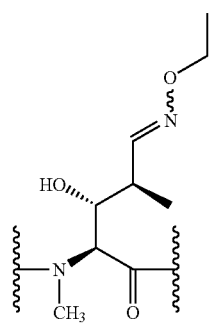

Example 53

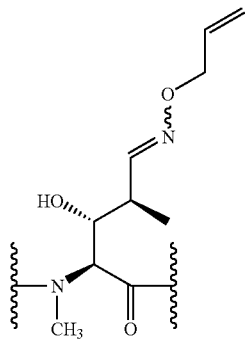

Example 54

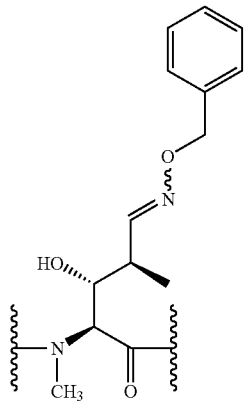

Example 55

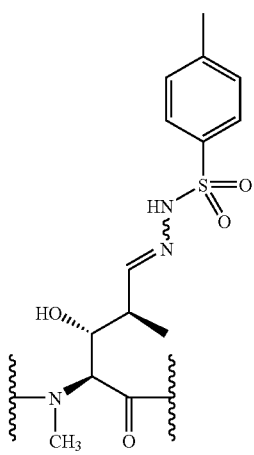

Another aspect of the present invention relates to the preparation of novel cyclosporine diene analogues of Formula X. Dehydration of cyclosporine alcohol of Formula IV with Burgess reagent at 60-80° C. in benzene affords cyclosporine diene (X=OAc), as shown in Scheme 13. The acetyl protecting group can be removed by treatment with potassium carbonate in methanol to give cyclosporine diene (X=OH). Olefin metathesis of cyclosporine diene with various olefin species in the presence of Grubbs' catalyst provides substituted diene of Formula X smoothly. It is interesting that olefin metathesis only occurs on outside carbon-carbon double bond moiety, while the inside carbon-carbon double bond remains unchanged.

Scheme 13

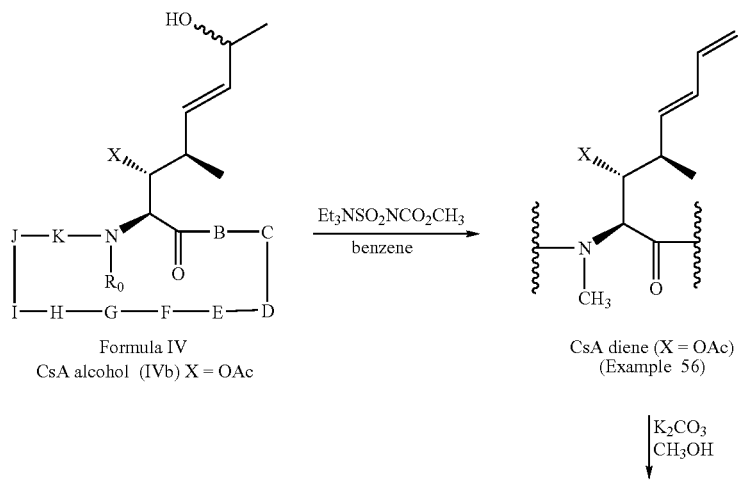

-continued
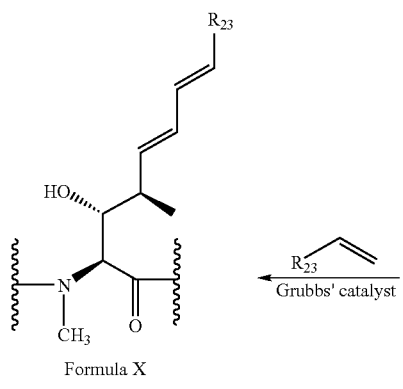 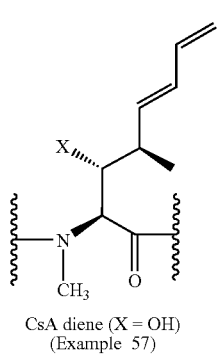
Formula X   CsA diene (X = OH) (Example 57)
Examples of compounds of Formula X include the following compounds:
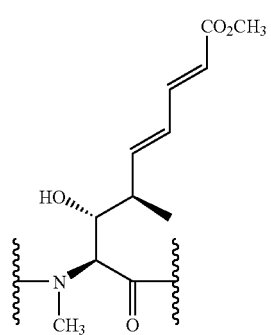
Example 58
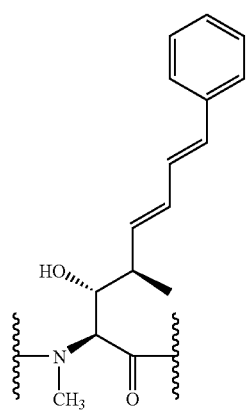
Example 59
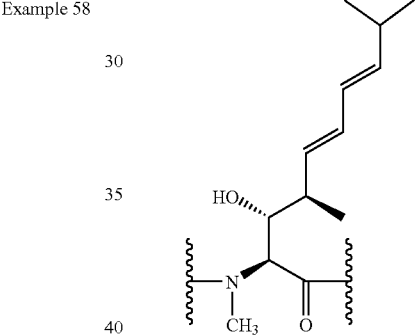
Example 60
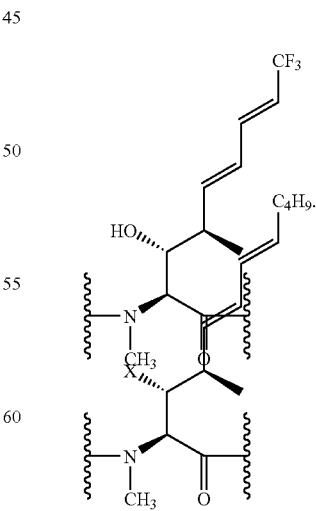
Example 61
Example 62 (X = OAc)
Example 63 (X = OH)

Another aspect of the present invention relates to the preparation of novel cyclosporine methyl ketones of Formula XI. Conversion of cyclosporine methyl vinyl ketone of Formula III to cyclosporine methyl ketone of Formula X can be conducted under hydrogenation with palladium on carbon, as shown in Scheme 14.

Scheme 14

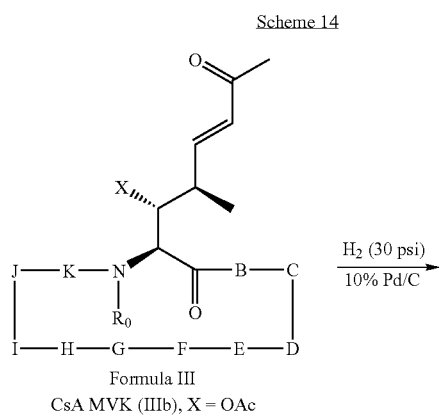

Formula III
CsA MVK (IIIb), X = OAc

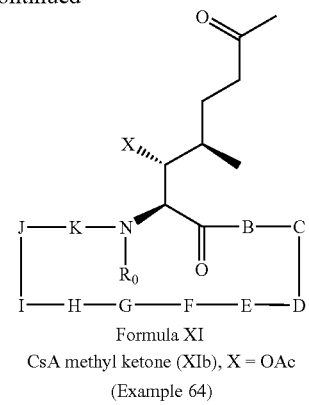

Formula XI
CsA methyl ketone (XIb), X = OAc
(Example 64)

The cyclosporine methyl ketone of Formula XI is another useful synthetic intermediate which can be converted to novel cyclosporine analogues of the present invention. Wittig reaction of cyclosporine methyl ketone of Formula XI with various phosphorous ylide species provides novel olefin of Formula XII (Scheme 15). Cyclosporine olefin of Formula XII can be prepared via an alternative synthetic passway, as shown in Scheme 15. Treatment of cyclosporine methyl ketone of Formula XI with Grignard reagents or organozinc reagents affords novel alcohol of Formula XIII smoothly. Dehydration of alcohol of Formula XIII with Burgess reagent generates cyclosporine olefin of Formula XII.

Scheme 15

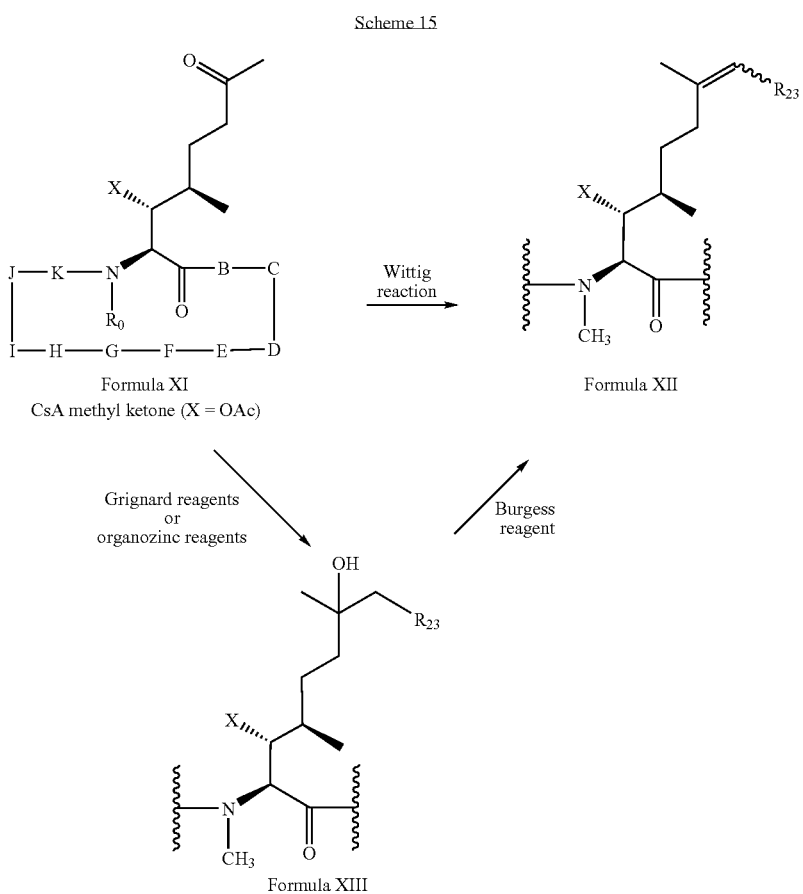

Examples of compounds of Formula XIII include the following compounds:

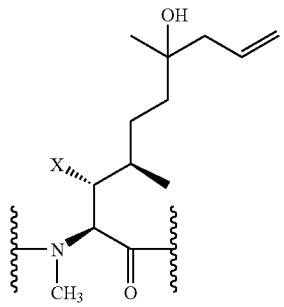

X = OH (Example 65)

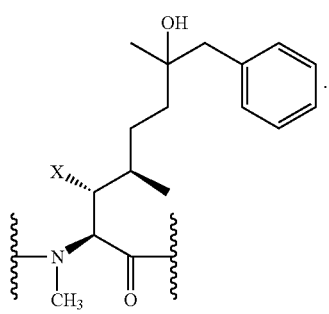

X = OAc (Example 66)

Examples of compounds of Formula XII include the following compounds:

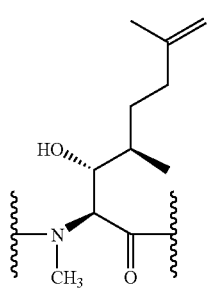

Example 67

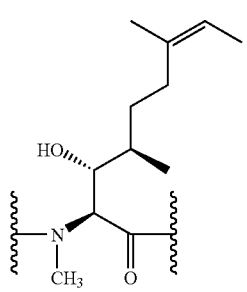

Example 68

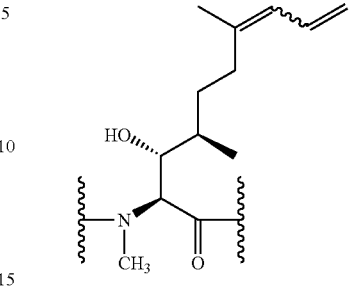

Example 69

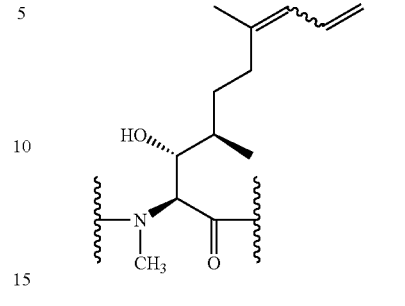

Example 70

The present invention also discloses compounds prepared from cyclosporin A methyl ketone of Formula X, where the position one amino acid is an amino acid of the following formula:

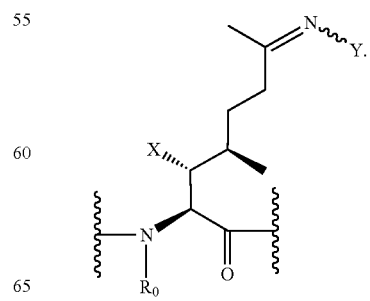

Other examples of compounds prepared from cyclosporin A methyl ketone of Formula X include the following compounds:

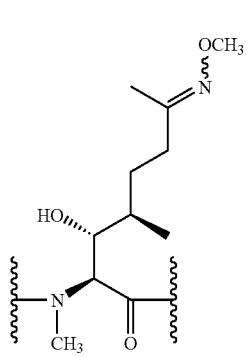

Example 71

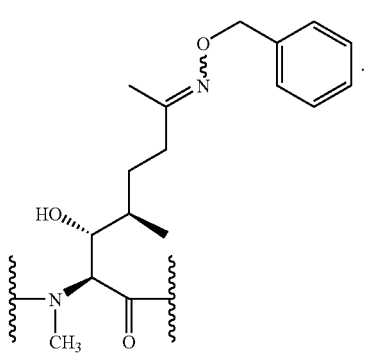

Example 73

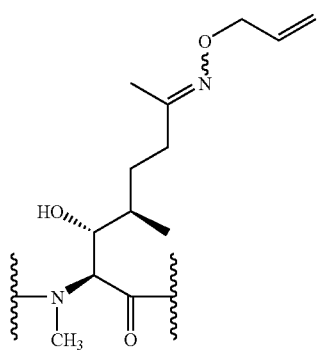

Example 72

Another aspect of the present invention relates to the alternative method of preparing the novel cyclosporin olefins of Formula VI from cyclosporine aldehyde of Formula XIV. Transformation of cyclosporin A (X=OAc) into cyclosporine aldehyde of Formula XIV (X=OAc) can be performed under standard ozonation conditions. Treatment of aldehyde of Formula XIV with Grignard reagents at −78° C. or organozinc reagents at 0° C. provides alcohol of Formula XV in good yield. Organozinc reagents used in this reaction can be either commercially available or generated from the corresponding Grignard reagent and zinc chloride. Dehydration of alcohol of Formula XV with Burgess reagent in benzene affords olefin of Formula VI smoothly (Scheme 16).

Scheme 16

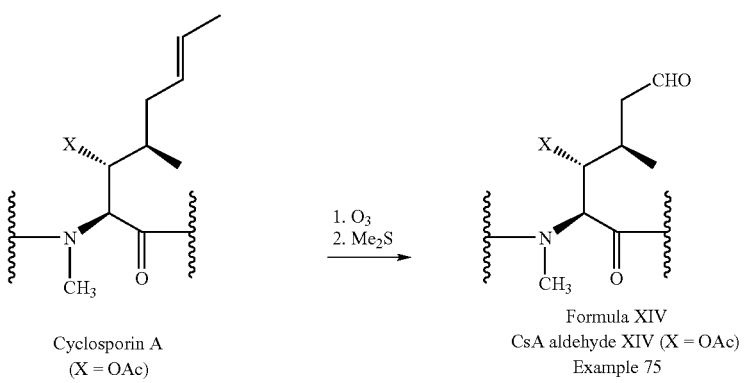

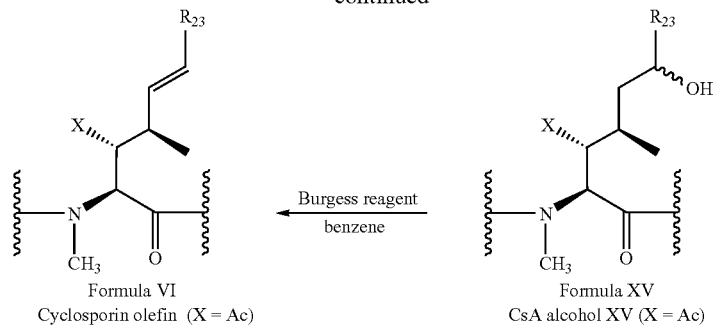
Examples of compounds of Formula XV include the following compounds:
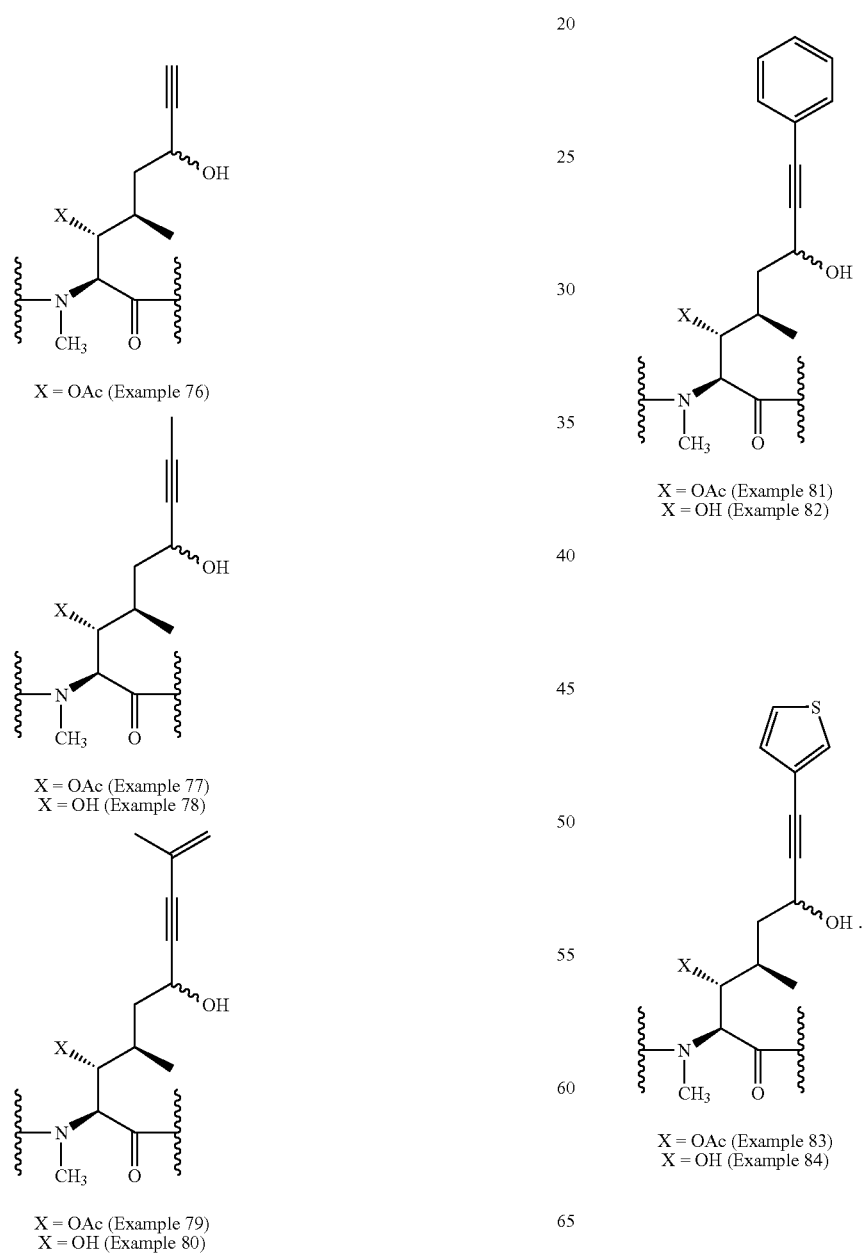

Examples of compounds of Formula VI include the following compounds:
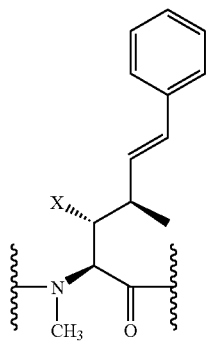
X = OAc (Example 85)
X = OH (Example 86)
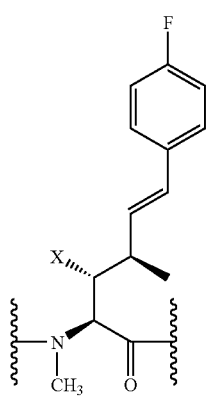
X = OAc (Example 87)
X = OH (Example 88)
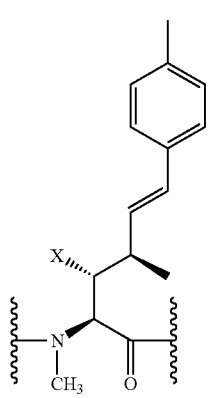
X = OAc (Example 89)
X = OH (Example 90)
-continued
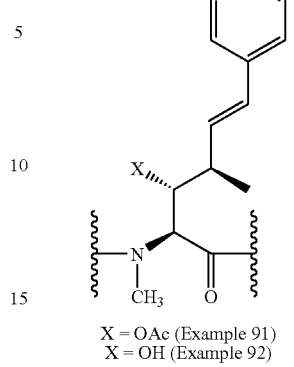
X = OAc (Example 91)
X = OH (Example 92)
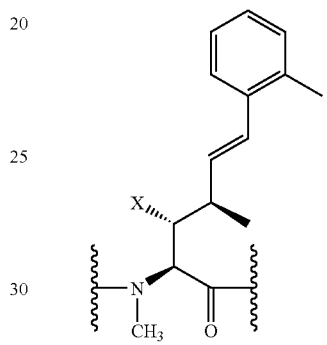
X = OAc (Example 93)
X = OH (Example 94)
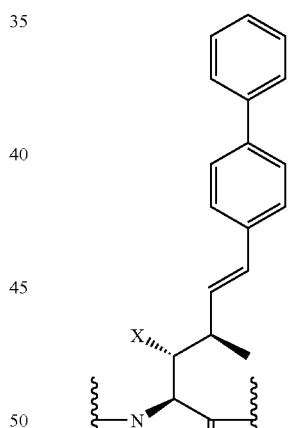
X = OAc (Example 95)
X = OH (Example 96)
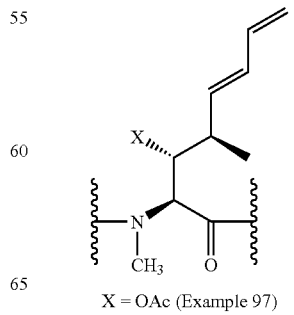
X = OAc (Example 97)

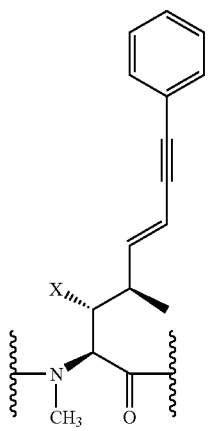

X = OAc (Example 98)
X = OH (Example 99)

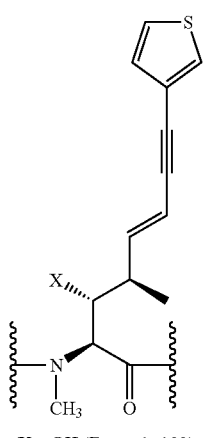

X = OH (Example 100)

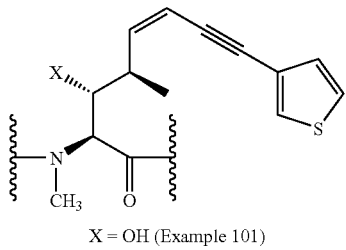

X = OH (Example 101)

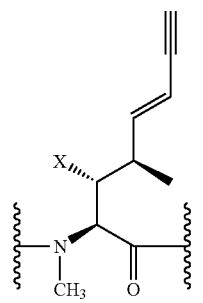

X = OAc (Example 102)
X = OH (Example 103)

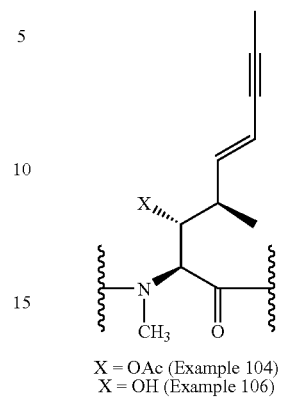

X = OAc (Example 104)
X = OH (Example 106)

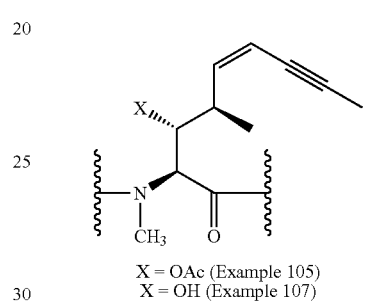

X = OAc (Example 105)
X = OH (Example 107)

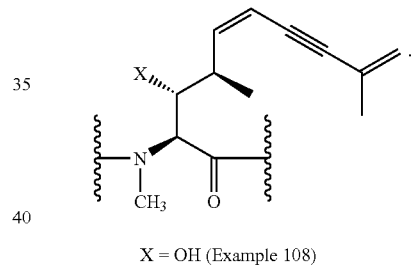

X = OH (Example 108)

The carbon-carbon double bond in novel cyclosporine olefin of Formula VI can be reduced by hydronation with palladium on carbon to afford novel closporine analogues of Formula XVI, as shown in Scheme 17.

Scheme 17

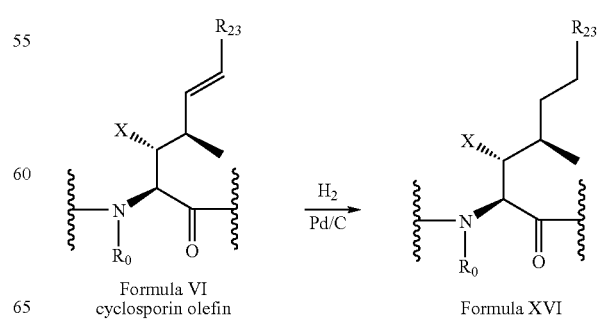

Formula VI
cyclosporin olefin

Formula XVI

Examples of compounds of Formula XVI include the following compounds:

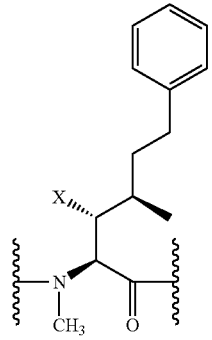

X = OH (Example 109)

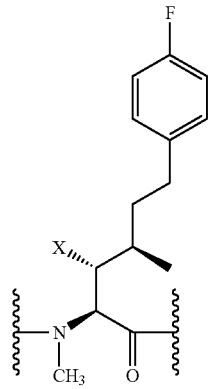

X = OH (Example 110)

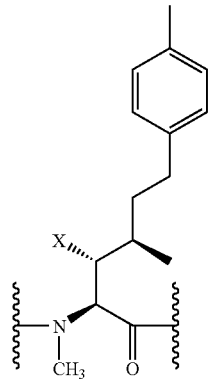

X = OH (Example 111)

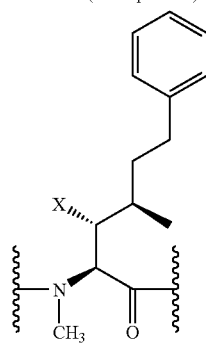

X = OH (Example 112)

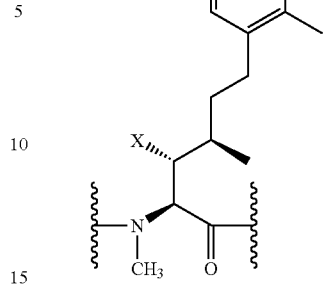

X = OH (Example 113)

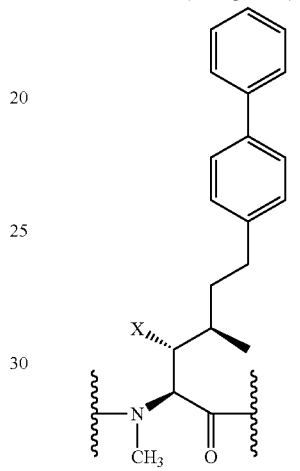

X = OH (Example 114)

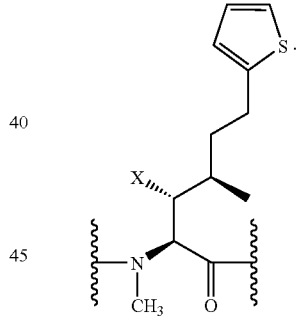

X = OH (Example 115)

EXAMPLES

The following examples are provided to illustrate embodiments of the present invention but are by no means intended to limit its scope.

Example 1

Materials and Methods (for Examples 3-14)

Reagents were purchased from commercial sources and used as received. Solvents for reactions and isolations were of reagent or spectrophotometric grade and used without further treatment. Anhydrous tert-butyl methyl ether was maintained dry over molecular sieves, previously activated at 105° C. for at least 12 h. Solvents were removed under vacuum with either a Buchi Rotavapor R-114 with Waterbath B-480, GeneVac HT-12 Atlas Evaporator with Vapour Condenser VC3000D and CVP 100 pump, or a Savant SpeedVac® Plus SC210A with VaporTrap RVT4104. $^1$H and $^{13}$C-NMR spectra were collected in CDCl$_3$, on a Bruker WM-360 spectrometer, with signals reported in ppm and internally referenced to TMS (δ 0.0), or CDCl$_3$ (δ 77.23). Centrifugation was accomplished using either a Beckman J2-MC Centrifuge, Fisher Scientific Marathon 26KM Centrifuge or Eppendorf Centrifuge 5810. Microbial cultures were shaken on a New Brunswick Innova 5000 rotary shaker inside a thermostatically controlled room maintained at 29° C. Aseptic transfer and inoculation techniques were performed inside a Nuaire NU-425-400 biological safety cabinet. Semi-preparative reversed-phase HPLC purifications were performed on a Gilson system with model 306 pumps, model 215 liquid handler, and a Perkin-Elmer LC Oven 101 column heater, employing a Zorbax StableBond Rx-C8 column, 21.2×250 mm, 7 μm packing. Analytical HPLC was performed on a Shimadzu system with SCL-10A system controller, SPD-M10A diode array detector, SIL-10AD auto injector, LC-10AT liquid chromatograph, DGU-14A degasser, and CTO-10A column oven, employing a Zorbax StableBond Rx-C8 column, 4.6× 150 mm, 3 μm packing. LC/MS analysis was performed using a Perkin-Elmer SciEx API 2000 LC/MS/MS system with a Perkin Elmer Series 2000 Micropump and Zorbax StableBond Rx-C8 columns, 4.6×50 mm, 3 μm packing, at 70° C.

Example 2

Culture Growth and Maintenance

Cultures were maintained on agar slants stored at 4° C. or as suspensions in 10% glycerol at −85° C. Mycelium and/or spores from slants were used to inoculate 125 mL DeLong flasks containing 12.5 mL soybean flour-glucose growth medium. Stage I cultures were shaken at 250 rpm for 48-72 h. A 10% inoculum was transferred from Stage I culture to 125 mL DeLong flasks containing 12.5 mL soybean flour-glucose medium to start Stage II cultures. Stage II cultures were grown at 250 rpm for 24 hours before being dosed with cyclosporin-type molecules. Cultures from cryo-preserved vials were initiated by aseptically transferring the contents of one vial (appropriately warmed to room temperature beforehand) to a 125 mL DeLong flask to start Stage II cultures. The growth medium was prepared in two parts. Part A consisted of soybean flour (1%), yeast extract (1%), NaCl (1%) and K$_2$HPO$_4$ (1%) in deionized water. The pH was adjusted to 7 with 50% HCl. Part B consisted of a 4% glucose solution in deionized water. Parts A and B were autoclaved separately at 121° C. and 15 psi for 20 min, mixed together under a sterile environment and allowed to cool to room temperature prior to use.

Example 3

Preparation of Cyclosporin A Methyl Vinyl Ketone (IIIa) by a Biocatalytic Method Cyclosporin A (1.0 g) and 1-hydroxybenzo-triazole (500 mg) were dissolved in 70 mL tert-butanol in a 500 mL reaction vessel equipped with a stir bar. Sodium citrate/sodium phosphate buffer (80 mM, 250 mL, pH 5.6) was added while stirring, resulting in a thick white suspension. Laccase C (1.8 g, ASA Spezialenzyme) was added as a solution in 35.5 mL of the same buffer, turning the reaction mixture slightly yellow in appearance. The reaction was mechanically stirred enough to create a vortex, open to ambient atmosphere and room temperature for a period of 20 h, after which time the reaction mixture had become orange in appearance. After removing a portion of the tert-butanol via rotavapor, the orange reaction mixture was loaded onto a pre-conditioned VARIAN BondElut® C8 solid-phase extraction cartridge (60 cc, 10 g of sorbent). After a wash with water, the cyclosporin-related products were eluted using acetonitrile. The acetonitrile eluate was concentrated in vacuo, transferred to a tared scintillation vial and dried in vacuo inside a Savant dryer to provide 913.0 mg of crude product as tan solids. The solids were re-dissolved in a minimal volume of acetonitrile and purified over the course of two injections by reversed-phase semi-prep chromatography under the following conditions: column: Zorbax StableBond Rx C8, 250×21.2 mm, 7 μm packing, flow rate 20 mL/min, column temperature 70° C., wavelength 210 nm, mobile phase A=water, B=acetonitrile, gradient profile: 0-2 min: 60% B, 2-15 min: 60-70% B; 15-30 min: 70-80% B; 30-31 min: 80-100% B; 31-34 min: 100% B; 34-35 min: 100-60% B. Product-containing fractions were dried down separately in the GeneVac dryer, then pooled together to provide 551.3 mg of CsA-MVK: $^1$H-NMR (CDCl$_3$, 300 MHz): δ 8.03 (1H, d, J=9.9 Hz), 7.79 (1H, d, J=7.8 Hz), 7.44 (1H, d, J=8.0 Hz), 7.13 (1H, d, J=8.0 Hz), 6.89 (1H, dd, J=16.1, 7.6 Hz), 6.06 (1H, d, J=16.1 Hz), 5.71 (1H, dd, J=11.0, 3.8 Hz), 5.65 (1H, bs), 5.22 (1H, dd, J=11.5, 3.8 Hz), 5.10 (2H, d, J=11.0 Hz), 5.05 (1H, dd, J=15.7, 9.1 Hz), 4.96 (1H, dd, J=10.1, 5.7 Hz), 4.85 (1H, q, J=7.2 Hz), 4.73 (1H, d, J=14.1 Hz), 4.65 (1H, q, J=8.7 Hz), 4.55 (1H, q, J=7.4 Hz), 4.04 (2H, bs), 3.52 (3H, s), 3.39 (3H, s), 3.31 (3H, s), 3.20 (1H, d, J=13.9 Hz), 3.12 (3H, s), 3.11 (3H, s), 2.72 (3H, s), 2.68 (3H, s), 2.54-2.34 (3H, m), 2.26 (3H, s), 2.20-1.76 (11H, m), 1.75-1.35 (6H, m), 1.32 (3H, d, J=7.3 Hz), 1.26 (3H, d, J=7.3 Hz), 1.10-0.81 (39H, m); $^{13}$C-NMR (CDCl$_3$, 90 MHz): δ 198.6, 174.7, 174.1 (2C), 173.8, 171.7, 171.6, 171.3, 170.6, 170.5, 170.3, 170.2, 148.9, 131.8, 74.9, 59.6, 58.2, 57.8, 55.7 (2C), 55.2, 50.6, 48.9, 48.6, 48.3, 45.3, 40.7, 39.7, 39.5, 39.2, 38.0, 36.2, 35.0, 31.7, 31.6, 31.3, 30.1 (2C), 29.8, 29.6, 27.5, 25.3, 25.1, 24.9 (2C), 24.6, 24.0 (4C), 23.8, 23.6, 22.0 (2C), 21.3, 20.8, 20.0, 18.8 (2C), 18.6, 18.4, 16.1.

Example 4

Preparation of Cyclosporin A Methyl Vinyl Ketone (IIIa) by a Chemical Method Using N-Hydroxypthalimide and Benzoyl Peroxide A solution of N-hydroxypthalimide (68 mg, 0.41 mmoles) and CsA (500 mg, 0.41 mmoles) in isobutyl methyl ketone (5.0 mL) was heated at 54° C. The solution was treated with dibenzoyl peroxide (75% in water) (80 mg, 0.27 mmoles) and subsequently; air was bubbled through the reaction mixture while stirring vigorously for 15 h. When consumption of CsA was complete as determined by TLC (3% methanol in chloroform), the reaction was concentrated to an oily residue. The latter was diluted with carbon tetrachloride and the reaction mixture was stirred for 1 h at 40° C. The excess N-hydroxypthalimide was filtered and the filtrate was concentrated to dryness under reduced pressure. The resulting oily residue was purified by column chromatography eluting with 2% methanol in chloroform. The main fraction was concentrated to give 380 mg of a white solid. $^1$H NMR and MS indicated the presence of a new product that was probably the cyclosporin A methyl vinyl ketone-N-hydroxyphthalimide adduct. A small amount of this product (100 mg) was subjected once again to the same protocol. A new spot was observed by TLC, which upon purification by column chromatography (2% methanol in chloroform on silica gel) gave the product CsA-MVK (25 mg) that matched by in all respects the CsA-MVK isolated from the biocatalysis method.

Example 5

Preparation of Cyclosporin A Methyl Vinyl Ketone(IIIa) by a Chemical Method Using tert-Butyl Hydroperoxide and Sodium Periodate To a mixture of CsA (400 mg, 0.33 mmoles) in isobutyl methyl ketone (5.0 mL) was added tert-butyl hydroperoxide (70% aqueous solution, 2.5 mL). Upon addition of sodium periodate (425 mg, 1.99 mmoles) at room temperature, the resulting mixture was stirred vigourously at 50° C. for 72 h. The mixture was diluted with dichloromethane (10 mL) and the organic layer was separated, washed thoroughly with water and then stirred with an aqueous sodium sulfite solution (15% aqueous solution, 30 mL) for 2 h. The organic layer was separated, dried over sodium sulfate and concentrated to dryness. The resulting residue was purified on silica gel eluting with 10% methanol in dichloromethane. The product isolated (370 mg) showed 70% of desired product as determined by $^1$HNMR along with unreacted cyclosporin A.

Example 6

Preparation of Cyclosporin A Methyl Vinyl Ketone (IIIa) by a Chemical Method Using tert-Butyl Hydroperoxide and Sodium Periodate (Optimized Method)

Cyclosporin A (5 g, 4.2 mmol) was dissolved in acetone (25 mL), benzene (25 mL), H$_2$O (37.5 mL). tert-Butyl hydroperoxide (31.25 mL of 70% aqueous solution, 258 mmol), potassium periodate (6.5 g, 28.3 mmol), and 18-crown-6 ether (4.38 g, 16.5 mmol) were added to the reaction mixture at room temperature. The resulting mixture was stirred vigorously at room temperature under N$_2$ atmosphere for 3 h. Organic solvents were removed from the reaction mixture in vacuo. The remaining mixture was poured into ice water (1 L) and extracted twice with a mixture of EtOAc/hexanes (200 mL, 1:1). The combined extracts were stirred in a 10% sodium sulfite solution for 2 h. The organic layer was separated, dried over Na$_2$SO$_4$, and concentrated to recover crude product (3.5-4 g, 70-80%). The crude product was purified by either preparative or semi-preparative HPLC, using acetonitrile (containing 0.05% TFA)/water (containing 0.05% TFA) solvent system.

Example 7

Preparation of Cyclosporin C Methyl Vinyl Ketone

Cyclosporin C (100 mg, 0.08 mmol) was dissolved in benzene (0.5 mL), acetone (0.5 mL), and water (0.8 mL). Mixture was then treated with KIO$_4$ (140 mg, 0.57 mmol), 18-crown-6 (90 mg, 0.32 mmol), and tert-butyl hydroperoxide (70% in water, 0.7 mL). Reaction was kept stirring for 4 d under N$_2$ atmosphere at room temp. Organic solvent was removed from the reaction mixture in vacuo. The remaining mixture was poured into ice water (50 mL) and extracted twice with a mixture of ethyl acetate and hexane (10 mL, 1:1). Combined extracts were stirred in a sodium sulfite solution (10% in water) for 2 h. Organic layer was separated, washed with brine, dried over sodium sulfate, and concentrated in vacuo. The crude product was purified by semi-preparative HPLC to afford CsC methyl vinyl ketone (21 mg, 21%) as a white solid: $^1$H NMR (300 MHz, CDCl$_3$) δ 8.29 (d, J=10.1 Hz, 1H), 7.79 (d, J=7.2 Hz, 1H), 7.75-7.62 (m, 4H), 7.58-7.33 (m, 5H), 7.28 (d, hidden by solvent peak, 1H), 7.03 (d, J=8.6 Hz, 1H), 6.87 (q, J=9.3 Hz, 2H), 6.15 (s, 1H), 6.10 (s, 1H), 5.70 (d, J=7.2 Hz, 6H), 5.28-5.06 (m, 9H), 4.98-4.71 (m, 10H), 4.33 (s, 1H), 4.19-4.02 (m, 10 H), 3.51 (s, 3H), 3.40 (s, 3H), 3.27 (s, 3H), 3.15 (s, 3H), 3.05 (s, 3H), 2.72 (s, 3H), 2.68 (s, 3H), 2.20 (s, 2H), 1.53-1.34 (m, 10 H), 1.25 (s, 3H), 1.09 (d, J=6.3 Hz, 2H), 1.04-0.77 (m, 18H); ESI MS m/z 1233 [C$_{62}$H$_{109}$N$_{11}$O$_{14}$+H]$^+$; HPLC 96.5% (AUC), t$_R$=12.76 min.

Example 8

Preparation of Cyclosporin D Methyl Vinyl Ketone

Cyclosporin D (200 mg, 0.16 mmol) was dissolved in benzene (1 mL), acetone (1 mL), and water (1.6 mL). Mixture was then treated with KIO$_4$ (280 mg, 1.15 mmol), 18-crown-6 (180 mg, 0.66 mmol), and tert-butyl hydroperoxide (70% in water, 1.4 mL). Reaction was kept stirring for 2 d under N$_2$ atmosphere at room temp. Organic solvent was removed from the reaction mixture in vacuo. The remaining mixture was poured into ice water (100 mL) and extracted twice with a mixture of ethyl acetate and hexane (20 mL, 1:1). Combined extracts were stirred in a sodium sulfite solution (10% in water) for 2 h. Organic layer was separated, washed with brine, dried over sodium sulfate, and concentrated in vacuo. The crude product was purified by semi-preparative HPLC to afford CsD methyl vinyl ketone (12 mg, 6%) as a white solid: $^1$H NMR (300 MHz, CDCl$_3$) δ 8.09 (d, J=9.9 Hz, 1H), 7.84 (d, J=7.7 Hz, 1H), 7.54 (d, J=7.9 Hz, 1H), 7.10 (d, J=8.0 Hz, 1H), 6.92 (d, J=7.4 Hz, 1H), 6.87 (d, J=7.4 Hz, 1H), 6.07 (s, 1H), 6.01 (s, 1H), 5.77-5.64 (m, 3H), 5.21 (dd, J=11.5, 3.9 Hz, 2H), 5.10 (s, 1H), 5.06 (s, 1H), 4.96 (dd, J=10.2, 5.3 Hz, 2H), 4.85 (t, J=14.6 Hz, 2H), 4.76 (s, 2H), 4.71-4.49 (m, 8H), 4.15-3.92 (m, 4H), 3.52 (s, 3H), 3.38 (s, 3H), 3.31 (s, 3H), 3.11 (s, 3H), 3.10 (s, 3H), 2.72 (s, 3H), 2.67 (s, 3H), 2.27 (s, 4H), 1.32 (d, J=7.2 Hz, 8H), 1.26 (d, J=5.6 Hz, 10H), 1.04-0.76 (m, 35H); ESI MS m/z 1231 [C$_{63}$H$_{111}$N$_{11}$O$_{13}$+H]$^+$; HPLC>99% (AUC), t$_R$32 13.35 mm.

Example 9

Preparation of Cyclosporin A Alcohol Isomers A (IVa-A) and B (IVa-B)

A solution of cyclosporin methyl vinyl ketone from Example 3, 4, 5, or 6 (37.5 mg) in methanol (1.0 mL) at 0° C. was treated with successive 10 mg portions of sodium borohydride, allowing for reaction time between portions, until TLC analysis indicated a completed reaction. After 18 h, 1N HCl (1.0 mL) was added dropwise and the reaction mixture was extracted with ethyl acetate. The ethyl acetate extract was evaporated to dryness in vacuo, giving white solids. The solids were triturated with chloroform, transferred with filtration and the solvent was again removed in vacuo to give 29.8 mg of a white, crystalline solid. The solids were redissolved in a minimal volume of acetonitrile and purified by reversed-phase semi-prep chromatography under the following conditions: column: Zorbax StableBond Rx C8, 250×21.2 mm, 7 μm packing, flow rate 20 mL/min, column temperature 70° C., wavelength 210 nm, mobile phase A=water, B=acetonitrile, gradient profile: 0-2 min: 55% B, 2-15 min:

55-62% B; 15-30 min: 62-70% B; 30-31 min: 70-100% B; 31-34 min: 100% B; 34-35 min: 100-60% B. Product-containing fractions were dried down separately in the GeneVac dryer, then pooled together to provide 11.8 mg each of both CsA alcohol isomers. $^1$H-NMR (CDCl$_3$, 300 MHz) for isomer A (Va-A): δ 8.49 (1H, d, J=9.7 Hz), 8.01 (1H, d, J=7.8 Hz), 7.75 (1H, d, J=8.4 Hz), 7.34 (1H, d, J=8.2 Hz), 5.71 (1H, dd, J=10.8, 4.1 Hz), 5.58 (2H, d, J=2.4 Hz), 5.35 (1H, d, J=8.1 Hz), 5.24 (1H, dd, J=11.7, 3.8 Hz), 5.18 (1H, d, J=11.0 Hz), 5.10 (3H, m), 5.01 (2H, q, J=8.2 Hz), 4.86 (1H, q, J=7.0 Hz), 4.73 (1H, d, J=13.6 Hz), 4.60 (1H, t, J=8.8 Hz), 4.50 (1H, t, J=7.2 Hz), 4.25 (1H, bs), 3.93 (1H, t, J=8.5 Hz), 3.49 (3H, s), 3.43 (3H, s), 3.29 (3H, s), 3.20 (1H, d, J=13.9 Hz), 3.14 (3H, s), 3.10 (3H, s), 2.71 (3H, s), 2.68 (3H, s), 2.46 (2H, m), 2.20-1.40 (18H, m), 1.33 (3H, d, J=7.2 Hz), 1.26 (3H, d, J=7.0 Hz), 1.22 (3H, d, J=6.6 Hz), 1.08 (3H, t, J=5.0 Hz), 1.05-0.82 (33H, m), 0.77 (3H, d, J=6.5 Hz); $^{13}$C-NMR (CDCl$_3$, 90 MHz): δ 174.2, 174.0, 173.8, 173.4, 172.0, 171.7, 171.4 (2C), 170.8, 170.2, 170.1, 137.9, 127.2, 73.7, 67.3, 60.5, 58.1, 57.6, 55.8, 55.7, 55.0, 50.3, 48.8, 48.5, 48.2, 45.0, 40.9, 39.8, 39.3, 37.6, 37.5, 36.4, 34.3, 31.6, 31.5, 31.4, 30.4, 30.0, 29.9, 29.8, 25.1, 25.0, 24.9 (2C), 24.6, 24.1 (2C), 24.0, 23.9, 23.6, 23.1, 22.1, 21.7, 21.3, 20.7, 20.2, 19.2, 18.9, 18.5, 18.2, 15.8, 10.2; $^1$H-NMR (CDCl$_3$, 300 MHz) for isomer B (IVa-B): δ 8.62 (1H, d, J=9.8 Hz), 8.14 (1H, d, J=7.2 Hz), 7.93 (1H, d, J=8.2 Hz), 7.39 (1H, d, J=8.2 Hz), 5.70 (1H, dd, J=11.1 4.1 Hz), 5.51 (1H, dd, J=15.8, 7.5 Hz), 5.36 (1H, dd, J=15.6, 4.8 Hz), 5.29-5.12 (5H, m), 5.08 (1H, t, J=7.0 Hz), 4.98 (1H, q, J=8.0 Hz), 4.85 (1H, q, J=7.6 Hz), 4.72 (1H, d, J=13.8 Hz), 4.62 (1H, t, J=9.0 Hz), 4.47 (1H, t, J=7.2 Hz), 4.03 (1H, d, J=5.4 Hz), 3.97 (2H, m), 3.46 (6H, two eclipsing s), 3.34 (3H, s), 3.18 (1H, d, J=13.9 Hz), 3.17 (3H, s), 3.07 (3H, s), 2.70 (3H, s), 2.67 (3H, s), 2.60-1.80 (12H, m), 1.68 (2H, q, J=7.4 Hz), 1.57 (3H, bs), 1.33 (3H, d, J=7.2 Hz), 1.26 (3H, d, J=7.0 Hz), 1.22 (3H, d, J=6.2 Hz), 1.15 (3H, d, J=6.6 Hz), 1.08 (3H, d, J=6.5 Hz), 1.01 (3H, dd, J=6.4, 4.6 Hz), 0.97-0.80 (30H, m), 0.70 (3H, d, J=6.5 Hz); $^{13}$C-NMR (CDCl$_3$, 90 MHz): δ 174.1, 173.9, 173.8 (2C), 172.2, 171.6, 171.3 (2C), 171.0, 170.2, 169.6, 138.9, 128.2, 72.8, 68.9, 60.2, 58.1, 57.5, 55.8, 55.6, 54.6, 50.3, 48.9, 48.4, 48.0, 44.9, 40.9, 39.9, 39.4, 38.0, 36.4 (2C), 33.3, 31.5 (2C), 31.4, 30.4, 30.0 (2C), 29.8, 25.0 (2C), 24.9, 24.6, 24.5, 24.1 (3C), 24.0, 23.9, 23.7, 22.0, 21.4, 21.2, 20.6, 20.2, 18.9, -18.4, 18.3, 18.0, 15.5, 10.3.

Example 10

Preparation of Cyclosporin Monoacetyl Ester 1, Monoacetyl Ester 2, and Diacetyl Ester of IVa-A Cyclosporin A alcohol isomer IVa-A (22 mg) was dissolved in methylene chloride (10 mL). To this solution was added acetic anhydride (1.5 equiv.), DMAP (0.1 equiv.) and pyridine (1.5 equiv.). The reaction proceeded at room temperature, and was monitored by LC/MS. The amount of reagents was eventually added in excess (17 equiv. of Ac$_2$O, 17 equiv. pyridine and 4.0 equiv. DMAP) to drive the reaction to 81% consumption of starting material. The solvent was removed in vacuo. The crude product was purified by reversed-phase semi-prep chromatography under the following conditions: column: Zorbax StableBond Rx C8, 7u 250× 21.2 mm, 7 μm packing; flow rate 20 mL/min; column temperature 70° C.; wavelength 210 nm; mobile phase A=water, B=acetonitrile; gradient profile: 0-2 min: 60-68% B, 2-15 min: 68-73% B; 15-30 min: 73-83% B; 30-31 min: 80-100% B; 31-34 min: 100% B; 34-35 min: 100-60% B. Product-containing fractions were dried down separately in the GeneVac dryer, then pooled together as appropriate to provide 4.0 mg of CsA monoacetyl ester 1, 1.4 mg of CsA monoacetyl ester 2 and 7.8 mg of diacetyl ester. $^1$H-NMR (CDCl$_3$, 300 MHz) for CsA monoacetyl ester 1: δ 8.08 (1H, d, J=9.7 Hz), 7.84 (1H, d, J=7.6 Hz), 7.45 (1H, d, J=8.3 Hz), 7.17 (1H, d, J=8.0 Hz), 5.71 (1H, dd, J=10.9, 4.1 Hz), 5.62 (1H, d, J=7.2 Hz), 5.58 (1H, d, J=7.4 Hz), 5.49 (1H, d, J=7.2 Hz), 5.47 (1H, d, J=6.7 Hz), 5.23 (1H, dd, J=11.5, 3.8 Hz), 5.21 (1H, d, J=6.6 Hz), 5.17 (1H, d, J=4.8 Hz), 5.10-4.95 (3H, m), 4.84 (1H, q, J=7.5 Hz), 4.72 (1H, d, J=14.1 Hz), 4.66 (1H, d, J=8.9 Hz), 4.51 (1H, q, J=7.3 Hz), 3.90 (1H, m), 3.49 (3H, s), 3.39 (3H, s), 3.29 (3H, s), 3.21 (1H, d, J=11.0 Hz), 3.17 (1H, d, J=9.7 Hz), 3.13 (3H, s), 3.10 (3H, s), 2.72 (3H, s), 2.69 (3H, s), 2.46-2.02 (5H, m), 2.01 (3H, s), 2.00 (3H, s), 1.98-1.40 (6H, m), 1.34 (7H, d, J=7.3 Hz), 1.28 (7H, d, J=6.5 Hz), 1.09-0.77 (39H, m); $^1$H-NMR (CDCl$_3$, 300 MHz) for diacetyl ester: δ 8.44 (1H, d, J=9.6 Hz), 8.13 (1H, d, J=6.9 Hz), 7.58 (1H, d, J=9.0 Hz), 7.48 (1H, d, J=7.9 Hz), 5.68 (1H, dd, J=11.2, 4.3 Hz), 5.49 (1H, d, J=11.0 Hz), 5.43 (1H, d, J=6.2 Hz), 5.39 (1H, d, J=3.9 Hz), 5.37-5.27 (2H, m), 5.20 (1H, d, J=11.4, 3.8 Hz), 5.15-5.05 (2H, m), 5.00 (2H, m), 4.97-4.77 (2H, m), 4.64 (1H, d, J=13.8 Hz), 4.43 (1H, q, J=7.0 Hz), 3.46 (3H, s), 3.30 (3H, s), 3.24 (3H, s), 3.20 (3H, s), 3.21 (1H, d, J=12.6 Hz), 3.03 (3H, s), 2.68 (3H, s), 2.66 (3H, s), 2.47-2.05 (5H, m), 2.01 (3H, s), 2.00 (3H, s), 1.92 (3H, s), 1.90-1.40 (12H, m), 1.33 (3H, d, J=7.1 Hz), 1.27 (3H, d, J=6.9 Hz), 1.21 (3H, d, J=6.3 Hz), 1.09 (3H, d, J=6.8 Hz), 1.03 (3H, d, J=6.5 Hz), 1.00-0.81 (30H, m), 0.79 (3H, d, J=6.4 Hz).

Example 11

Preparation of Cyclosporin A Monobutyrate Ester of IVa-B

Cyclosporin alcohol isomer IVa-B (20 mg) and 114 μL of vinyl butyrate (TCI) were dissolved in 9 mL anhydrous tert-butyl methyl ether. To this solution were added 400 mg each of immobilized lipases AH and AK (lipases from Amano; immobilization procedure as described in Sergeeva et al., *Biotechnol. Lett.*, 22:1419-1422 (2000), which is hereby incorporated by reference in its entirety). The reaction was incubated with 250 rpm shaking at 45° C. for 5 days. The enzyme was removed by filtration through a 0.45 μm PTFE syringe filter. The retained solids were rinsed four times with approx. 10 mL anhydrous tert-butyl methyl ether. The filtrate and rinsings were pooled and the solvent was removed in vacuo to obtain a tan oil. The oil was dissolved in a minimal volume of acetonitrile and purified by reversed-phase semi-prep chromatography under the following conditions: column: Zorbax StableBond Rx C8, 250×21.2 mm, 7 μm packing, flow rate 20 mL/min, column temperature 70° C., wavelength 210 nm, mobile phase A=water, B=acetonitrile, gradient profile: 0-2 min: 60-68% B, 2-15 min: 68-73% B; 15-30 min: 73-83% B; 30-31 min: 80-100% B; 31-34 min: 100% B; 34-35 min: 100-60% B. Product-containing fractions were dried down separately in the GeneVac dryer, then pooled together to provide 17.6 mg of the CsA monobutyrate ester: $^1$H-NMR (CDCl$_3$, 300 MHz): δ 8.06 (1H, d, J=9.8 Hz), 7.81 (1H, d, J=7.3 Hz), 7.44 (1H, d, J=8.2 Hz), 7.18 (1H, d, J=7.9 Hz), 5.71 (1H, dd, J=11.0, 4.2 Hz), 5.67 (1H, d, J=7.0 Hz), 5.62 (1H, d, J=7.0 Hz), 5.56 (1H, d, J=6.4 Hz), 5.50 (1H, dd, J=9.0, 6.4 Hz), 5.30-4.96 (6H, m), 4.85 (1H, q, J=7.4 Hz), 4.72 (1H, d, J=14.0 Hz), 4.66 (1H, t, J=8.7 Hz), 4.51 (1H, q, J=7.3 Hz), 3.91 (1H, t, J=6.0 Hz), 3.50 (3H, s), 3.39 (3H, s), 3.30 (3H, s), 3.18 (1H, d, J=13.9 Hz), 3.13 (3H, s), 3.09 (3H, s), 2.71 (3H, s), 2.69 (3H, s), 2.50-1.40 (17H, m), 1.36-1.20 (16H, m), 1.10-0.77 (42H, m); $^{13}$C-NMR (CDCl$_3$, 90 MHz): δ 174.2, 174.1 (2C), 173.7, 173.1, 171.6, 171.3 (2C), 170.7, 170.3 (2C), 170.2, 133.5, 131.5, 74.3, 71.1, 59.5, 57.9, 57.7, 55.5 (2C), 55.0, 50.5, 48.9, 48.7, 48.3, 45.2, 40.8, 39.7, 39.3 (2C), 37.9, 36.8, 36.2, 34.6, 31.7, 31.5, 31.4, 30.1 (2C), 29.8, 29.7, 25.2, 25.1 (2C), 24.9, 24.6, 24.0 (3C), 23.8, 23.7, 22.0, 21.9, 21.4, 20.7, 20.6, 20.0, 18.8, 18.7 (2C), 18.6, 18.3, 16.0, 13.9, 10.1.

Example 12

Preparation of [γ-Hydroxy-MeLeu⁴]CsA-MVK

A solution of CsA methyl vinyl ketone (from Example 3, 4, 5, or 6, 237.2 mg) in 2.8 mL DMF was aseptically distributed among three (3) different 2.8 L Fermbach flasks, each containing 280 mL of Stage II liquid cultures of *Saccharopolyspora hirsuta* subsp. *hirsuta* (ATCC 27875). Each of the three flasks also received 100 μL of antifoam solution. After dosing cyclosporin methyl ketone into these cultures, all three (3) flasks were placed on an orbital shaker at 250 rpm and 29° C. After four (4) days of continuous shaking, all three flasks were removed and ending pH values were taken, which ranged from 7.75 to 8.43. The contents of each Fermbach flask were treated, separately, in the following way: The cells were removed via centrifugation at 7500 rpm for 15 min. The pelleted cells were extracted with methanol (2×25 mL) inside centrifuge tubes. After centrifugation at 6000 rpm for 5 min, the supernatants were pooled and the solvent was removed in vacuo to give 316.0 mg (Flask 1), 86.9 mg (Flask 2) and 153.9 mg (Flask 3) of residues, respectively. The bulk, aqueous supernatant was extracted with ethyl acetate (2×200 mL), in 300 mL portions inside a separatory funnel, using centrifugation when necessary to break severe emulsions. The combined organic extracts were shaken with brine and reduced to a small volume via rotavapor. The pool was transferred to a tared scintillation vial and the solvent was completely removed in vacuo to give 65.4 mg (Flask 1), 108.6 mg (Flask 2) and 158.5 mg (Flask 3) of residues, respectively. The contents of Flasks 2 and 3 were each purified by reversed-phase semi-prep chromatography under the following conditions: column: Zorbax StableBond Rx C8, 250×21.2 mm, 7 mm packing, flow rate 20 mL/min, column temperature 70° C., wavelength 210 nm, mobile phase A=water, B=acetonitrile, gradient profile: 0-2 min: 40% B, 2-15 min: 40-50% B; 15-30 min: 50-60% B; 30-31 min: 60-100% B; 31-34 min: 100% B; 34-35 min: 100-40% B. Product-containing fractions were dried down separately in the GeneVac dryer, then pooled together to provide 11.2 mg of product. $^1$H-NMR (CDCl$_3$, 300 MHz): δ 8.12 (1H, d, J=9.9 Hz), 7.82 (1H, d, J=7.6 Hz), 7.55 (1H, d, J=8.4 Hz), 7.18 (1H, d, J=8.0 Hz), 6.89 (1H, dd, J=16.1, 7.5 Hz), 6.11 (1H, d, J=16.0 Hz), 5.71 (1H, dd, J=10.8, 3.8 Hz), 5.54 (1H, d, J=6.4 Hz), 5.45 (1H, t, J=5.5 Hz), 5.10-4.92 (5H, m), 4.85 (1H, q, J=7.3 Hz), 4.74 (1H, d, J=8.9 Hz), 4.69 (1H, d, J=13.4 Hz), 4.55 (1H, q, J=7.4 Hz), 4.06 (1H, m), 3.75 (1H, bs), 3.51 (3H, s), 3.39 (3H, s), 3.30 (3H, s), 3.18 (1H, d, J=8.3 Hz), 3.14 (3H, s), 3.13 (3H, s), 2.72 (3H, s), 2.68 7.2 Hz), 1.26 (6H, d, J=4.4 Hz), 1.19 (3H, s), 1.07 (3H, d, J=6.5 Hz), 1.05-0.82 (33H, m), 0.80 (3H, d, J=6.5 Hz); $^{13}$C-NMR (CDCl$_3$, 90 MHz): δ 198.4, 174.6, 174.0, 173.8, 173.7, 171.9, 171.3, 171.2, 170.9, 170.7, 170.5, 170.0, 148.4, 131.5, 74.5, 68.9, 59.5, 58.3, 57.7, 55.8, 55.0, 54.1, 50.4, 48.9, 48.5, 48.3, 45.2, 41.7, 40.7, 39.6, 39.2 (2C), 37.9, 34.5, 32.5, 31.7, 31.3, 31.1, 30.2, 30.0, 29.8, 29.7, 29.0, 28.2, 25.2, 25.0, 24.9, 24.6, 24.0, 23.9 (2C), 23.8, 22.0 (2C), 20.7, 19.7, 18.8, 18.7, 18.6, 18.3, 16.0, 10.1.

Example 13

Preparation of [γ-hydroxy-MeLeu⁹] CsA

A solution of cyclosporin A (143.7 mg) in 1.0 mL of ethanol was aseptically distributed between two different 2.8 L Fermbach culture flasks, each containing 280 mL of Stage II liquid culture of *Streptomyces catenulae* (ATCC-23893). Additionally, a second solution of cyclosporin A (141.0 mg) in 1.0 mL of DMF was aseptically distributed between two additional Stage II cultures of the same microorganism in two different 2.8 L Fermbach culture flasks. After dosing cyclosporin A into these cultures, all four (4) flasks were placed on an orbital shaker at 250 rpm and 29° C. After seven (7) days of continuous shaking, all four flasks were removed and ending pH values were taken, which ranged from 8.32 to 8.38. The cells were removed via centrifugation at 7500 rpm for 10 min. The pelleted cells were extracted with methanol (2×20 mL) inside centrifuge tubes. After centrifugation at 6000 rpm for 5 min, the supernatants were pooled and the solvent was removed in vacuo. The bulk, aqueous supernatant was extracted with ethyl acetate (2×400 mL), in 300 mL portions inside a separatory funnel. The combined organic extracts were shaken with brine and reduced to a small volume via rotavapor. The small pool was combined with the extract from the pelleted cells and dried in vacuo to give 723.1 mg a crude product. The crude was re-dissolved in a minimal volume of acetonitrile and purified by reversed-phase semi-prep chromatography under the following conditions: column: Zorbax StableBond Rx C8, 250×21.2 mm, 7 μm packing, flow rate: 20 mL/min, column temperature 70° C., wavelength 210 nm, mobile phase A=water, B=acetonitrile, gradient profile: 0-2 min: 50% B, 2-15 min: 50-75% B; 15-30 min: 75-100% B; 30-36 min:100% B; 36-37 min: 100-50% B. Product-containing fractions were dried down separately in the GeneVac dryer, then pooled together to provide 22.6 mg of [γ-hydroxy-MeLeu⁹] CsA: $^1$H-NMR (CDCl$_3$, 300 MHz): δ 7.90 (1H, d, J=9.6 Hz), 7.55 (1H, d, J=7.8 Hz), 7.48 (1H, d, J=8.2 Hz), 7.02 (1H, d, J=8.5 Hz), 5.88 (1H, dd, J=8.0, 5.4 Hz), 5.50 (1H, d, J=6.0 Hz), 5.34 (3H, bs), 5.31 (1H, d, J=4.0 Hz), 5.18 (1H, d, J=11.0 Hz), 5.04 (1H, dt, 9.4, 7.5 Hz), 5.00-4.90 (2H, m), 4.85 (1H, dd, J=7.6, 7.4 Hz), 4.72 (1H, d, J=14.2 Hz), 4.63 (1H, dd, J=9.7, 8.6 Hz), 4.55 (1H, t, J=7.5 Hz), 3.94 (1H, d, J=6.5 Hz), 3.78 (1H, q, J=6.6 Hz), 3.51 (3H, s), 3.39 (3H, s), 3.26 (3H, s), 3.20 (1H, d, J=13.9 Hz), 3.12 (3H, s), 3.11 (3H, s), 3.05-2.85 (2H, m), 2.72 (6H, two eclipsing s), 2.43 (2H, m), 2.14 (2H, m), 2.07-1.90 (4H, m), 1.70 (1H, sextet, J=7.0 Hz), 1.63 (7H, m), 1.55-1.40 (3H, m), 1.37 (3H, d, J=7.3 Hz), 1.24 (3H, d, J=7.2 Hz), 1.08 (3H, d, J=6.5 Hz), 1.05-0.80 (36H, m), 0.70 (3H, d, J=6.1 Hz); $^{13}$C-NMR (CDCl$_3$, 90 MHz): δ 174.0, 174.1, 173.6, 173.4, 171.9, 171.5, 171.3, 170.6, 170.3, 170.2, 169.9, 129.8, 126.5, 75.1, 69.9, 59.1, 58.0, 57.8, 55.7 (3C), 50.6, 49.0, 48.9, 47.6, 45.3, 42.7, 40.5, 39.7, 37.6, 36.5, 36.2, 36.0, 34.4, 31.8, 31.5, 31.3, 30.8, 30.4, 30.3, 30.2, 29.9, 29.3, 25.8, 25.1 (3C), 24.2, 24.1, 23.7, 23.2, 22.3, 21.3, 20.3, 20.2, 18.9, 18.6, 18.1, 17.9, 16.9, 16.3, 10.1.

Example 14

Preparation of [γ-hydroxy-MeLeu⁹] CsA-MVK

[γ-hydroxy-MeLeu⁹] CsA (21.0 mg) was dissolved in 2.2 mL of a solution of 1-hydroxybenzotriazole (23 mg) in tert-butanol (3.2 mL). Sodium citrate/sodium phosphate buffer (80 mM, 7.83 mL, pH 5.6) was added while stirring, resulting in a thick white suspension. Laccase C (56.7 mg, ASA Spezialenzyme) was added as a solution in 1.11 mL of the same buffer, turning the reaction mixture slightly yellow in appearance. The reaction was mechanically stirred enough to create a vortex, open to ambient atmosphere and room temperature for a period of ~18 h, after which time the reaction mixture had become orange in appearance. A portion of the tert-butanol was removed from the reaction mixture in vacuo. The orange reaction mixture was then divided in two portions. Each portion was loaded onto a pre-conditioned VARIAN Bond-Elut® C8 solid-phase extraction cartridge (30 cc, 500 mg of sorbent). After a 1 mL wash with water, the cyclosporin-related products were eluted with 3 mL methanol. The methanol eluate was concentrated in vacuo, transferred to a tared scintillation vial and dried in vacuo inside a Savant SpeedVac to provide 27.9 mg of crude product as orange-brown solids. The solids were purified by reversed-phase semi-prep chromatography under the following conditions: column: Zorbax StableBond Rx C8, 250×21.2 mm, 7 µm packing, flow rate 20 mL/min, column temperature 70° C., wavelength 210 nm, mobile phase A=water, B=acetonitrile, gradient profile: 0-2 min: 40% B, 2-15 min: 40-50% B; 15-30 min: 50-60% B; 30-31 min: 60-100% B; 31-34 min: 100% B; 34-35 min: 100-40% B. Product-containing fractions were dried down separately in the GeneVac dryer, then pooled together to provide 7.0 mg of [γ-hydroxy-MeLeu$^9$] CsA-MVK: $^1$H-NMR (CDCl$_3$, 300 MHz): δ 7.98 (1H, d, J=9.9 Hz), 7.74 (1H, d, J=7.8 Hz), 7.45 (1H, d, J=8.0 Hz), 7.06 (1H, d, J=8.1 Hz), 6.88 (1H, dd, J=16.1, 7.5 Hz), 6.07 (1H, d, J=16.1 Hz), 5.90 (1H, dd, J=8.2, 4.8 Hz), 5.62 (1H, bs), 5.21 (1H, dd, J=11.6, 3.8 Hz), 5.15 (1H, d, J=11.1 Hz), 5.07-4.92 (4H, m), 4.87 (1H, q, J=7.5 Hz), 4.73 (1H, d, J=14.0 Hz), 4.65 (1H, t, J=9.0 Hz), 4.57 (1H, t, J=7.5 Hz), 4.04 (2H, bs), 3.52 (3H, s), 3.38 (3H, s), 3.29 (3H, s), 3.20 (1H, d, J=14.1 Hz), 3.13 (3H, s), 3.11 (3H, s), 2.74 (3H, s), 2.71 (3H, s), 2.56-2.32 (2H, m), 2.25 (3H, s), 2.19-1.40 (14H, m), 1.34 (3H, d, J=7.2 Hz), 1.24 (6H, dd, J=6.9, 1.4 Hz), 1.08 (3H, d, J=6.5 Hz), 1.05-0.82 (36H, m); $^{13}$C-NMR (CDCl$_3$, 90 MHz): δ 198.6, 174.5, 174.2, 174.0, 173.6, 171.7, 171.5, 171.2, 170.4 (2C), 170.2, 170.1, 149.0, 131.8, 74.8, 69.9, 59.4, 58.0 (2C), 55.7 (2C), 55.3, 50.6, 49.0, 48.7, 47.5, 45.3, 42.7, 40.4, 39.6 (2C), 37.9, 36.2, 35.0, 31.7, 31.6, 31.3, 30.7, 30.5, 30.4, 30.2, 30.1, 29.6, 27.5, 25.5, 25.1, 25.0 (2C), 24.2, 23.9, 23.6, 23.4, 22.2, 21.3, 20.6, 20.0, 18.8, 18.7, 18.5, 17.9, 16.3, 10.1.

Example 15

Materials and Methods (for Examples 16-115)

Unless otherwise noted, reagents and solvents were used as received from commercial suppliers. Proton and $^{19}$F nuclear magnetic resonance spectra were obtained on a Bruker AC 300 or a Bruker AV 300 spectrometer at 300 MHz for proton and 282 MHz for fluorine, or on a Bruker AMX 500 spectrometer at 500 MHz for proton. Spectra are given in ppm (δ) and coupling constants, J, are reported in Hertz. Tetramethylsilane was used as an internal standard for proton spectra and the solvent peak was used as the reference peak for carbon spectra. Mass spectra were obtained on a Perkin Elmer Sciex 100 atmospheric pressure ionization (APCI) mass spectrometer, or a Finnigan LCQ Duo LCMS ion trap electrospray ionization (ESI) mass spectrometer. HPLC analyses were obtained using a Dynamax C18 column (200×4.5 mm) or Luna C18(2) column (250×4.6 mm) with UV detection at 210 nm using a standard solvent gradient program (Method A; Table 2) and oven temperature at 65° C. Semi-prepare HPLC were performed using a Dynamax C18 column (60 A, 8 um) or a Luna C18(2) column (250×21.2 mm) with a standard solvent gradient program (Method B; Table 3) and oven temperature at 70° C. Elemental analyses were performed by Quantitative Technologies, Inc. (Whitehouse, N.J.).

TABLE 2

Method A

| Time (min) | Flow (mL/min) | Percentage of 0.05% (v/v) trifluoroacetic acid in water | Percentage of 0.05% (v/v) trifluoroacetic acid in acetonitrile |
| --- | --- | --- | --- |
| 0.0 | 1.0 | 100 | 0 |
| 15 | 1.0 | 0 | 100 |
| 25 | 1.0 | 0 | 100 |
| 30 | 1.0 | 100 | 0 |

TABLE 3

Method B

| Time (min) | Flow (mL/min) | Percentage of 0.05% (v/v) trifluoroacetic acid in water | Percentage of 0.05% (v/v) trifluoroacetic acid in acetonitrile |
| --- | --- | --- | --- |
| 0.0 | 10 | 60 | 40 |
| 30 | 10 | 0 | 100 |
| 45 | 10 | 0 | 100 |
| 50 | 10 | 60 | 40 |

Example 16

Preparation of Cyclosporin A Aldehyde (Va) from CsA MVK

Ozone was bubbled into a solution of CsA methyl vinyl ketone (300 mg, 0.247 mmol) in methylene chloride (30 mL) at −78° C. until a blue color was developed. The mixture was degassed with nitrogen for a few min and then methyl sulfide (0.5 mL) was added at −78° C. The reaction mixture was allowed to warm to room temperature and stirred overnight. Solvents were removed in vacuo and the residue was dissolved in ethyl acetate, washed with water and brine, dried over sodium sulfate, filtered, and concentrated in vacuo to afford the crude CsA aldehyde Va (280 mg, 96%) as a white solid: $^1$H NMR (300 MHz, CDCl$_3$) δ $^1$H NMR (300 MHz, CDCl$_3$) δ 9.65 (s, 1H), 8.58 (d, J=9.5 Hz, 1H), 7.96 (d, J=6.8 Hz, 1H), 7.49 (d, J=8.4 Hz, 1H), 7.47 (d, J=9.0 Hz, 1H), 5.69-4.00 (m, 12H) 3.48 (s, 3H), 3.46-2.50 (m, 4H), 3.44 (s, 3H), 3.29 (s, 3H), 3.19 (s, 3H), 3.10 (s, 3H), 2.68 (s, 3H), 2.68 (s, 3H), 2.30-1.70 (m, 5H), 1.60-0.75 (m, 58H); ESI MS m/z 1176 [C$_{59}$H$_{105}$N$_{11}$O$_{13}$+H]$^+$.

Example 17

Preparation of Cyclosporin A Aldehyde (Vb) from CsA Alcohol

Ozone was bubbled into a solution of CsA alcohol IVb (X=OAc, R$_0$=CH$_3$, 500 mg, 0.4 mmol) in methanol (50 mL) at −78° C. until a blue color was developed. The mixture was degassed with nitrogen for a few min and then zinc dust (52 mg, 0.8 mmol) followed by 50% of acetic acid (20 mL)

were added at −78° C. The reaction mixture was allowed to warm to room temperature. Solvents were removed in vacuo and the residue was dissolved in ethyl acetate, washed with water, saturated sodium bicarbonate and brine, dried over sodium sulfate, filtered, and concentrated in vacuo. The residue was purified by chromatography on silica gel (95:5 ethyl acetate/methanol) to afford CsA aldehyde Vb (X=OAc, $R_0$=CH$_3$, 250 mg, 52%) as a white solid: $[\alpha]^{25}{}_D$ −287.5° (c 0.35, CHCl$_3$); $^1$H NMR (300 MHz, CDCl$_3$) δ 9.55 (s, 1H), 8.63 (d, J=9.5 Hz, 1H), 7.96 (d, J=6.8 Hz, 1H), 7.56 (d, J=8.4 Hz, 1H), 7.52 (d, J=9.3 Hz, 1H), 5.92-4.66 (m, 12H), 3.47 (s, 3H), 3.40-2.50 (m, 4H), 3.31 (s, 3H), 3.30 (s, 3H), 3.20 (s, 3H), 3.02 (s, 3H), 2.68 (s, 3H), 2.65 (s, 3H), 2.30-1.70 (m, 5H), 1.96 (s, 3H), 1.60-0.75 (m, 57H); APCI MS m/z 1218 $[C_{61}H_{107}N_{11}O_{14}+H]^+$; HPLC 98.6% (AUC), $t_R$=14.56 min; Anal. Calcd for $C_{61}H_{107}N_{11}O_{14}$: C, 60.12; H, 8.85; N, 12.64. Found: C, 59.20; H, 8.87; N, 12.11.

Example 18

Reaction of CsA Aldehyde (Va) with a Phosphorus Ylide

To a suspension of methyltriphenylphosphonium bromide (136 mg, 0.38 mmol) in THF (2 mL) was added sodium bis(trimethylsilyl)amide (1.0 M in THF, 0.38 mL, 0.38 mmol) dropwise at room temperature. The mixture was stirred under nitrogen for 2 h and then cooled to 0° C. CsA aldehyde Va (X=OH, 45 mg, 0.038 mmol) in THF (2 mL) was added dropwise and the mixture was stirred at 0° C. for 15 min. The mixture was quenched with saturated ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product, which was purified by semi-preparative HPLC to afford CsA olefin (20 mg, 44%) as a white solid: $^1$H NMR (500 MHz, CDCl$_3$) δ 8.34 (d, J=9.5 Hz, 1H), 7.94 (d, J=7.0 Hz, 1H), 7.68 (d, J=8.5 Hz, 1H), 7.39 (d, J=8.5 Hz, 1H), 5.80-3.98 (m, 15H), 3.49 (s, 3H), 3.45 (s, 3H), 3.33 (s, 3H), 3.25-2.35 (m, 4H), 3.15 (s, 3H), 3.08 (s, 3H), 2.69 (s, 3H), 2.68 (s, 3H), 2.20-1.40 (m, 6H), 1.30-0.84 (m, 57H); APCI MS m/z 1174 $[C_{61}H_{107}N_{11}O_{12}+H]^+$; HPLC 97.6% (AUC), $t_R$=14.01 min.

Example 19

Reaction of CsA Aldehyde Va with a Phosphorus Ylide

To a suspension of ethyltriphenylphosphonium bromide (189 mg, 0.51 mmol) in THF (5 mL) was added sodium bis(trimethylsilyl)amide (1.0 M in THF, 0.51 mL, 0.51 mmol) dropwise at room temperature. The mixture was stirred under nitrogen for 4 h and then cooled to 0° C. CsA aldehyde Va (X=OH, 60 mg, 0.051 mmol) in THF (3 mL) was added dropwise and the mixture was stirred at 0° C. for 1 h. The mixture was quenched with saturated ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product, which was purified by semi-preparative HPLC to afford CsA olefin (18 mg, 30%) as a white solid: $^1$H NMR (300 MHz, CDCl$_3$) δ 7.87 (d, J=9.5 Hz, 1H), 7.65 (d, J=7.0 Hz, 1H), 7.51 (d, J=8.5 Hz, 1H), 7.09 (d, J=8.5 Hz, 1H), 5.75-4.00 (m, 14H), 3.80-2.35 (m, 4H), 3.57 (s, 3H), 3.37 (s, 3H), 3.27 (s, 3H), 3.11 (s, 3H), 3.09 (s, 3H), 2.73 (s, 3H), 2.70 (s, 3H), 2.20-1.50 (m, 9H), 1.40-0.84 (m, 57H); APCI MS m/z 1188 $[C_{61}H_{109}N_{11}O_{12}+H]^+$; HPLC 98.3% (AUC), $t_R$=14.06 min.

Example 20

Reaction of CsA Aldehyde Va with a Phosphorus Ylide

To a suspension of n-propyltriphenylphosphonium bromide (196 mg, 0.51 mmol) in THF (5 mL) was added sodium bis(trimethylsilyl)amide (1.0 M in THF, 0.51 mL, 0.51 mmol) dropwise at room temperature. The mixture was stirred under nitrogen for 4 h and then cooled to 0° C. CsA-aldehyde (60 mg, 0.051 mmol) in THF (3 mL) was added dropwise and the mixture was stirred at 0° C. for 1 h. The mixture was quenched with saturated ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product, which was purified by semi-preparative HPLC to afford CsA olefin (15 mg, 24%) as a white solid: $^1$H NMR (300 MHz, CDCl$_3$) δ 7.86 (d, J=9.5 Hz, 1H), 7.66 (d, J=7.0 Hz, 1H), 7.56 (d, J=8.0 Hz, 1H), 7.18 (d, J=8.0 Hz, 1H), 5.80-4.50 (m, 14H), 3.56 (s, 3H), 3.36 (s, 3H), 3.27 (s, 3H), 3.25-2.35 (m, 4H), 3.11 (s, 3H), 3.09 (s, 3H), 2.74 (s, 3H), 2.71 (s, 3H), 2.20-1.40 (m, 9H), 1.30-0.84 (m, 59H); APCI MS m/z 1202 $[C_{62}H_{111}N_{11}O_{12}+H]^+$; HPLC 91.2% (AUC), $t_R$=14.65 min.

Example 21

Reaction of CsA Aldehyde Va with a Phosphorus Ylide

To a suspension of n-butyltriphenylphosphonium bromide (237 mg, 0.595 mmol) in THF (4 mL) was added sodium bis(trimethylsilyl)amide (1.0 M in THF, 0.6 mL, 0.6 mmol) dropwise at room temperature. The mixture was stirred under nitrogen for 2 h and then cooled to 0° C. CsA aldehyde Va (140 mg, 0.119 mmol) in THF (1 mL) was added dropwise and the mixture was stirred at 0° C. for 5 min. The mixture was quenched with saturated aqueous ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product (30 mg), which was purified by semi-preparative HPLC to afford CsA olefin (5 mg, 3%) as a white solid: $^1$H NMR (300 MHz, CDCl$_3$) δ 7.89 (d, J=9.8 Hz, 1H), 7.64 (d, J=7.2 Hz, 1H), 7.51 (d, J=7.6 Hz, 1H), 7.10 (d, J=7.8 Hz, 1H), 5.73-3.70 (m, 13H), 3.58 (s, 3H), 3.37 (s, 3H), 3.27 (s, 3H), 3.11 (s, 3H), 3.08 (s, 3H), 2.73 (s, 3H), 2.70 (s, 3H), 2.50-1.50 (m, 12H), 1.40-0.70 (m, 63H); ESI MS m/z 1217 $[C_{63}H_{113}N_{11}O_{12}+H]^+$; HPLC 95.6% (AUC), $t_R$=16.02 min.

Example 22

Reaction of CsA Aldehyde Vb with a Phosphorus Ylide

To a suspension of sodium hydride (95%, 16 mg, 0.66 mmol) in THF (2 mL) was added methyl diethylphosphonoacetate (0.12 mL, 0.66 mmol) dropwise at room temperature. The mixture was stirred under nitrogen for 15 min and then cooled to 0° C. CsA aldehyde Vb (X=OAc, 80 mg, 0.066 mmol) in THF (3 mL) was added dropwise and the mixture was stirred at 0C for 30 min. The mixture was quenched with 10% NaH$_2$PO$_4$, extracted with ether. The combined ether layers were washed with 1 N NaOH and brine, dried over sodium sulfate, filtered and concentrated in vacuo. The residue was pre-purified by preparative thin layer chromatography (1:1 hexanes/acetone) to give the crude product (17 mg), which was purified by semi-preparative HPLC to afford CsA methyl ester (10 mg, 12%) as a white solid: mp 150-152° C.; $^1$H NMR (300 MHz, CDCl$_3$) δ 8.61 (d, J=9.5 Hz, 1H), 7.97 (d, J=7.0 Hz, 1H), 7.64 (d, J=8.2 Hz, 1H), 7.19 (d, J=9.4 Hz, 1H), 6.85 (dd, J=16.5, 6.7 Hz, 1H), 5.98 (d, J=16.5 Hz, 1H), 5.75-4.45 (m, 12H), 3.65 (s, 3H), 3.44 (s, 3H), 3.29 (s, 3H), 3.25-2.20 (m, 4H), 3.22 (s, 3H), 3.20 (s, 3H), 3.04 (s, 3H), 2.67 (s, 3H), 2.65 (s, 3H), 2.20-1.50 (m, 5H), 2.00 (s, 3H), 1.60-0.83 (m, 57H); APCI MS m/z 1274 [C$_{64}$H$_{111}$N$_{11}$O$_{15}$+H]$^{30}$ ; HPLC 98.0% (AUC), t$_R$=15.50 min.

Example 23

Reaction of CsA Aldehyde Va with a Phosphorus Ylide

To a suspension of sodium hydride (95%, 11 mg, 0.43 mmol) in THF (2 mL) was added methyl diethylphosphonoacetate (0.08 mL, 0.43 mmol) dropwise at room temperature. The mixture was stirred under nitrogen for 15 min and then cooled to 0° C. CsA aldehyde Va (X=OH, 50 mg, 0.043 mmol) in THF (2 mL) was added dropwise and the mixture was stirred at 0° C. for 5 min. The mixture was quenched with saturated ammonium chloride, extracted with ether. The combined organic layers were washed with 0.5 N NaOH and brine, dried over sodium sulfate, filtered and concentrated in vacuo. The residue was pre-purified by preparative thin layer chromatography (1:1 hexanes/acetone) to give the crude product, which was purified by semi-preparative HPLC to afford CsA methyl ester (22 mg, 42%) as a white solid: $^1$H NMR (300 MHz, CDCl$_3$) δ 8.21 (d, J=9.5 Hz, 1H), 7.81 (d, J=7.0 Hz, 1H), 7.31 (d, J=8.0 Hz, 1H), 7.28 (d, J=9.0 Hz, 1H), 7.01 (dd, J=15.8, 7.5 Hz, 1H), 5.88 (d, J=15.8 Hz, 1H), 5.75-4.00 (m, 12H), 3.67 (s, 3H), 3.50 (s, 3H), 3.40 (s, 3H), 3.25-2.20 (m, 4H), 3.27 (s, 3), 3.14 (s, 3H), 3.09 (s, 3H), 2.70 (s, 3H), 2.68 (s, 3H), 2.20-1.40 (m, 7H), 1.30-0.84 (m, 56H); ESI MS m/z 1232 [C$_{62}$H$_{109}$N$_{11}$O$_{14}$+H]$^+$; HPLC 92.5% (AUC), t$_R$=15.29 min.

Example 24

Reaction of CsA Aldehyde Va with a Phosphorus Ylide

To a solution of diethyl(cyanomethyl)phosphonate (0.083 mL, 0.51 mmol) in THF (2 mL) was added sodium bis(trimethylsilyl)amide (1.0 M in THF, 0.51 mL, 0.51 mmol) dropwise at 0° C., and the mixture was stirred under nitrogen at 0° C. for 15 min. CsA aldehyde Va (X=OH, 60 mg, 0.051 mmol) in THF (3 mL) was added dropwise and the mixture was stirred at 0C for 15 min. The mixture was quenched with saturated ammonium chloride, extracted with ether. The combined organic layers were washed with 1 N NaOH and brine, dried over sodium sulfate, filtered and concentrated in vacuo. The residue was pre-purified by preparative thin layer chromatography (1:1 hexanes/acetone) to give the crude product, which was purified by semi-preparative HPLC to afford the target compound (30 mg, 49%) as a white solid: $^1$H NMR (500 MHz, CDCl$_3$) δ 8.21 (d, J=9.5 Hz, 1H), 7.84 (d, J=7.0 Hz, 1H), 7.46 (d, J=8.0 Hz, 1H), 7.40 (d, J=9.0 Hz, 1H), 6.73 (dd, J=16.5, 7.8 Hz, 1H), 5.72-4.03 (m, 12H), 5.44 (d, J=16.5 Hz, 1H), 3.49 (s, 3H), 3.43 (s, 3H), 3.31 (s, 3H), 3.25-2.35 (m, 4H), 3.16 (s, 3H), 3.12 (s, 3H), 2.72 (s, 3H), 2.68 (s, 3H), 2.20-1.40 (m, 7H), 1.30-0.79 (m, 56H); APCI MS m/z 1199 [C$_{61}$H$_{106}$N$_{12}$O$_{12}$+H]$^+$; HPLC>99% (AUC), t$_R$=13.48 min.

Example 25

Reaction of CsA Aldehyde Va with a Phosphorus Ylide

To a suspension of [3-(dimethylamino)propyl]triphenylphosphonium bromide (330 mg, 0.77 mmol) in THF (3 mL) was added sodium bis(trimethylsilyl)amide (1.0 M in THF, 0.77 mL, 0.77 mmol) dropwise at room temperature. The mixture was stirred under nitrogen for 2 h and then cooled to 0° C. CsA aldehyde Va (X=OH, 90 mg, 0.077 mmol) in THF (2 mL) was added dropwise and the mixture was stirred at 0° C. for 5 h. The mixture was quenched with saturated ammonium chloride, extracted with ether. The combined organic layers were washed with brine, dried over sodium sulfate, filtered, and concentrated in vacuo. The residue was pre-purified by preparative thin layer chromatography (1:1 hexanes/acetone) to give the crude product, which was purified by semi-preparative HPLC to afford CsA nitrile (5 mg, 5%) as a white solid: $^1$H NMR (300 MHz, CDCl$_3$) δ 7.85 (d, J=9.5 Hz, 1H), 7.53 (d, J=8.0 Hz, 2H), 7.08 (d, J=8.0 Hz, 1H), 5.75-4.55 (m, 14H), 3.75-2.35 (m, 6H), 3.58 (s, 3H), 3.36 (s, 3H), 3.27 (s, 3H), 3.11 (s, 3H), 3.08 (s, 3H), 2.83 (s, 6H), 2.74 (s, 3H), 2.69 (s, 3H), 2.20-1.40 (m, 7H), 1.30-0.84 (m, 58H); ESI MS m/z 1246 [C$_{64}$H$_{116}$N$_{12}$O$_{12}$+H]$^+$; HPLC>99% (AUC), t$_R$=14.15 min.

Example 26

Reaction of CsA Aldehyde Va with a Phosphorus Ylide

To a suspension of (3,3-dimethylallyl)triphenylphosphonium bromide (279 mg, 0.68 mmol) in THF (3 mL) was added sodium bis(trimethylsilyl)amide (1.0 M in THF, 0.68 mL, 0.68 mmol) dropwise at room temperature. The mixture was stirred under nitrogen for 1 h and then cooled to 0° C. CsA aldehyde Va (80 mg, 0.068 mmol) in THF (2 mL) was added dropwise and the mixture was stirred at 0° C. for 5 min. The mixture was quenched with saturated ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product, which was purified by semi-preparative HPLC to afford the trans-olefin (5 mg, 5%) as a white solid: $^1$H NMR (300 MHz, CDCl$_3$) δ 8.34 (d, J=9.5 Hz, 1H), 7.91 (d, J=7.0 Hz, 1H), 7.53 (d, J=8.5 Hz, 1H), 7.45 (d, J=8.5 Hz, 1H), 6.26 (dd, J=15.2, 10.8 Hz, 1H), 5.75-3.95 (m, 14H), 3.51 (s, 3H), 3.42 (s, 3H), 3.35-2.50 (m, 4H), 3.32 (s, 3H), 3.15 (s, 3H), 3.05 (s, 3H), 2.69 (s, 3H), 2.69 (s, 3H), 2.20-1.50 (m, 7H), 1.74 (s, 3H), 1.72 (s, 3H), 1.40-0.82 (m, 56H); ESI MS m/z 1229 [C$_{64}$H$_{113}$N$_{11}$O$_{12}$+H]$^+$; HPLC 98.1% (AUC), t$_R$=17.09 min.

Example 27

Reaction of CsA Aldehyde Va with a Phosphorus Ylide

To a suspension of (3,3-dimethylallyl)triphenylphosphonium bromide (279 mg, 0.68 mmol) in THF (3 mL) was added sodium bis(trimethylsilyl)amide (1.0 M in THF, 0.68 mL, 0.68 mmol) dropwise at room temperature. The mixture was stirred under nitrogen for 1 h and then cooled to 0° C. CsA aldehyde Va (80 mg, 0.068 mmol) in THF (2 mL) was added dropwise and the mixture was stirred at 0° C. for 5 min. The mixture was quenched with saturated ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product, which was purified by semi-preparative HPLC to afford the cis-olefin (5 mg, 5%) as a white solid: $^1$H NMR (300 MHz, CDCl$_3$) δ 7.86 (d, J=9.5 Hz, 1H), 7.62 (d, J=7.0 Hz, 1H), 7.50 (d, J=8.5 Hz, 1H), 7.12 (d, J=8.5 Hz, 1H), 6.18 (t, J=11.5 Hz, 1H), 6.09 (d, J=11.5 Hz), 5.74-3.95 (m, 13H), 3.60 (s, 3H), 3.36 (s, 3H), 3.35-2.50 (m, 4H), 3.28 (s, 3H), 3.12 (s, 3H), 3.09 (s, 3H), 2.73 (s, 3H), 2.71 (s, 3H), 2.20-1.50 (m, 7H), 1.79 (s, 3H), 1.71 (s, 3H), 1.40-0.82 (m, 56H); ESI MS m/z 1229 [C$_{64}$H$_{113}$N$_{11}$O$_{12}$+H]$^+$; HPLC 92.2% (AUC), t$_R$=16.65 min.

Example 28

Reaction of CsA Aldehyde Va with a Phosphorus Ylide

To a suspension of 2-butenyltriphenylphosphonium bromide (180 mg, 0.51 mmol) in THF (3 mL) was added sodium bis(trimethylsilyl)amide (1.0 M in THF, 0.43 mL, 0.43 mmol) dropwise at room temperature. The mixture was stirred under nitrogen for 1 h and then cooled to 0° C. CsA aldehyde (Va, 100 mg, 0.085 mmol) in THF (2 mL) was added dropwise and the mixture was stirred at 0° C. for 10 min. The mixture was quenched with saturated aqueous ammonium chloride, extracted with ether. The combined organic layers were washed with brine, dried over sodium sulfate, filtered and concentrated in vacuo. The residue was pre-purified by preparative thin layer chromatography (1:1 hexanes/acetone) to give the crude product (26 mg), which was purified by semi-preparative HPLC to afford CsA diene (5 mg, 5%) as a white solid: $^1$H NMR (300 MHz, CDCl$_3$) δ 7.84 (d, J=9.5 Hz, 1H), 7.64 (d, J=7.0 Hz, 1H), 7.54 (d, J=7.7 Hz, 1H), 7.15 (d, J=7.4 Hz, 1H), 6.40-5.92 (m, 3H), 5.80-4.60 (m, 12H), 3.85-3.75 (m, 1H), 3.61 (s, 1.5H), 3.57 (s, 1.5H), 3.35 (s, 3H), 3.27 (s, 1.5H), 3.26 (s, 1.5H), 3.11 (s, 3H), 3.10 (s, 3H), 2.74 (s, 3H), 2.71 (s, 3H), 2.45-1.50 (m, 10H), 1.40-0.82 (m, 60H); ESI MS m/z 1215 [C$_{63}$H$_{111}$N$_{11}$O$_{12}$+H]$^+$; HPLC 96.0% (AUC), t$_R$=16.67 min.

Example 29

Preparation of Cyclosporin A Methyl Ester

A solution of CsA aldehyde (Va, 0.20 g, 0.17 mmol) in CCl$_4$ (6 mL) was treated with t-BuOCl (92 mg, 0.85 mmol). Resulting mixture was stirred at room temperature for 5 min under N$_2$ atmosphere. A mixture of methanol (68 μl, 1.7 mmol) and pyridine (138 μl, 1.70 mmol) was added to the reaction and allowed to stir for an additional 30 min. Mixture was then poured into H$_2$O (10 mL), extracted with ether, dried over sodium sulfate, and concentrated in vacuo. The crude product was purified by semi-preparative HPLC to afford the target compound (30 mg, 15%) as an off-white solid: $^1$H NMR (300 MHz, CDCl$_3$) δ 8.43 (d, J=9.6 Hz, 1H), 8.00 (d, J=7.1 Hz, 1H), 7.47 (d, J=8.8 Hz, 1H), 7.34 (d, J=7.8 Hz, 1H), 5.71 (d, J=5.7 Hz, 1H), 5.55 (d, J=3.8 Hz, 1H), 5.51 (d, J=3.9 Hz, 1H), 5.47 (d, J=9.0 Hz, 1H), 5.23 (d, J=10.9 Hz, 2H), 5.10-5.05 (m, 4H), 5.01-4.66 (m, 12H), 4.46 (t, J=14.2 Hz, 2H), 4.04 (d, J=3.4 Hz, 2H), 3.46 (s, 3H), 3.43 (s, 3H), 3.25 (s, 3H), 3.17 (s, 3H), 3.06 (s, 3H), 2.70 (s, 3H), 2.69 (s, 3H), 1.35-1.25 (m, 4H), 1.06-0.77 (m, 52H); ESI MS m/z 1207 [C$_{60}$H$_{107}$N$_{11}$O$_{14}$+H]$^+$; HPLC >99% (AUC), t$_R$=18.55 min.

Example 30

Preparation of Cyclosporin A Diol

To an ice-cooled solution of CsA aldehyde (Va, 200 mg, 0.170 mmol) in methanol (2 mL) was added sodium borohydride (64 mg, 1.7 mmol). The mixture was stirred at 0° C. under nitrogen atmosphere for 1 h, quenched with saturated ammonium chloride, extracted with ethyl acetate (2×50 mL). The combined organic layers were dried over sodium sulfate, filtered and concentrated under reduced pressure to afford the alcohol (190 mg, 95%) as a white solid: $^1$H NMR (300 MHz, CDCl$_3$) δ 8.24 (d, J=9.5 Hz, 1H), 7.88 (d, J=7.1 Hz, 1H), 7.48 (d, J=8.7 Hz, 1H), 7.42 (d, J=7.8 Hz, 1H), 5.69 (d, J=7.6 Hz, 1H), 5.40-4.92 (m, 8H), 4.85 (t, J=6.5 Hz, 1H), 4.74-4.60 (m, 2H), 4.46 (t, J=7.2 Hz, 1H), 4.12-4.04 (m, 1H), 3.49 (s, 3H), 3.41 (s, 3H), 3.28 (s, 3H), 3.17 (s, 3H), 3.10 (s, 3H), 2.68 (s, 6H), 2.50-2.35 (m, 1H), 2.24-1.52 (m, 12H), 1.50-0.70 (m, 55H); ESI MS m/z 1179 [C$_{59}$H$_{107}$N$_{11}$O$_{13}$+H]$^+$.

Example 31

Preparation of Cyclosporin A Monoester

A solution of CsA diol from Example 30 (0.10 g, 0.85 mmol) in methylene chloride (2 mL) was cooled to 0° C. Solution was treated with acryloyl chloride (76 mg, 0.84 mmol), pyridine (90 μl, 1.1 mmol) and DMAP (5 mg). Reaction was stirred under N$_2$ atmosphere and was allowed to slowly warm to room temperature overnight. Reaction was quenched with saturated sodium bicarbonate solution, extracted with methylene chloride. The combined organic layers were washed with a 10% solution of NaH$_2$PO$_4$ and brine, dried over sodium sulfate, and concentrated in vacuo. The crude product was purified by semi-preparative HPLC to afford CsA monoester (5.2 mg, 15%) as a white solid: $^1$H NMR (300 MHz, CDCl$_3$) δ 8.04 (d, J=9.7 Hz, 1H), 7.67 (d, J=7.3 Hz, 1H), 7.44 (d, J=8.5 Hz, 1H), 7.19 (d, J=7.9 Hz 1H), 6.40 (d, J=1.5 Hz, 1H), 6.35-6.10 (m, 2H), 5.83 (d, J=1.5 Hz, 1H), 5.80 (d, J=1.6 Hz, 1H), 5.69 (d, J=7.1 Hz, 1H), 5.32-4.64 (m, 8H), 4.51 (t, J=14.5 Hz, 2H), 4.40 (dd, J=11.0, 3.7 Hz, 1H), 3.52 (s, 3H), 3.39 (s, 3H), 3.25 (s, 3H), 3.11 (s, 3H), 3.10 (s, 3H), 2.70 (s, 3H), 2.69 (s, 3H), 2.14-1.97 (m, 7H), 1.72-1.39 (m, 8H), 1.37-0.68 (m, 52H); ESI MS m/z 1233 [C$_{62}$H$_{109}$N$_{11}$O$_{14}$+H]$^+$; HPLC>99% (AUC), t$_R$=15.56 min.

Example 32

Preparation of Cyclosporin A Monoester

A solution of CsA diol from Example 30 (0.10 g, 0.85 mmol) in methylene chloride (2 mL) was cooled to 0° C. Solution was treated with trans-crotonyl chloride (29 mg, 0.28 mmol), pyridine (34 μl, 0.42 mmol) and DMAP (5 mg). Reaction was stirred under N$_2$ atmosphere and was allowed to slowly warm to room temperature overnight. Reaction was quenched with saturated sodium bicarbonate solution, extracted with methylene chloride. The combined organic layers were washed with a 10% solution of NaH$_2$PO$_4$ and brine, dried over sodium sulfate, and concentrated in vacuo. The crude product was purified by semi-preparative HPLC to afford CsA monoester (3.8 mg, 11%) as a white solid: $^1$H NMR (300 MHz, CDCl$_3$) δ 8.05 (d, J=9.5 Hz, 1H), 7.67 (d, J=7.3 Hz, 1H), 7.43 (d, J=8.5 Hz, 1H), 7.21 (d, J=7.8 Hz, 1H), 6.98-6.90 (m, 2H), 5.83 (d, J=1.6 Hz, 1H), 5.74 (d, J=24.2 Hz, 1H), 5.45 (d, J=6.7 Hz, 1H), 5.29-4.50 (m, 13H), 3.52 (s, 3H), 3.39 (s, 3H), 3.25 (s, 3H), 3.12 (s, 3H), 3.09 (s, 3H), 2.70 (s, 3H), 2.69 (s, 3H), 1.89 (dd, J=6.8, 1.6 Hz, 1H), 1.47-1.18 (m, 15H), 1.08-0.77 (m, 52H); ESI MS m/z 1247 [C$_{63}$H$_{111}$N$_{11}$O$_{14}$+H]$^+$; HPLC>99% (AUC), t$_R$=15.89 min.

Example 33

Preparation of Cyclosporin A Monoester

A solution of CsA diol from Example 30 (45 mg, 0.038 mmol) in methylene chloride (1 mL) was cooled to 0° C. Solution was treated with benzoyl chloride (5.0 mg, 0.03 mmol) and pyridine (10 μl, 0.14 mmol). Reaction was stirred under N$_2$ atmosphere and allowed to slowly warm to room temperature overnight. Reaction was quenched with saturated sodium bicarbonate solution, extracted with methylene chloride, washed with a 10% solution of NaH$_2$PO$_4$ and brine, dried over sodium sulfate, and concentrated in vacuo. The crude product was purified by semi-preparative HPLC to afford CsA monoester (4.2 mg, 6%) as a white solid: $^1$H NMR (300 MHz, CDCl$_3$) δ 8.17 (d, J=7.2 Hz, 1H), 8.00 (d, J=7.9 Hz, 1H), 7.76-7.68 (m, 4H), 7.53 (t, J=13.6 Hz, 2H), 7.42 (t, J=15.9 Hz, 2H), 7.22 (d, J=7.9 Hz, 1H), 5.51 (d, J=6.7 Hz, 1H), 5.14 (d, J=10.8 Hz, 1H), 5.0-4.06 (m, 14H), 3.55 (s, 3H), 3.41 (s, 3H), 3.27 (s, 3H), 3.12 (s, 3H), 3.09 (s, 3H), 2.69 (s, 3H), 2.68 (s, 3H), 1.43-1.25 (m, 9H), 1.08-0.70 (m, 54H); ESI MS m/z 1283 [C$_{66}$H$_{111}$N$_{11}$O$_{14}$+H]$^+$; HPLC 94.9% (AUC), t$_R$=17.39 min.

Example 34

Preparation of Cyclosporin A Amine

A mixture of CsA aldehyde (Va, 200 mg, 0.17 mmol), ammonium acetate (131 mg, 1.70 mmol), sodium cyanoborohydride (21 mg, 0.34 mmol), and acetic acid (48 μl) in methanol (3 mL) was stirred for 24 h at room temperature under N$_2$ atmosphere. Mixture was diluted with ether and then extracted with 1 N HCl. Aqueous layer was neutralized with saturated sodium bicarbonate solution and extracted with ethyl acetate. Organic layer was washed with brine, dried over sodium sulfate, and concentrated in vacuo. The crude product was purified by semi-preparative HPLC to afford CsA amine (19 mg, 9.5%) as a white solid: $^1$H NMR (300 MHz, CDCl$_3$) δ 8.25 (d, J=9.8 Hz, 1H), 8.01 (d, J=6.6 Hz, 1H), 7.53 (d, J=8.7 Hz, 1H), 7.47 (d, J=7.9 Hz, 1H), 5.68 (d, J=10.1 Hz, 2H), 5.29-5.07 (m, 10H), 4.97 (d, J=7.9 Hz, 2H), 4.84 (t, J=14.5 Hz, 2H), 4.69 (s, 1H), 4.45 (t, J=13.9 Hz, 2H), 4.21 (s, 1H), 4.14-3.83 (m, 6H), 3.46 (s, 3H), 3.40 (s, 3H), 3.28 (s, 3H), 3.18 (s, 3H), 3.10 (s, 3H), 2.69 (s, 3H), 2.68 (s, 3H), 1.50 (d, J=6.8 Hz, 1H), 1.43 (s, 1H), 1.30 (dd, J=19.8, 6.8 Hz, 1H), 1.05-0.74 (m, 54H); ESI MS m/z 1178 [C$_{59}$H$_{108}$N$_{12}$O$_{12}$+H]$^+$; HPLC 98.8% (AUC), t$_R$=13.58 min.

Example 35

Preparation of Cyclosporin A Methylamine

A solution of CsA aldehyde (Va, 0.20 g, 0.17 mmol) in CH$_3$OH (3 mL) was treated with methylamine (0.4 mL, 2 M in THF, 0.8 mmol) and allowed to stir for 30 min at room temperature. Reaction was then cooled to 0° C. and treated with NaBH$_4$ (16 mg, 0.85 mmol). Mixture was stirred for an additional 2 h under N2 atmosphere. Mixture was quenched with H$_2$O and diluted with ether. Crude product was extracted with 1 N HCl and then neutralized with saturated sodium bicarbonate solution. Crude product was then extracted with ethyl acetate, washed with brine, dried over sodium sulfate, and concentrated in vacuo. The crude product was purified by semi-preparative HPLC to afford CsA methylamine (6.3 mg, 3%) as an off-white solid: $^1$H NMR (300 MHz, CDCl$_3$) δ 8.04 (d, J=10.1 Hz, 1H), 7.74 (d, J=7.2 Hz, 1H), 7.55 (d, J=8.1 Hz, 1H), 7.46 (d, J=7.8 Hz, 1H), 5.67 (d, J=7.0 Hz, 1H), 5.16-4.81 (m, 7H), 4.68-4.47 (m, 4H), 4.16-4.04 (m, 6H), 3.48 (s, 3H), 3.37 (s, 3H), 3.32 (s, 3H), 3.18 (s, 3H), 3.16 (s, 3H), 2.65 (s, 3H), 2.63 (s, 3H), 2.08 (s, 1H), 2.04 (s, 3H), 1.32-1.23 (m, 9H), 1.06-0.84 (m, 54H); ESI MS m/z 1192 [C$_{60}$H$_{110}$N$_{12}$O$_{12}$+H]$^+$; HPLC 90.6% (AUC), t$_R$=13.32 min.

Example 36

Preparation of Cyclosporin Benzylamine

A solution of CsA amine from Example 34 (50 mg, 0.042 mmol), benzaldehyde (9 mg, 0.84 mmol), sodium cyanoborohydride (13 mg, 0.21 mmol), and acetic acid (100 μl) in methanol (1.5 mL) was allowed to stir overnight at room temperature under N$_2$ atmosphere. Reaction was quenched with saturated sodium bicarbonate solution, extracted with ethyl acetate, washed with brine, dried over sodium sulfate, and concentrated in vacuo. The crude product was purified by semi-preparative HPLC to afford CsA amine (8.4 mg, 15.6%) as an off-white solid: $^1$H NMR (300 MHz, CD$_2$Cl$_2$) δ 8.03 (d, J=8.7 Hz, 1H), 7.80 (d, J=6.5 Hz, 1H), 7.70 (dd, J=5.6, 3.3 Hz, 2H), 7.60 (d, J=7.7 Hz, 1H), 7.55 (dd, J=5.6, 3.2 Hz, 2H), 7.44 (d, J=8.0 Hz, 1H), 7.35 (s, 2H), 5.66 (d, J=7.1 Hz, 1H), 5.24 (d, J=8.1 Hz, 1H), 5.17-4.64 (m, 6H), 4.39 (t, J=14.3 Hz, 2H), 4.34 (s, 1H), 4.24-3.90 (m, 6H), 3.42 (s, 3H), 3.35 (s, 3H), 3.22 (s, 3H), 3.14 (s, 3H), 3.07 (s, 3H), 2.67 (s, 3H), 2.66 (s, 3H), 1.51 (s, 1H), 1.45 (d, J=4.8 Hz, 1H), 1.42-1.18 (m, 10H), 1.05-0.60 (m, 54H); ESI MS m/z 1268 [C$_{66}$H$_{114}$N$_{12}$O$_{12}$+H]$^+$; HPLC 96.5% (AUC), t$_R$=14.89 min.

Example 37

Preparation of Cyclosporin Amide

A solution of CsA amine from Example 34 (65 mg, 0.055 mmol) in methylene chloride (2 mL) was treated with benzoyl chloride (38 mg, 0.28 mmol) and pyridine (45 μl, 0.55 mmol). Reaction mixture was allowed to stir overnight at room temperature under N$_2$ atmosphere. Mixture was diluted with ethyl acetate, washed with 1 N HCl, neutralized with saturated sodium bicarbonate solution, washed with brine, dried over sodium sulfate, and concentrated in vacuo. The crude product was purified by semi-preparative HPLC to afford CsA amide (18.6 mg, 26%) as a white solid: $^1$H NMR (300 MHz, CD$_2$Cl$_2$) δ 8.20 (d, J=9.7 Hz, 1H), 7.79-7.66 (m, 2H), 7.56-7.35 (m, 6H), 7.27 (d, J=7.8 Hz, 1H), 5.67 (dd, J=10.7, 4.1 Hz, 1H), 5.41 (d, J=7.7 Hz, 1H), 5.16-4.94 (m, 9H), 4.81 (t, J=14.5 Hz, 2H), 4.72-4.06 (m, 4H), 3.49 (s, 3H), 3.39 (s, 3H), 3.23 (s, 3H), 3.12 (s, 3H), 3.09 (s, 3H), 2.67 (s, 3H), 2.64 (s, 3H), 2.11 (s, 1H), 1.77-1.54 (m, 8H), 1.47 (d, J=7.41 Hz, 1H), 1.35-1.19 (m, 4H), 1.12-0.68 (m, 50H); ESI MS m/z 1282 [C$_{66}$H$_{112}$N$_{12}$O$_{13}$+H]$^+$; HPLC 99% (AUC), t$_R$=14.69 min.

Example 38

Preparation of Cyclosporin Sulfonamide

A solution of CsA amine from Example 34 (65 mg, 0.055 mmol) in methylene chloride (2 mL) was treated with benzenesulfonyl chloride (49 mg, 0.28 mmol) and pyridine (45 µl, 0.55 mmol). Reaction mixture was allowed to stir overnight at room temperature under N$_2$ atmosphere. Mixture was diluted with ethyl acetate, washed with 1 N HCl, neutralized with saturated sodium bicarbonate solution, washed with brine, dried over sodium sulfate, and concentrated in vacuo. The crude product was purified by semi-preparative HPLC to afford CsA sulfonamide (12.4 mg, 17%) as an off white solid: $^1$H NMR (300 MHz, CD$_2$Cl$_2$) δ 8.36 (d, J=9.9 Hz, 1H), 7.77 (dd, J=7.6, 1.2 Hz, 2H), 7.70 (d, J=6.9 Hz, 1H), 7.56-7.37 (m, 5H), 7.29 (d, J=8.9 Hz, 1H), 6.51 (d, J=7.1 Hz, 1H), 5.64 (dd, J=11.2, 3.9 Hz, 1H), 5.39 (dd, J=11.6, 4.1 Hz, 1H), 5.20 (d, J=10.1 Hz, 1H), 5.14-4.58 (m, 10 H), 4.35 (t, J=14.1 Hz, 2H), 4.03 (d, J=10.1 Hz, 1H), 3.81 (d, J=6.7 Hz, 1H), 3.41 (s, 3H), 3.34 (s, 3H), 3.16 (s, 3H), 3.15 (s, 3H), 3.13 (s, 3H), 2.60 (s, 3H), 2.59 (s, 3H), 2.02 (s, 1H), 1.54 (s, 1H), 1.47 (d, J=7.5 Hz, 3H), 1.44-0.60 (m, 54H), 0.57 (d, J=6.4 Hz, 4H); ESI MS m/z 1318 [C$_{65}$H$_{112}$N$_{12}$O$_{14}$S+H]$^+$; HPLC 97.6% (AUC), t$_R$=15.17 min.

Example 39

Preparation of Cyclosporin Amine

A solution of CsA methylamine from Example 35 (50 mg, 0.042 mmol) in methylene chloride (1.5 mL) was treated with crotyl chloride (38 mg, 0.42 mmol) and allowed to stir for 24 h at room temperature under N$_2$ atmosphere. Reaction was quenched with water, extracted with ether, washed with brine, dried over sodium sulfate, and concentrated in vacuo. The crude product was purified by semi-preparative HPLC to afford CsA amine (5.4 mg, 10%) as a pale yellow solid: $^1$H NMR (300 MHz, CDCl$_3$) δ 7.92 (d, J=9.2 Hz, 1H), 7.86 (d, J=7.3 Hz, 1H), 7.48 (d, J=5.4 Hz, 1H), 7.26 (d, J=covered by solvent peak, 1H), 5.70 (d, J=7.1 Hz, 1H), 5.24-4.84 (m, 12H), 4.72 (d, J=12.8 Hz, 2H), 4.42 (d, J=6.5 Hz, 1H), 4.14-4.06 (m, 2H), 3.62 (s, 3H), 3.40 (s, 3H), 3.24 (s, 3H), 3.18 (s, 3H), 3.14 (s, 3H), 3.10 (s, 3H), 2.70 (s, 3H), 2.16-1.92 (m, 8H), 1.77-1.62 (m, 7H), 1.34 (d, J=5.2 Hz, 2H), 1.26 (d, J=5.1 Hz, 2H), 1.07-0.67 (m, 54H); ESI MS m/z 1246 [C$_{64}$H$_{116}$N$_{12}$O$_{12}$+H]$^+$; HPLC 96.8% (AUC), t$_R$=13.67 min.

Example 40

Preparation of Cyclosporin Amine

A solution of CsA methylamine from Example 35 (50 mg, 0.042 mmol) in methylene chloride (1.5 mL) was treated with benzyl bromide (72 mg, 0.42 mmol) and allowed to stir for 24 h at room temperature under N2 atmosphere. Reaction was quenched with water, extracted with ether, washed with brine, dried over sodium sulfate, and concentrated in vacuo. The crude product was purified by semi-preparative HPLC to afford CsA amine (3.5 mg, 7%) as an off-white solid: $^1$H NMR (300 MHz, CD$_2$Cl$_2$) δ 7.68 (d, J=6.3 Hz, 1H), 7.31 (d, J=7.3 Hz, 6H), 7.18 (d, J=7.9 Hz, 1H), 5.68 (d, J=7.1 Hz, 1H), 5.16-5.02 (m, 4H), 4.82 (t, J=14.6 Hz, 2H), 4.74-4.64 (m, 4H), 3.56 (s, 3H), 3.38 (s, 3H), 3.19 (s, 3H), 3.11 (s, 3H), 3.06 (s, 3H), 2.69 (s, 3H), 2.66 (s, 3H), 1.69-1.55 (m, 8H), 1.33-1.22 (m, 14H), 1.06-0.73 (m, 54H); ESI MS m/z 1282 [C$_{67}$H$_{116}$N$_{12}$O$_{12}$+H]$^+$; HPLC 98.6% (AUC), t$_R$=13.85 min.

Example 41

Preparation of Cyclosporin Amide

A solution of CsA methylamine from Example 35 (75 mg, 0.063 mmol) in methylene chloride (2 mL) was treated with benzoyl chloride (45 mg, 0.32 mmol) and pyridine (51 µl, 0.63 mmol). Reaction mixture was allowed to stir for 24 h at room temperature under N$_2$ atmosphere. Mixture was diluted with ethyl acetate, washed with 1 N HCl, neutralized with saturated sodium bicarbonate solution, washed with brine, dried over sodium sulfate, and concentrated in vacuo. The crude product was purified by semi-preparative HPLC to afford CsA amide (9.6 mg, 11%) as a pale yellow solid: $^1$H NMR (300 MHz, CD$_2$Cl$_2$) δ 8.16 (d, J=8.9 Hz, 1H), 7.70 (dd, J=5.6, 3.3 Hz, 1H), 7.55 (dd, J=5.6, 3.2 Hz, 1H), 7.49 (d, J=8.1 Hz, 1H), 7.39 (s, 5H), 7.32 (d, J=8.0 Hz, 1H), 5.67 (d, J=7.6 Hz, 1H), 5.24-4.90 (m, 12), 4.79 (t, J=13.4 Hz, 2H), 4.71 (s, 1H), 4.66 (s, 1H), 4.60 (s, 1H), 4.31 (s, 2H), 4.19 (dd, J=5.6, 3.4 Hz, 1H), 4.14 (s, 2H), 3.44 (s, 3H), 3.36 (s, 3H), 3.21 (s, 3H), 3.14 (s, 3H), 3.08 (s, 3H), 2.90 (s, 3H), 2.66 (s, 3H), 1.51-1.39 (m, 4H), 1.35-1.22 (m, 6H), 1.05-0.82 (m, 50H); ESI MS m/z 1296 [C$_{67}$H$_{114}$N$_{12}$O$_{13}$+H]$^+$; HPLC 95.9% (AUC), t$_R$=14.42 min.

Example 42

Preparation of Cyclosporin Sulfonamide

A solution of CsA methylamine from Example 35 (70 mg, 0.059 mmol) in methylene chloride (2 mL) was treated with benzenesulfonyl chloride (53 mg, 0.30 mmol) and pyridine (48 µl, 0.59 mmol). Reaction mixture was allowed to stir for 24 h at room temperature under N$_2$ atmosphere. Triethylamine (82 µl, 0.30 mmol) was added and stirred for an additional hour to push the reaction to completion. Mixture was diluted with ethyl acetate, washed with 1 N HCl, neutralized with saturated sodium bicarbonate solution, washed with brine, dried over sodium sulfate, and concentrated in vacuo. The crude product was purified by semi-preparative HPLC to afford CsA sulfonamide (6.6 mg, 8.5%) as an off-white solid: $^1$H NMR (300 MHz, CD$_2$Cl$_2$) δ 7.89 (d, J=9.6 Hz, 1H), 7.77 (d, J=9.68 Hz, 3H), 7.61-7.47 (m, 5H), 7.38 (d, J=8.2 Hz, 1H), 7.07 (d, J=7.8 Hz, 1H), 5.71-5.66 (m, 2H), 5.52 (d, J=4.7 Hz, 1H), 5.22-4.37 (m, 18H), 4.20 (s, 2H), 4.13 (s, 3H), 3.90 (d, J=9.1 Hz, 1H), 3.45 (s, 3H), 3.32 (s, 3H), 3.24 (s, 3H), 3.08 (s, 3H), 2.70 (s, 3H), 2.68 (s, 3H), 2.65 (s, 3H), 1.97 (s, 1H), 1.53-1.22 (m, 12H), 1.14-0.71 (m, 42H); ESI MS m/z 1332 [C$_{66}$H$_{114}$N$_{12}$O$_{14}$S+H]$^+$; HPLC 60.5% (AUC), t$_R$=14.63 min.

Example 43

Preparation of Cyclosporin Vinyl Iodide (cis-Isomer)

To a vigorously stirred suspension of iodomethyltriphenylphosphonium iodide (612 mg, 1.1 mmol) in dry THF (8 mL) under nitrogen, was added sodium bis(trimethylsilyl)amide (1.1 mL, 1 M in THF, 1.1 mmol). After 10 min at room temperature, the mixture was cooled to 0° C. and CsA aldehyde (Va, 136 mg, 0.11 mmol) in anhydrous THF (5 mL) was added dropwise. After 15 min at −78° C., the reaction was allowed to warm up to room temperature. After 5 min, a saturated solution of ammonium chloride (5 mL) was added. The residue was extracted with ethyl acetate (3×200 mL), the combined organic extracts were filtered through a plug of diatomaceous earth, washed with an aqueous solution of sodium hydrogensulfite (20%, 200 mL), then dried over anhydrous sodium sulfate and concentrated under vacuum to afford crude product (145 mg). The material was purified by preparative thin layer chromatography (silica gel, 1:1 acetone/hexanes) followed by semi-preparative HPLC to afford cis-vinyl iodide (7.1 mg, 5%) as a colorless oil: $^1$H NMR (300 MHz, CDCl$_3$) δ 7.85 (d, J=9.5 Hz, 1H), 7.61 (d, J=7.4 Hz, 1H), 7.55 (d, J=8.0 Hz, 1H), 7.09 (d, J=7.9 Hz, 1H), 6.22 (d, J=6.2 Hz, 1H), 6.06 (t, J=8.0 Hz, 1H), 5.74-4.54 (m, 12H), 4.02 (m, 1H), 3.59 (s, 3H), 3.36 (s, 3H), 3.27 (s, 3H), 3.12 (s, 3H), 3.09 (s, 3H), 2.74 (s, 3H), 2.71 (s, 3H), 2.42-0.79 (m, 66H); ESI MS m/z 1301 [C$_{60}$H$_{106}$IN$_{11}$O$_{12}$+H]$^+$; HPLC>92% (AUC), t$_R$=15.85 min.

Example 44

Preparation of Cyclosporin Vinyl Iodide
(trans-Isomer)

To a suspension of chromium chloride (314 mg, 2.55 mmol) in THF (5 mL) under stirring and nitrogen, was added a solution of iodoform (334 mg, 0.85 mmol) and CsA aldehyde (Va, 100 mg, 0.085 mmol) in THF (10 mL) at 0° C. After 1 h at 0° C., the reaction was poured into ice water and extracted with ethyl acetate (2×200 mL). The organic layer was separated, dried over anhydrous sodium sulfate, and concentrated under vacuum. The crude material was purified by preparative thin layer chromatography (SiO$_2$, 1:1 hexanes/acetone) followed by semi-preparative HPLC to afford trans-vinyl iodide (3.5 mg, 3%) as a pale yellow oil: $^1$H NMR (300 MHz, CDCl$_3$) δ 8.21 (d, J=9.7 Hz, 1H), 7.85 (d, J=9.0 Hz, 1H), 7.41-7.31 (m, 2H), 7.19 (d, J=7.8 Hz, 1H), 6.50 (dd, J=14.5 Hz, 7.4 Hz, 1H), 6.12 (d, J=14.5 Hz, 1H), 5.72-5.65 (m, 1H), 5.31-5.24 (m, 1H), 5.50-4.67 (m, 12H), 4.49 (m, 1H), 3.48 (s, 3H), 3.40 (s, 3H), 3.28 (s, 3H), 3.14 (s, 6H), 2.69 (s, 3H), 2.68 (s, 3H), 2.35-0.70 (m, 63H); ESI MS m/z 1301 [C$_{60}$H$_{106}$IN$_{11}$O$_{12}$+H]$^+$; HPLC 97.4% (AUC), t$_R$=17.59 min.

Example 45

Preparation of Cyclosporin Pyrimidine

To a solution of trans-vinyl iodide from Example 44 (48 mg, 0.036 mmol) in toluene (10 mL) under nitrogen, were added 5-pyrimidyltrimethylstannane (180 mg, 0.73 mmol) and tetrakis(triphenylphosphine)palladium (6 mg, 5.5 μmol). After 15 h at 80° C., the mixture was cooled down to room temperature and solvent was removed under reduced pressure. The crude material was purified by semi-preparative HPLC to afford CsA pyrimidine (6.8 mg, 15%) as a pale yellow oil: $^1$H NMR (300 MHz, CDCl$_3$) δ 9.03 (s, 1H), 8.83 (s, 2H), 8.10 (d, J=9.6 Hz, 1H), 7.87 (d, J=7.8 Hz, 1H), 7.50 (d, J=7.9 Hz, 1H), 7.10 (d, J=8.0 Hz, 1H), 6.65 (dd, J$_1$=16.3 Hz, 7.6 Hz, 1H), 6.37 (d, J=16.2 Hz, 1H), 5.81-5.75 (m, 2H), 5.30-4.50 (m, 13H), 3.48 (s, 3H), 3.39 (s, 3H), 3.33 (s, 3H), 3.12 (s, 3H), 3.10 (s, 3H), 2.73 (s, 3H), 2.68 (s, 3H), 2.40-0.70 (m, 64H); ESI MS m/z 1253 [C$_{64}$H$_{109}$N$_{13}$O$_{12}$+H]$^+$; HPLC>99% (AUC), t$_R$=15.13 min.

Example 46

Preparation of Cyclosporin Thiazole

To a solution of trans-vinyl iodide from Example 44 (41 mg, 0.031 mmol) in THF (2 mL) under stirring and nitrogen, were added 2-thiazolylzinc bromide (0.31 mL, 1 M in THF, 0.31 mmol) and dichlorobis(triphenylphosphine)palladium (II) (3 mg, 0.047 mmol). After 4 h at room temperature, the solvent was removed under reduced pressure. The crude material was purified by semi-preparative HPLC to afford CsA thiazole (12 mg, 30%) as a white solid: $^1$H NMR (300 MHz, CD$_2$Cl$_2$) δ 7.95-7.89 (m, 1H), 7.73-7.66 (m, 1H), 7.53-7.47 (m, 3H), 7.21 (d, J=7.6 Hz, 1H), 6.95 (dd, J$_1$=16.1 Hz, 7.5 Hz, 1H), 6.82 (d, J=16.0 Hz, 1H), 5.73-5.65 (m, 1H), 5.62-5.59 (m, 1H), 5.10-4.20 (m, 11H), 3.35 (s, 3H), 3.24 (s, 3H), 3.10 (s, 3H), 3.08 (s, 3H), 2.71 (s, 3H), 2.70 (s, 3H), 2.66-0.70 (m, 69H). ESI MS m/z 1258 [C$_{63}$H$_{108}$N$_{12}$O$_{12}$S+H]$^+$; HPLC 90% (AUC), t$_R$=14.94 min.

Example 47

Preparation of Cyclosporin Thiophene

To a solution of trans-vinyl iodide from Example 44 (38 mg, 0.029 mmol) in THF (2 mL) under stirring and nitrogen, were added 2-thiophenylzinc bromide (0.58 mL, 0.5 M in THF, 0.58 mmol) and dichlorobis(triphenylphosphine)palladium(II) (20 mg, 0.028 mmol). After 18 h at room temperature, the solvent was removed under reduced pressure. The crude material was purified by semi-preparative HPLC to afford CsA thiophene (3.9 mg, 10%) as a yellowish solid: $^1$H NMR (300 MHz, CDCl$_3$) δ 8.01 (d, J=9.9 Hz, 1H), 7.90 (d, J=7.2 Hz, 1H), 7.49 (d, J=8.4 Hz, 1H), 7.32-7.29 (m, 1H), 7.08-7.05 (m, 1H), 6.97-6.90 (m, 2H), 6.50 (d, J=15.8 Hz, 1H), 6.05 (dd, J$_1$=8.0 Hz, J$_2$=15.9 Hz, 1H), 5.77-5.68 (m, 1H), 5.48-4.45 (m, 16H), 4.05-4.01 (m, 1H), 3.65 (m, 1H), 3.51 (s, 3H), 3.38 (s, 3H), 3.23 (s, 3H), 3.11 (s, 3H), 3.08 (s, 3H), 2.70 (s, 6H), 2.65-0.71 (m, 63H); ESI MS m/z 1257 [C$_{64}$H$_{109}$N$_{11}$O$_2$S+H]$^+$; HPLC 96.8% (AUC), t$_R$=15.98 min.

Example 48

Preparation of Cyclosporin Diol

To a solution of phenylmagnesium bromide (1.0 M in ether, 1.29 mL, 1.29 mmol) in THF (4 mL), was added zinc chloride (1.0 M in ether, 1.29 mL, 1.29 mmol) at 0° C. The mixture was stirred under nitrogen at 0° C. for 30 min and CsA aldehyde (Va, 50 mg, 0.043 mmol) was added. The mixture was allowed to slowly warm to room temperature and stirred for 4 h, quenched with saturated aqueous ammonium chloride, extracted with ether. The combined organic layers were washed with brine, dried over sodium sulfate, filtered and concentrated in vacuo. The residue was purified by semi-preparative HPLC to afford CsA diol (7 mg, 13%) as a white solid: $^1$H NMR (300 MHz, CDCl$_3$) δ 8.09 (d, J=9.8 Hz, 1H), 7.68 (d, J=6.8 Hz, 1H), 7.55-7.10 (m, 7H), 5.75-4.15 (m, 11H), 3.62 (s, 3H), 3.5-2.2 (m, 2H), 3.42 (s, 3H), 3.24 (s, 3H), 3.13 (s, 3H), 3.09 (s, 3H), 2.69 (s, 3H), 2.68 (s, 3H), 2.10-1.50

(m, 8H), 1.40-0.75 (m, 60H); APCI MS m/z 1254 $[C_{65}H_{111}N_{11}O_{13}+H]^+$; HPLC>99% (AUC), $t_R$=15.85 min.

Example 49

Preparation of Cyclosporin Diol

To a solution of zinc chloride (1.0 M in ether, 0.85 mL, 0.85 mmol) in THF (4 mL), was added benzylmagnesium chloride (1.0 M in ether, 0.85 mL, 0.85 mmol) at 0° C. The mixture was stirred under nitrogen at 0° C. for 30 min and CsA aldehyde (Va, 50 mg, 0.043 mmol) was added. The mixture was allowed to slowly warm to room temperature and quenched with saturated aqueous ammonium chloride, extracted with ether. The combined organic layers were washed with brine, dried over sodium sulfate, filtered and concentrated in vacuo. The residue was purified by semi-preparative HPLC to afford CsA diol (5 mg, 10%) as a white solid: $^1$H NMR (300 MHz, CDCl$_3$) δ 8.03 (d, J=9.8 Hz, 1H), 7.68 (d, J=6.8 Hz, 1H), 7.55-7.10 (m, 7H), 5.75-4.10 (m, 11H), 3.52 (s, 3H), 3.5-2.2 (m, 4H), 3.35 (s, 3H), 3.28 (s, 3H), 3.10 (s, 3H), 3.09 (s, 3H), 2.71 (s, 3H), 2.69 (s, 3H), 2.10-1.50 (m, 8H), 1.40-0.75 (m, 60H); APCI MS m/z 1268 $[C_{66}H_{113}N_{11}O_{13}+H]^+$; HPLC>99% (AUC), $t_R$=15.90 min.

Example 50

Preparation of Cyclosporin Oxime

A solution of CsA aldehyde (Va, 460 mg, 0.39 mmol) in pyridine (2 mL) was treated with hydroxylamine hydrochloride (27 mg, 0.39 mmol). Reaction mixture was allowed to stir for 1.5 h at room temperature under N$_2$ atmosphere. Mixture was then diluted with ether, washed with 1 N HCl, neutralized with saturated sodium bicarbonate solution, washed with brine, dried over sodium sulfate, and concentrated in vacuo to afford 516 mg of crude product. 50 mg of the crude product was purified by semi-preparative HPLC to afford CsA oxime (6.3 mg, 12.6%) as a white solid: $^1$H NMR (300 MHz, CD$_2$Cl$_2$) δ 8.28 (s, 1H), 8.17 (d, J=9.8 Hz, 1H), 7.90 (d, J=7.6 Hz, 1H), 7.59 (d, J=7.8 Hz, 1H), 7.28 (d, J=7.3 Hz, 1H), 7.16 (d, J=8.2 Hz, 1H), 5.67-5.57 (m, 3H), 5.45 (d, J=7.0 Hz, 1H), 5.36-4.93 (m, 8H), 4.69 (s, 1H), 4.64 (s, 1H), 4.59-4.41 (m, 4H), 4.07-3.97 (m, 2H), 3.36 (s, 3H), 3.35 (s, 3H), 3.23 (s, 3H), 3.07 (s, 3H), 3.04 (s, 3H), 2.68 (s, 3H), 2.62 (s, 3H), 1.99 (s, 1H), 1.97 (s, 1H), 1.44-1.67 (m, 5H), 1.08-0.62 (m, 52H); ESI MS m/z 1192 $[C_{59}H_{106}N_{12}O_{13}+H]^+$; HPLC 97.8% (AUC), $t_R$=13.97 min.

Example 51

Preparation of Cyclosporin Oxime

A mixture of CsA aldehyde (Va, 50 mg, 0.043 mmol), O-methylhydroxyamine hydrochloride (3.6 mg, 0.043 mmol) and pyridine (0.5 mL) was stirred at room temperature for 1 h, and then diluted with ether, washed with 0.5 N HCl, saturated aqueous sodium bicarbonate and brine, dried over sodium sulfate, filtered and concentrated in vacuo. The residue was pre-purified by preparative thin layer chromatography (1:1 hexanes/acetone) to give the crude product (15 mg), which was purified by semi-preparative HPLC to afford CsA oxime (10 mg, 20%) as a white solid: $^1$H NMR (300 MHz, CDCl$_3$) δ 8.40 (d, J=9.8 Hz, 1H), 7. 86 (d, J=7.0 Hz, 1H), 7.50-7.47 (m, 2H), 7.32 (d, J=5.0 Hz, 1H), 5.75-4.15 (m, 11H), 3.69 (s, 3H), 3.49 (s, 3H), 3.42 (s, 3H), 3.25 (s, 3H), 3.16 (s, 3H), 3.06 (s, 3H), 2.69 (s, 3H), 2.68 (s, 3H), 2.25-1.50 (m, 8H), 1.40-0.75 (m, 60H); APCI MS m/z 1205 $[C_{60}H_{108}N_{12}O_{13}S+H]^+$; HPLC 91.7% (AUC), $t_R$=15.66 min.

Example 52

Preparation of Cyclosporin Oxime

A mixture of CsA aldehyde (Va, 50 mg, 0.043 mmol), O-ethylhydroxyamine hydrochloride (4.2 mg, 0.043 mmol) and pyridine (0.5 mL) was stirred at room temperature for 1 h, and then diluted with ether, washed with 0.5 N HCl, saturated aqueous sodium bicarbonate and brine, dried over sodium sulfate, filtered and concentrated in vacuo. The residue was purified by semi-preparative HPLC to afford CsA oxime (16 mg, 31%) as a white solid: $^1$H NMR (300 MHz, CDCl$_3$) δ 8.44 (d, J=9.8 Hz, 1H), 7.88 (d, J=6.8 Hz, 1H), 7.57-7.52 (m, 2H), 7.32 (d, J=5.0 Hz, 1H), 5.80-4.10 (m, 11H), 3.94 (q, J=6.8 Hz, 2H), 3.48 (s, 3H), 3.42 (s, 3H), 3.24 (s, 3H), 3.16 (s, 3H), 3.06 (s, 3H), 2.69 (s, 3H), 2.68 (s, 3H), 2.25-1.50 (m, 8H), 1.40-0.75 (m, 63H); APCI MS m/z 1219 $[C_{61}H_{110}N_{12}O_{13}+H]^+$; HPLC 90.4% (AUC), $t_R$=15.98 min.

Example 53

Preparation of Cyclosporin Oxime

A mixture of CsA aldehyde (Va, 50 mg, 0.043 mmol), O-allylhydroxyamine hydrochloride (4.7 mg, 0.043 mmol) and pyridine (0.5 mL) was stirred at room temperature for 1 h, and then diluted with ether, washed with 0.5 N HCl, saturated aqueous sodium bicarbonate and brine, dried over sodium sulfate, filtered and concentrated in vacuo. The residue was purified by semi-preparative HPLC to afford CsA oxime (14 mg, 27%) as a white solid: $^1$H NMR (300 MHz, CDCl$_3$) δ 8.41 (d, J=9.8 Hz, 1H), 7.86 (d, J=6.8 Hz, 1H), 7.50-7.47 (m, 2H), 7.36 (d, J=5.0 Hz, 1H), 6.05-4.10 (m, 16H), 3.49 (s, 3H), 3.42 (s, 3H), 3.22 (s, 3H), 3.16 (s, 3H), 3.06 (s, 3H), 2.69 (s, 6H), 2.35-1.50 (m, 8H), 1.40-0.75 (m, 60H); APCI MS m/z 1231 $[C_{62}H_{110}N_{12}O_{13}+H]^+$; HPLC 95.0% (AUC), $t_R$=16.20 min.

Example 54

Preparation of Cyclosporin Oxime

A mixture of CsA aldehyde (Va, 50 mg, 0.043 mmol), O-benzylhydroxyamine hydrochloride (6.9 mg, 0.043 mmol) and pyridine (0.5 mL) was stirred at room temperature for 1 h, and then diluted with ether, washed with 0.5 N HCl, saturated aqueous sodium bicarbonate and brine, dried over sodium sulfate, filtered and concentrated in vacuo. The residue was purified by semi-preparative HPLC to afford CsA oxime (13 mg, 24%) as a white solid: $^1$H NMR (300 MHz, CDCl$_3$) δ 8.44 (d, J=9.8 Hz, 1H), 7.85 (d, J=6.8 Hz, 1H), 7.38-7.29 (m, 8H), 5.80-4.10 (m, 13H), 3.49 (s, 3H), 3.42 (s, 3H), 3.16 (s, 3H), 3.06 (s, 3H), 2.93 (s, 3H), 2.68 (s, 3H), 2.67 (s, 3H), 2.35-1.50 (m, 8H), 1.40-0.75 (m, 60H); APCI MS m/z 1281 $[C_{66}H_{112}N_{12}O_{13}+H]^+$; HPLC 95.7% (AUC), $t_R$=16.97 min.

Example 55

Preparation of Cyclosporin Hydrazone

A mixture of CsA aldehyde (Va, 50 mg, 0.043 mmol), p-toluenesulfonhydrazide (7.9 mg, 0.043 mmol) and ethanol (1 mL) was stirred at 60° C for 30 min, and then cooled to room temperature. The solvents were removed in vacuo and the crude product was purified by preparative thin layer chromatography (4:1 ethyl acetate/acetone) to give CsA hydrazone (10 mg, 18%) as a white solid: $^1$H NMR (300 MHz, CDCl$_3$) δ 8.55 (d, J=9.8 Hz, 1H), 8.45 (s, 1H), 8.04-8.00 (m, 2H), 7.86 (d, J=8.2 Hz, 2H), 7.47 (d, J=8.0 Hz, 1H), 7.27 (d, J=8.2 Hz, 2H), 6.91 (d, J=5.0 Hz, 1H), 5.75-4.05 (m, 1H), 3.44 (s, 3H), 3.43 (s, 3H), 3.39 (s, 3H), 3.18 (s, 3H), 3.09 (s, 3H), 2.68 (s, 3H), 2.67 (s, 3H), 2.38 (s, 3H), 2.25-1.50 (m, 10H), 1.40-0.60 (m, 58H); APCI MS m/z 1344 [C$_{66}$H$_{113}$N$_{13}$O$_{14}$S+H]$^+$; HPLC>99% (AUC), t$_R$=16.08 min.

Example 56

Preparation of Cyclosporin Diene (X=OAc)

A solution of CsA alcohol IVb (X=OAc, 180 mg) in benzene (10 mL) was treated with Burgess reagent (50 mg, 0.21 mmol) at reflux for 24 h under N$_2$, and then cooled to room temperature, quenched with 4 mL of H$_2$O, separated. The aqueous layer was extracted with EtOAc (3×10 mL), and the combined organic layers were dried over Na$_2$SO$_4$, concentrated to dryness. The residue was purified via semi-preparative HPLC to give CsA diene (X=OAc, 25 mg, 14%) as a white solid: $^1$H NMR (CDCl$_3$, 300 MHz) δ 8.55 (d, J=9.6 Hz, 11H), 8.05 (d, J=6.7 Hz, 1H), 7.62 (dd, J=7.9 Hz, 2.0 Hz, 2H), 5.92 (dd, J=15.1, 4.6, Hz, 1H), 5.68 (dd, J=10.9, 4.0, Hz, 1H), 5.60 (d, J=5.6 Hz, 1H), 5.54 (d, J=10.1 Hz, 1H), 5.36 (d, J=11.4 Hz, 1 H), 5.31 (dd, J=10.7, 4.0, Hz, 1H), 5.16 (dd, J=10.9, 4.0, Hz, 1H), 5.10-4.93 (m, 4H), 4.85 (dt, J=15.0, 7.3 Hz, 2H), 4.65 (d, J=13.7 Hz, 1H), 4.43 (t, J=7.0 Hz, 1H), 3.45 (s, 3H), 3.29 (s, 3H), 3.28 (s, 3H), 3.20 (s, 3H), 3.02 (s, 3H), 2.67 (s, 3H),.2.65 (s, 3H), 2.13-1.99 (m, 5H), 1.95 (s, 3H), 1.83-0.70 (m, 63H); ESI MS m/z 1243 [C$_{64}$H$_{111}$N$_{11}$O$_{13}$+H]$^+$; HPLC>99% (AUC), t$_R$=17.6 min.

Example 57

Preparation of Cyclosporin Diene (X=OH)

CsA diene from Example 56(X=OAc, 28 mg, 0.022 mmol) was dissolved in 2 mL of methanol, and then K$_2$CO$_3$ (155 mg, 1.127 mmol) was added. The mixture was stirred at room temperature for 5 h, diluted with 50 mL of ethyl acetate, washed with water (10 mL), brine (10 mL) and dried over Na$_2$SO$_4$. The solvent was removed in vacuo, the residue was purified via semi-preparative HPLC to give CsA diene (X=OH, 9.0 mg, 33%) as a white solid: $^1$H NMR (CDCl$_3$, 300 MHz) δ 8.27 (d, J=9.8 Hz, 1H), 7.90 (d, J=7.2 Hz, 1H), 7.54 (d, J=8.6 Hz, 1H), 7.36 (d, J=8.0 Hz, 1H), 6.09 (t, J=5.6 Hz, 1 H), 6.05 (d, J=4.8 Hz, 2H), 5.71 (dd, J=11.1, 4.1 Hz, 1H), 5.62 (dd, J=14.4, 6.8 Hz, 1H), 5.78-4.98 (m, 12H), 4.85 (t, J=7.0 Hz, 2H), 4.72 (t, J=8.5 Hz, 1H), 4.68 (d, J=3.4 Hz, 1H), 4.48 (t, J=7.2 Hz, 1H), 3.96 (dd, J=8.2, 3.6 Hz, 1H), 3.49 (s, 3H), 3.41(s, 3H), 3.31 (s, 3H), 3.14 (s, 3H), 3.07 (s, 3H), 2.70 (s, 3H), 2.69 (s, 3H), 2.66-2.44 (m, 6H), 2.15-2.05 (m, 7H), 1.71-1.62 (m, 6H), 1.42-0.72 (m, 42H); ESI MS m/z 1201 [C$_{62}$H$_{109}$N$_{11}$O$_{12}$+H]$^+$; HPLC 98.2% (AUC), t$_R$=15.2 min.

Example 58

Preparation of Cyclosporin Diene (X=OH)

Cyclosporine diene from Example 57 (X=OH, 11 mg, 0.009 mmol) was dissolved in 2 mL of CH$_2$Cl$_2$, then methyl acrylate (8 mg, 0.09 mmol) and Grubbs' catalyst 3$^{rd}$ generation (3 mg, 0.0045 mmol) were added. The mixture was refluxed for 1.5 h, and then the solvent was removed in vacuo. The residue was purified via semi-preparative HPLC to give CsA diene (X=OH, 3.4 mg, 29%) as a white solid: $^1$H NMR (CDCl$_3$, 300 MHz) δ 8.20 (d, J=10.1 Hz, 1H), 7.86 (d, J=8.0 Hz, 1H), 7.45 (d, J=8.5 Hz, 1H), 7.10 (dd, J=15.5, 10.2 Hz, 1H), 6.13 (t, J=5.2 Hz, 1H), 5.85 (d, J=15.4 Hz, 1H), 5.70 (d, J=7.7 Hz, 1H), 5.45 (d, J=7.5 Hz, 1H), 5.18-4.97 (m, 8H), 4.85 (t, J=6.8 Hz, 2H), 4.73 (m, 3H), 4.52 (t, J=7.4 Hz, 1H), 3.99 (m, 1H), 3.73 (s, 3H), 3.48 (s, 3H), 3.40 (s, 3H), 3.35 (s, 3H), 3.14 (s, 3H), 3.08 (s, 3H), 2.70 (s, 3H), 2.69 (s, 3H), 2.12-0.62 (m, 64H); ESI MS m/z 1259 [C$_{64}$H$_{111}$N$_{11}$O$_{14}$+H]$^+$; HPLC 98.1% (AUC), t$_R$=14.7 min.

Example 59

Preparation of Cyclosporin Diene (X=OH)

Cyclosporin diene from Example 57 (X=OH, 11 mg, 0.009 mmol) was dissolved in 3 mL of CH$_2$Cl$_2$, and then styrene (10 mg, 0.09 mmol) and Grubbs' catalyst 2$^{nd}$ generation (17 mg, 0.02 mmol) were added. The mixture was refluxed for 8 h. After that, the solvent was removed in vacuo, and the residue was purified via semi-preparative HPLC to give ALB 16085 (11 mg, 99%) as a white solid: $^1$H NMR (CD$_2$Cl$_2$, 500 MHz) δ 8.28 (d, J=9.0 Hz, 1H), 7.96 (d, J=6.83 Hz, 1H), 7.52 (d, J=8.9 Hz, 1H), 7.42 (d, J=7.5 Hz, 1H), 7.38 (d, J=6.5 Hz, 3H), 7.30 (t, J=7.6 Hz, 3H), 7.22 (m, 1H), 6.45 (d, J=15.6 Hz, 1H), 6.24 (dd, J=15.9, 6.4 Hz, 1H), 5.66 (dd, J=1.1, 3.8 Hz, 1H), 5.21 (m, 4H), 5.04 (t, J=7.3 Hz, 1H), 5.01-4.90 (m, 4H), 4.82 (t, J=7.0 Hz, 2H), 4.64 (d, J=13.8 Hz, 2H), 4.35 (m, 3H), 4.14 (t, J=4.5 Hz, 1H), 3.48 (s, 3H), 3.32 (s, 3H), 3.23 (s, 3H), 3.14 (s, 3H), 3.13 (m, 2H), 3.04 (s, 3H), 2.65 (s, 3H),2.63 (s, 3H), 2.32 (m, 2H), 2.22-0.62 (m, 57H); ESI MS m/z 1276 [C$_{68}$H$_{113}$N$_{11}$O$_{12}$+H]$^+$; HPLC>99% (AUC), t$_R$=16.2 min.

Example 60

Preparation of Cyclosporin Diene (X=OH)

CsA diene from Example 57 (X=OH, 50 mg, 0.042 mmol) was dissolved in 4 mL of CH$_2$Cl$_2$, then vinylcyclopentane (40 mg, 0.42 mmol) and Grubbs' catalyst 2$^{nd}$ generation (18 mg, 0.021 mmol) were added. The mixture was refluxed overnight. After that, the solvent was removed in vacuo, and the residue was purified via semi-preparative HPLC to give CsA diene (10 mg, 18%) as a white solid: $^1$H NMR (CDCl$_3$, 500 MHz) δ 8.38 (d, J=9.5 Hz, 1H), 8.07 (d, J=6.7 Hz, 1H), 7.61 (d, J=9.1 Hz, 1H), 7.47 (d, J=8.0 Hz, 1H), 5.70 (dd, J=11.0, 4.1 Hz, 1H), 5.48 (d, J=7.2 Hz, 1H), 5.40 (d, J=7.2 Hz, 1H), 5.34 (dd, J=11.3, 4.1 Hz, 1H), 5.23 (d, J=11.0 Hz, 1H), 5.14 (m, 2H), 5.08 (t, J=7.0 Hz, 1H), 4.98 (m, 2H), 4.86 (t, J=7.3 Hz, 1H), 4.68 (d, J=13.8 Hz, 1H), 4.41 (t, J=7.1 Hz, 1H), 4.04 (m, 2H), 3.50 (s, 3H), 3.38 (s, 3H), 3.25 (s, 3H), 3.18 (s, 3H), 3.07 (s, 3H), 2.70 (s, 3H), 2.68 (s, 3H), 2.40 (q, J=7.8 Hz, 1H), 2.31 (q, J=6.7 Hz, 1H), 2.22-0.62 (m, 75H); ESI MS m/z 1269 [C$_{67}$H$_{117}$N$_{11}$O$_{12}$+H]$^+$; HPLC>99% (AUC), t$_R$=17.3 min.

Example 61

Preparation of Cyclosporin Diene (X=OH)

A 25 mL round bottom flask was charged with CsA diene from Example 57 (X=OH, 40 mg, 0.033 mmol), CH$_2$Cl$_2$ (4 mL), 3,3,3-trifluoropropene (100 mg, 1.04 mmol), and Grubbs' catalyst 3$^{rd}$ generation (5 mg, 0.008 mmol). The mixture was stirred at 40° C. overnight under the atmosphere of 3,3,3-trifluoropropene. After cooling down to room temperature, solvent was removed in vacuo. The residue was pre-purified by column chromatography (silica gel, 6:1 EtOAc/CH$_3$CN) to give 40 mg of light brown solid. The obtained solid was purified via semi-preparative HPLC to give CsA diene (8 mg, 19%) as a white solid: $^1$H NMR (CDCl$_3$, 500 MHz) δ 8.33 (d, J=9.7 Hz, 1H), 8.00 (d, J=6.9 Hz, 1H), 7.71 (d, J=8.8 Hz, 1H), 7.48 (d, J=8.0 Hz, 2H), 6.40 (m, 1H), 5.85 (m, 1H), 5.70 (dd, J=11.0, 4.1 Hz, 1H), 5.33 (dd, J=11.2, 3.9 Hz, 1H), 5.26 (d, J=7.6 Hz, 1H), 5.20 (d, J=10.9 Hz, 1H), 5.15-5.05 (m, 2H), 5.00 (m, 1H), 4.88 (d, J=2.2 Hz, 1H), 4.86 (d, J=8.2 Hz, 1H), 4.70 (d, J=14.0 Hz, 2H), 4.44 (t, J=7.1 Hz, 2H), 4.28 (m, 1H), 4.18 (t, J=6.9 Hz, 1H), 3.50 (s, 3H), 3.36 (s, 3H), 3.23 (s, 3H), 3.17 (s, 3H), 3.08 (s, 3H), 2.98 (m, 2H), 2.70 (S, 3H), 2.69 (s, 3H), 2.32 (m, 1H), 2.22-0.62 (m, 62H); ESI MS m/z 1269 [C$_{63}$H$_{108}$F$_3$N$_{11}$O$_{12}$+H]$^+$; HPLC>99% (AUC), t$_R$=16.2 min.

Example 62

Preparation of Cyclosporin Diene (X=OAc)

A 25 mL round bottom flask was charged with CsA diene from Example 56 (X=OAc, 22 mg, 0.018 mmol), CH$_2$Cl$_2$ (2 mL), 1-hexene (15 mg, 0.178 mmol), and tricyclohexylphosphine[1,3-bis(2,4,6-trimethylphenyl)-4,5-dihydroimidazol-2-yl-ene][benzylidine]ruthenium(IV) dichloride (6.8 mg, 0.008 mmol). The mixture was refluxed for 24 h. After cooling down to room temperature, solvent was removed in vacuo. The residue was purified via semi-preparative HPLC to give CsA diene (X=OAc, 10 mg, 43.5%) as a white solid: $^1$H NMR (CDCl$_3$, 300 MHz) δ 8.56 (d, J=9.5 Hz, 1H), 8.05 (d, J=6.6 Hz, 1H), 7.64 (dd, J=9.1, 8.1 Hz, 2H), 5.86 (dd, J=10.1, 5.2 Hz, 1H), 5.68 (dd, J=11.1, 3.9 Hz, 1H), 5.63-5.28 (m, 6H), 5.16 (dd, J=10.2, 4.0 Hz, 1H), 5.08 (t, J=7.7 Hz, 1H), 4.99 (dt, J=9.9, 11.3 Hz, 2H), 4.85 (q, J=9.6 Hz, 1H), 4.65 (d, J=13.7 Hz, 1H), 4.43 (t, J=6.8 Hz, 1H), 3.44 (s, 3H), 3.35 (s, 3H), 3.30 (s, 3H), 3.21 (s, 3H), 3.01 (s, 3H), 2.67 (s, 3H), 2.65 (s, 3H), 2.13-1.99 (m, 8H), 1.94 (s, 3H), 1.83-0.70 (m, 68H); ESI MS m/z 1298 [C$_{68}$H$_{119}$N$_{11}$O$_{13}$+H]$^+$; HPLC>99% (AUC), t$_R$=20.6 min.

Example 63

Preparation of Cyclosporin Diene (X=OAc)

CsA diene from Example 62 (X=OAc, 5 mg, 0.0038 mmol) was dissolved in 2 mL of methanol, and then K$_2$CO$_3$ (5 mg, 0.038 mmol) was added. The mixture was stirred at room temperature for 63 h, solvent was removed in vacuo, the residue was purified via semi-preparative HPLC to give CsA diene (X=OH, 3.0 mg, 62%) as a white solid: $^1$H NMR (CDCl$_3$, 300 MHz) δ 8.36 (d, J=9.76 Hz, 1H), 7.94 (d, J=7.1 Hz, 1H), 7.55 (d, J=8.5 Hz, 1H), 7.45 (d, J=8.1 Hz, 1H), 6.00 (dd, J=15.5, 5.6 Hz, 1 H), 5.70 (dt, J=9.5, 5.6 Hz, 2H), 5.58 (t, J=6.7 Hz, 1H), 5.42 (dd, J=15.2, 5.3 Hz, 1H), 5.20-4.97 (m, 6H), 4.87-4.67 (m, 3H), 4.46 (t, J=6.6 Hz, 1H), 3.98 (m, 1H), 3.50 (s, 3H), 3.41(s, 3H), 3.33 (s, 3H), 3.15 (s, 3H), 3.05 (s, 3H), 2.69 (s, 6H), 1.69 (m, 4H), 1.35-0.84 (m, 72H); ESI MS m/z 1257 [C$_{66}$H$_{117}$N$_{11}$O$_{12}$+H]$^+$; HPLC 97.4% (AUC), t$_R$=18.7 min.

Example 64

Preparation of Cyclosporin Methyl Ketone XIb

To a suspension of 10% Pd/C (70 mg) in methanol (10 mL) was added a solution of CsA methyl vinyl ketone IIIb (X=OAc, 740 mg, 0.58 mmol) in methanol (10 mL). The mixture was shaken under 30 psi of hydrogen for 2 h. The solution was filtered through a 0.2 μm syringe pack then concentrated to dryness to give CsA methyl ketone XIb (X=OAc, 680 mg, 92%) as a yellowish oil, which was pure enough to be carried over the next step. $^1$H NMR (300 MHz, CDCl$_3$) δ 8.56 (d, J=9.6 Hz, 1H), 8.08 (d, J=6.7 Hz, 1H), 7.72 (d, J=9.0 Hz, 1H), 7.65 (d, J=7.7 Hz, 1H), 5.72-5.67 (m, 1H), 5.50-4.42 (m, 14H), 3.43 (s, 3H), 3.25 (s, 3H), 3.22 (s, 3H), 3.19 (s, 3H), 3.14 (s, 3H), 2.67 (s, 6H), 2.50-0.64 (m, 71H); ESI MS m/z 1219 [C$_{62}$H$_{111}$N$_{11}$O$_{13}$+H]$^+$.

Example 65

Preparation of Cyclosporin Tertiary Alcohol

To a solution of allylmagnesium bromide (2.3 mL, 1 M in diethyl ether, 2.3 mmol) in anhydrous THF (4 mL) under stirring and nitrogen, was added zinc chloride (2.3 mL, 1 M in THF, 2.3 mmol) dropwise. After having stirred the mixture at room temperature for 10 min, a solution of CsA methyl ketone from Example 64 (100 mg, 0.079 mmol) in THF (4 mL) was added dropwise. After 24 h, the reaction was quenched with water added dropwise and extracted with ethyl acetate. The organic layer was washed with water, separated, dried over anhydrous sodium sulfate and concentrated under vacuum. The crude material was purified by semi-preparative HPLC to afford CsA tertiary alcohol (X=OAc, 23 mg, 22%) as a colorless oil.

To a stirred solution of the acetate (23 mg, 0.01 mmol) in methanol (4 mL) was added potassium carbonate (30 mg, 0.2 mmol) at room temperature. After 18 h, ethyl acetate (50 mL) and water (30 mL) were added. The organic layer was separated, dried over anhydrous sodium sulfate, and concentrated under vacuum to afford crude product. The material was purified by semi-preparative HPLC to afford CsA tertiary alcohol (X=OH, 7.9 mg, 35%) as a colorless oil: $^1$H NMR (300 MHz, CDCl$_3$) δ 8.06-8.01 (m, 1H), 7.75 (d, J=7.3 Hz, 1H), 7.67-7.61 (m, 1H), 7.31-7.26 (m, 1H), 5.91-4.50 (m, 14H), 3.93-3.89 (m, 1H), 3.51 (s, 3H), 3.39 (s, 3H), 3.25 (s, 3H), 3.13 (s, 3H), 3.11 (s, 3H), 2.70 (s, 3H), 2.68 (s, 3H), 2.40-0.70 (m, 77H); ESI MS m/z 1261 [C$_{65}$H$_{117}$N$_{11}$O$_{13}$+H]$^+$; HPLC 96.4% (AUC), t$_R$=14.99 min.

Example 66

Preparation of Cyclosporin Tertiary Alcohol

To a solution of benzylmagnesium bromide (5.2 mL, 1 M in diethyl ether, 5.2 mmol) in THF (25 mL) under stirring and nitrogen at −78° C., was added a solution of CsA methyl ketone from Example 64 (550 mg, 0.43 mmol) in THF (10 mL) dropwise. Two additional portions of benzylmagnesium bromide (0.8 mL each) were added after 2 and 3 h respectively. After 5 h overall, the reaction was quenched with a saturated aqueous solution of ammonium chloride added dropwise. The reaction was extracted with ethyl acetate (100 mL) and washed with water. The organic layer was separated, dried over anhydrous sodium sulfate, and concentrated under vacuum to afford crude product. The material was purified by semi-preparative HPLC to afford CsA tertiary alcohol (X=OAc, 133 mg, 22%) as a pale yellowish oil: ESI MS m/z 1353 $[C_{71}H_{121}N_{11}O_{14}+H]^+$.

Example 67

Preparation of Cyclosporin Olefin

To a stirred suspension of methyltriphenylphosphonium bromide (600 mg, 1.68 mmol) in dry THF (4 mL) under nitrogen, was added sodium bis(trimethylsilyl)amide (1.68 mL, 1 M in THF, 1.68 mmol). After 1 h at room temperature, the mixture was cooled to 0C and CsA methyl ketone from Example 64 (X=OAc, 212 mg, 0.16 mmol) in anhydrous THF (4 mL) was added dropwise. After 1 h at 0° C., a saturated solution of ammonium chloride (5 mL) and then water were added. The residue was extracted with ethyl acetate (3×200 mL), and the combined organic extracts were dried over anhydrous sodium sulfate and concentrated under vacuum to afford crude product. The material was purified by semi-preparative HPLC to afford the CsA olefin (X=OAc, 27 mg, 12%) as a colorless oil.

To a stirred solution of CsA olefin (X=OAc, 24 mg, 0.02 mmol) in methanol (3 mL) was added potassium carbonate (30 mg, 0.2 mmol) at room temperature. After 18 h, ethyl acetate (50 mL) and water (30 mL) were added. The organic layer was separated, dried over anhydrous sodium sulfate, and concentrated under vacuum to afford crude product. The material was purified by semi-preparative HPLC to afford CsA olefin (X=OH, 8.1 mg, 35%) as a colorless oil: $^1$H NMR (300 MHz, CDCl$_3$) δ 7.94 (d, J=9.2 Hz, 1H), 7.67-7.62 (m, 2H), 5.72-5.64 (m, 1H), 5.54-5.50 (m, 1H), 5.40-4.55 (m, 14H), 3.77-3.71 (m, 1H), 3.50 (s, 3H), 3.38 (s, 3H), 3.26 (s, 3H), 3.12 (s, 3H), 3.08 (s, 3H), 2.72 (s, 3H), 2.70 (s, 3H), 2.50-0.66 (m, 72H); ESI MS m/z 1217 $[C_{63}H_{113}N_{11}O_{12}+H]^+$; HPLC>95% (AUC), $t_R$=15.88 min.

Example 68

Preparation of Cyclosporin Olefin

To a stirred suspension of ethyltriphenylphosphonium bromide (633 mg, 1.7 mmol) in dry THF (5 mL) under nitrogen, was added sodium bis(trimethylsilyl)amide (1.7 mL, 1 M in THF, 1.7 mmol). After 15 min at room temperature, the mixture was cooled to 0° C. and CsA methyl ketone from Example 64 (215 mg, 0.17 mmol) in anhydrous THF (4 mL) was added dropwise. After 24 h at 0° C., a saturated solution of ammonium chloride (5 mL) then water were added. The residue was extracted with ethyl acetate (3×200 mL), and the combined organic extracts were dried over anhydrous sodium sulfate and concentrated under vacuum to afford crude product. The material was purified by semi-preparative HPLC to afford CsA olefin (X=OAc, 12 mg, 5%) as a colorless oil.

To a stirred solution of the acetate (12 mg, 9.6 μmol) in methanol (2 mL) was added potassium carbonate (12 mg, 96 μmol) at room temperature. After 18 h, ethyl acetate (50 mL) and water (30 mL) were added. The organic layer was separated, dried over anhydrous sodium sulfate, and concentrated under vacuum to afford crude product. The material was purified by semi-preparative HPLC to afford CsA olefin (X=OH, 2.5 mg, 21%) as a colorless oil: $^1$H NMR (300 MHz, CDCl$_3$) δ 7.92-7.88 (m, 1H), 7.69-7.65 (m, 1H), 7.54-7.49 (m, 1H), 7.19-7.13 (m, 1H), 5.74-5.69 (m, 1H), 5.59-5.55 (m, 1H), 5.40-4.50 (m, 14H), 3.83-3.78 (m, 1H), 3.50 (s, 3H), 3.38 (s, 3H), 3.26 (s, 3H), 3.12 (s, 3H), 3.08 (s, 3H), 2.72 (s, 3H), 2.70 (s, 3H), 2.50-0.66 (m, 73H); ESI MS m/z 1231 $[C_{64}H_{115}N_{11}O_{12}+H]^+$; HPLC>91% (AUC), $t_R$=16.27 min.

Example 69

Preparation of Cyclosporin Diene

To a solution of CsA tertiary alcohol from Example 65 (X=OAc, 65 mg, 0.05 mmol) in benzene (7 mL) under stirring and nitrogen was added Burgess reagent (60 mg, 0.25 mmol). The mixture was stirred at 60° C. for 2 h. After cooling down, the reaction was extracted with ethyl acetate (100 mL) and washed with water. The organic layer was separated, dried over anhydrous sodium sulfate, and concentrated under vacuum to afford crude product. The material was purified by semi-preparative HPLC to afford CsA diene (X=OAc, 28 mg, 44%) as a yellowish oil.

To a stirred solution of the acetate (28 mg, 0.02 mmol) in methanol (4 mL) was added potassium carbonate (35 mg, 0.2 mmol) at room temperature. After 18 h, the ethyl acetate (50 mL) and water (10 mL) were added. The organic layer was washed with water, separated, dried over anhydrous sodium sulfate, and concentrated under vacuum to afford crude product. The material was purified three times by semi-preparative HPLC to afford CsA diene (2.2 mg, 8%) as a mixture of cis and trans isomers (colorless oil): $^1$H NMR (300 MHz, CDCl$_3$) δ 8.03-7.99 (m, 1H), 7.68-7.60 (m, 1H), 7.51-7.46 (m, 1H), 7.18-7.11 (m, 1H), 5.90-4.50 (m, 15H), 3.51 (s, 3H), 3.39 (s, 3H), 3.11 (s, 6H), 2.69 (s, 6H), 2.50-0.65 (m, 78H); ESI MS m/z 1243 $[C_{65}H_{115}N_{11}O_{12}+H]^+$; HPLC 18.4% and 76.4% (AUC), $t_R$=14.78 and 16.34 min.

Example 70

Preparation of Cyclosporin Olefin

To a solution of CsA tertiary alcohol from Example 66 (X=OAc, 133 mg, 0.09 mmol) in benzene (15 mL) under stirring and nitrogen was added Burgess reagent (117 mg, 0.49 mmol). The mixture was stirred at 60° C. for 1.5 h. After cooling down, the reaction was diluted with ethyl acetate (100 mL) and washed with water. The organic layer was separated, dried over anhydrous sodium sulfate, and concentrated under vacuum to afford CsA olefin (X=OAc, 67 mg, 51%), which was pure enough to be carried over without purification: ESI MS m/z 1353 $[C_{71}H_{121}N_{11}O_{14}+H]^+$.

To a stirred solution of CsA olefin (X=OAc, 67 mg, 0.05 mmol) in methanol (8 mL) was added potassium carbonate (67 mg, 0.48 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford CsA olefin (31 mg, 47%) as a mixture of cis and trans isomers (colorless oil): $^1$H NMR (300 MHz, CDCl$_3$) δ 8.09-7.97 (m, 1H), 7.75-7.67 (m, 1H), 7.57-7.53 (m, 1H), 7.24-10 (m, 7H), 5.70-4.60 (m, 14H), 3.82-3.78 (m, 1H), 3.51 (s, 3H), 3.39 (s, 3H), 3.25 (s, 3H), 3.10 (s, 3H), 3.08 (s, 3H), 2.72 (s, 3H), 2.70 (s, 3H), 2.45-0.71 (m, 71H); ESI MS m/z 1293 $[C_{69}H_{117}N_{11}O_{12}+H]^+$; HPLC 19.2% and 80.7% (AUC), $t_R$=15.25 and 16.86 min.

Example 71

Preparation of Cyclosporin Oxime

To a stirred solution of CsA methyl ketone from Example 64 (100 mg, 0.079 mmol) in pyridine (1 mL) was added methoxylamine hydrochloride (8.0 mg, 0.079 mmol). After 1 h at room temperature, the mixture was diluted with diethyl ether and washed with 1 N aqueous hydrochloric acid then water. The organic layer was separated, dried over anhydrous sodium sulfate, and concentrated under vacuum to afford crude product. The material was purified by semi-preparative HPLC to afford CsA oxime (X=OAc, 19 mg, 18%) as a yellowish oil: ESI MS m/z 1290 $[C_{65}H_{116}N_{11}O_{14}+H]^+$.

To a stirred solution of CsA oxime (X=OAc, 19 mg, 0.014 mmol) in methanol (2 mL) was added potassium carbonate (20 mg, 0.14 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford CsA oxime (X=OH, 4.2 mg, 23%) as a colorless oil: $^1$H NMR (300 MHz, CDCl$_3$) δ 7.99 (d, J=10.0 Hz, 1H), 7.70 (d, J=7.7 Hz, 1H), 7.47 (d, J=6.7 Hz, 1H), 7.13 (d, J=7.8 Hz, 1H), 5.73-5.69 (m, 1H), 5.56-5.52 (m, 1H), 5.35-4.52 (m, 12H), 3.80 (s, 3H), 3.51 (s, 3H), 3.38 (s, 3H), 3.19 (s, 6H), 2.71 (s, 3H), 2.69 (s, 3H), 2.45-0.71 (m, 75H); ESI MS m/z 1248 $[C_{63}H_{114}N_{12}O_{13}+H]^+$; HPLC>93% (AUC), $t_R$=14.82 min.

Example 72

Preparation of Cyclosporin Oxime

To a stirred solution of CsA methyl ketone from Example 64 (100 mg, 0.079 mmol) in pyridine (1 mL) was added O-allylhydroxylamine hydrochloride hydrate (8.6 mg, 0.079 mmol). After 2 h at room temperature, the mixture was diluted with diethyl ether and washed with 1 N aqueous hydrochloric acid then water. The organic layer was separated, dried over anhydrous sodium sulfate, and concentrated under vacuum to afford crude product. The material was purified by semi-preparative HPLC to afford CsA oxime (X=OAc, 19 mg, 18%) as a yellowish oil: ESI MS m/z 1316 $[C_{67}H_{118}N_{12}O_{14}+H]^+$.

To a stirred solution of CsA oxime (X=OAc, 19 mg, 0.014 mmol) in methanol (4 mL) was added potassium carbonate (18 mg, 0.13 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford CsA (X=OH, 9.7 mg, 53%) as a colorless oil: $^1$H NMR (500 MHz, CDCl$_3$) δ 8.02 (d, J=9.0 Hz, 1H), 7.71 (d, J=6.0 Hz, 1H), 7.58 (d, J=6.4 Hz, 1H), 7.21 (d, J=7.6 Hz, 1H), 5.98-5.90 (m, 1H), 5.78-5.70 (m, 1H), 5.59-5.52 (m, 1H), 5.31-4.50 (m, 12H), 3.66-3.60 (m, 1H), 3.51 (s, 3H), 3.40 (s, 3H), 3.25 (s, 3H), 3.09 (s, 3H), 3.08 (s, 3H), 2.71 (s, 3H), 2.69 (s, 3H), 2.45-0.69 (m, 75H); ESI MS m/z 1274 $[C_{65}H_{116}N_{12}O_{13}+H]^+$; HPLC>93% (AUC), $t_R$=15.32 min.

Example 73

Preparation of Cyclosporin Oxime

To a stirred solution of CsA methyl ketone from Example 64 (100 mg, 0.079 mmol) in pyridine (1 mL) was added O-benzylhydroxylamine hydrochloride (13 mg, 0.079 mmol). After 2 h at room temperature, the mixture was diluted with diethyl ether and washed with 1 N aqueous hydrochloric acid then water. The organic layer was separated, dried over anhydrous sodium sulfate, and concentrated under vacuum to afford crude product. The material was purified by semi-preparative HPLC to afford CsA oxime (X=OAc, 35 mg, 32%) as a yellowish oil: ESI MS m/z 1366 $[C_{71}H_{120}N_{12}O_{14}+H]^+$.

To a stirred solution of CsA oxime (X=OAc, 35 mg, 0.025 mmol) in methanol (4 mL) was added potassium carbonate (40 mg, 0.28 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford CsA oxime (X=OH, 18 mg, 53%) as a colorless oil: $^1$H NMR (300 MHz, CDCl$_3$) δ 8.00 (d, J=9.8 Hz, 1H), 7.70 (d, J=7.7 Hz, 1H), 7.50 (d, J=8.0 Hz, 1H), 7.37-7.29 (m, 5H), 7.17 (d, J=7.9 Hz, 1H), 5.78-5.70 (m, 1H), 5.65-5.60 (m, 1H), 5.35-4.55 (m, 12H), 3.83-3.78 (m, 1H), 3.51 (s, 3H), 3.37 (s, 3H), 3.20 (s, 3H), 3.10 (s, 6H), 2.69 (s, 3H), 2.67 (s, 3H), 2.40-0.70 (m, 73H); ESI MS m/z 1324 $[C_{69}H_{118}N_{12}O_{13}+H]^+$; HPLC>94% (AUC), $t_R$=15.84 min.

Example 74

Acetylation of Cyclosporin A

A solution of cyclosporin A (5.0 g, 4.16 mmol), acetic anhydride (7.80 mL, 83.2 mmol), and DMAP (760 mg, 6.2 mmol) in methylene chloride (40 mL) was stirred overnight at room temperature under N$_2$ atmosphere. Saturated sodium bicarbonate solution (200 mL) was added to the solution and stirred for an additional 2 h. The mixture was extracted with ether, washed with 1 N HCl, neutralized with saturated sodium bicarbonate solution, washed with brine, dried over sodium sulfate, and concentrated in vacuo to afford CsA acetate (4.92 g, 95%) as a white solid: $^1$H NMR (300 MHz, CDCl$_3$) δ 8.57 (d, J=9.6 Hz, 1H), 8.04 (d, J=6.9 Hz, 1H), 7.51 (d, J=9.4 Hz, 1H), 7.47 (d, J=7.8 Hz, 1H), 5.67 (dd, J=11.0, 4.0 Hz, 1H), 5.60-5.44 (m, 2H), 5.39 (dd, J=11.7, 3.7 Hz, 1H), 5.32-5.13 (m, 4H), 5.06-4.93 (m, 2H), 4.85 (t, J=7.2 Hz, 1H), 4.77 (t, J=9.6 Hz, 1H), 4.65 (d, J=13.7 Hz, 1H), 4.41 (t, J=7.0 Hz, 1H), 3.46 (s, 3H), 3.26 (s, 3H), 3.24 (s, 3H), 3.21 (s, 3H), 3.10 (s, 3H), 2.68 (s, 3H), 2.66 (s, 3H), 2.50-2.35 (m, 1H), 2.25-1.80 (m, 6H), 2.08 (s, 3H), 2.01 (s, 3H), 1.75-1.55 (m, 6H), 1.45-0.75 (m, 55H); ESI MS m/z 1245 $[C_{64}H_{113}N_{11}O_{13}+H]^+$.

Example 75

Preparation of Cyclosporin A Aldehyde (Formula XIV)

Ozone was bubbled into a solution of CsA acetate from Example 74 (3.0 g, 2.4 mmol) in methylene chloride (70 mL) at −78° C. until a blue color was developed. The mixture was degassed with nitrogen for a few min and dimethylsulfide (3 mL) was added at −78° C. The reaction mixture was allowed to warm to room temperature and stirred for 3 h. The reaction mixture was concentrated in vacuo and the residue was dissolved in ethyl acetate (300 mL), washed with water (2×70 mL) and brine (70 mL), dried over sodium sulfate, filtered, and concentrated in vacuo to afford CsA aldehyde XIV (2.79 g, 94%) as a white solid. The crude was carried to the next step without further purification: $^1$H NMR (300 MHz, CDCl$_3$) δ 9.60 (d, J=3.5 Hz, 1H), 8.55 (d, J=9.7 Hz, 1H), 7.96 (d, J=6.8 Hz, 1H), 7.52 (d, J=7.7 Hz, 1H), 7.46 (d, J=9.0 Hz, 1H), 5.67 (dd, J=11.0, 3.8 Hz, 1H), 5.60-5.45 (m, 2H), 5.32 (dd, J=12.1, 3.3 Hz, 1H), 5.24-5.10 (m, 2H), 5.08-4.90 (m, 2H), 4.84 (t, J=7.1 Hz, 1H), 4.73 (t, J=9.6 Hz, 1H), 4.64 (d, J=13.8 Hz, 1H), 4.41 (t, J=7.0 Hz, 1H), 3.46 (s, 3H), 3.29 (s, 6H), 3.21 (s, 3H), 3.08 (s, 3H), 2.67 (s, 3H), 2.65 (s, 3H), 2.50-2.35 (m, 2H), 2.25-1.80 (m, 6H), 1.99 (s, 3H), 1.75-1.55 (m, 3H), 1.50-0.75 (m, 57H); ESI MS m/z 1233 $[C_{62}H_{109}N_{11}O_{14}+H]^+$.

Example 76

Preparation of CsA Alcohol from Aldehyde of Formula XIV

Zinc chloride (1.0 M in ether, 6.5 mL, 6.5 mmol) was added dropwise to a solution of ethynylmagnesium bromide (0.5 M in THF, 13 mL, 6.5 mmol) at 0° C. and the mixture was stirred under nitrogen at 0° C. for 5 min. CsA aldehyde (XIV, 400 mg, 0.325 mmol) in THF (5 mL) was added and the mixture was allowed to slowly warm to room temperature for 1 h, quenched with saturated aqueous ammonium chloride, extracted with ethyl acetate. The combined organic layers were washed with brine, dried over sodium sulfate, filtered and concentrated in vacuo to give CsA alcohol (X═OAc, 390 mg, 95%) as a white solid: $^1$H NMR (300 MHz, CDCl$_3$) δ 8.44 (d, J=9.8 Hz, 1H), 7.95 (d, J=6.8 Hz, 1H), 7.76-7.73 (m, 2H), 5.70-4.15 (m, 13H), 3.45 (s, 3H), 3.29 (s, 3H), 3.21 (s, 3H), 3.20 (s, 3H), 3.14 (s, 3H), 2.67 (s, 6H), 2.50-1.50 (m, 10H), 1.99 (s, 3H), 1.40-0.75 (m, 60H); ESI MS m/z 1259 $[C_{64}H_{111}N_{11}O_{14}+H]^+$.

Example 77

Preparation of CsA Alcohol from Aldehyde of Formula XIV

Zinc chloride (1.0 M in ether, 4.8 mL, 4.8 mmol) was added to a solution of propynylmagnesium bromide (0.5 M in ether, 9.6 mL, 4.8 mmol) at 0° C. and the mixture was stirred under nitrogen at 0° C. for 5 min. CsA aldehyde (XIV, 300 mg, 0.24 mmol) in THF (4 mL) was added and the mixture was allowed to slowly warm to room temperature, quenched with saturated aqueous ammonium chloride, extracted with ethyl acetate. The combined organic layers were washed with brine, dried over sodium sulfate, filtered and concentrated in vacuo to give CsA alcohol (290 mg, 94%) as a white solid. A part of crude product (40 mg) was purified by semi-preparative HPLC to afford CsA alcohol (X═OAc, 20 mg, 50%) as a white solid: $^1$H NMR (300 MHz, CDCl$_3$) δ 8.47 (d, J=9.8 Hz, 1H), 7.96 (d, J=6.8 Hz, 1H), 7.70 (d, J=7.5 Hz, 1H), 7.58 (d, J=7.5 Hz, 1H), 5.70-4.10 (m, 13H), 3.44 (s, 3H), 3.29 (s, 3H), 3.23 (s, 3H), 3.22 (s, 3H), 3.13 (s, 3H), 2.67 (s, 6H), 2.50-1.50 (m, 9H), 1.99 (s, 3H), 1.80 (s, 3H), 1.40-0.75 (m, 60H); ESI MS m/z 1273 $[C_{65}H_{113}N_{11}O_{14}+H]^+$.

Example 78

Preparation of CsA Alcohol of Formula XV

A mixture of CsA alcohol from Example 77 (X═OAc, 20 mg, 0.016 mmol), potassium carbonate (100 mg, 0.724 mmol) and methanol (2 mL) was stirred at room temperature for 5 h, and then diluted with ethyl acetate, washed with water and brine, dried over sodium sulfate, filtered and concentrated in vacuo. The residue was purified by semi-preparative HPLC to afford CsA alcohol (X═OH, 8 mg, 42%) as a white solid: $^1$H NMR (300 MHz, CDCl$_3$) δ 8.15 (d, J=9.8 Hz, 1H), 7.80 (d, J=6.8 Hz, 1H), 7.49 (d, J=7.5 Hz, 1H), 7.38 (d, J=7.5 Hz, 1H), 5.70-3.95 (m, 12H), 3.53 (s, 3H), 3.37 (s, 3H), 3.25 (s, 3H), 3.16 (s, 3H), 3.13 (s, 3H), 2.68 (s, 6H), 2.50-1.50 (m, 11H), 1.80 (d, J=1.5 Hz, 3H), 1.40-0.75 (m, 60H); ESI MS m/z 1231 $[C_{63}H_{111}N_{11}O_{13}+H]^+$; HPLC>99% (AUC), $t_R$=15.49 min.

Example 79

Preparation of CsA Alcohol from Aldehyde of Formula XIV

Ethylmagnesium bromide (1.0 M in ether, 2.43 mL, 2.43 mmol) was added to a solution of 2-methyl-1-buten-3-yne (0.23 mL, 2.43 mmol) in THF (5 mL) at 0° C. and the mixture was stirred under nitrogen at 0° C. for 1 h. Zinc chloride (1.0 M in ether, 2.43 mL, 2.43 mmol) was added and the mixture was stirred at 0° C. for 5 min. CsA aldehyde (XIV, 300 mg, 0.24 mmol) in THF (4 mL) was added and the mixture was allowed to warm to room temperature and stirred overnight. The mixture was quenched with saturated aqueous ammonium chloride, extracted with ethyl acetate. The combined organic layers were washed with brine, dried over sodium sulfate, filtered and concentrated in vacuo. The crude product was purified by semi-preparative HPLC to afford CsA alcohol (X═OAc, 145 mg, 46%) as a white solid: $^1$H NMR (300 MHz, CDCl$_3$) δ 8.51 (t, J=9.8 Hz, 1H), 7.97 (d, J=6.8 Hz, 1H), 7.82 (t, J=8.5 Hz, 1H), 7.67 (t, J=7.2 Hz, 1H), 5.70-4.35 (m, 15H), 3.45 (s, 3H), 3.29 (s, 3H), 3.21 (s, 6H), 3.15 (s, 3H), 2.68 (s, 6H), 2.50-1.50 (m, 9H), 2.01 (s, 1.5H), 2.00 (s, 1.5H), 1.87 (s, 3H), 1.40-0.75 (m, 60H); ESI MS m/z 1299 $[C_{67}H_{115}N_{11}O_{14}+H]^+$.

Example 80

Preparation of CsA Alcohol of Formula XV

A mixture of CsA alcohol from Example 79 (X═OAc, 20 mg, 0.016 mmol), potassium carbonate (100 mg, 0.724 mmol) and methanol (2 mL) was stirred at room temperature for 5 h, and then diluted with ethyl acetate, washed with water and brine, dried over sodium sulfate, filtered and concentrated in vacuo. The residue was purified by semi-preparative HPLC to afford CsA alcohol (X═OH, 8 mg, 42%) as a white solid: $^1$H NMR (300 MHz, CDCl$_3$) δ 8.13 (d, J=9.8 Hz, 1H), 7.82 (d, J=6.8 Hz, 1H), 7.50 (t, J=8.5 Hz, 1H), 7.40 (t, J=8.5 Hz, 1H), 5.75-3.95 (m, 15H), 3.53 (s, 3H), 3.37 (s, 3H), 3.24 (s, 3H), 3.15 (s, 3H), 3.14 (s, 3H), 2.69 (s, 3H), 2.68 (s, 3H), 2.50-1.50 (m, 10H), 1.86 (s, 1.5H), 1.83 (s, 1.5H), 1.40-0.75 (m, 60H); ESI MS m/z 1257 $[C_{65}H_{113}N_{11}O_{13}+H]^+$; HPLC>99% (AUC), $t_R$=14.93 min.

Example 81

Preparation of CsA Alcohol from Aldehyde of Formula XIV

Zinc chloride (1.0 M in ether, 6.5 mL, 6.5 mmol) was added dropwise to a solution of phenylethynylmagnesium bromide (1.0 M in THF, 6.5 mL, 6.5 mmol) at 0° C. and the mixture was stirred under nitrogen at 0° C. for 5 min. CsA aldehyde (XIV, 400 mg, 0.325 mmol) in THF (10 mL) was added and the mixture was allowed to slowly warm to room temperature for 1 h, quenched with saturated aqueous ammonium chloride, extracted with ethyl acetate. The combined organic layers were washed with brine, dried over sodium sulfate, filtered and concentrated in vacuo to give the crude product (400 mg, 94%) as a white solid. A part of the crude product (100 mg) was purified by semi-preparative HPLC to afford CsA alcohol (X═OAc, 27 mg, 29%) as a white solid: $^1$H NMR (300 MHz, CDCl$_3$) δ 8.51 (d, J=9.8 Hz, 1H), 7.94 (d, J=9.2 Hz, 1H), 7.85 (d, J=8.5 Hz, 1H), 7.50-7.27 (m, 6H), 5.70-4.30 (m, 13H), 3.46 (s, 3H), 3.29 (s, 3H), 3.20 (s, 3H), 3.16 (s, 3H), 3.05 (s, 3H), 2.69 (s, 3H), 2.68 (s, 3H), 2.50-1.50 (m, 9H), 2.02 (s, 3H), 1.40-0.75 (m, 60H); ESI MS m/z 1335 $[C_{70}H_{115}N_{11}O_{14}+H]^+$.

Example 82

Preparation of CsA Alcohol of Formula XV

A mixture of CsA alcohol from Example 81 (X=OAc, 27 mg, 0.02 mmol), potassium carbonate (100 mg, 0.724 mmol) and methanol (2 mL) was stirred at room temperature for 15 h, and then diluted with ethyl acetate, washed with water and brine, dried over sodium sulfate, filtered and concentrated in vacuo. The residue was purified by semi-preparative HPLC to afford CsA alcohol (11 mg, 42%) as a white solid: $^1$H NMR (300 MHz, CDCl$_3$) δ 8.20 (d, J=9.8 Hz, 1H), 7.83 (d, J=8.5 Hz, 1H), 7.46-7.25 (m, 7H), 5.75-4.05 (m, 12H), 3.55 (s, 3H), 3.41 (s, 3H), 3.16 (s, 3H), 3.15 (s, 3H), 3.11 (s, 3H), 2.67 (s, 3H), 2.66 (s, 3H), 2.50-1.50 (m, 11H), 1.40-0.75 (m, 60H); ESI MS m/z 1293 $[C_{68}H_{113}N_{11}O_{13}+H]^+$; HPLC>99% (AUC), $t_R$=15.29 min.

Example 83

Preparation of CsA Alcohol from Aldehyde of Formula XIV

Ethylmagnesium bromide (1.0 M in ether, 2.43 mL, 2.43 mmol) was added to a solution of 3-ethynylthiophene (0.3 mL, 2.43 mmol) in THF (5 mL) at 0° C. and the mixture was stirred under nitrogen at 0° C. for 1 h. Zinc chloride (1.0 M in ether, 2.43 mL, 2.43 mmol) was added and the mixture was stirred at 0° C. for 5 min. CsA aldehyde (XIV, 300 mg, 0.24 mmol) in THF (4 mL) was added and the mixture was allowed to warm to room temperature and stirred overnight. The mixture was quenched with saturated aqueous ammonium chloride, extracted with ethyl acetate. The combined organic layers were washed with brine, dried over sodium sulfate, filtered and concentrated in vacuo. The crude product was purified by semi-preparative HPLC to afford CsA alcohol (X=OAc, 168 mg, 52%) as a white solid: $^1$H NMR (300 MHz, CDCl$_3$) δ 8.49 (d, J=9.8 Hz, 1H), 7.95 (d, J=6.8 Hz, 1H), 7.83 (d, J=8.5 Hz, 1H), 7.55-7.12 (m, 4H), 5.70-4.40 (m, 13H), 3.45 (s, 3H), 3.29 (s, 3H), 3.20 (s, 3H), 3.16 (s, 3H), 3.02 (s, 3H), 2.68 (s, 3H), 2.67 (s, 3H), 2.50-1.50 (m, 9H), 2.02 (s, 3H), 1.40-0.75 (m, 60H); ESI MS m/z 1341 $[C_{68}H_{113}N_{11}O_{14}S+H]^+$.

Example 84

Preparation of CsA Alcohol of Formula XV

A mixture of CsA alcohol from Example 83 (X=OAc, 20 mg, 0.015 mmol), potassium carbonate (50 mg, 0.36 mmol) and methanol (1 mL) was stirred at room temperature for 5 h, and then diluted with ethyl acetate, washed with water and brine, dried over sodium sulfate, filtered and concentrated in vacuo. The residue was purified by semi-preparative HPLC to afford CsA alcohol (X=OH, 13 mg, 67%) as a white solid: $^1$H NMR (300 MHz, CDCl$_3$) δ 8.17 (d, J=9.8 Hz, 1H), 7.80 (d, J=6.8 Hz, 1H), 7.65 (d, J=8.5 Hz, 1H), 7.55-7.12 (m, 4H), 5.75-3.95 (m, 12H), 3.51 (s, 3H), 3.38 (s, 3H), 3.11 (s, 6H), 3.09 (s, 3H), 2.69 (s, 6H), 2.50-1.50 (m, 10H), 1.40-0.75 (m, 61H); ESI MS m/z 1299 $[C_{66}H_{111}N_{11}O_{13}S+H]^+$; HPLC 93.4% (AUC), $t_R$=15.15 min.

Example 85

Preparation of CsA Olefin

Zinc chloride (1.0 M in ether, 9.7 mL, 9.7 mmol) was added to a solution of phenylmagnesium bromide (1.0 M in THF, 9.7 mL, 9.7 mmol) at 0° C. and the mixture was stirred under nitrogen at 0° C. for 5 min. CsA aldehyde (XIV, 400 mg, 0.325 mmol) in THF (5 mL) was added and the mixture was allowed to slowly warm to room temperature and stirred for 4 h. The mixture was quenched with saturated aqueous ammonium chloride, extracted with ethyl acetate. The combined organic layers were washed with brine, dried over sodium sulfate, filtered and concentrated in vacuo to give the crude alcohol as a white solid: ESI MS m/z 1311 $[C_{68}H_{115}N_{11}O_{14}+H]^+$.

A mixture of the crude alcohol, Burgess reagent (218 mg, 0.916 mmol) and benzene (10 mL) was heated at reflux for 5 h, and then cooled to room temperature, diluted with ether, washed with water and brine, dried over sodium sulfate, filtered and concentrated in vacuo. The residue was purified by semi-preparative HPLC to afford CsA olefin (X=OAc, 70 mg, 18%) as a white solid: $^1$H NMR (300 MHz, CDCl$_3$) δ 8.43 (d, J=9.5 Hz, 1H), 7.93 (d, J=7.0 Hz, 1H), 7.63 (d, J=7.2 Hz, 1H), 7.25-7.15 (m, 6H), 6.27 (d, J=16.8 Hz, 1H), 6.01 (dd, J=16.8, 8.0 Hz, 1H), 5.70-4.30 (m, 12H), 3.44 (s, 3H), 3.29 (s, 3H), 3.17 (s, 3H), 3.10 (s, 3H), 3.09 (s, 3H), 2.66 (s, 3H), 2.65 (s, 3H), 2.50-1.50 (m, 8H), 2.01 (s, 3H), 1.40-0.82 (m, 58H); ESI MS m/z 1293 $[C_{68}H_{113}N_{11}O_{13}+H]^+$.

Example 86

Preparation of CsA Olefin

A mixture of CsA olefin from Example 85 (X=OAc, 70 mg, 0.054 mmol), potassium carbonate (200 mg, 1.45 mmol) and methanol (2 mL) was stirred at room temperature for 8 h, and then diluted with ethyl acetate, washed with water and brine, dried over sodium sulfate, filtered and concentrated in vacuo. The residue was purified by semi-preparative HPLC to afford CsA olefin (X=OH, 37 mg, 54%) as a white solid: $^1$H NMR (300 MHz, CDCl$_3$) δ 8.10 (d, J=9.8 Hz, 1H), 7.78 (d, J=7.5 Hz, 1H), 7.60 (d, J=7.2 Hz, 1H), 7.35-7.17 (m, 6H), 6.44 (d, J=16.0 Hz, 1H), 6.17 (dd, J=16.0, 7.8 Hz, 1H), 5.75-4.35 (m, 12H), 3.52 (s, 3H), 3.39 (s, 3H), 3.23 (s, 3H), 3.11 (s, 6H), 2.70 (s, 6H), 2.50-1.50 (m, 9H), 1.40-0.82 (m, 58H); ESI MS m/z 1251 $[C_{66}H_{111}N_{11}O_{12}+H]^+$; HPLC>99% (AUC), $t_R$=15.76 min.

Example 87

Preparation of CsA Olefin

Zinc chloride (1.0 M in ether, 4.9 mL, 4.9 mmol) was added to a solution of p-fluorophenylmagnesium bromide (1.0 M in THF, 4.9 mL, 4.9 mmol) at 0° C. and the mixture was stirred under nitrogen at 0° C. for 5 min. CsA aldehyde (XIV, 300 mg, 0.243 mmol) in THF (5 mL) was added and the mixture was allowed to slowly warm to room temperature and stirred for 24 h. The mixture was quenched with saturated aqueous ammonium chloride, extracted with ethyl acetate. The combined organic layers were washed with brine, dried over sodium sulfate, filtered and concentrated in vacuo to give the crude alcohol as a white solid: ESI MS m/z 1329 $[C_{68}H_{114}FN_{11}O_{14}+H]^+$.

A mixture of the crude alcohol, Burgess reagent (160 mg, 0.68 mmol) and benzene (10 mL) was heated at reflux for 3 h, and then cooled to room temperature, diluted with ether, washed with water and brine, dried over sodium sulfate, filtered and concentrated in vacuo. The residue was purified by semi-preparative HPLC to afford CsA olefin (X=OAc, 62 mg, 21%) as a white solid: $^1$H NMR (300 MHz, CDCl$_3$) δ 8.47 (d, J=9.8 Hz, 1H), 7.95 (d, J=7.0 Hz, 1H), 7.81 (d, J=8.0 Hz, 1H), 7.65 (d, J=8.0 Hz, 1H), 7.10 (t, J=8.6 Hz, 2H), 6.98 (d, J=8.6 Hz, 2H), 6.23 (d, J=16.0 Hz, 1H), 5.91 (dd, J=16.0, 7.8 Hz, 1H), 5.70-4.35 (m, 12H), 3.45 (s, 3H), 3.28 (s, 3H), 3.17 (s, 3H), 3.12 (s, 3H), 3.11 (s, 3H), 2.66 (s, 3H), 2.64 (s, 3H), 2.50-1.50 (m, 8H), 2.00 (s, 3H), 1.40-0.82 (m, 58H); ESI MS m/z 1307 $[C_{68}H_{112}FN_{11}O_{13}+H]^+$.

Example 88

Preparation of CsA Olefin

A mixture of CsA olefin from Example 87 (X=OAc, 62 mg, 0.047 mmol), potassium carbonate (60 mg, 0.43 mmol) and methanol (2 mL) was stirred at room temperature overnight, and then diluted with ethyl acetate, washed with water and brine, dried over sodium sulfate, filtered and concentrated in vacuo. The residue was purified by semi-preparative HPLC to afford CsA olefin (X=OH, 38 mg, 63%) as a white solid: $^1$H NMR (300 MHz, CDCl$_3$) δ 8.13 (d, J=9.8 Hz, 1H), 7.86 (d, J=7.0 Hz, 1H), 7.70 (d, J=8.0 Hz, 1H), 7.40 (d, J=8.0 Hz, 1H), 7.28 (t, J=8.6 Hz, 2H), 6.96 (t, J=8.6 Hz, 2H), 6.38 (d, J=16.0 Hz, 1H), 6.10 (dd, J=16.0, 7.8 Hz, 1H), 5.70-4.00 (m, 12H), 3.51 (s, 3H), 3.38 (s, 3H), 3.24 (s, 3H), 3.11 (s, 6H), 2.72 (s, 3H), 2.70 (s, 3H), 2.50-1.50 (m, 9H), 1.40-0.82 (m, 58H); ESI MS m/z 1269 $[C_{66}H_{110}FN_{11}O_{12}+H]^+$; HPLC 94.2% (AUC), $t_R$=15.44 min.

Example 89

Preparation of CsA Olefin

Zinc chloride (1.0 M in ether, 4.9 mL, 4.9 mmol) was added to a solution of p-tolylmagnesium bromide (1.0 M in THF, 4.9 mL, 4.9 mmol) at 0° C. and the mixture was stirred under nitrogen at 0° C. for 5 min. CsA aldehyde (XIV, 300 mg, 0.243 mmol) in THF (5 mL) was added and the mixture was allowed to slowly warm to room temperature and stirred overnight. The mixture was quenched with saturated aqueous ammonium chloride, extracted with ethyl acetate. The combined organic layers were washed with brine, dried over sodium sulfate, filtered and concentrated in vacuo to give the crude alcohol as a white solid: ESI MS m/z 1325 $[C_{69}H_{117}N_{11}O_{14}+H]^+$.

A mixture of the crude alcohol, Burgess reagent (162 mg, 0.68 mmol) and benzene (10 mL) was heated at reflux for 2 h, and then cooled to room temperature, diluted with ether, washed with water and brine, dried over sodium sulfate, filtered and concentrated in vacuo. The residue was purified by semi-preparative HPLC to afford CsA olefin (X=OAc, 118 mg, 40%) as a white solid: $^1$H NMR (300 MHz, CDCl$_3$) δ 8.46 (d, J=9.8 Hz, 1H), 7.95 (d, J=7.0 Hz, 1H), 7.85 (d, J=8.0 Hz, 1H), 7.72 (d, J=8.0 Hz, 1H), 7.11 (d, J=8.0 Hz, 2H), 7.07 (d, J=8.0 Hz, 2H), 6.24 (d, J=16.0 Hz, 1H), 5.90 (dd, J=16.0, 7.8 Hz, 1H), 5.75-4.30 (m, 12H), 3.47 (s, 3H), 3.28 (s, 3H), 3.17 (s, 3H), 3.10 (s, 3H), 3.09 (s, 3H), 2.67 (s, 3H), 2.65 (s, 3H), 2.50-1.50 (m, 8H), 2.31 (s, 3H), 2.00 (s, 3H), 1.40-0.82 (m, 58H); ESI MS m/z 1307 $[C_{69}H_{115}N_{11}O_{13}+H]^+$.

Example 90

Preparation of CsA Olefin

A mixture of CsA olefin from Example 89 (X=OAc, 118 mg, 0.09 mmol), potassium carbonate (100 mg, 0.724 mmol) and methanol (3 mL) was stirred at room temperature overnight, and then diluted with ethyl acetate, washed with water and brine, dried over sodium sulfate, filtered and concentrated in vacuo. The residue was purified by semi-preparative HPLC to afford CsA olefin (X=OH, 60 mg, 53%) as a white solid: $^1$H NMR (300 MHz, CDCl$_3$) δ 8.08 (d, J=9.8 Hz, 1H), 7.81 (d, J=7.0 Hz, 1H), 7.75 (d, J=8.0 Hz, 1H), 7.48 (d, J=8.0 Hz, 1H), 7.17 (d, J=8.0 Hz, 2H), 7.07 (d, J=8.0 Hz, 2H), 6.41 (d, J=16.0 Hz, 1H), 6.07 (dd, J=16.0, 7.8 Hz, 1H), 5.75-4.00 (m, 12H), 3.51 (s, 3H), 3.38 (s, 3H), 3.22 (s, 3H), 3.11 (s, 6H), 2.70 (s, 6H), 2.50-1.50 (m, 9H), 2.30 (s, 3H), 1.40-0.82 (m, 58H); ESI MS m/z 1265 $[C_{67}H_{113}N_{11}O_{12}+H]^+$; $^{HPLC}$>99% (AUC), $t_R$=15.44 min.

Example 91

Preparation of CsA Olefin m-Tolylmagnesium bromide (1.0 M in THF, 3.65 mL, 3.65 mmol) was added to a solution of CsA aldehyde (XIV, 300 mg, 0.243 mmol) in THF (10 mL) at 0° C. and the mixture was stirred under nitrogen at 0° C. for 1 h. The mixture was quenched with saturated aqueous ammonium chloride, extracted with ethyl acetate. The combined organic layers were washed with brine, dried over sodium sulfate, filtered and concentrated in vacuo to give the crude alcohol as a white solid: ESI MS m/z 1325 $[C_{69}H_{117}N_{11}O_{14}+H]^+$.

A mixture of the crude alcohol, Burgess reagent (160 mg, 0.68 mmol) and benzene (10 mL) was heated at reflux for 2 h, and then cooled to room temperature, diluted with ether, washed with water and brine, dried over sodium sulfate, filtered and concentrated in vacuo. The residue was purified by semi-preparative HPLC to afford CsA olefin (X=OAc, 42 mg, 14%) as a white solid: $^1$H NMR (300 MHz, CDCl$_3$) δ 8.50 (d, J=9.8 Hz, 1H), 7.98 (d, J=7.0 Hz, 1H), 7.69 (d, J=8.0 Hz, 1H), 7.61 (d, J=8.0 Hz, 1H), 7.00-7.20 (m, 4H), 6.22 (d, J=16.0 Hz, 1H), 5.96 (dd, J=16.0, 7.8 Hz, 1H), 5.75-4.30 (m, 12H), 3.45 (s, 3H), 3.28 (s, 3H), 3.17 (s, 3H), 3.10 (s, 3H), 3.06 (s, 3H), 2.66 (s, 3H), 2.65 (s, 3H), 2.50-1.50 (m, 8H), 2.34 (s, 3H), 2.03 (s, 3H), 1.40-0.82 (m, 58H); ESI MS m/z 1307 $[C_{69}H_{115}N_{11}O_{13}+H]^+$.

Example 92

Preparation of CsA Olefin

A mixture of CsA olefin from Example 91 (X=OAc, 42 mg, 0.032 mmol), potassium carbonate (50 mg, 0.36 mmol) and methanol (1 mL) was stirred at room temperature for 7 h, and then diluted with ethyl acetate, washed with water and brine, dried over sodium sulfate, filtered and concentrated in vacuo. The residue was purified by semi-preparative HPLC to afford CsA olefin (X=OH, 25 mg, 41%) as a white solid: $^1$H NMR (300 MHz, CDCl$_3$) δ 8.07 (d, J=9.8 Hz, 1H), 7.80 (d, J=7.0 Hz, 1H), 7.54 (d, J=8.0 Hz, 1H), 7.28 (d, J=8.0 Hz, 1H), 7.16-6.98 (m, 4H), 6.39 (d, J=16.0 Hz, 1H), 6.16 (dd, J=16.0, 7.8 Hz, 1H), 5.70-3.95 (m, 12H), 3.53 (s, 3H), 3.39 (s, 3H), 3.23 (s, 3H), 3.11 (s, 3H), 3.10 (s, 3H), 2.70 (s, 6H), 2.50-1.50

(m, 9H), 2.32 (s, 3H), 1.40-0.82 (m, 58H); ESI MS m/z 1265 $[C_{67}H_{113}N_{11}O_{12}+H]^+$; HPLC 95.3% (AUC), $t_R$=15.76 min.

Example 93

Preparation of CsA Olefin

Zinc chloride (1.0 M in ether, 4.9 mL, 4.9 mmol) was added to a solution of o-tolylmagnesium bromide (1.0 M in THF, 4.9 mL, 4.9 mmol) at 0° C. and the mixture was stirred under nitrogen at 0° C. for 5 min. CsA aldehyde (XIV, 300 mg, 0.243 mmol) in THF (5 mL) was added and the mixture was allowed to slowly warm to room temperature and stirred overnight. The mixture was quenched with saturated aqueous ammonium chloride, extracted with ethyl acetate. The combined organic layers were washed with brine, dried over sodium sulfate, filtered and concentrated in vacuo to give the crude alcohol as a white solid: ESI MS m/z 1325 $[C_{69}H_{117}N_{11}O_{14}+H]^+$.

A mixture of crude alcohol, Burgess reagent (160 mg, 0.68 mmol) and benzene (10 mL) was heated at reflux for 2 h, and then cooled to room temperature, diluted with ether, washed with water and brine, dried over sodium sulfate, filtered and concentrated in vacuo. The residue was purified by semi-preparative HPLC to afford CsA olefin (X=OAc, 28 mg, 9%) as a white solid: $^1$H NMR (300 MHz, CDCl$_3$) δ 8.51 (d, J=9.8 Hz, 1H), 7.96 (d, J=7.0 Hz, 1H), 7.82 (d, J=8.0 Hz, 1H), 7.69 (d, J=8.0 Hz, 1H), 7.00-7.20 (m, 4H), 6.48 (d, J=16.0 Hz, 1H), 5.88 (dd, J=16.0, 7.8 Hz, 1H), 5.75-4.30 (m, 12H), 3.45 (s, 3H), 3.28 (s, 3H), 3.17 (s, 3H), 3.11 (s, 3H), 3.10 (s, 3H), 2.66 (s, 3H), 2.64 (s, 3H), 2.50-1.50 (m, 8H), 2.26 (s, 3H), 1.98 (s, 3H), 1.40-0.82 (m, 58H); ESI MS m/z 1307 $[C_{69}H_{115}N_{11}O_{13}+H]^+$.

Example 94

Preparation of CsA Olefin

A mixture of CsA olefin from Example 93 (X=OAc, 28 mg, 0.021 mmol), potassium carbonate (30 mg, 0.22 mmol) and methanol (1 mL) was stirred at room temperature overnight, and then diluted with ethyl acetate, washed with water and brine, dried over sodium sulfate, filtered and concentrated in vacuo. The residue was purified by semi-preparative HPLC to afford CsA olefin (X=OH, 12 mg, 44%) as a white solid: $^1$H NMR (300 MHz, CDCl$_3$) δ 8.19 (d, J=9.8 Hz, 1H), 7.81 (d, J=7.0 Hz, 1H), 7.63 (d, J=8.0 Hz, 1H), 7.41 (d, J=8.0 Hz, 1H), 7.20-7.10 (m, 4H), 6.66 (d, J=16.0 Hz, 1H), 5.98 (dd, J=16.0, 7.8 Hz, 1H), 5.70-3.95 (m, 12H), 3.54 (s, 3H), 3.39 (s, 3H), 3.18 (s, 3H), 3.12 (s, 3H), 3.11 (s, 3H), 2.70 (s, 6H), 2.50-1.50 (m, 9H), 2.30 (s, 3H), 1.40-0.82 (m, 58H); ESI MS m/z 1265 $[C_{67}H_{113}N_{11}O_{12}+H]^+$; HPLC>99% (AUC), $t_R$=15.77 min.

Example 95

Preparation of CsA Olefin

A solution of CsA aldehyde (XIV, 400 mg, 0.32 mmol) in THF (10 mL) was cooled to −78° C. and treated with 4-biphenylmagnesium bromide and allowed to stir for 30 min under N$_2$ atmosphere. Reaction was quenched with saturated ammonium chloride solution at −78° C., extracted with ethyl acetate, washed with brine, dried over sodium sulfate, and concentrated in vacuo. The crude product was purified by washing through a short silica gel column (9:1 hexanes/ethyl acetate to 9:1 ethyl acetate/methanol) to afford the crude alcohol (415 mg, 92%) as a pale yellow solid.

A solution of the crude alcohol (400 mg, 0.29 mmol) in benzene (11 mL) was heated to 50° C. Reaction mixture was then treated with Burgess reagent (200 mg, 0.087 mmol) and allowed to keep stirring at 50° C. for 3 h. Reaction was then heated to 70° C. and stirred for an additional 1.5 h. Reaction was allowed to slowly cool to room temperature. Reaction was diluted with ether, washed with water and brine, dried over sodium sulfate and concentrated in vacuo. The crude product was purified by semi-preparative HPLC to afford CsA olefin (X=OAc, 73.4 mg, 19%) as a pale yellow solid: $^1$H NMR (300 MHz, CD$_2$Cl$_2$) δ 8.02-7.51 (m, 6H), 7.45 (d, J=8.1 Hz, 4H), 7.42-7.30 (m, 6H), 5.66 (d, J=7.5 Hz, 1H), 5.25 (d, J=7.8 Hz, 1H), 5.16-4.93 (m, 14H), 4.41 (d, J=7.1 Hz, 1H), 4.34 (s, 2H), 4.16 (s, 2H), 4.12-3.82 (m, 2H), 3.41 (s, 3H), 3.35 (s, 3H), 3.22 (s, 3H), 3.13 (s, 3H), 3.07 (s, 3H), 2.66 (s, 3H), 2.65 (s, 3H), 1.51 (s, 1H), 1.46 (d, J=7.1 Hz, 2H), 1.34-0.69 (m, 54H); ESI MS m/z 1369 $[C_{74}H_{117}N_{11}O_{13}+H]^+$.

Example 96

Preparation of CsA Olefin

A solution of CsA olefin from Example 95 (X=OAc, 74 mg, 0.054 mmol) in methanol (2 mL) was stirred at room temperature and treated with potassium carbonate (82 mg, 0.59 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford CsA olefin (X=OH, 33 mg, 46%) as a pale yellow solid: $^1$H NMR (300 MHz, CD$_2$Cl$_2$) δ 7.98 (t, J=23.1 Hz, 1H), 7.69 (d, J=6.5 Hz, 1H), 7.60 (d, J=7.7 Hz, 4H), 7.55 (d, J=1.6 Hz, 1H), 7.52 (d, J=1.7 Hz, 1H), 7.47-7.39 (m, 4H), 7.34 (d, J=8.1 Hz, 1H), 7.24 (d, J=7.7 Hz, 1H), 6.45 (d, J=16.1 Hz, 1H), 6.30-6.24 (m, 1H), 5.69 (d, J=3.6 Hz, 1H), 5.66 (d, J=3.7 Hz, 1H), 5.16-4.59 (m, 8H), 4.39 (t, J=14.3 Hz, 1H), 4.10-4.01 (m, 2H), 3.49 (d, J=9.5 Hz, 4H), 3.36 (d, J=6.3 Hz, 4H), 3.20 (s, 3H), 3.11 (s, 3H), 3.09 (s, 3H), 2.68 (s, 3H), 2.67 (s, 3H), 2.66 (s, 3H), 2.64 (s, 3H), 1.35-1.20 (m, 3H), 1.04-0.65 (m, 50H); ESI MS m/z 1327 $[C_{72}H_{115}N_{11}O_{12}+H]^+$; HPLC>99% (AUC), $t_R$=16.71 min.

Example 97

Preparation of CsA Diene

Vinylmagnesium bromide (1.0 M in THF, 1.0 mL, 1.0 mmol) was added in 4 portions to a solution of CsA aldehyde (XIV, 300 mg, 0.24 mmol) in THF (10 mL) at −78° C. under nitrogen in 1 h. After addition the resulted mixture was stirred at −78° C. for 15 min., and then was quenched with saturated aqueous NH$_4$Cl solution (2 mL) at −78° C. The mixture was allowed to warm up to room temperature, and then poured in 10 mL of saturated aqueous NH$_4$Cl solution, extracted with EtOAc (3×25 mL). The combined organic layers were washed with saturated aqueous H$_4$Cl solution and brine, dried over NaSO$_4$. Concentrated to dryness to give 300 mg of white solid. The crude alcohol was used for next step without further purification.

To a solution of the crude alcohol (300 mg) in benzene (5 mL) was added Burgess reagent (100 mg, 0.42 mmol), and then the resulting mixture was stirred at 60° C. for 1 h under nitrogen. After that another portion of Burgess reagent (100 mg, 0.42 mmol) was added to the reaction mixture, and then the resulting mixture was stirred at 60° C. for an additional 2 h under nitrogen. The reaction mixture was allowed to cool down to room temperature, diluted with EtOAc (50 mL), washed with water, separated. The aqueous layer was extracted with EtOAc (3×10 mL), and the combined organic layers were dried over $Na_2SO_4$, concentrated to dryness. The residue was purified via semi-preparative HPLC to give CsA diene (X=OAc, 28 mg, 9% over 2 steps) as a white solid: $^1$H NMR ($CDCl_3$, 300 MHz) δ 8.55 (d, J=9.6 Hz, 1H), 8.05 (d, J=6.7 Hz, 1H), 7.62 (dd, J=7.9 Hz, 2.0 Hz, 2H), 5.92 (dd, J=15.1, 4.6, Hz, 1H), 5.68 (dd, J=10.9, 4.0, Hz, 1H), 5.60 (d, J=5.6 Hz, 1H), 5.54 (d, J=10.1 Hz, 1H), 5.36 (d, J=11.4 Hz, 1 H), 5.31 (dd,J=10.7, 4.0 Hz, 1H), 5.16 (dd, J=10.9, 4.0 Hz, 1H), 5.10-4.93 (m, 4H), 4.85 (dt, J=15.0, 7.3 Hz, 2H), 4.65 (d, J=13.7 Hz, 1H), 4.43 (t, J=7.0 Hz, 1H), 3.45 (s, 3H), 3.29 (s, 3H), 3.28 (s, 3H), 3.20 (s, 3H), 3.02 (s, 3H), 2.67 (s, 3H), 2.65 (s, 3H), 2.13-1.99 (m, 5H), 1.95 (s, 3H), 1.83-0.70 (m, 63H); ESI MS m/z 1243 $[C_{64}H_{111}N_{11}O_{13}+H]^+$; HPLC>99% (AUC), $t_R$=17.6 min.

Example 98

Preparation of CsA Alkyne

A mixture of CsA alcohol from Example 81 (300 mg, 0.225 mmol), Burgess reagent (268 mg, 1.12 mmol) and benzene (10 mL) was heated at reflux for 4 h, and then cooled to room temperature, diluted with ether, washed with water and brine, dried over sodium sulfate, filtered and concentrated in vacuo. The residue was purified by semi-preparative HPLC to afford CsA alkyne (X=OAc, 12 mg, 4%) as a white solid: $^1$H NMR (300 MHz, $CDCl_3$) δ 8.65 (d, J=9.8 Hz, 1H), 7.94 (d, J=7.0 Hz, 1H), 7.77 (d, J=8.0 Hz, 1H), 7.59 (d, J=9.2 Hz, 1H), 7.52-7.25 (m, 5H), 6.03 (dd, J=16.0, 6.8 Hz, 1H), 5.81 (d, J=16.0 Hz, 1H), 5.71-4.35 (m, 12H), 3.46 (s, 3H), 3.28 (s, 3H), 3.18 (s, 3H), 3.10 (s, 3H), 2.87 (s, 3H), 2.67 (s, 6H), 2.50-1.50 (m, 8H), 2.05 (s, 3H), 1.40-0.82 (m, 58H); ESI MS m/z 1317 $[C_{70}H_{113}N_{11}O_{13}+H]^+$.

Example 99

Preparation of CsA Alkyne

A mixture of CsA alkyne from Example 98 (12 mg, 0.009 mmol), potassium carbonate (50 mg, 0.36 mmol) and methanol (1 mL) was stirred at room temperature for 8 h, and then diluted with ethyl acetate, washed with water and brine, dried over sodium sulfate, filtered and concentrated in vacuo. The residue was purified by semi-preparative HPLC to afford CsA alkyne (5 mg, 43%) as a white solid: $^1$H NMR (300 MHz, $CDCl_3$) δ 8.37 (d, J=9.8 Hz, 1H), 7.84 (d, J=7.2 Hz, 1H), 7.51-7.48 (m, 2H), 7.44-7.27 (m, 5H), 6.16 (dd, J=16.0, 7.4 Hz, 1H), 5.79 (d, J=16.0 Hz, 1H), 5.72-3.95 (m, 12H), 3.51 (s, 3H), 3.42 (s, 3H), 3.14 (s, 3H), 3.10 (s, 3H), 3.02 (s, 3H), 2.68 (s, 6H), 2.50-1.50 (m, 9H), 1.40-0.82 (m, 58H); ESI MS m/z 1275 $[C_{68}H_{111}N_{11}O_{12}+H]^+$; HPLC>99% (AUC), $t_R$=16.20 min.

Example 100

Preparation of CsA Alkyne

A mixture of CsA alcohol from Example 83 (100 mg, 0.075 mmol), Burgess reagent (35 mg, 0.15 mmol) and benzene (4 mL) was heated at 50° C. for 1 h, and then cooled to room temperature, diluted with ether, washed with water and brine, dried over sodium sulfate, filtered and concentrated in vacuo. The residue was purified by semi-preparative HPLC to afford trans-isomer (20 mg, 20%) as a white solid: ESI MS m/z 1323 $[C_{68}H_{111}N_{11}O_{13}S+H]^+$; and cis-isomer (47 mg, 47%) as a white solid: ESI MS m/z 1323 $[C_{68}H_{111}N_{11}O_{13}S+H]^+$.

A mixture of acetate of the trans-isomer (20 mg, 0.008 mmol), potassium carbonate (50 mg, 0.36 mmol) and methanol (1 mL) was stirred at room temperature for 5 h, and then diluted with ethyl acetate, washed with water and brine, dried over sodium sulfate, filtered and concentrated in vacuo. The residue was purified by semi-preparative HPLC to afford the trans-isomer (5 mg, 25%) as a white solid: $^1$H NMR (300 MHz, $CDCl_3$) δ 8.38 (d, J=9.8 Hz, 1H), 7.84 (d, J=7.2 Hz, 1H), 7.58 (d, J=3.0 Hz, 1H), 7.46 (d, J=8.0 Hz, 1H), 7.39 (d, J=8.7 Hz, 1H), 7.23 (dd, J=5.0, 3.0 Hz, 1H), 7.18 (dd, J=5.0, 1.0 Hz, 1H), 6.15 (dd, J=16.0, 7.4 Hz, 1H), 5.78 (d, J=16.0 Hz, 1H), 5.72-3.95 (m, 12H), 3.50 (s, 3H), 3.43 (s, 3H), 3.15 (s, 3H), 3.09 (s, 3H), 2.98 (s, 3H), 2.68 (s, 6H), 2.50-1.50 (m, 9H), 1.40-0.82 (m, 58H); ESI MS m/z 1281 $[C_{66}H_{109}N_{11}O_{12}S+H]^+$; HPLC 98.9% (AUC), $t_R$=16.11 min.

Example 101

Preparation of CsA Alkyne

A mixture of CsA alcohol from Example 83 (100 mg, 0.075 mmol), Burgess reagent (35 mg, 0.15 mmol) and benzene (4 mL) was heated at 50° C. for 1 h, and then cooled to room temperature, diluted with ether, washed with water and brine, dried over sodium sulfate, filtered and concentrated in vacuo. The residue was purified by semi-preparative HPLC to afford trans-isomer (20 mg, 20%) as a white solid: ESI MS m/z 1323 $[C_{68}H_{111}N_{11}O_{13}S+H]^+$; and cis-isomer (47 mg, 47%) as a white solid: ESI MS m/z 1323 $[C_{68}H_{111}N_{11}O_{13}S+H]^+$.

A mixture of acetate of the cis-isomer (47 mg, 0.008 mmol), potassium carbonate (100 mg, 0.72 mmol) and methanol (1 mL) was stirred at room temperature for 5 h, and then diluted with ethyl acetate, washed with water and brine, dried over sodium sulfate, filtered and concentrated in vacuo. The residue was purified by semi-preparative HPLC to afford the cis-isomer (5 mg, 11%) as a white solid: $^1$H NMR (300 MHz, $CDCl_3$) δ 7.91 (d, J=9.8 Hz, 1H), 7.69-7.60 (m, 3H), 7.27-7.24 (m, 2H), 7.18 (dd, J=5.0, 1.0 Hz, 1H), 5.75-3.95 (m, 14H), 3.61 (s, 3H), 3.35 (s, 3H), 3.26 (s, 3H), 3.12 (s, 3H), 3.09 (s, 3H), 2.73 (s, 3H), 2.72 (s, 3H), 2.50-1.50 (m, 9H), 1.40-0.82 (m, 58H); ESI MS m/z 1281 $[C_{66}H_{109}N_{11}O_{12}S+H]^+$; HPLC 98.3% (AUC), $t_R$=15.86 min.

Example 102

Preparation of CsA Alkyne

A mixture of CsA alcohol from Example 76 (390 mg, 0.31 mmol), Burgess reagent (220 mg, 0.93 mmol) and benzene (10 mL) was heated at reflux for 4 h, and then cooled to room temperature, diluted with ether, washed with water and brine, dried over sodium sulfate, filtered and concentrated in vacuo. The residue was purified by semi-preparative HPLC to afford CsA alkyne (26 mg, 7%) as a white solid: $^1$H NMR (300 MHz, $CDCl_3$) δ 8.55 (d, J=9.8 Hz, 1H), 7.97 (d, J=7.0 Hz, 1H), 7.90 (d, J=7.8 Hz, 1H), 7.82 (d, J=9.3 Hz, 1H), 6.09 (dd, J=16.0, 6.4 Hz, 1H), 5.75-4.45 (m, 13H), 3.43 (s, 3H), 3.27 (s, 3H), 3.19 (s, 6H), 3.08 (s, 3H), 2.68 (s, 6H), 2.50-1.50 (m, 9H), 1.99 (s, 3H), 1.40-0.82 (m, 58H); ESI MS m/z 1241 $[C_{64}H_{109}N_{11}O_{13}+H]^+$.

Example 103

Preparation of CsA Alkyne

A mixture of CsA acetate from Example 102 (26 mg, 0.021 mmol), potassium carbonate (50 mg, 0.36 mmol) and methanol (1 mL) was stirred at room temperature for 8 h, and then diluted with ethyl acetate, washed with water and brine, dried over sodium sulfate, filtered and concentrated in vacuo. The residue was purified by semi-preparative HPLC to afford CsA alkyne (14 mg, 54%) as a white solid: $^1$H NMR (300 MHz, CDCl$_3$) δ 8.29 (d, J=9.8 Hz, 1H), 7.84 (d, J=7.2 Hz, 1H), 7.43-7.37 (m, 2H), 6.20 (dd, J=16.0, 7.4 Hz, 1H), 5.73-3.95 (m, 13H), 3.49 (s, 3H), 3.41 (s, 3H), 3.25 (s, 3H), 3.15 (s, 3H), 3.08 (s, 3H), 2.69 (s, 3H), 2.68 (s, 3H), 2.50-1.50 (m, 10H), 1.40-0.82 (m, 58H); ESI MS m/z 1199 $[C_{62}H_{107}N_{11}O_{12}+H]^+$; HPLC>99% (AUC), $t_R$=14.77 min.

Example 104

Preparation of CsA Alkyne

A mixture of CsA alcohol from Example 77 (200 mg, 0.157 mmol), Burgess reagent (187 mg, 0.786 mmol) and benzene (5 mL) was heated at reflux for 5 h, and then cooled to room temperature, diluted with ether, washed with water and brine, dried over sodium sulfate, filtered and concentrated in vacuo. The residue was purified by semi-preparative HPLC to afford trans-isomer (30 mg, 15%) as a white solid: $^1$H NMR (300 MHz, CDCl$_3$) δ 8.60 (d, J=9.8 Hz, 1H), 7.95 (d, J=7.0 Hz, 1H), 7.68 (d, J=7.8 Hz, 1H), 7.45 (d, J=9.4 Hz, 1H), 5.83 (dd, J=16.0, 6.8 Hz, 1H), 5.71-3.95 (m, 13H), 3.44 (s, 3H), 3.28 (s, 3H), 3.24 (s, 3H), 3.20 (s, 3H), 3.04 (s, 3H), 2.67 (s, 3H), 2.65 (s, 3H), 2.50-1.50 (m, 8H), 1.95 (s, 3H), 1.90 (d, J=1.6 Hz, 3H), 1.40-0.82 (m, 58H); ESI MS m/z 1255 $[C_{65}H_{111}N_{11}O_{13}+H]^+$.

Example 105

Preparation of CsA Alkyne

A mixture of CsA alcohol from Example 77 (200 mg, 0.157 mmol), Burgess reagent (187 mg, 0.786 mmol) and benzene (5 mL) was heated at reflux for 5 h, and then cooled to room temperature, diluted with ether, washed with water and brine, dried over sodium sulfate, filtered and concentrated in vacuo. The residue was purified by semi-preparative HPLC to afford cis-isomer (10 mg, 5%) as a white solid: $^1$H NMR (300 MHz, CDCl$_3$) δ 8.41 (d, J=9.8 Hz, 1H), 8.02 (d, J=7.0 Hz, 1H), 7.82 (d, J=8.6 Hz, 1H), 7.55 (d, J=8.5 Hz, 1H), 5.70-3.95 (m, 14H), 3.47 (s, 3H), 3.29 (s, 3H), 3.28 (s, 3H), 3.20 (s, 3H), 3.04 (s, 3H), 2.67 (s, 3H), 2.66 (s, 3H), 2.50-1.50 (m, 8H), 1.99 (s, 3H), 1.90 (d, J=2.3 Hz, 3H), 1.40-0.82 (m, 58H); ESI MS m/z 1255 $[C_{65}H_{111}N_{11}O_{13}+H]^+$.

Example 106

Preparation of CsA Alkyne

A mixture of the trans-isomer from Example 104 (10 mg, 0.008 mmol), potassium carbonate (50 mg, 0.36 mmol) and methanol (1 mL) was stirred at room temperature for 8 h, and then diluted with ethyl acetate, washed with water and brine, dried over sodium sulfate, filtered and concentrated in vacuo. The residue was purified by semi-preparative HPLC to afford the trans-isomer (6 mg, 60%) as a white solid: $^1$H NMR (300 MHz, CDCl$_3$) δ 8.29 (d, J=9.8 Hz, 1H), 7.85 (d, J=7.0 Hz, 1H), 7.51-7.46 (m, 2H), 5.92 (dd, J=16.0, 7.2 Hz, 1H), 5.73-3.95 (m, 12H), 3.48 (s, 3H), 3.40 (s, 3H), 3.26 (s, 3H), 3.14 (s, 3H), 3.08 (s, 3H), 2.69 (s, 6H), 2.50-1.50 (m, 10H), 1.89 (d, J=1.9 Hz, 3H), 1.40-0.82 (m, 58H); ESI MS m/z 1213 $[C_{63}H_{109}N_{11}O_{12}+H]^+$; HPLC 97.9% (AUC), $t_R$=16.50 min.

Example 107

Preparation of CsA Alkyne

A mixture of the cis-isomer from Example 105 (10 mg, 0.008 mmol), potassium carbonate (50 mg, 0.36 mmol) and methanol (1 mL) was stirred at room temperature for 8 h, and then diluted with ethyl acetate, washed with water and brine, dried over sodium sulfate, filtered and concentrated in vacuo. The residue was purified by semi-preparative HPLC to afford the cis-isomer (5 mg, 50%) as a white solid: $^1$H NMR (300 MHz, CDCl$_3$) δ 7.98 (d, J=9.8 Hz, 1H), 7.66 (d, J=7.4 Hz, 1H), 7.56 (d, J=8.0 Hz, 1H), 7.18 (d, J=8.0 Hz, 1H), 5.74-3.90 (m, 13H), 3.58 (s, 3H), 3.37 (s, 3H), 3.27 (s, 3H), 3.11 (s, 6H), 2.72 (s, 3H), 2.70 (s, 3H), 2.50-1.50 (m, 10H), 1.98 (d, J=2.0 Hz, 3H), 1.40-0.82 (m, 58H); ESI MS m/z 1255 $[C_{63}H_{109}N_{11}O_{12}+H]^+$; HPLC>99% (AUC), $t_R$=16.38 min.

Example 108

Preparation of CsA Alkyne

A mixture of CsA alcohol from Example 79 (100 mg, 0.077 mmol), Burgess reagent (27 mg, 0.115 mmol) and benzene (4 mL) was heated at reflux for 1 h, and then cooled to room temperature, diluted with ether, washed with water and brine, dried over sodium sulfate, filtered and concentrated in vacuo. The residue was purified by semi-preparative HPLC to afford the cis-isomer (10 mg, 10%) as a white solid: ESI MS m/z 1281 $[C_{67}H_{113}N_{11}O_{13}+H]^+$.

A mixture of acetate of the cis-isomer (26 mg, 0.021 mmol), potassium carbonate (50 mg, 0.36 mmol) and methanol (1 mL) was stirred at room temperature for 8 h, and then diluted with ethyl acetate, washed with water and brine, dried over sodium sulfate, filtered and concentrated in vacuo. The residue was purified by semi-preparative HPLC to afford CsA alkyne (14 mg, 54%) as a white solid: $^1$H NMR (300 MHz, CDCl$_3$) δ 7.98 (d, J=9.8 Hz, 1H), 7.69 (d, J=6.8 Hz, 1H), 7.59 (d, J=8.0 Hz, 1H), 7.18 (d, J=8.0 Hz, 1H), 5.75-3.95 (m, 15H), 3.59 (s, 3H), 3.38 (s, 3H), 3.28 (s, 3H), 3.10 (s, 6H), 2.72 (s, 3H), 2.70 (s, 3H), 2.50-1.50 (m, 10H), 1.92 (s, 3H), 1.40-0.75 (m, 58H); ESI MS m/z 1239 $[C_{65}H_{111}N_{11}O_{12}+H]^+$; HPLC>99% (AUC), $t_R$=15.40 min.

Example 109

Reduction of Cyclosporin Olefin

Hydrogenation of CsA olefin from Example 86 (20 mg, 0.016 mmol) with 10% of palladium on carbon (10 mg) was carried out in methanol (1 mL) under hydrogen (30 psi) on a parr shaker for 2 h. The mixture was filtered and the filtrate was concentrated in vacuo. The residue was purified by semi-preparative HPLC to afford the target (12 mg, 60%) as a light yellow solid: $^1$H NMR (300 MHz, CDCl$_3$) δ 7.97 (d, J=9.8 Hz, 1H), 7.67 (d, J=7.5 Hz, 1H), 7.51 (d, J=8.0 Hz, 1H), 7.25-7.10 (m, 6H), 5.80-3.80 (m, 12H), 3.52 (s, 3H), 3.38 (s, 3H), 3.25 (s, 3H), 3.10 (s, 3H), 3.09 (s, 3H), 2.72 (s, 3H), 2.70 (s, 3H), 2.50-1.50 (m, 10H), 1.40-0.82 (m, 61H); ESI MS m/z 1253 $[C_{66}H_{113}N_{11}O_{12}+H]^+$; HPLC>99% (AUC), $t_R$=16.12 min.

Example 110

Reduction of Cyclosporin Olefin

Hydrogenation of CsA olefin from Example 88 (20 mg, 0.016 mmol) with 10% of palladium on carbon (5 mg) was carried out in methanol (2 mL) under hydrogen (25 psi) on a parr shaker for 1 h. The mixture was filtered and the filtrate was concentrated in vacuo. The residue was purified by semi-preparative HPLC to afford the target (12 mg, 60%) as a light yellow solid: $^1$H NMR (300 MHz, CDCl$_3$) δ 7.97 (d, J=9.8 Hz, 1H), 7.66 (d, J=7.5 Hz, 1H), 7.53 (d, J=8.0 Hz, 1H), 7.22 (d, J=8.0 Hz, 1H), 7.10 (t, J=8.6 Hz, 2H), 6.91 (t, J=8.6 Hz, 2H), 5.75-3.80 (m, 12H), 3.51 (s, 3H), 3.38 (s, 3H), 3.26 (s, 3H), 3.09 (s, 6H), 2.72 (s, 3H), 2.69 (s, 3H), 2.50-1.50 (m, 10H), 1.40-0.82 (m, 61H); ESI MS m/z 1271 $[C_{66}H_{112}FN_{11}O_{12}+H]^+$; HPLC>99% (AUC), $t_R$=15.99 min.

Example 111

Reduction of Cyclosporin Olefin

Hydrogenation of CsA olefin from Example 90 (20 mg, 0.016 mmol) with 10% of palladium on carbon (5 mg) was carried out in methanol (2 mL) under hydrogen (25 psi) on a parr shaker for 1 h. The mixture was filtered and the filtrate was concentrated in vacuo. The residue was purified by semi-preparative HPLC to afford the target (14 mg, 70%) as a light yellow solid: $^1$H NMR (300 MHz, CDCl$_3$) δ 7.97 (d, J=9.8 Hz, 1H), 7.67 (d, J=7.5 Hz, 1H), 7.59 (d, J=8.0 Hz, 1H), 7.25-7.02 (m, 5H), 5.80-3.80 (m, 12H), 3.51 (s, 3H), 3.37 (s, 3H), 3.24 (s, 3H), 3.09 (s, 6H), 2.72 (s, 3H), 2.70 (s, 3H), 2.50-1.50 (m, 10H), 2.28 (s, 3H), 1.40-0.82 (m, 61H); ESI MS m/z 1267 $[C_{67}H_{115}N_{11}O_{12}+H]^+$; HPLC 95.2% (AUC), $t_R$=16.25 min.

Example 112

Reduction of Cyclosporin Olefin

Hydrogenation of CsA olefin from Example 92 (12 mg, 0.009 mmol) with 10% of palladium on carbon (3 mg) was carried out in methanol (1 mL) under hydrogen (20 psi) on a parr shaker for 1 h. The mixture was filtered and the filtrate was concentrated in vacuo. The residue was purified by semi-preparative HPLC to afford the target (10 mg, 83%) as a light yellow solid: $^1$H NMR (500 MHz, CDCl$_3$) δ 7.97 (d, J=9.8 Hz, 1H), 7.64 (d, J=7.5 Hz, 1H), 7.44 (d, J=8.0 Hz, 1H), 7.20-6.92 (m, 5H), 5.75-3.70 (m, 12H), 3.53 (s, 3H), 3.38 (s, 3H), 3.25 (s, 3H), 3.09 (s, 3H), 3.08 (s, 3H), 2.71 (s, 3H), 2.69 (s, 3H), 2.50-1.50 (m, 10H), 2.30 (s, 3H), 1.40-0.82 (m, 61H); ESI MS m/z 1267 $[C_{67}H_{115}N_{11}O_{12}+H]^+$; HPLC 98.9% (AUC), $t_R$=16.24 min.

Example 113

Reduction of Cyclosporin Olefin

Hydrogenation of CsA olefin from Example 94 (8 mg, 0.006 mmol) with 10% of palladium on carbon (2 mg) was carried out in methanol (1 mL) under hydrogen (25 psi) on a parr shaker for 1 h. The mixture was filtered and the filtrate was concentrated in vacuo. The residue was purified by semi-preparative HPLC to afford the target (6 mg, 75%) as a light yellow solid: $^1$H NMR (500 MHz, CDCl$_3$) δ 7.93 (d, J=9.8 Hz, 1H), 7.64 (d, J=7.5 Hz, 1H), 7.50 (d, J=8.0 Hz, 1H), 7.17 (d, J=8.0 Hz, 1H), 7.10-7.05 (m, 4H), 5.75-3.70 (m, 12H), 3.53 (s, 3H), 3.37 (s, 3H), 3.26 (s, 3H), 3.09 (s, 3H), 3.07 (s, 3H), 2.73 (s, 3H), 2.70 (s, 3H), 2.50-1.50 (m, 10H), 2.27 (s, 3H), 1.40-0.82 (m, 61H); ESI MS m/z 1267 $[C_{67}H_{115}N_{11}O_{12}+H]^+$; HPLC>99% (AUC), $t_R$=16.22 min.

Example 114

Reduction of Cyclosporin Olefin

A solution of CsA olefin from Example 96 (20 mg, 0.015 mmol) in methanol (2 ml) was treated with 10% Pd/C (5 mg) and kept under pressure with H$_2$ gas (25 psi). Reaction was run in Parr-shaker at room temperature for 1 h. Mixture was filtered through a micro-filter and rinsed with methanol. Filtrate was concentrated in vacuo. The crude product was purified by semi-preparative HPLC to afford the target compound (6.3 mg, 31%) as an off white solid: $^1$H NMR (300 MHz, CD$_2$Cl$_2$) δ 8.01 (d, J=9.0 Hz, 1H), 7.84 (d, J=6.0 Hz, 1H), 7.71 (d, J=9.0 Hz, 1H), 7.62-7.31 (m, 10H), 7.22 (d, J=7.9 Hz, 1H), 5.33 (d, J=2.6 Hz, 1H), 5.11 (d, J=10.7 Hz, 1H), 5.04-4.45 (m, 12H), 3.48 (d, J=8.8 Hz, 4H), 3.35 (s, 3H), 3.20 (d, J=2.2 Hz, 4H), 3.12-3.06 (m, 12H), 2.70-2.64 (m, 12H), 1.34-1.21 (m, 4H), 1.08-0.75 (m, 50H); ESI MS m/z 1329 $[C_{72}H_{117}N_{11}O_{12}+H]^+$; HPLC 98.1% (AUC), $t_R$=17.32 min.

Example 115

Reduction of Cyclosporin Olefin

To a suspension of 10% Pd/C (5 mg) in methanol (3 mL) was added a solution of CsA olefin from Example 47 (10 mg, 0.012 mmol) in methanol (2 mL). The mixture was stirred under hydrogen for 2 d. The solution was filtered through a 0.2 μm syringe pack and then concentrated to dryness. The material was purified by semi-preparative HPLC to afford CsA thiophene (2.4 mg, 24%) as a colorless oil: $^1$H NMR (300 MHz, CDCl$_3$) δ 7.99 (d, J=9.6 Hz, 1H), 7.67 (d, J=7.2 Hz, 1H), 7.46 (d, J=8.8 Hz, 1H), 7.19 (d, J=7.9 Hz, 1H), 7.04 (d, J=5.2 Hz, 1H), 6.88 (m, 1H), 6.78-6.73 (m, 1H), 5.72-5.67 (m, 1H), 5.25 (dd, J=11.7 Hz, 3.7 Hz, 1H), 5.23-4.49 (m, 14H), 3.87-3.82 (m, 1H), 3.51 (s, 3H), 3.38 (s, 3H), 3.23 (s, 3H), 3.10 (s, 6H), 2.70 (s, 3H), 2.69 (s, 3H), 2.45-0.71 (m, 66H); ESI MS m/z 1259 $[C_{64}H_{111}N_{11}O_{12}S+H]^+$; HPLC 97.8% (AUC), $t_R$=15.58 min.

Example 116

Determination of Immunosuppressive Activity

Cyclosporin A and cyclosporin derivatives of the present invention were tested for biological activity in the mixed lymphocyte reaction (MLR) assay. The MLR assay was designed to measure $^3$H-thymidine uptake by human lymphocytes or murine splenocytes that are undergoing cell proliferation in an immune response to allogeneic stimulation. The murine system uses the H2 disparate inbred mouse strains: Balb/c (H2$^d$) and C57B1/6 (H2$^b$). The results of testing cyclosporin A and cyclosporin derivatives of the present invention in human and murine MLR were comparable. The MLR assay is useful for identifying CsA derivatives with immunosuppressive activity and to quantify this activity relative to the immunosuppressive activity of CsA.

For the purposes of testing compounds of the present invention, a one-way MLR was performed. In this method, the splenocytes of the C57B1/6 mice are γ-irradiated so as to act as stimulators of an immune response from the splenocytes from the Balb/c mice. First, spleens from Balb/C and C57B1/6 mice were surgically removed. Next, splenocytes were isolated by meshing each spleen and suspending with RPMI/HEPES/0.01% human serum albumin. Then, C57B1/6 splenocyte cells (stimulators) were γ-irradiated at 2000 rads. Cells were washed after irradiation. Next, stimulator and responder cells were counted at 1:20 dilution in Trypan. Cell populations were established at 5.12×10⁶ cells per mL. Then, samples were plated in 96 well sterile tissue culture plates. To each well was added an aliquot (100 μL) of splenocytes (responders) from Balb/c mice and an aliquot (100 μL) of γ-irradiated splenocytes (stimulators) from C57B1/6 mice (final volume=200 μL with cell population of 2.5×10⁵ cells). Aliquots of a 4 μg/mL stock solution of cyclosporin A and cyclosporin derivatives were measured and combined with the amount of media that resulted in 200 μL final volume. Concentrations of cyclosporin A in test wells tested were: 10.0, 20.0, 30.0, 40.0, and 60.0 ng/mL. Cyclosporin derivatives of the present invention were initially tested at 10, 100, and 1000 ng/mL drug concentrations to determine the range of potency and then retested at tighter concentration intervals to determine $IC_{50}$ values (the inhibitory concentration of test compound determined to inhibit proliferation by 50% relative to control). To measure the effect of drug on proliferation, the plate was incubated for 3 days at 37° C. in 5% $CO_2$. On day 4, 1 μCi/well of ³H-Thymidine was added and the plate was incubated for 24 hours. On day 5, cells were harvested onto a glass microfiber filtermat using a cell harvester. Dried filtermat and scintillation fluid were placed into sample bag and sealed. Then, the amount of radioactivity incorporated in the splenocytes was measured using a beta counter for 1 minute. Finally, averages and standard deviations for each drug were calculated and results were expressed as:

% Inhibition (% control)=(1−[average *CPM* of test drug÷average *CPM* of 0 drug])×100;

% Proliferation=100−% Inhibition

Initial screens were done at a fixed value of 100 ng/ml test compound. IC50s are calculated from 7 point concentration-response curves using GraphPad software. $IC_{50}$ values for cyclosporin A, which was routinely run as the positive control in this immunosuppression assay, fell between 8-35 ng/ml. $IC_{50}$ values for compounds of the present invention tested in this immunosuppression assay typically fall in the range: 100 ng/ml≦$IC_{50}$≦1000 ng/ml. Compound IIIa of the present invention (synthesized according to methods described in Examples 3, 4, 5, and 6) gave an $IC_{50}$ value of 310 ng/ml (cyclosporin A $IC_{50}$=14 ng/ml) in this assay. The compound exemplified in Example 109 gave an $IC_{50}$ value of 160 ng/ml (cyclosporin A $IC_{50}$=16 ng/ml).

An alternative assay that was used to determine immunosuppression activity was the concanavalin A-stimulated splenocyte assay. In this assay, male BALB/c mice, at 5 to 7 weeks of age, are sacrificed by $CO_2$ inhalation. Spleens are removed and dissociated by pushing through a nylon cell strainer. The splenocytes are washed in RPMI 1640/5% fetal calf serum (FCS) and pelleted at 400g. Red blood cells are then lysed by resuspending the cell pellet in ACK lysis buffer (150 mM $NH_4Cl$, 1 mM $KHCO_3$, 0.1 mM EDTA, 3 ml per spleen) for 10 min at room temperature. After pelleting at 400 g, the cells are washed by resuspending in RPMI 1640/5% FCS and repelleting. The cell pellet is resuspended in RPMI 1640/5% FCS and again passed through a cell strainer to remove cell aggregates. The cells are then counted and adjusted to 2×10⁶ cells/ml in RPMI 1640/10% FCS/50 μM 2-mercaptoethanol. Cell viability is assessed by Trypan blue staining. Cyclosporin A or test compound and two micrograms of concanavalin A are added to the wells of a 96 well plate prior to the addition of 2×10⁵ splenocytes. The cells are cultured in a 37° C. $CO_2$ incubator for 2 days and then pulsed with 1 μCi of [³H]-thymidine for 6 hours. Cells are harvested onto filtermats with a TomTec 96 well plate harvester and lysed with $H_2O$. The filtermat and scintillation fluid are sealed in a plastic sleeve. [³H]thymidine incorporation is measured with a Wallac Trilux plate counter. Initial screens are done at a fixed value of 100 ng/ml test compound. IC50s are calculated from 7 point concentration-response curves using GraphPad software. $IC_{50}$ values for this immunosuppressive assay were consistent with those determined in the previous method.

Although the invention has been described in detail for the purpose of illustration, it is understood that such detail is solely for that purpose, and variations can be made therein by those skilled in the art without departing from the spirit and scope of the invention which is defined by the following claims.

What is claimed:
1. A compound of Formula (I):

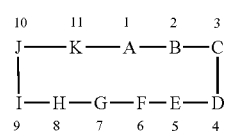

Formula I wherein A is an amino acid of Formula (II):

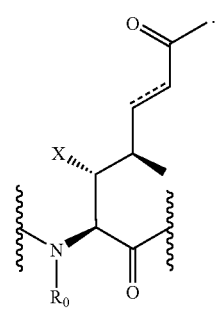

Formula III wherein:
$R_0$ is H or $CH_3$;
X=hydrogen;
hydroxyl; or
hydroxyl group derivatized with an alkanoyl, aryloyl, alkylaminocarbonyl, arylaminocarbonyl, arylalkylaminocarbonyl, alkyloxycarbonyl, aryloxycarbonyl, or arylalkyloxycarbonyl group;
CO— in Formula II is covalently bound to an α-amino group of B in Formula I to form an amide linkage, and —N—R₀ in Formula II is covalently bound to a carboxylic acid of K to form an amide linkage;

B is an amino acid selected from the group consisting of:
α-aminobutyric acid;
alanine;
threonine;
valine;
norvaline; and
a modified α-aminobutyric acid, alanine, valine, or norvaline, wherein a carbon atom in a side chain is substituted with a hydroxyl group;

C is a sarcosine;

D is an amino acid selected from the group consisting of:
leucine;
N-methyl leucine;
valine;
γ-hydroxy-N-methyl leucine; and
γ-hydroxy leucine;

E is an amino acid selected from the group consisting of:
valine;
norvaline; and
a modified valine or norvaline, wherein a carbon atom in a side chain is substituted with a hydroxyl group;

F is an amino acid selected from the group consisting of:
leucine;
N-methyl leucine;
γ-hydroxy-N-methyl leucine; and
γ-hydroxy leucine;

G is α-aminobutyric acid or alanine;

H is D-alanine;

I and J are independently selected from the group consisting of:
leucine;
N-methyl leucine;
γ-hydroxy-N-methyl leucine; and
γ-hydroxy leucine;

K is N-methyl valine or valine;
or a pharmaceutically acceptable salt thereof.

2. A compound according to claim 1, wherein the compound has the following formula:

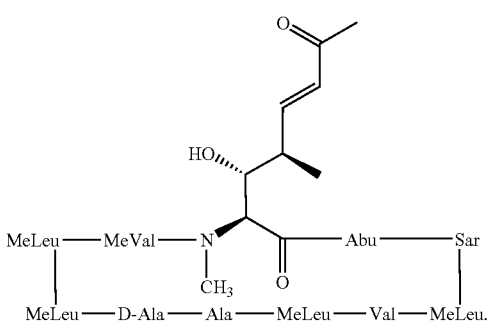

3. A compound according to claim 1, wherein the compound has the following formula:

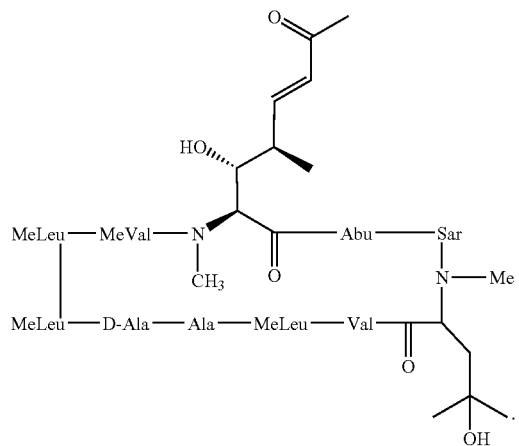

4. A compound according to claim 1, wherein the compound has the following formula:

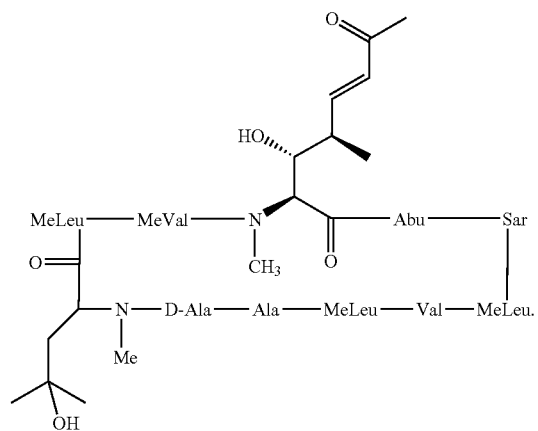

5. A compound according to claim 1, wherein the compound has the following formula:

Formula XI

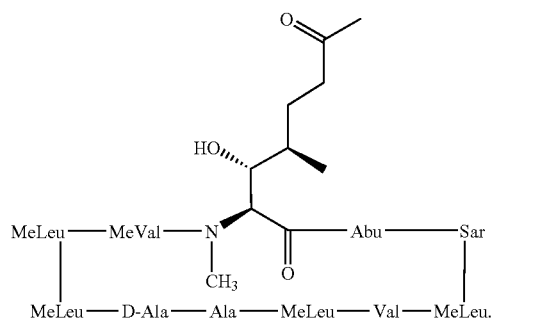

6. A pharmaceutical composition comprising a therapeutically effective amount of the compound of claim 1 and one or more pharmaceutical excipients.

7. A method of treating a mammal with a chronic inflammatory disease comprising:

administering a therapeutically effective amount of the compound of claim 1 to the mammal under conditions effective to treat the chronic inflammatory disease.

8. The method of claim 7, wherein the chronic inflammatory disease is selected from the group consisting of asthma, rheumatoid arthritis, multiple sclerosis, psoriasis, and ulcerative colitis.

* * * * *